US009617248B2

(12) United States Patent
Chessari et al.

(10) Patent No.: US 9,617,248 B2
(45) Date of Patent: *Apr. 11, 2017

(54) BICYCLIC HETEROCYCLE COMPOUNDS AND THEIR USES IN THERAPY

(71) Applicant: ASTEX THERAPEUTICS LIMITED, Cambridge (GB)

(72) Inventors: Gianni Chessari, Cambridge (GB); Christopher Norbert Johnson, Cambridge (GB); Lee William Page, Cambridge (GB); Ildiko Maria Buck, Cambridge (GB); James Edward Harvey Day, Cambridge (GB); Steven Howard, Cambridge (GB); Gordon Saxty, Zagreb (HR); Christopher William Murray, Cambridge (GB)

(73) Assignee: ASTEX THERAPEUTICS LIMITED, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/436,319

(22) PCT Filed: Oct. 18, 2013

(86) PCT No.: PCT/GB2013/052723
§ 371 (c)(1),
(2) Date: Apr. 16, 2015

(87) PCT Pub. No.: WO2014/060770
PCT Pub. Date: Apr. 24, 2014

(65) Prior Publication Data
US 2015/0353537 A1 Dec. 10, 2015

Related U.S. Application Data

(60) Provisional application No. 61/716,084, filed on Oct. 19, 2012.

(30) Foreign Application Priority Data

Oct. 19, 2012 (GB) .................................. 1218850.4

(51) Int. Cl.
C07D 403/14 (2006.01)
C07D 471/04 (2006.01)
C07D 519/00 (2006.01)

(52) U.S. Cl.
CPC ......... C07D 403/14 (2013.01); C07D 471/04 (2013.01); C07D 519/00 (2013.01)

(58) Field of Classification Search
CPC ........................... C07D 403/14; C07D 471/04
See application file for complete search history.

(56) References Cited

U.S. PATENT DOCUMENTS

| 4,080,330 | A | 3/1978 | Kubela et al. |
| 4,138,494 | A | 2/1979 | Kubela et al. |
| 4,153,789 | A | 5/1979 | Kubela et al. |
| 6,084,098 | A | 7/2000 | Kover et al. |
| 7,935,819 | B2 | 5/2011 | Halley et al. |
| 7,977,477 | B2 | 7/2011 | Berdini et al. |
| 8,044,206 | B2 | 10/2011 | Kikuchi et al. |
| 8,415,486 | B2 | 4/2013 | Condon et al. |
| 9,018,214 | B2 | 4/2015 | Woolford et al. |
| 9,155,743 | B2 | 10/2015 | Buck et al. |
| 9,458,158 | B2 | 10/2016 | Buck et al. |
| 2005/0245537 | A1 | 11/2005 | Tsuchimori et al. |
| 2014/0045831 | A1 | 2/2014 | Buck et al. |
| 2014/0179666 | A1 | 6/2014 | Woolford et al. |
| 2015/0259359 | A1 | 9/2015 | Chessari et al. |
| 2015/0266873 | A1 | 9/2015 | Chessari et al. |
| 2015/0291586 | A1 | 10/2015 | Woolford et al. |
| 2015/0353537 | A1 | 12/2015 | Chessari et al. |
| 2016/0083377 | A1 | 3/2016 | Buck et al. |
| 2017/0029419 | A1 | 2/2017 | Chessari et al. |

FOREIGN PATENT DOCUMENTS

| CA | 2433090 A1 | 7/2002 |
| EP | 302008 A2 | 2/1989 |
| EP | 560235 A1 | 9/1993 |
| EP | 778277 A1 | 6/1997 |
| GB | 1550230 | 8/1979 |
| JP | S52-012162 A | 1/1977 |
| WO | 97/16440 A1 | 5/1997 |
| WO | 97/30971 A1 | 8/1997 |
| WO | 97/38665 A2 | 10/1997 |
| WO | 98/00401 A1 | 1/1998 |
| WO | 98/50346 A1 | 11/1998 |
| WO | 98/50358 A1 | 11/1998 |
| WO | 99/28313 A1 | 6/1999 |
| WO | 99/50247 A1 | 10/1999 |
| WO | 00/15612 A1 | 3/2000 |

(Continued)

OTHER PUBLICATIONS

Flygare, J., et al., "Small-molecule pan-IAP antagonists: a patent review", Expert Opinion on Therapeutic Patents, Informa Healthcare, GB, vol. 20 (2), pp. 251-267 (2010).

Eckelman, B.P., et al "The mechanism of peptide-binding specificity of IAP-BIR domains", Cell Death and Differentiation, Nature Publishing Group, GB, vol. 15(5), pp. 920-928 (2008).

Ashton, K., et al., "Small Molecule Disruptors of the Glucokinase-Glucokinase Regulatory Protein Interaction: 1. Discovery of a Novel Tool Compound for in Vivo Proof-of-Concept", Journal of Medicinal Chemistry, vol. 57(2), pp. 309-324 (2014).

(Continued)

Primary Examiner — Rebecca Anderson
(74) Attorney, Agent, or Firm — Heslin Rothenberg Farley & Mesiti P.C.

(57) ABSTRACT

The invention relates to new bicyclic heterocycle compounds, to pharmaceutical compositions comprising the compounds and to the use of the compounds in the treatment of diseases, e.g. cancer.

20 Claims, No Drawings

(56) References Cited

FOREIGN PATENT DOCUMENTS

| | | |
|---|---|---|
| WO | 00/51984 A1 | 9/2000 |
| WO | 00/55143 A1 | 9/2000 |
| WO | 01/05763 A2 | 1/2001 |
| WO | 01/12600 A1 | 2/2001 |
| WO | 01/17942 A1 | 3/2001 |
| WO | 01/44226 A1 | 6/2001 |
| WO | 02/50061 A1 | 6/2002 |
| WO | 02/080853 A2 | 10/2002 |
| WO | 02/088101 A2 | 11/2002 |
| WO | 2005/019167 A2 | 3/2005 |
| WO | 2005/039572 A1 | 5/2005 |
| WO | 2006/010118 A2 | 1/2006 |
| WO | 2006/032987 A1 | 3/2006 |
| WO | 2006/069063 A1 | 6/2006 |
| WO | 2007/054453 A1 | 5/2007 |
| WO | 2007/073405 A1 | 6/2007 |
| WO | 2007/090617 A2 | 8/2007 |
| WO | 2008/045905 A1 | 4/2008 |
| WO | 2008/109181 A2 | 9/2008 |
| WO | 2008/116107 A2 | 9/2008 |
| WO | 2009/094287 A1 | 7/2009 |
| WO | 2009/147476 A1 | 12/2009 |
| WO | 2010/011666 A2 | 1/2010 |
| WO | 2010/048149 A2 | 4/2010 |
| WO | 2010/121212 A2 | 10/2010 |
| WO | 2010/129467 A1 | 11/2010 |
| WO | 2012/143725 A1 | 10/2012 |
| WO | 2012/143726 A1 | 10/2012 |
| WO | 2013/052110 A1 | 4/2013 |
| WO | 2013/102242 A1 | 7/2013 |
| WO | 2014/060767 A1 | 4/2014 |
| WO | 2014/060768 A1 | 4/2014 |
| WO | 2014/060770 A1 | 4/2014 |
| WO | 2015/092420 A1 | 6/2015 |
| WO | 2015/106025 A1 | 7/2015 |

OTHER PUBLICATIONS

Moore, C., et al., "Structural and Biophysical Characterization of XIAP BIR3 G306E Mutant: Insights in Protein Dynamics and Application for Fragment-Based Drug Design", Chem. Biol. Drug Design, vol. 74(3), pp. 212-223 (2009).

Zhao, H., et al., "Indoline and Piperazine Containing Derivatives as a Novel Class of Mixed D2/D4 Receptor Antagonists. Part 1: Identification and Structure-Activity Relationships" Bioorganic & Medicinal Chemistry Letters, vol. 12, pp. 3105-3109 (2002).

International Search Report for PCT/GB2013/052723 dated Dec. 20, 2013.

GB Search Report for GB1218850.4 dated Feb. 7, 2013.

Vippagunta, S.R. et al., Crystalline Solids, *Advanced Drug Delivery Reviews*, vol. 48, pp. 3-26 (2001).

BICYCLIC HETEROCYCLE COMPOUNDS AND THEIR USES IN THERAPY

CROSS REFERENCE TO RELATED APPLICATIONS

This application is a national stage filing under section 371 of International Application No. PCT/GB2013/052723, filed on Oct. 18, 2013, and published in English on Apr. 24, 2014 as WO 2014/060770, and claims priority to U.S. Provisional Application No. 61/716,084 filed on Oct. 19, 2012 and to British Application No. 1218850.4 filed on Oct. 19, 2012.

FIELD OF THE INVENTION

The invention relates to new bicyclic heterocycle compounds, to pharmaceutical compositions comprising said compounds and to the use of said compounds in the treatment of diseases, e.g. cancer.

BACKGROUND OF THE INVENTION

IAP Family

The family of inhibitor of apoptosis (IAP) proteins comprises 8 members, XIAP, cIAP1, cIAP2, NAIP, ILP2, ML-IAP, survivin and BRUCE (also known as apollon). Members of the IAP family have been shown to inhibit programmed cell death through their ability to directly inhibit members of the caspase family of apoptotic enzymes, although the precise role of all 8 members is yet to be fully defined. The common structural feature of all IAP family members is a ~70 amino acid zinc-binding fold termed the baculovirus IAP repeat (BIR) domain, which is present in one to three copies.

Many interactions between IAPs and other proteins are mediated via a surface groove on the BIR domain. BIR domains may be classified by their peptide-binding specificity. There are three types of BIR domains; type III domains (capable of binding caspase (and caspase-like) peptides with a specificity for proline in the third (P3) position (e.g. XIAP BIR3), type II domains (like type III domains but lacking the proline requirement e.g. XIAP BIR2) and type I domains (which do not bind caspases or similar peptides, e.g. XIAP BIR1) (Eckelman et al. Cell Death and Differentiation 2008; 15: 920-928). BIRs are small (~70 amino acids) Zn-coordinated domains and a variety of proteins use their N-terminal to interact with the BIR domains grooves. BIR antagonists prevent caspases binding to BIRs and hence result in increased caspase activity thereby inducing auto-ubiquitination and proteasomal degradation of IAPs.

IAPs are overexpressed in many cancers including renal, melanoma, colon, lung, breast, ovarian and prostate cancers (Tamm et al., Clin. Cancer Research 2000; 6(5): 1796-803), and have been implicated in tumour growth, pathogenesis and resistance to chemo- and radio-therapy (Tamm 2000).

XIAP

XIAP is a 57 kDa protein with three BIR domains, the second and third of which bind caspases and a RING-type zinc finger (E3 ligase). XIAP binds several proteins in addition to caspases, including ligation substrates such as TAK1 and cofactor TAB1, MURR1 involved in copper homeostasis (Burstein et al., EMBO 2004; 23: 244-254), endogenous inhibitors such as second mitochondria-derived activator of caspases (SMAC), and those of less clear function such as MAGE-D1, NRAGE (Jordan et al., J. Biol. Chem. 2001; 276: 39985-39989).

The BIR3 domain binds and inhibits caspase-9, an apical caspase in the mitochondrial pathway of caspase activation. A groove on the surface of the BIR3 domain interacts with the N-terminus of the small subunit of caspase-9, locking capsase-9 in its inactive monomeric form with an incompetent catalytic site (Shiozaki et al., Mol. Cell 2003; 11: 519-527).

In addition to caspase-binding, XIAP also inhibits apoptosis through other mechanisms. XIAP forms a complex with TAK1 kinase and its cofactor TAB1 that leads to activation of JNK and MAPK signal transduction pathways, in turn leading to activation of NFκB (Sanna et al., Mol Cell Biol 2002; 22: 1754-1766). XIAP also activates NFκB by promoting NFκB translocation to the nucleus and degradation of IκB (Hofer-Warbinek et al., J. Biol. Chem. 2000; 275: 22064-22068, Levkau et al., Circ. Res. 2001; 88: 282-290).

Cells transfected with XIAP are able to block programmed cell death in response to a variety of apoptotic stimuli (Duckett et al., EMBO 1996; 15: 2685-2694, Duckett et al., MCB 1998; 18: 608-615, Bratton, Lewis, Butterworth, Duckett and Cohen, Cell Death and Differentiation 2002; 9: 881-892).

XIAP is ubiquitously expressed in all normal tissues, but it is pathologically elevated in many acute and chronic leukaemias, prostate, lung, renal, and other types of tumours (Byrd et al., 2002; Ferreira et al., 2001; Hofmann et al., 2002; Krajewska et al., 2003; Schimmer et al., 2003; Tamm et al., 2000). In de novo acute myeloid leukaemia (AML), XIAP expression correlates with myelomonocytic French-American-British (FAB) subtypes M4/M5 ($P<0.05$) and expression of monocytic markers in AML blasts. In addition, XIAP was found to be overexpressed in normal monocytes but undetectable in granulocytes. In AML, XIAP expression was significantly lower in patients with favourable rather than intermediate or poor cytogenetics (n=74; $P<0.05$) (Tamm et al., Hematol. J. 2004; 5(6): 489-95).

Overexpression renders cells resistant to multi-agent therapy and is associated with poor clinical outcome in disease including AML, renal cancer, melanoma (Tamm et al., Clin. Cancer Research 2000; 6: 1796-1803) and lung cancer (Hofmann et al., J. Cancer Res. Clin. Oncology 2002; 128(10): 554-60).

XIAP is translated by a cap-independent mechanism of translation initiation that is mediated by a unique internal ribosome entry site (IRES) sequence element located in its 5' untranslated region. This allows XIAP mRNA to be actively translated during conditions of cellular stress when the majority of cellular protein synthesis is inhibited. Translational upregulation of XIAP in response to stress increases resistance to radiation induced cell death (Holcik et al., Oncogene 2000; 19: 4174-4177).

XIAP inhibition has been investigated in vitro via several techniques including RNA silencing, gene knockout, peptidic ligand mimetics and small molecule antagonists, and has been shown to promote apoptosis as a monotherapy and to sensitise many tumour types to chemotherapy, including bladder (Kunze et al., 2008; 28(4B): 2259-63). XIAP knockout mice are born at the expected Mendelian frequency, with no obvious physical or histological defects, and normal life spans (Harlin et al., Mol. Cell Biol. 2001; 21(10): 3604-3608). This indicates that lacking XIAP activity is not toxic in normal tissues and suggests a therapeutic window over tumour cells. Further studies have shown XIAP is a critical discriminator between apoptosis in type 1 and type 2 cells including hepatocytes and therefore should be used with caution in patients with underlying liver conditions (Jost et al., Nature, 2009, 460, 1035-1041). It was noted that the cIAP1 and cIAP2 levels are upregulated in the XIAP knockout mouse and may protect from pathology via a compensatory mechanism, suggesting pan-inhibition may be required for functional knockout. Similarly, cIAP1 and cIAP2 knockout mice are also asympotomatic (Conze et al., Mol. Biol. Cell 2005; 25(8): 3348-56). While lack of any one of the IAPs produced no overt phenotype in mice, deletion of cIAP1 with cIAP2 or XIAP resulted in mid embryonic lethality (Moulin, EMBO J., 2012).

Endogenous IAP antagonists such as SMAC have been used to validate members of this family as targets for therapeutic agents. SMAC peptides chemosensitise tumour cells, and in combination with platins and Tumour Necrosis Factor α-related apoptosis inducing ligand (TRAIL) in xenografts, results in tumour growth delay (Fulda et al., Nat. Med. 2002; 808-815; Yang et al., Cancer Res. 2003; 63: 831-837).

A natural product, embellin, was identified as binding at the surface groove of the BIR3 domain of XIAP with similar affinity to the natural SMAC peptide. Embellin induces apoptosis in cell lines in vitro and results in tumour growth delay in xenografts (Nikolovska-Coleska et al., J. Med. Chem. 2004; 47(10): 2430-2440; Chitra et al., Chemotherapy 1994; 40: 109-113).

XIAP antisense oligonucleotides have been developed as therapeutic agents for solid tumour and haematological malignancies. In vitro these antisense oligonucleotides have been shown to knockdown protein expression levels by 70%, induce apoptosis and sensitise cells to chemotherapy and delay tumour growth in vivo. One of these agents, AEG351156, has been studied in clinical trials (Hu et al., Clin. Cancer Res. 2003; 9: 2826-2836; Cummings et al., Br. J. Cancer 2005; 92: 532-538).

Small molecule antagonists of XIAP developed include peptidomimetics as well as synthetic agents. The peptidomimetics target the BIR3 domain, mimicking SMAC disruption of caspase-9 binding to XIAP, have shown induction of apoptosis in a variety of tumour cell lines as a single agent, as well as chemosensitisers and are being further investigated clinically (Oost et al., J. Med. Chem. 2004; 47: 4417-4426; Sun et al., Bioorg. Med. Chem. Lett. 2005; 15: 793-797).

Synthetic small molecule antagonists of BIR3 and BIR2 domains also demonstrate anti-tumour activity in several different models, including induction of apoptosis by annexin-V staining and IC50s of <10 µM against over one-third of the NCI60 cell line panel. XIAP antagonists also induced dose-dependent cell death of primary-cultured leukaemia cells in 5 out of 5 chronic lymphocytic leukaemia cell lines and 4 out of 5 acute myeloid leukaemia cell lines (Schimmer et al., Cancer Cell 2004; 5: 25-35; Berezovskaya et al., Cancer Res. 2005; 65(6): 2378-86).

High levels of XIAP protein in tumour cell lines were inversely correlated with sensitivity to some anti-cancer drugs, particularly cytarabine and other nucleosides (Tamm et al., Clin. Cancer Research 2000; 6: 1796-1803). XIAP inhibition potentiates TRAIL-induced antitumor activity in two preclinical models of pancreatic cancer in vivo (Vogler 2008). Gene expression and transfection studies suggest that the increased expression of apoptosis suppressor XIAP plays an important role in anoikis resistance and in the survival of circulating human prostate carcinoma cells, thereby promoting metastasis. Small molecule antagonists were found to be anti-metastatic in these models (Berezovskaya et al., Cancer Res. 2005; 65(6): 2378-86).

XIAP has also been found to be involved in other pathways associated with cancer and other diseases and these may also benefit from XIAP targeted agents. The E3 ligase activity of the RING finger domain of XIAP is able to bind both to TAB1 and to an upstream BMP receptor (type 1), suggesting that XIAP may signal in a TGF-β-mediated pathway (Yamaguchi et al., EMBO 1999; 179-187). Focal adhesion kinase (FAK) overexpression has been shown to result in upregulated XIAP expression (Sonoda et al., J. Biol. Chem. 2000; 275: 16309-16315). E3 ligases are attractive therapeutic targets and molecules which target this activity in other proteins such as MDM2 are being developed (Vassilev et al., Science 2004; 303: 844-848). Direct or indirect inhibition of the XIAP ligase activity may also be useful in the treatment of cancer and other diseases. Dysregulated apoptotic signalling, which would result from inhibition of IAP function in controlling programmed cell death, has also been implicated in many diseases, including disorders associated with cell accumulation (e.g. cancer, autoimmunity, inflammation and restenosis) or disorders where excessive apoptosis results in cell loss (e.g. stroke, heart failure, neurodegeneration such as Alzheimer's disease, Parkinson's disease, Huntington's disease, amyotrophic lateral sclerosis, AIDS, ischaemia (stroke, myocardial infarction) and osteoporosis).

XIAP is an important apoptotic regulator in experimental autoimmune encephalomyelitis and a potential pharmacological target for treating autoimmune diseases such as multiple sclerosis (MS) (Moore et al., 2004; 203(1): 79-93). Antisense-mediated knockdown of XIAP reverses paralysis in an animal model of MS suggesting that treatments targeting XIAP, and perhaps other IAPs, may have utility in the treatment of MS (Hebb et al., Curr. Drug Disc. Tech. 2008; 5(1): 75-7).

cIAP1, cIAP-2, XIAP and survivin are overexpressed in malignant pleural mesothelioma and are responsible for a large degree of the resistance of cultured mesothelioma cells to cisplatin. Levels of circulating TNF-α are significantly higher in mesothelioma patients prior to surgical tumor debulking compared with those after surgery. TNF-α increases mRNA and protein levels of IAP-1, IAP-2 and XIAP (Gordon et al., 2007). NF-Kb upregulation plays an important survival role in mesotheliomas in response to the inflammatory effects of exposure to asbestos fibres (Sartore-Bianchi et al., 2007). IAP antagonists have the potential to reverse the pro-survival effect of TNF-α.

The ability of cell lines to upregulate TNF-alpha expression sufficiently to act in an autocrine fashion and kill the cells, once cIAP1 & 2 are depleted, is believed to be important for IAP activity (Nature Reviews Cancer (2010), 10(8), 561-74, Gryd-Hansen, M). In vivo, however, certain tumour types are surrounded by a pro-inflammatory cytokine network and hence the tumour cells which, on depletion of cIAP1/2 are switched towards cell killing by apoptosis, may be triggered to apoptose by TNF-alpha (or other Death Receptor cytokine agonists) already being produced by surrounding cells in the tumour microenvironment, such as tumour-associated macrophages, or indeed by the tumour cells themselves. Certain tumour types such as breast, ovarian and melanoma display this "inflammatory phenotype" which could potentially be targeted by IAP antagonists.

cIAP1 and cIAP2

Cellular IAP (cIAP) 1 and 2 are closely related members of the IAP family with three BIR domains, a RING domain and a caspase-recruitment (CARD) domain. A functional nuclear export signal exists within the CARD domain of cIAP1 which appears to be important for cell differentiation (Plenchette et al., Blood 2004; 104: 2035-2043). The presence of this CARD domain is unique to cIAP1 and cIAP2 within the IAP family of proteins. These two genes reside in tandem on chromosome 11q22 and given their high degree of similarity are thought to have arisen via gene duplication.

cIAP1, like XIAP and survivin, is widely expressed in tumour cell lines, and has been found to be expressed at high levels in colorectal cancers in particular, as well as lung, ovarian, renal, CNS and breast cancers (Tamm et al., Clin. Cancer Res. 2000; 6: 1796-1803). cIAP2 expression is generally more restricted and is thought to be regulated though constitutive ubiquitination and degradation by cIAP1 (Conze et al., Mol. Biol. Cell 2005; 25(8): 3348-56; Mahoney et al., PNAS 2008; 105: 11778-11783). Immunohistochemistry and western blot analysis identified cIAP1 and cIAP2 as potential oncogenes as both are overexpressed in multiple lung cancers with or without higher copy numbers (Dia et al., Human Mol. Genetics 2003; 12(7): 791-801). cIAP1 expression level preferentially seems to play an important role in low-stage adenocarcinoma (Hofmann et al., J. Cancer Res. Clin. Oncology 2002; 128(10): 554-60).

Increased levels of cIAP1 and cIAP2 and reduced levels of endogenous inhibitors are associated with chemoresistance as has been seen for XIAP. cIAP overexpression has been found to correlate in vitro to resistance to DNA alkylating agents such as carboplatin, cisplatin and topoisomerase inhibitor VP-16 (Tamm et al., Clin. Cancer Res. 2000; 6: 1796-1803). Levels of cIAP1 and survivin were found to be high in thyroid cancer cells after cisplatin and doxorubicin treatment. Cells resistant to chemotherapy such as taxol showed reduced expression of SMAC and released minimal amounts of this protein from the mitochondria. Down-regulation of cIAP1 and survivin has been found to increase the cytotoxicity of cisplatin and doxorubicin, whereas overexpression of SMAC improved the efficacy of taxol. However, silencing of cIAP1 and survivin by RNA interference restored sensitivity to doxorubicin and cisplatin (TirrO et al.; Cancer Res. 2006; 66(8): 4263-72).

SMAC mimetics such as LBW242 were originally thought to primarily target XIAP. However studies have shown that cIAP1 was targeted for degradation by autoubiquitination in cells (Yang et al., J. Biol. Chem. 2004; 279(17): 16963-16970) and may have contributed to the apoptotic effects that resulted. SiRNA of cIAP1 and Tumour Necrosis Factor (TNF)-alpha induction (or stimulation) were found to combine synergistically and render cell lines more sensitive (Gaither et al. Cancer Res. 2007; 67 (24): 11493-11498).

cIAP1 and cIAP2 have been demonstrated to be critical regulators of the NFκB signalling pathway which is involved in a diverse range of biological processes, particularly in innate and adaptive immunity as well as in proliferation and survival. NFκB pathway deregulation is associated with inflammation and cancers including hepatitis and ulcerative colitis, gastritis, hepatocellular carcinoma colorectal cancer and gastric cancers, as well as angiogenesis and metastasis (Shen et al., Apoptosis 2009; 14: 348-363).

On ligand binding, the TNF Receptor (TNFR) recruits TNFR-associated Death Domain (TRADD) and receptor-interacting protein (RIP) 1. TRAF2 and cIAP1/cIAP2 are then recruited to form a large membrane complex. RIP1 is ubiquitinated and these polyubiquitin chains serve as a docking site for downstream kinases, resulting in NFκB pathway signalling effects (Ea et al., Mol. Cell 2006; 22: 245-257; Wu et al., Nat. Cell Biol. 2006; 8: 398-406). The extended roles are complex and yet to be fully defined but cIAP1 and cIAP2 are identified as key components of TNF-alpha mediated NFκB signalling regulation as well as constitutive (ligand-independent/classical) NFκB signalling (Varfolomeev et al., Cell 2007; 131(4): 669-81). cIAP1 and cIAP2 have been shown to bind TRAF2, an adapter protein that functions in both the classical and alternative NFκB pathways as well as MAPK pathway signalling pathway (Rothe et al., Cell 2005; 83: 1243-1252). cIAP1 and cIAP2 directly target RIP1 for ubiquitination in vitro (Betrand et al., Mol. Cell 2008; 30: 689-700).

TNF-alpha regulates many cellular functions, including apoptosis, inflammation, immune response, and cell growth and differentiation (Trace et al., Annu. Rev. Med. 1994; 45: 491-503) and therapeutic IAP antagonists may be of benefit in conditions where these functions are affected.

Production of TNF-alpha is seen in many malignant tumours, and is one of the key drivers of cancer-related inflammation that drives tumour development and/or progression. cIAPs protect cancer cells from the lethal effects of TNF-alpha.

NAIP

NAIP was the first IAP to be discovered (Roy et al., Cell 1995; 80: 167-178). NAIP is unique among the IAPs in that it possesses a nucleotide-binding and oligomerisation domain, as well as leucine rich repeats which are similar to those contained in proteins normally involved in innate immunity. There are indications that NAIP may also be over expressed in some cancers including breast and oesophageal cancer (Nemoto et al., Exp. Mol. Pathol. 2004; 76(3): 253-9) as well as MS (Choi et al., J. Korean Med. 2007; 22 Suppl: S17-23; Hebb et al., Mult. Sclerosis 2008; 14(5): 577-94).

ML-IAP

Melanoma inhibitor of apoptosis protein (ML-IAP) contains a single BIR and RING finger motif. ML-IAP is a powerful inhibitor of apoptosis induced by death receptors and chemotherapeutic agents, probably functioning as a direct inhibitor of downstream effector caspases (Vucic et al., Curr. Biol. 2000; 10(21): 1359-66). ML-IAP is also known as Baculoviral IAP repeat-containing protein 7 (BIRC7), Kidney inhibitor of apoptosis protein (KIAP), RING finger protein 50 (RNF50) and Livin. The BIR domain of ML-IAP possesses an evolutionarily conserved fold that is necessary for anti-apoptotic activity. It has been found that the majority of melanoma cell lines express high levels of ML-IAP in contrast to primary melanocytes, which expressed undetectable levels. These melanoma cells were significantly more resistant to drug-induced apoptosis. Elevated expression of ML-IAP renders melanoma cells resistant to apoptotic stimuli and thereby potentially contributes to the pathogenesis of this malignancy.

ILP-2

ILP-2, also known as BIRC8, has a single BIR domain and a RING domain. ILP-2 is expressed only in testis in normal cells, and binds to caspase 9 (Richter et al, Mol. Cell. Biol. 2001; 21: 4292-301).

Survivin

Survivin, also known as BIRC5, inhibits both caspase 3 and caspase 7, but its primary function is mitotic progression regulation, rather than the regulation of apoptosis. Survivin promotes formation of microtubules in the mitotic spindle, counteracting apoptosis during cell cycle. Apoptosis inhibition by survivin is predictive of poor outcome in colorectal cancer (Kawasaki et al., Cancer Res. 1998; 58(22): 5071-5074) and stage III gastric cancer (Song et al., Japanese J. Clin. Oncol. 2009; 39(5): 290-296).

BRUCE

BRUCE (BIR repeat-containing ubiquitin-conjugating enzyme) is a peripheral membrane protein in the trans-Golgi network with a single BIR domain, most similar to that of survivin. BRUCE is inhibited via three mechanisms: (i) SMAC binding, (ii) HtrA2 protease and (iii) caspase-mediated cleavage. In addition, BRUCE acts as a E2/E3 ubiquitin ligase via ubiquitin-conjugating (UBC) domain.

SUMMARY OF THE INVENTION

The present invention provides compounds of formula (I). The present invention provides compounds which are useful in therapy, in particular in the treatment of cancer. The compounds of formula (I) may be antagonists of the IAP family of proteins (IAP), and especially XIAP, and/or cIAP (such as cIAP1 and/or cIAP2) and may be useful in the treatment of IAP-mediated conditions.

According to a first aspect of the invention, there is provided a compound of formula (I):

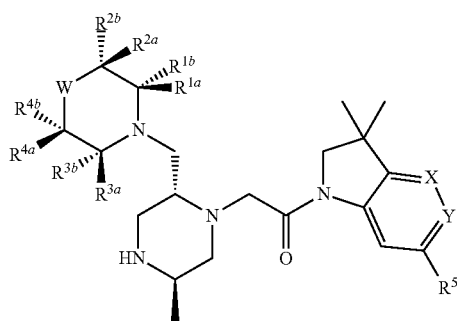

(I)

or tautomeric or stereochemically isomeric forms, N-oxides, pharmaceutically acceptable salts or the solvates thereof; wherein X is CH and Y is $CR^9$, or one of X or Y is $CR^9$ and the other is nitrogen, or X and Y are nitrogen;

W is either absent or selected from $CR^6R^7$, $CH_2$—$CH_2$, $CH_2$—O, O—$CH_2$, C=O, $SO_2$, O, $NR^8$, $CH_2$—$NR^8$ and $NR^8$—$CH_2$;

when W is $CR^6R^7$, $CH_2$—$CH_2$, $CH_2$—O, O—$CH_2$, C=O, $SO_2$, $CH_2$—$NR^8$ or $NR^8$—$CH_2$, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{1a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, when W is $NR^8$, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, or $R^{2a/2b}$ or $R^{4a/4b}$ can join together with the nitrogen atom at W to form a fused heterocyclic group with 5 or 6 ring members which can be optionally substituted by one or more substituents $R^{10}$, provided that except for when X and Y are other than both nitrogen, $R^{4a}$ and $R^{4b}$ do not together represent =O when $R^5$ is 1,1-difluoroethyl and $R^8$ is methyl;

when W is O, then $R^{1a}$, $R^{1b}$, $R^{2a}$, $R^{2b}$, $R^{3a}$, $R^{3b}$, $R^{4a}$, and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, provided that except for when X and Y are other than both nitrogen:

$R^{1a}$, $R^{1b}$, $R^{2a}$, $R^{2b}$, $R^{3a}$, $R^{3b}$, $R^{4a}$ and $R^{4b}$ are not all hydrogen, or when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen, or when $R^{2a}$ and $R^{4a}$ are methyl then $R^{1a}$, $R^{2b}$, $R^{3a}$, $R^{3b}$ and $R^{4b}$ are not all hydrogen, or $R^{2a}$ or $R^{3b}$ is not methoxymethyl when $R^5$ is 1,1-difluoropropyl;

when W is absent, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, or $R^{2a/2b}$ and $R^{4a/4b}$ can join together to form a fused phenyl or pyridinyl group which can be optionally substituted by one or more substituents $R^{10}$, provided that except for when X and Y are other than both nitrogen:

$R^{1a}$, $R^{1b}$, $R^{2a}$, $R^{2b}$, $R^{3a}$, $R^{3b}$, $R^{4a}$ and $R^{4b}$ are not all hydrogen, or when one of $R^{2a}$ or $R^{2b}$ or $R^{4a}$ or $R^{4b}$ is fluorine the remaining $R^{1a}$, $R^{1b}$, $R^{2a}$, $R^{2b}$, $R^{3a}$, $R^{3b}$, $R^{4a}$ and $R^{4b}$ groups are not all hydrogen, or when $R^{2a}$ and $R^{2b}$, or $R^{4a}$ and $R^{4b}$ join to form =O then the remaining $R^{1a}$, $R^{1b}$, $R^{2a}$, $R^{2b}$, $R^{3a}$, $R^{3b}$, $R^{4a}$ and $R^{4b}$ groups are not all hydrogen, or $R^{2a}$ and $R^{2b}$, or $R^{4a}$ and $R^{4b}$ are not both fluorine when $R^5$ is 2,4-difluorobenzyl;

$R^5$ is selected from: benzyl optionally substituted on the phenyl group by one or two substituents selected from fluorine and nitrile, and optionally substituted on the methylene by hydroxyl; and $C_{2-4}$ alkyl substituted by one or two substituents selected from fluorine and hydroxyl;

$R^6$ and $R^7$ are independently selected from hydrogen, hydroxyl and fluorine;

$R^8$ is selected from hydrogen, $C_{1-4}$ alkyl, —$SO_2$—$C_{1-4}$ alkyl, —$SO_2$—$NH(C_{1-4}$ alkyl), —$SO_2$—$N(C_{1-4}$ alkyl$)_2$, —C(=O)—NH—$SO_2$—$C_{1-4}$ alkyl, —C(=O)—NH—$SO_2$-phenyl, —C(=O)—N($C_{1-4}$ alkyl$)_2$, pyrimidinyl, —C(=O)-phenyl, —C(=O)—$C_{3-6}$ cycloalkyl and —C(=O)—$C_{1-4}$ alkyl, wherein the alkyl or cyclic groups can be optionally substituted by one or more $R^{19}$;

$R^9$ is selected from hydrogen and nitrile; and $R^{10}$ is independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile.

In a further aspect of the invention there is provided a compound of formula (I) for use in the prophylaxis or treatment of a disease or condition as described herein, pharmaceutical compositions comprising a compound of formula (I) and processes for the synthesis of compound of formula (I).

DEFINITIONS

Unless the context indicates otherwise, references to formula (I) in all sections of this document (including the uses, methods and other aspects of the invention) include references to all other sub-formula, sub-groups, preferences, embodiments and examples as defined herein.

By "IAP" we mean any of the IAP family members XIAP, cIAP (cIAP1 and/or cIAP2), NAIP, ILP2, ML-IAP, survivin and/or BRUCE, in particular XIAP, cIAP1, cIAP2, ML-IAP, more particularly XIAP, cIAP1 and/or cIAP2, most particularly XIAP and/or cIAP1. In particular we mean the BIR domains of IAP, in particular the BIR domains of XIAP, cIAP1, or cIAP2.

By "one or more IAP family members" we mean any of the IAP family members in particular XIAP, cIAP1 and/or cIAP2, more particularly XIAP and/or cIAP1.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "antagonist" refers to a type of receptor ligand or drug that blocks or dampens agonist-mediated biological responses. Antagonists have affinity but no agonistic efficacy for their cognate receptors, and binding will disrupt the interaction and inhibit the function of any ligand (e.g. endogenous ligands or substrates, an agonist or inverse agonist) at receptors. The antagonism may arise directly or indirectly, and may be mediated by any mechanism and at any physiological level. An example of indirect antagonism, would be the indirect antagonism of cIAP as a consequence of ubiquination of cIAP resulting in its degradation. As a result, antagonism of ligands may under different circumstances manifest itself in functionally different ways. Antagonists mediate their effects by binding to the active site or to allosteric sites on receptors, or they may interact at unique binding sites not normally involved in the biological regulation of the receptors activity. Antagonist activity may be reversible or irreversible depending on the longevity of the antagonist receptor complex, which, in turn, depends on the nature of antagonist receptor binding.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurance of a disease or guarding from a disease. Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence of cancer.

As used herein, the term "mediated", as used e.g. in conjunction with IAP as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The term "optionally substituted" as used herein refers to a group which may be unsubstituted or substituted by a substituent as herein defined.

The prefix "$C_{x-y}$" (where x and y are integers) as used herein refers to the number of carbon atoms in a given group. Thus, a $C_{1-4}$ alkyl group contains from 1 to 4 carbon atoms, a $C_{3-6}$ cycloalkyl group contains from 3 to 6 carbon atoms, a halo$C_{1-4}$ alkyl group contains from 1 to 4 carbon atoms, and so on.

The term "halo" or "halogen" as used herein refers to fluorine, chlorine, bromine or iodine.

The term "$C_{1-4}$ alkyl" as used herein as a group or part of a group refers to a linear or branched saturated hydrocarbon group containing from 1 to 4 carbon atoms, respectively. Examples of such groups include methyl, ethyl, n-propyl, isopropyl, n-butyl, isobutyl, sec-butyl, tert butyl and the like.

The term "$C_{3-6}$cycloalkyl" as used herein refers to a saturated monocyclic hydrocarbon ring of 3 to 6 carbon atoms. Examples of such groups include cyclopropyl, cyclobutyl, cyclopentyl or cyclohexyl and the like.

The term "halo$C_{1-4}$ alkyl" as used herein as a group or part of a group refers to a $C_{1-4}$ alkyl group as defined herein wherein one or more than one hydrogen atom is replaced with a halogen. The term 'halo$C_{1-4}$ alkyl' therefore includes monohalo$C_{1-4}$ alkyl and also polyhalo$C_{1-4}$ alkyl. There may be one, two, three or more hydrogen atoms replaced with a halogen, so the halo$C_{1-4}$ alkyl may have one, two, three or more halogens. Examples of such groups include fluoroethyl, fluoromethyl, trifluoromethyl or trifluoroethyl and the like.

The term "heterocyclyl" as used herein shall, unless the context indicates otherwise, include both aromatic and non-aromatic ring systems. Thus, for example, the term "heterocyclyl group" include within their scope aromatic, non-aromatic, unsaturated, partially saturated and fully saturated heterocyclyl ring systems. In general, unless the context indicates otherwise, reference to 5 to 6 ring members include 5, or 6 atoms in the ring. The heterocyclyl groups can be heteroaryl groups having 5 or 6 ring members. Where reference is made herein to heterocyclyl groups, the heterocyclyl ring can, unless the context indicates otherwise, be optionally substituted i.e. unsubstituted or substituted by one or more (e.g. 1, 2, 3, or 4 in particular one or two) substituents as defined herein.

The heterocyclyl group can be, for example, a five membered or six membered monocyclic ring. Each ring may contain up to three heteroatoms typically selected from nitrogen, sulfur and oxygen. Typically the heterocyclyl ring will contain up to 2, for example a single heteroatom. In one embodiment, the heterocyclyl ring will contain one or two heteroatoms selected from N, O, S and oxidised forms of N or S. In one embodiment, the heterocyclyl ring contains at least one ring nitrogen atom. The nitrogen atoms in the heterocyclyl rings can be basic, as in the case of an imidazole or pyridine, or essentially non-basic as in the case of an indole or pyrrole nitrogen. In general the number of basic nitrogen atoms present in the heterocyclyl group, including any amino group substituents of the ring, will be less than five.

The heterocyclyl groups can be attached via a carbon atom or a heteroatom (e.g. nitrogen). Equally the heterocyclyl groups can be substituted on a carbon atom or on a heteroatom (e.g. nitrogen).

The term "heteroaryl" is used herein to denote a heterocyclyl group having aromatic character. Examples of heteroaryl groups are monocyclic containing from five to six ring members.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A nitrogen-containing heteroaryl ring must contain at least one ring nitrogen atom. The nitrogen-containing heteroaryl ring can be N-linked or C-linked. Each ring may, in addition, contain up to about four other heteroatoms typically selected from nitrogen, sulfur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), and tetrazolyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine. Partially saturated heterocyclyl groups include pyrazolines, for example pyrazolin-2-yl and pyrazolin-3-yl.

Examples of non-aromatic heterocyclyl groups are groups having from 5 to 6 ring members. Such groups typically have from 1 to 3 heteroatom ring members, usually selected from nitrogen, oxygen and sulfur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides and combinations thereof (e.g. thiomorpholine).

Particular examples include morpholine, piperidine (e.g. piperidin-1-yl, piperidin-2-yl, piperidin-3-yl and piperidin-4-yl), piperidinone, pyrrolidine (e.g. pyrrolidin-1-yl, pyrrolidin-2-yl and pyrrolidin-3-yl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. tetrahydropyran-4-yl), imidazoline, imidazolidinone, oxazoline, thiazoline, pyrazolin-2-yl, pyrazolidine, piperazinone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The nitrogen-containing heterocyclyl ring can be N-linked or C-linked. The heterocylic groups can contain, for example cyclic amine moieties (e.g. as in pyrrolidine), cyclic amides (such as a pyrrolidinone, piperidinone or caprolactam), cyclic sulfonamides (such as an isothiazolidine 1,1-dioxide, [1,2]thiazinane 1,1-dioxide or [1,2]thiazepane 1,1-dioxide) and combinations thereof.

Particular examples of nitrogen-containing non-aromatic heterocyclyl groups include aziridine, morpholine, thiomorpholine, piperidine (e.g. piperidin-1-yl, piperidin-2-yl, piperidin-3-yl and piperidin-4-yl), pyrrolidine (e.g. pyrrolidin-1-yl, pyrrolidin-2-yl and pyrrolidin-3-yl), pyrrolidone, dihydrothiazole, imidazoline, imidazolidinone, oxazoline, thiazoline, 6H-1,2,5-thiadiazine, pyrazolin-2-yl, pyrazolin-3-yl, pyrazolidine, piperazine, and N-alkyl piperazines such as N-methyl piperazine.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see *Advanced Organic Chemistry*, by Jerry March, 4th Edition, Wiley Interscience, pages 131-133, 1992.

The heterocyclyl groups can each be unsubstituted or substituted by one or more substituent groups. For example, heterocyclyl or carbocyclyl groups can be unsubstituted or substituted by 1, 2, 3 or 4 substituents. Where the heterocyclyl or carbocyclyl group is monocyclic or bicyclic, typically it is unsubstituted or has 1, 2 or 3 substituents as defined herein.

A combination of substituents is permissible only if such a combination results in a stable or chemically feasible compound (e.g. one that is not substantially altered when kept at 40° C. or less for at least a week).

The various functional groups and substituents making up the compounds of the invention are typically chosen such that the molecular weight of the compound of the invention does not exceed 1000 Daltons (Da). More usually, the molecular weight of the compound will be less than 750 Da, for example less than 700 Da, or less than 650 Da, or less than 600 Da, or less than 550 Da.

DETAILED DESCRIPTION OF THE INVENTION

In one embodiment, X is CH and Y is $CR^9$; X is nitrogen and Y is $CR^9$; or X is $CR^9$ and Y is nitrogen. In a further embodiment, X is CH and Y is C—CN; or X is nitrogen and Y is CH; or X is nitrogen and Y is C—CN; or X is CH and Y is nitrogen; or X and Y are nitrogen. In a further embodiment, X is CH and Y is CH; X is nitrogen and Y is CH; X is nitrogen and Y is C—CN; or X is CH and Y is nitrogen. In a yet further embodiment, X is nitrogen and Y is CH; or X is CH and Y is nitrogen. In a still yet further embodiment, X is nitrogen and Y is CH. In one embodiment, X and Y are nitrogen. In another embodiment, X is CH and Y is nitrogen.

In one embodiment, X is nitrogen and Y is $CR^9$, or X and Y are nitrogen, or X is $CR^9$ and Y is nitrogen. In one embodiment, X and Y are nitrogen. In one embodiment, X is nitrogen and Y is CH, or X and Y are nitrogen, or X is CH and Y is nitrogen.

In one embodiment the compound of formula (I) is an N-oxide of a compound of formula (I). Thus, X can become $N^+$—$O^-$.

In one embodiment, $R^9$ represents hydrogen. In an alternative embodiment, $R^9$ represents nitrile.

In one embodiment, W is either absent or is selected from $CR^6R^7$, $CH_2$—O, C=O, $SO_2$, O, $NR^8$ and $CH_2$—$NR^8$. In one embodiment W is absent, O or $NR^8$. In one embodiment, W represents O or $NR^8$. In a further embodiment, W represents O. In a further embodiment, W represents $NR^8$.

In one embodiment, $R^{1a}$, $R^{1b}$, $R^{2a}$, $R^{2b}$, $R^{3a}$, $R^{3b}$, $R^{4a}$ and $R^{4b}$ independently represent hydrogen, $C_{1-4}$ alkyl (such as methyl or isopropyl), halogen (such as fluorine), halo$C_{1-4}$ alkyl (such as monofluoromethyl or trifluoromethyl), hydroxy$C_{1-4}$ alkyl (such as hydroxymethyl), $C_{1-4}$ alkyoxy (such as methoxy), methoxymethyl, carboxyl or nitrile;
or $R^{1a}$ and $R^{1b}$ join together to form cyclopropyl;
or $R^{1a}$ and $R^{3a}$ or $R^{1b}$ and $R^{3b}$ join together to form a $C_{1-4}$ bridged alkyl group (such as ethylene);
or $R^{2a}$ and $R^{3a}$ or $R^{2b}$ and $R^{3b}$ join together to form a $C_{1-4}$ bridged alkyl group (such as methylene);
or $R^{3a}$ and $R^{4a}$ or $R^{1b}$ and $R^{4b}$ join together to form a $C_{1-4}$ bridged alkyl group (such as methylene);
or $R^{2a}$ and $R^{4a}$ or $R^{2b}$ and $R^{4b}$ join together to form a $C_{1-4}$ bridged alkyl group (such as ethylene);
or $R^{2a}/R^{2b}$ join together with the nitrogen atom at W to form a fused heteroaromatic group with 5 or 6 ring members (such as triazolyl) which can be optionally substituted by one or more substituents $R^{10}$;
or $R^{2a}$ and $R^{2b}$ together represent =O;
or $R^{4a}$ and $R^{4b}$ together represent =O.

In a further embodiment, $R^{1a}$, $R^{1b}$, $R^{2a}$, $R^{2b}$, $R^{3a}$, $R^{3b}$, $R^{4a}$ and $R^{4b}$ independently represent hydrogen or $C_{1-4}$ alkyl (such as methyl). In a yet further embodiment, $R^{3a}$ and $R^{3b}$ both represent $C_{1-4}$ alkyl (such as methyl) and $R^{1b}$, $R^{2a}$, $R^{2b}$, $R^{3a}$, $R^{4a}$ and $R^{4b}$ each represent hydrogen.

In a further embodiment, $R^{2a}$ and $R^{4a}$, or $R^{2b}$ and $R^{4b}$ join together to form a $C_{1-4}$ bridged alkyl group (such as ethylene).

In one embodiment, $R^{3a}$ and $R^{3b}$ are methyl. In another embodiment, $R^{3a}$ and $R^{3b}$ are methyl, and $R^{1b}$, $R^{2a}$, $R^{2b}$, $R^{3a}$, $R^{4a}$, $R^{4b}$ are hydrogen.

In one embodiment, X and Y are nitrogen and W is either absent or selected from $CR^6R^7$, $CH_2$—$CH_2$, $CH_2$—O, O—$CH_2$, C=O, $SO_2$, O, $NR^8$, $CH_2$—$NR^8$ and $NR^8$—$CH_2$; then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile,
or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group,
or when W is $NR^8$, $R^{2a/2b}$ or $R^{4a/4b}$ can join together with the nitrogen atom at W to form a fused heterocyclic group with 5 or 6 ring members which can be optionally substituted by one or more substituents $R^{10}$,
or when W is absent $R^{2a/2b}$ and $R^{4a/4b}$ can join together to form a fused phenyl or pyridinyl group which can be optionally substituted by one or more substituents $R^{10}$.

In one embodiment, when W is $CR^6R^7$, $CH_2$—$CH_2$, $CH_2$—O, O—$CH_2$, C=O, $SO_2$, $CH_2$—$NR^8$ or $NR^8$—$CH_2$, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen (such as fluorine), $C_{1-4}$ alkyl (such as methyl, ethyl, isopropyl), carboxyl, hydroxyl, hydroxy$C_{1-4}$ alkyl (such as hydroxymethyl), $C_{1-4}$ alkyoxy (such as methoxy), $C_{3-6}$ cycloalkyl (such as cyclopropyl), halo$C_{1-4}$ alkyl (such as monofluoromethyl, trifluoromethyl), methoxymethyl and nitrile,
or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group.

In one embodiment when W is $NR^8$,
then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, or $R^{2a/2b}$ or $R^{4a/4b}$ can join together with the nitrogen atom at W to form a fused heterocyclic group with 5 or 6 ring members which can be optionally substituted by one or more substituents $R^{10}$.

In one embodiment, when W is $NR^8$, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen (such as fluorine), $C_{1-4}$ alkyl (such as methyl, ethyl, isopropyl), carboxyl, hydroxyl, hydroxy$C_{1-4}$ alkyl (such as hydroxymethyl), $C_{1-4}$ alkyoxy (such as methoxy), $C_{3-6}$ cycloalkyl (such as cyclopropyl), halo$C_{1-4}$ alkyl (such as monofluoromethyl, trifluoromethyl), methoxymethyl and nitrile, or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group,
or $R^{2a/2b}$ or $R^{4a/4b}$ can join together with the nitrogen atom at W to form a fused heteroaromatic group with 5 or 6 ring members which can be optionally substituted by one or more substituents $R^{10}$, provided that except for when X and Y are other than both nitrogen, $R^{4a}$ and $R^{4b}$ do not together represent =O when $R^5$ is difluoroethyl and $R^8$ is methyl and
when one of $R^{2a}$, $R^{2b}$, $R^{4a}$ and $R^{4b}$ are methyl then the remaining $R^{1a}$, $R^{1b}$, $R^{2a}$, $R^{2b}$, $R^{3a}$, $R^{3b}$, $R^{4a}$ and $R^{4b}$ are not all hydrogen.

In one embodiment, when W represents $NR^8$, $R^{2a/2b}$ or $R^{4a/4b}$ join together with the nitrogen atom at W to form a fused heteroaromatic group with 5 or 6 ring members which can be optionally substituted by one or more substituents $R^{10}$. In such an embodiment, it will be appreciated that the $R^8$ group of W joins with either the $R^{2a/2b}$ or $R^{4a/4b}$ groups to form the fused heteroaromatic group with 5 or 6 ring members which can be optionally substituted by one or more substituents $R^{10}$.

In one embodiment when W is O,
then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, and nitrile wherein at least one is selected from $C_{3-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile or at least two of $R^{1a}$, $R^{1b}$, $R^{2b}$, $R^{3a}$, $R^{3b}$ and $R^{4b}$ are selected from $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group.

In one embodiment, when W is O,
then $R^{1a}$, $R^{1b}$, $R^{2a}$, $R^{2b}$, $R^{3a}$, $R^{3b}$, $R^{4a}$ and $R^{4b}$ are independently selected from hydrogen, halogen (such as fluorine), $C_{1-4}$ alkyl (such as methyl, ethyl, isopropyl), carboxyl, hydroxyl, hydroxy$C_{1-4}$ alkyl (such as hydroxymethyl), $C_{1-4}$ alkyoxy (such as methoxy), $C_{3-6}$ cycloalkyl (such as cyclopropyl), halo$C_{1-4}$ alkyl (such as monofluoromethyl, trifluoromethyl), methoxymethyl and nitrile, or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, provided that except for when X and Y are other than both nitrogen:
$R^{1a}$, $R^{1b}$, $R^{2a}$, $R^{2b}$, $R^{3a}$, $R^{3b}$, $R^{4a}$ and $R^{4b}$ are not all hydrogen, or
when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen, or
when $R^{3a}$ and $R^{4a}$ are methyl then $R^{1a}$, $R^{1b}$, $R^{2b}$, $R^{3b}$ and $R^{4b}$ are not all hydrogen, or
$R^{1a}$ or $R^{3b}$ is not methoxymethyl when $R^5$ is 1,1-difluoropropyl.

In one embodiment when W is absent,
then $R^{1a}$, $R^{1b}$, $R^{2a}$, $R^{2b}$, $R^{3a}$, $R^{3b}$, $R^{4a}$ and $R^{4b}$ are independently selected from hydrogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile wherein at least one is selected from $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group,
or $R^{2a/2b}$ and $R^{4a/4b}$ can join together to form a fused phenyl or pyridinyl group which can be optionally substituted by one or more substituents $R^{10}$.

In one embodiment, when W is absent, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen (such as fluorine, chlorine), $C_{1-4}$ alkyl (such as methyl, ethyl, isopropyl), carboxyl, hydroxyl, hydroxy$C_{1-4}$ alkyl (such as hydroxymethyl), $C_{1-4}$ alkyoxy (such as methoxy), $C_{3-6}$ cycloalkyl (such as cyclopropyl), halo$C_{1-4}$ alkyl (such as monofluoromethyl, trifluoromethyl), methoxymethyl and nitrile,
or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group,
or $R^{2a/2b}$ and $R^{4a/4b}$ can join together to form a fused phenyl or pyridinyl group which can be optionally substituted by one or more substituents $R^{10}$, provided that except for when X and Y are other than both nitrogen:
$R^{1a}$, $R^{1b}$, $R^{2a}$, $R^{2b}$, $R^{3a}$, $R^{3b}$, $R^{4a}$ and $R^{4b}$ are not all hydrogen, or
when one of $R^{2a}$ or $R^{2b}$ or $R^{4a}$ or $R^{4b}$ is fluorine the remaining $R^{1a}$, $R^{1b}$, $R^{2a}$, $R^{2b}$, $R^{3a}$, $R^{3b}$, $R^{4a}$ and $R^{4b}$ groups are not all hydrogen, or
when $R^{2a}$ and $R^{2b}$, or $R^{4a}$ and $R^{4b}$ join to form =O then the remaining $R^{1a}$, $R^{1b}$, $R^{2a}$, $R^{2b}$, $R^{3a}$, $R^{3b}$, $R^{4a}$ and $R^{4b}$ groups are not all hydrogen, or $R^{2a}$ and $R^{2b}$, or $R^{4a}$ and $R^{4b}$ are not both fluorine when $R^5$ is 2,4-difluorobenzyl.

In one embodiment when W is $NR^8$, then $R^{1a}$, $R^{1b}$, $R^{2a}$, $R^{2b}$, $R^{3a}$, $R^{3b}$, $R^{4a}$ and $R^{4b}$ are independently selected from hydrogen, $C_{1-4}$ alkyl (such as methyl, ethyl, isopropyl), carboxyl, hydroxy$C_{1-4}$ alkyl (such as hydroxymethyl), $C_{3-6}$ cycloalkyl (such as cyclopropyl), halo$C_{1-4}$ alkyl (such as monofluoromethyl, trifluoromethyl), methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, or $R^{2a/2b}$ or $R^{4a/4b}$ can join together with the nitrogen atom at W to form a fused heteroaromatic group with 5 or 6 ring members which can be optionally substituted by one or more substituents $R^{10}$, provided that except for when X and Y are other than both nitrogen, $R^{4a}$ and $R^{4b}$ do not together represent =O when $R^5$ is difluoroethyl and $R^8$ is methyl.

In one embodiment when W is O, then $R^{1a}$, $R^{1b}$, $R^{2a}$, $R^{2b}$, $R^{3a}$, $R^{3b}$, $R^{4a}$ and $R^{4b}$ are independently selected from hydrogen, $C_{1-4}$ alkyl (such as methyl, ethyl, isopropyl), carboxyl, hydroxy$C_{1-4}$ alkyl (such as hydroxymethyl), $C_{3-6}$ cycloalkyl (such as cyclopropyl), halo$C_{1-4}$ alkyl (such as monofluoromethyl, trifluoromethyl), methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, provided that except for when X and Y are other than both nitrogen:

$R^{1a}$, $R^{1b}$, $R^{2a}$, $R^{2b}$, $R^{3a}$, $R^{3b}$, $R^{4a}$ and $R^{4b}$ are not all hydrogen, or when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen, or when $R^{2a}$ and $R^{4a}$ are methyl then $R^{1a}$, $R^{1b}$, $R^{2b}$, $R^{3a}$, $R^{3b}$ and $R^{4b}$ are not all hydrogen, or $R^{1a}$ or $R^{3b}$ is not methoxymethyl when $R^5$ is 1,1-difluoropropyl.

In a further embodiment, when W is 0:

(i) X and Y are both nitrogen, then:

$R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile; or $R^{2a}$ and $R^{2b}$, or $R^{4a}$ and $R^{4b}$ can together represent =O; or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl; or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$; or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group; or (ii) X is CH and Y is $CR^9$, or one of X or Y is $CR^9$ and the other is nitrogen, then:

at least one of $R^{1a}$, $R^{1b}$, $R^{2a}$, $R^{2b}$, $R^{3a}$, $R^{3b}$, $R^{4a}$ and $R^{4b}$ are independently selected from halogen, $C_{3-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl and nitrile, and the remaining $R^{1a}$, $R^{1b}$, $R^{2a}$, $R^{2b}$, $R^{3a}$, $R^{3b}$, $R^{4a}$ and $R^{4b}$ groups are hydrogen; or $R^{2a}$ and $R^{2b}$, or $R^{4a}$ and $R^{4b}$ can together represent =O; or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl; or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$; or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group; or (iii) X is CH and Y is $CR^9$, or one of X or Y is $CR^9$ and the other is nitrogen, then:

two of $R^{1a}$, $R^{1b}$, $R^{2a}$, $R^{2b}$, $R^{3a}$, $R^{3b}$, $R^{4a}$ and $R^{4b}$ groups are independently selected from halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile and $R^{2a}$ and the remaining groups represent hydrogen; or $R^{2a}$ and $R^{2b}$, or $R^{4a}$ and $R^{4b}$ can together represent =O; or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl; or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$; or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group; or (iv) X is CH and Y is $CR^9$, or one of X or Y is $CR^9$ and the other is nitrogen, then:

at least three of $R^{1a}$, $R^{1b}$, $R^{2a}$, $R^{2b}$, $R^{3a}$, $R^{3b}$, $R^{4a}$ and $R^{4b}$ groups are independently selected from halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile and the remaining groups are hydrogen; or $R^{2a}$ and $R^{2b}$, or $R^{4a}$ and $R^{4b}$ can together represent =O; or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl; or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$; or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group; or (v) X is CH and Y is $CR^9$, or one of X or Y is $CR^9$ and the other is nitrogen, then: $R^{2a}$ and $R^{4a}$ are methyl and the remaining $R^{1a}$, $R^{1b}$, $R^{2b}$, $R^{3a}$, $R^{3b}$ and $R^{4b}$ groups are selected from halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile; or $R^{2a}$ and $R^{2b}$, or $R^{4a}$ and $R^{4b}$ can together represent =O; or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl; or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$; or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group; or (vi) X is CH and Y is $CR^9$, or one of X or Y is $CR^9$ and the other is nitrogen and $R^5$ is selected from: benzyl optionally substituted on the phenyl group by one or two substituents selected from fluorine and nitrile, and optionally substituted on the methylene by hydroxyl; and $C_{2-4}$ alkyl substituted by a single fluorine or one or two hydroxyl substituents, then:

at least one of $R^{1a}$, $R^{1b}$, $R^{2a}$, $R^{2b}$, $R^{3a}$, $R^{3b}$, $R^{4a}$ and $R^{4b}$ are independently selected from halogen, $C_{3-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, and the remaining $R^{1a}$, $R^{1b}$, $R^{2a}$, $R^{2b}$, $R^{3a}$, $R^{3b}$, $R^{4a}$ and $R^{4b}$ groups are hydrogen; or $R^{2a}$ and $R^{2b}$, or $R^{4a}$ and $R^{4b}$ can together represent =O; or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl; or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$; or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group.

In a further embodiment, when W is O and X is CH and Y is $CR^9$, or one of X or Y is $CR^9$ and the other is nitrogen, then:

at least one of $R^{1a}$, $R^{1b}$, $R^{2a}$, $R^{2b}$, $R^{3a}$, $R^{3b}$, $R^{4a}$ and $R^{4b}$ are independently selected from $C_{3-4}$ alkyl (such as isopropyl), hydroxy$C_{1-4}$ alkyl (such as $CH_2OH$), halo$C_{1-4}$ alkyl (such as $CH_2F$ and $CF_3$) and nitrile, and the remaining $R^{1a}$, $R^{1b}$, $R^{2a}$, $R^{2b}$, $R^{3a}$, $R^{3b}$, $R^{4a}$ and $R^{4b}$ groups are hydrogen; or two of $R^{1a}$, $R^{1b}$, $R^{2b}$, $R^{3a}$, $R^{3b}$, $R^{4a}$ and $R^{4b}$ groups are independently selected from $C_{1-4}$ alkyl (such as methyl), carboxyl, hydroxy$C_{1-4}$ alkyl (such as $CH_2OH$) and methoxymethyl and $R^{2a}$ and the remaining groups represent hydrogen; or three of $R^{1a}$, $R^{1b}$, $R^{2a}$, $R^{2b}$, $R^{3a}$, $R^{3b}$, $R^{4a}$ and $R^{4b}$ groups are independently selected from $C_{1-4}$ alkyl (such as methyl) and the remaining groups are hydrogen; or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl; or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$; or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group.

In one embodiment, W is $CR^6R^7$.

When W is $CR^6R^7$, in one embodiment:
$R^{1a}$ and $R^{1b}$ both represent hydrogen or one represents hydrogen and the other represents halo$C_{1-4}$ alkyl (such as trifluoromethyl);
$R^{2a}$ and $R^{2b}$ both represent hydrogen or one represents hydrogen and the other represents halogen (such as fluorine);
$R^{3a}$ and $R^{3b}$ both represent hydrogen;
$R^{4a}$ and $R^{4b}$ both represent hydrogen or halogen (such as fluorine); and
$R^6$ and $R^7$ both represent hydrogen, fluorine or one represents hydrogen and the other represents hydroxyl.

In one embodiment, $R^6$ and $R^7$ both represent hydrogen, fluorine or one represents hydrogen and the other represents hydroxyl.

In one embodiment, W is $CH_2$—O.

When W is $CH_2$—O, in one embodiment:
$R^{1a}$ and $R^{1b}$ both represent hydrogen;
$R^{2a}$ and $R^{2b}$ both represent hydrogen;
$R^{3a}$ and $R^{3b}$ both represent hydrogen; and
$R^{4a}$ and $R^{4b}$ both represent halogen (such as fluorine).

In one embodiment, W is C=O.

When W is C=O, in one embodiment:
one of $R^{1a}$ and $R^{1b}$ represents hydrogen and the other represents $C_{1-4}$ alkyl (such as methyl);
$R^{2a}$ and $R^{2b}$ both represent hydrogen;
$R^{3a}$ and $R^{3b}$ both represent hydrogen; and
$R^{4a}$ and $R^{4b}$ both represent hydrogen.

In one embodiment, W is $SO_2$.

When W is $SO_2$, in one embodiment:
one of $R^{1a}$ and $R^{1b}$ represents hydrogen and the other represents $C_{1-4}$ alkyl (such as methyl);
$R^{2a}$ and $R^{2b}$ both represent hydrogen;
$R^{3a}$ and $R^{3b}$ both represent hydrogen; and
$R^{4a}$ and $R^{4b}$ both represent hydrogen.

In one embodiment, W is O.

When W is O, in one embodiment:
$R^{1a}$ and $R^{1b}$ both represent hydrogen or $C_{1-4}$ alkyl (such as methyl) or one represents hydrogen and the other represents $C_{1-4}$ alkyl (such as methyl or isopropyl), hydroxy$C_{1-4}$ alkyl (such as hydroxymethyl), halo$C_{1-4}$ alkyl (such as monofluoromethyl or trifluoromethyl) or methoxymethyl, or one represents $C_{1-4}$ alkyl (such as methyl) and the other represents hydroxy$C_{1-4}$ alkyl (such as hydroxymethyl), methoxymethyl or carboxyl;

$R^{2a}$ and $R^{2b}$ both represent hydrogen or $C_{1-4}$ alkyl (such as methyl) or one represents hydrogen and the other represents nitrile;

$R^{3a}$ and $R^{3b}$ both represent hydrogen or one represents hydrogen and the other represents $C_{1-4}$ alkyl (such as methyl) or hydroxy$C_{1-4}$ alkyl (such as hydroxymethyl) or one represents $C_{1-4}$ alkyl (such as methyl) and the other represents hydroxy$C_{1-4}$ alkyl (such as hydroxymethyl);

$R^{4a}$ and $R^{4b}$ both represent hydrogen or one represents hydrogen and the other represents $C_{1-4}$ alkyl (such as methyl) or hydroxy$C_{1-4}$ alkyl (such as hydroxymethyl);

or $R^{1a}$ and $R^{1b}$ join together to form cyclopropyl;
or $R^{2a}$ and $R^{3a}$ or $R^{1b}$ and $R^{3b}$ join together to form a $C_{1-4}$ bridged alkyl group (such as ethylene);
or $R^{2a}$ and $R^{3a}$ or $R^{2b}$ and $R^{3b}$ join together to form a $C_{1-4}$ bridged alkyl group (such as methylene);
or $R^{1a}$ and $R^{4a}$ or $R^{1b}$ and $R^{4b}$ join together to form a $C_{1-4}$ bridged alkyl group (such as methylene);
or $R^{2a}$ and $R^{4a}$ or $R^{2b}$ and $R^{4b}$ join together to form a $C_{1-4}$ bridged alkyl group (such as ethylene) provided that except for when X and Y are other than both nitrogen:
  $R^{1a}$, $R^{1b}$, $R^{2a}$, $R^{2b}$, $R^{3a}$, $R^{3b}$, $R^{4a}$ and $R^{4b}$ are not all hydrogen, or
  when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen.

When W is O, in a further embodiment:
$R^{1a}$ and $R^{1b}$ both represent hydrogen or $C_{1-4}$ alkyl (such as methyl) or one represents hydrogen and the other represents $C_{1-4}$ alkyl (such as methyl or isopropyl), hydroxy$C_{1-4}$ alkyl (such as hydroxymethyl), halo$C_{1-4}$ alkyl (such as monofluoromethyl or trifluoromethyl) or methoxymethyl, or one represents $C_{1-4}$ alkyl (such as methyl) and the other represents hydroxy$C_{1-4}$ alkyl (such as hydroxymethyl), methoxymethyl or carboxyl;

$R^{2a}$ and $R^{2b}$ both represent hydrogen or $C_{1-4}$ alkyl (such as methyl) or one represents hydrogen and the other represents nitrile;

$R^{3a}$ and $R^{3b}$ both represent hydrogen or one represents hydrogen and the other represents $C_{1-4}$ alkyl (such as methyl) or hydroxy$C_{1-4}$ alkyl (such as hydroxymethyl) or one represents $C_{1-4}$ alkyl (such as methyl) and the other represents hydroxy$C_{1-4}$ alkyl (such as hydroxymethyl);

$R^{4a}$ and $R^{4b}$ both represent hydrogen or one represents hydrogen and the other represents $C_{1-4}$ alkyl (such as methyl);

or $R^{1a}$ and $R^{1b}$ join together to form cyclopropyl;
or $R^{1a}$ and $R^{3a}$ or $R^{1b}$ and $R^{3b}$ join together to form a $C_{1-4}$ bridged alkyl group (such as ethylene);
or $R^{2a}$ and $R^{3a}$ or $R^{2b}$ and $R^{3b}$ join together to form a $C_{1-4}$ bridged alkyl group (such as methylene);
or $R^{1a}$ and $R^{4a}$ or $R^{1b}$ and $R^{4b}$ join together to form a $C_{1-4}$ bridged alkyl group (such as methylene);
or $R^{2a}$ and $R^{4a}$ or $R^{2b}$ and $R^{4b}$ join together to form a $C_{1-4}$ bridged alkyl group (such as ethylene) provided that except for when X and Y are other than both nitrogen:
  $R^{1a}$, $R^{1b}$, $R^{2a}$, $R^{2b}$, $R^{3a}$, $R^{3b}$, $R^{4a}$ and $R^{4b}$ are not all hydrogen, or
  when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen.

When W is O, in a further embodiment:
$R^{1a}$ and $R^{1b}$ both represent hydrogen or $C_{1-4}$ alkyl (such as methyl) or one represents hydrogen and the other represents $C_{1-4}$ alkyl (such as methyl or isopropyl), hydroxy$C_{1-4}$ alkyl (such as hydroxymethyl), halo$C_{1-4}$ alkyl (such as monofluoromethyl or trifluoromethyl) or methoxymethyl, or one represents $C_{1-4}$ alkyl (such as methyl) and the other represents hydroxy$C_{1-4}$ alkyl (such as hydroxymethyl) or carboxyl;
$R^{2a}$ and $R^{2b}$ both represent hydrogen or $C_{1-4}$ alkyl (such as methyl) or one represents hydrogen and the other represents nitrile;
$R^{3a}$ and $R^{3b}$ both represent hydrogen or one represents hydrogen and the other represents $C_{1-4}$ alkyl (such as methyl) or hydroxy$C_{1-4}$ alkyl (such as hydroxymethyl) or one represents $C_{1-4}$ alkyl (such as methyl) and the other represents hydroxy$C_{1-4}$ alkyl (such as hydroxymethyl);
$R^{4a}$ and $R^{4b}$ both represent hydrogen or one represents hydrogen and the other represents $C_{1-4}$ alkyl (such as methyl);
or $R^{1a}$ and $R^{1b}$ join together to form cyclopropyl;
or $R^{1a}$ and $R^{3a}$ or $R^{1b}$ and $R^{3b}$ join together to form a $C_{1-4}$ bridged alkyl group (such as ethylene);
or $R^{2a}$ and $R^{3a}$ or $R^{2b}$ and $R^{3b}$ join together to form a $C_{1-4}$ bridged alkyl group (such as methylene);
or $R^{1a}$ and $R^{4a}$ or $R^{1b}$ and $R^{4b}$ join together to form a $C_{1-4}$ bridged alkyl group (such as methylene);
or $R^{2a}$ and $R^{4a}$ or $R^{2b}$ and $R^{4b}$ join together to form a $C_{1-4}$ bridged alkyl group (such as ethylene) provided that except for when X and Y are other than both nitrogen:
$R^{1a}$, $R^{1b}$, $R^{2a}$, $R^{2b}$, $R^{3a}$, $R^{3b}$, $R^{4a}$ and $R^{4b}$ are not all hydrogen, or
when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen.

When W is O, in a further embodiment:
$R^{1a}$ and $R^{1b}$ both represent hydrogen or $C_{1-4}$ alkyl (such as methyl) or one represents hydrogen and the other represents $C_{1-4}$ alkyl (such as methyl or isopropyl), hydroxy$C_{1-4}$ alkyl (such as hydroxymethyl), halo$C_{1-4}$ alkyl (such as monofluoromethyl or trifluoromethyl), or, methoxymethyl or one represents $C_{1-4}$ alkyl (such as methyl) and the other represents hydroxy$C_{1-4}$ alkyl (such as hydroxymethyl);
$R^{2a}$ and $R^{2b}$ both represent hydrogen or $C_{1-4}$ alkyl (such as methyl) or one represents hydrogen and the other represents nitrile;
$R^{3a}$ and $R^{3b}$ both represent hydrogen or one represents hydrogen and the other represents $C_{1-4}$ alkyl (such as methyl) or hydroxy$C_{1-4}$ alkyl (such as hydroxymethyl);
$R^{4a}$ and $R^{4b}$ both represent hydrogen or one represents hydrogen and the other represents $C_{1-4}$ alkyl (such as methyl);
or $R^{1a}$ and $R^{1b}$ join together to form cyclopropyl;
or $R^{1a}$ and $R^{3a}$ or $R^{1b}$ and $R^{3b}$ join together to form a $C_{1-4}$ bridged alkyl group (such as ethylene);
or $R^{2a}$ and $R^{3a}$ or $R^{2b}$ and $R^{3b}$ join together to form a $C_{1-4}$ bridged alkyl group (such as methylene);
or $R^{1a}$ and $R^{4a}$ or $R^{1b}$ and $R^{4b}$ join together to form a $C_{1-4}$ bridged alkyl group (such as methylene);
or $R^{2a}$ and $R^{4a}$ or $R^{2b}$ and $R^{4b}$ join together to form a $C_{1-4}$ bridged alkyl group (such as ethylene);
provided that except for when X and Y are other than both nitrogen:
$R^{1a}$, $R^{1b}$, $R^{2a}$, $R^{2b}$, $R^{3a}$, $R^{3b}$, $R^{4a}$ and $R^{4b}$ are not all hydrogen, or
when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen.

In a further embodiment, $R^{2a}$ and $R^{4a}$ or $R^{2b}$ and $R^{4b}$ join together to form a $C_{1-4}$ bridged alkyl group (such as ethylene).

In one embodiment when W is O,
$R^{3b}$ is methyl,
$R^{1a}$, $R^{1b}$, $R^{2a}$, $R^{2b}$, $R^{3a}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile,
or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group,
provided that except for when X and Y are other than both nitrogen:
when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen, or
$R^{1a}$ or $R^{3b}$ is not methoxymethyl when $R^5$ is 1,1-difluoropropyl.

In one embodiment when W is O,
$R^{3b}$ is methyl,
$R^{1a}$, $R^{1b}$, $R^{2a}$, $R^{2b}$, $R^{3a}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl and nitrile,
or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group,
provided that except for when X and Y are other than both nitrogen:
when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen.

In one embodiment when W is O,
$R^{3b}$ is methyl,
$R^{3a}$ is hydroxymethyl,
$R^{1b}$, $R^{2a}$, $R^{2b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl and nitrile (such as hydrogen),
or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group.

In one embodiment when W is O,
$R^{3b}$ is methyl,
$R^{3a}$ is hydroxymethyl,
$R^{1a}$, $R^{1b}$, $R^{2a}$, $R^{2b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl and nitrile (such as hydrogen).

In one embodiment when W is O,
$R^{3b}$ is methyl, $R^{1a}$ is methyl,
$R^{1b}$, $R^{2a}$, $R^{2b}$, $R^{3a}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl and nitrile (such as hydrogen),
or $R^{2a}$ and $R^{2b}$, or $R^{4a}$ and $R^{4b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group.

In one embodiment when W is O,
$R^{3b}$ is methyl,
$R^{1a}$ is methyl,
$R^{1b}$, $R^{2a}$, $R^{2b}$, $R^{3a}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl and nitrile (such as hydrogen).

When W is O, in a yet further embodiment:
$R^{1a}$ represents $C_{1-4}$ alkyl (such as methyl) and $R^{1b}$ represents hydrogen;
$R^{2a}$ and $R^{2b}$ both represent hydrogen;
$R^{3a}$ represents hydrogen and $R^{3b}$ represents $C_{1-4}$ alkyl (such as methyl); and
$R^{4a}$ and $R^{4b}$ both represent hydrogen.

In one embodiment, W is O and $R^{4b}$ is hydroxymethyl. In another embodiment, $R^{4b}$ is hydroxymethyl, $R^{1a}$ is methyl, and $R^{1b}$, $R^{2a}$, $R^{2b}$, $R^{3a}$, $R^{3b}$ and $R^{4a}$ are hydrogen.

In one embodiment, W is O and $R^{3a}$ is hydroxymethyl. In another embodiment, $R^{3a}$ is hydroxymethyl, $R^{3b}$ is methyl, and $R^{1a}$, $R^{1b}$, $R^{2a}$, $R^{2b}$, $R^{4a}$ and $R^{4b}$ are hydrogen.

In one embodiment, W is O and $R^{1a}$ and $R^{3b}$ are methyl. In another embodiment, W is O, $R^{1a}$ and $R^{3b}$ are methyl, and $R^{1b}$, $R^{2a}$, $R^{2b}$, $R^{3a}$, $R^{4a}$ and $R^{4b}$ are hydrogen.

In one embodiment, when W is $NR^8$, $R^8$ is selected from hydrogen, $C_{1-4}$ alkyl, $-SO_2-C_{1-4}$ alkyl, $-SO_2-NH(C_{1-4}$ alkyl), $-SO_2-N(C_{1-4}$ alkyl)$_2$, $-C(=O)-N(C_{1-4}$ alkyl)$_2$, $-C(=O)$-phenyl, $-C(=O)-C_{3-6}$ cycloalkyl and $-C(=O)-C_{1-4}$ alkyl, wherein the alkyl or cyclic groups can be optionally substituted by one or more $R^{10}$.

In one embodiment, W is $NR^8$.

When W is $NR^8$, in one embodiment:
$R^{1a}$ and $R^{1b}$ both represent hydrogen or one represents hydrogen and the other represents $C_{1-4}$ alkyl (such as methyl);
$R^{1a}$ and $R^{2b}$ both represent hydrogen or one represents hydrogen and the other represents $C_{1-4}$ alkyl (such as methyl) or $R^{2a}$ and $R^{2b}$ together represent =O;
$R^{3a}$ and $R^{3b}$ both represent hydrogen or one represents hydrogen and the other represents $C_{1-4}$ alkyl (such as methyl);
$R^{4a}$ and $R^{4b}$ both represent hydrogen or one represents hydrogen and the other represents $C_{1-4}$ alkyl (such as methyl) or $R^{4a}$ and $R^{4b}$ together represent =O provided that except for when X and Y are other than both nitrogen, $R^{4a}$ and $R^{4b}$ do not together represent =O when $R^5$ is 1,1-difluoroethyl and $R^8$ is methyl;
or $R^{2a}/R^{2b}$ join together with the nitrogen atom at W to form a fused heteroaromatic group with 5 or 6 ring members (such as triazolyl) which can be optionally substituted by one or more substituents $R^{10}$;
$R^8$ represents hydrogen, $C_{1-4}$ alkyl (such as methyl), $-SO_2-C_{1-4}$ alkyl (such as $-SO_2Me$), $-C(=O)-N(C_{1-4}$ alkyl)$_2$ (such as $C(=O)-N(Me)_2$), pyrimidinyl, $-C(=O)$-phenyl or $-C(=O)-C_{1-4}$ alkyl (such as $C(=O)-CH_3$).

When W is $NR^8$, in a further embodiment:
$R^{1a}$ and $R^{1b}$ both represent hydrogen or one represents hydrogen and the other represents $C_{1-4}$ alkyl (such as methyl);
$R^{2a}$ and $R^{2b}$ both represent hydrogen or one represents hydrogen and the other represents $C_{1-4}$ alkyl (such as methyl) or $R^{2a}$ and $R^{2b}$ together represent =O;
$R^{3a}$ and $R^{3b}$ both represent hydrogen;
$R^{4a}$ and $R^{4b}$ both represent hydrogen or one represents hydrogen and the other represents $C_{1-4}$ alkyl (such as methyl) or $R^{4a}$ and $R^{4b}$ together represent =O provided that except for when X and Y are other than both nitrogen, $R^{4a}$ and $R^{4b}$ do not together represent =O when $R^5$ is 1,1-difluoroethyl and $R^8$ is methyl;
$R^8$ represents hydrogen, $C_{1-4}$ alkyl (such as methyl), pyrimidinyl, or $-C(=O)-C_{1-4}$ alkyl (such as $C(=O)-CH_3$).

In one embodiment when W is $NR^8$ then $R^{2a/2b}$ or $R^{4a/4b}$ can join together with the nitrogen atom at W to form a fused heterocyclic group with 5 or 6 ring members which can be optionally substituted by one or more substituents $R^{10}$. In a further embodiment when W is $NR^8$ then $R^{2a/2b}$ or $R^{4a/4b}$ can join together with the nitrogen atom at W to form a fused heteroaromatic group with 5 or 6 ring members which can be optionally substituted by one or more substituents $R^{10}$. In a further embodiment when W is $NR^8$ then $R^{2a/2b}$ or $R^{4a/4b}$ can join together with the nitrogen atom at W to form a fused triazolyl group with 5 or 6 ring members which can be optionally substituted by one or more substituents $R^{10}$. In a further embodiment when W is $NR^8$ then $R^{2a/2b}$ or $R^{4a/4b}$ can join together with the nitrogen atom at W to form a fused saturated heterocyclic group with 5 or 6 ring members (e.g. morpholinyl) which can be optionally substituted by one or more substituents $R^{10}$.

In one embodiment when W is $NR^8$,
$R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile,
or $R^{2a}$ and $R^{2b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl,
or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a bridged alkyl group,
or $R^{2a/2b}$ or $R^{4a/4b}$ can join together with the nitrogen atom at W to form a fused heterocyclic group with 5 or 6 ring members which can be optionally substituted by one or more substituents $R^{10}$.

In one embodiment when W is $NR^8$, $R^8$ is selected from hydrogen, $C_{1-4}$ alkyl, $-SO_2-C_{1-4}$ alkyl, $-SO_2-NH(C_{1-4}$ alkyl), $-SO_2-N(C_{1-4}$ alkyl)$_2$, $-C(=O)-NH-SO_2-C_{1-4}$ alkyl, $-C(=O)-NH-SO_2$-phenyl, $-C(=O)-N(C_{1-4}$ alkyl)$_2$, pyrimidinyl, $-C(=O)$-phenyl, $-C(=O)-C_{3-6}$ cycloalkyl and $-C(=O)-C_{1-4}$ alkyl, wherein the alkyl or cyclic groups can be optionally substituted by one or more $R^{10}$
$R^{3b}$ is methyl,
$R^{1a}$, $R^{1b}$, $R^{2a}$, $R^{2b}$, $R^{3a}$, $R^{4a}$ and $R^{4b}$ are independently selected from hydrogen, halogen, alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile,
or $R^{2a}$ and $R^{2b}$ can together represent =O,
or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{2b}$, or $R^{2b}$ and $R^{4b}$, can join together to form a $C_{1-4}$ bridged alkyl group, and or $R^{2a/2b}$ or $R^{4a/4b}$ can join together with the nitrogen atom at W to form a fused heterocyclic group with 5 or 6 ring members which can be optionally substituted by one or more substituents $R^{10}$.

In one embodiment when W is $NR^8$,
$R^8$ is selected from hydrogen, $C_{1-4}$ alkyl, $-SO_2-C_{1-4}$ alkyl, $-SO_2-NH(C_{1-4}$ alkyl), $-SO_2-N(C_{1-4}$ alkyl$)_2$, $-C(=O)-NH-SO_2-C_{1-4}$ alkyl, $-C(=O)-NH-SO_2$-phenyl, $-C(=O)-N(C_{1-4}$ alkyl$)_2$, pyrimidinyl, $-C(=O)$-phenyl, $-C(=O)-C_{3-6}$ cycloalkyl and $-C(=O)-C_{1-4}$ alkyl, wherein the alkyl or cyclic groups can be optionally substituted by one or more $R^{10}$,
$R^{3b}$ is methyl,
$R^{1a}$ is hydrogen or methyl, and
$R^{1b}$, $R^{2a}$, $R^{2b}$, $R^{3a}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile (such as hydrogen).

In one embodiment when W is $NR^8$, wherein $R^8$ is $-C(=O)-C_{1-4}$ alkyl wherein the alkyl can be optionally substituted by one or more $R^{10}$,
$R^{3b}$ is methyl,
$R^{1a}$ is hydrogen or methyl,
$R^{1b}$, $R^{2a}$, $R^{2b}$, $R^{3a}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile (such as hydrogen).

In one embodiment when W is $NR^8$,
$R^8$ is $-C(=O)-C_{1-4}$ alkyl (such as $-C(=O)$-methyl), $R^{3b}$ is methyl,
$R^{1a}$ is hydrogen or methyl, and
$R^{1b}$, $R^{2a}$, $R^{2b}$, $R^{3a}$, $R^{4a}$ and $R^{4b}$ are hydrogen.

In one embodiment when W is $NR^8$,
$R^8$ is $-C(=O)-C_{1-4}$ alkyl (such as $-C(=O)$-methyl), $R^{3a}$ and $R^{3b}$ are methyl, and
$R^{1b}$, $R^{2a}$, $R^{2b}$, $R^{3a}$, $R^{4a}$ and $R^{4b}$ are hydrogen.

In one embodiment, W is $NR^8$ and $R^8$ is $-C(=O)-C_{1-4}$ alkyl (such as $C(=O)-CH_3$). In another embodiment, W is $NR^8$ and $R^8$ is $-C(=O)-C_{1-4}$ alkyl (such as $C(=O)-CH_3$), $R^{3b}$ is methyl and $R^{1a}$, $R^{1b}$, $R^{2a}$, $R^{2b}$, $R^{3a}$, $R^{4a}$ and $R^{4b}$ are hydrogen.

In another embodiment, W is $NR^8$ and $R^8$ is $-C(=O)-C_{1-4}$ alkyl (such as $C(=O)-CH_3$), $R^{1a}$ and $R^{3b}$ are methyl, and $R^{1b}$, $R^{2a}$, $R^{2b}$, $R^{3a}$, $R^{4a}$ and $R^{4b}$ are hydrogen.

In one embodiment, W is $NR^8$ and $R^{2a}$ and $R^{2b}$ or $R^{4a}$ and $R^{4b}$ together represent =O. In one embodiment, W is $NR^8$ and $R^{2a}$ and $R^{2b}$ together represent =O.

In one embodiment W is $NR^8$, $R^{1a}$ and $R^{1b}$ both represent hydrogen; $R^{2a}$ and $R^{2b}$ together represent C=O; $R^{3a}$ and $R^{3b}$ both represent hydrogen; and $R^{4a}$ and $R^{4b}$ represent hydrogen or fluorine.

In one embodiment W is $NR^8$ and $R^8$ represents hydrogen, $C_{1-4}$ alkyl (such as methyl), $-SO_2-C_{1-4}$ alkyl (such as $-SO_2Me$), $-C(=O)-N(C_{1-4}$ alkyl$)_2$ (such as $C(=O)-N(Me)_2$), pyrimidinyl, $-C(=O)$-phenyl or $-C(=O)-C_{1-4}$ alkyl (such as $C(=O)-CH_3$).

When W is $NR^8$, in a further embodiment $R^8$ represents hydrogen, $C_{1-4}$ alkyl (such as methyl), $-C(=O)-C_{3-6}$ cycloalkyl or $-C(=O)-C_{1-4}$ alkyl (such as $C(=O)-CH_3$). When W represents $NR^8$, in a further embodiment $R^8$ represents hydrogen, $C_{1-4}$ alkyl (such as methyl), or $-C(=O)-C_{1-4}$ alkyl (such as $C(=O)-CH_3$).

In one embodiment, W is $CH_2-NR^8$.

When W represents $CH_2-NR^8$, in one embodiment:
$R^{1a}$ and $R^{1b}$ both represent hydrogen;
$R^{2a}$ and $R^{2b}$ together represent C=O;
$R^{3a}$ and $R^{3b}$ both represent hydrogen;
$R^{4a}$ and $R^{4b}$ both represent hydrogen; and
$R^8$ represents hydrogen.

In one embodiment, W is absent.
When W is absent, in one embodiment:
$R^{1a}$ and $R^{1b}$ both represent hydrogen or one represents hydrogen and the other represents hydroxy$C_{1-4}$ alkyl (such as hydroxymethyl) or halo$C_{1-4}$ alkyl (such as monofluoromethyl or trifluoromethyl);
$R^{2a}$ and $R^{2b}$ both represent hydrogen or halogen (such as fluorine) or one represents hydrogen and the other represents halogen (such as fluorine);
$R^{3a}$ and $R^{3b}$ both represent hydrogen;
$R^{4a}$ and $R^{4b}$ both represent hydrogen or one represents hydrogen and the other represents $C_{1-4}$ alkyoxy (such as methoxy);
or $R^{2a}/R^{2b}$ and $R^{4a}/R^{4b}$ join together to form a pyridinyl group which can be optionally substituted by one or more substituents $R^{10}$; provided that except for when X and Y are other than both nitrogen:
$R^{1a}$, $R^{1b}$, $R^{2a}$, $R^{2b}$, $R^{3a}$, $R^{3b}$, $R^{4a}$ and $R^{4b}$ are not all hydrogen, or
when one of $R^{2a}$ or $R^{2b}$ or $R^{4a}$ or $R^{4b}$ is fluorine the remaining $R^{1a}$, $R^{1b}$, $R^{2a}$, $R^{2b}$, $R^{3a}$, $R^{3b}$, $R^{4a}$ and $R^{4b}$ groups are not all hydrogen, or
$R^{2a}$ and $R^{2b}$, or $R^{4a}$ and $R^{4b}$ are not both fluorine when $R^5$ is 2,4-difluorobenzyl.

In one embodiment when W is absent, then $R^{2a}/R^{2b}$ and $R^{4a}/R^{4b}$ join together to form a pyridinyl group (such as pyridin-6-yl) which can be optionally substituted by one or more substituents $R^{10}$. In one embodiment when W is absent, then $R^{2a}/R^{2b}$ and $R^{4a}/R^{4b}$ join together to form an unsubstituted pyridinyl group (such as pyridin-6-yl).

In one embodiment, W is absent and $R^{1a}$ and $R^{1b}$ both represent hydrogen; $R^{2a}$ and $R^{2b}$ together fluorine; $R^{3a}$ and $R^{3b}$ both represent hydrogen; and $R^{4a}$ and $R^{4b}$ both represent hydrogen.

In one embodiment, $R^5$ is selected from: benzyl optionally substituted on the phenyl group by one or two fluorine substituents, and optionally substituted on the methylene by hydroxyl; and $C_{2-4}$ alkyl substituted by one or two fluorine substituents.

In one embodiment, $R^5$ is benzyl optionally substituted on the phenyl group by one or two substituents selected from fluorine and nitrile, and optionally substituted on the methylene by hydroxyl.

In one embodiment, $R^5$ is benzyl optionally substituted on the phenyl group by one or two substituents which is fluorine, and optionally substituted on the methylene by hydroxyl. In another embodiment, $R^5$ is benzyl substituted on the phenyl group by one or two fluorine substituents, and optionally substituted on the methylene by hydroxyl.

In another embodiment, $R^5$ is benzyl substituted on the phenyl group by one or two fluorine substituents, and substituted on the methylene by hydroxyl.

In one embodiment, $R^5$ is benzyl optionally substituted (e.g. substituted) on the phenyl group by one or two fluorines.

In one embodiment, $R^5$ is benzyl optionally substituted on the phenyl group by one or two substituents selected from fluorine, and wherein the methylene is optionally substituted by a hydroxyl group (e.g. $R^5$ is selected from C(H)(OH)-2-fluorophenyl, C(H)(OH)-3-fluorophenyl, C(H)(OH)-4-fluorophenyl, $-C(H)(OH)$-2,3-difluorophenyl, $-C(H)(OH)$-2, 4-difluorophenyl, —C(H)(OH)-2,5-difluorophenyl, —C(H)(OH)-2,6-difluorophenyl and —C(H)(OH)-3,4-difluorophenyl).

In one embodiment, $R^5$ is benzyl optionally substituted on the phenyl group by one or two fluorines wherein the methylene is optionally substituted by a hydroxyl group (e.g. C(H)(OH)-4-fluorophenyl or —C(H)(OH)-2,4-difluorophenyl).

In a further embodiment, $R^5$ is benzyl optionally substituted on the phenyl group by one fluorine (such as 2-fluorobenzyl, 3-fluorobenzyl or 4-fluorobenzyl), two fluorines (such as 2,3-difluorobenzyl, 2,4-difluorobenzyl or 2,6-difluorobenzyl) or one fluorine and one nitrile (such as 2-cyano-4-fluorobenzyl).

In a further embodiment, $R^5$ is benzyl optionally substituted on the phenyl group by one fluorine (such as 4-fluorobenzyl), two fluorines (such as 2,4-difluorobenzyl) or one fluorine and one nitrile (such as 2-cyano-4-fluorobenzyl).

In one embodiment, $R^5$ is 2-fluorobenzyl. In one embodiment, $R^5$ is 4-fluorobenzyl. In one embodiment, $R^5$ is benzyl substituted on the methylene by an hydroxyl group and unsubstituted on the phenyl group.

In one embodiment, $R^5$ is CH(OH)-phenyl where the phenyl group is optionally substituted with one or two substituents selected from fluorine.

In one embodiment, $R^5$ is benzyl optionally substituted on the phenyl group by one or two fluorines (such as 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl or 3,4-difluorobenzyl) or one fluorine and one nitrile (such as 2-cyano-4-fluorobenzyl), wherein the methylene is optionally substituted by a hydroxyl group (such as C(H)(OH)-2-fluorophenyl, C(H)(OH)-3-fluorophenyl, C(H)(OH)-4-fluorophenyl, —C(H)(OH)-2,3-difluorophenyl, —C(H)(OH)-2,4-difluorophenyl or —C(H)(OH)-3,4-difluorophenyl) or the methylene is optionally substituted by a hydroxyl group or $R^5$ is $C_{2-4}$ alkyl substituted by a hydroxyl group (such as 1-hydroxybutyl) or one or two fluorines (such as 1,1-difluoropropyl or 1,1-difluorobutyl).

In a yet further embodiment, $R^5$ is selected from unsubstituted benzyl and benzyl substituted on the phenyl group by one fluorine. In one embodiment $R^5$ is benzyl optionally substituted on the phenyl group by one or two fluorines (such as 4-fluorobenzyl or 2,4-difluorobenzyl). In one embodiment $R^5$ is benzyl optionally substituted on the phenyl group by two fluorines (such as 2,4-difluorobenzyl). In a yet further embodiment, $R^5$ is benzyl optionally substituted on the phenyl group by one fluorine. In a still yet further embodiment, $R^5$ is 4-fluorobenzyl.

In one embodiment, $R^5$ is $C_{2-4}$ alkyl substituted by one or two substituents selected from fluorine and hydroxyl.

In one embodiment, $R^5$ is $C_{2-4}$ alkyl substituted by one hydroxyl (such as 1-hydroxybutyl).

In an alternative embodiment, $R^5$ is $C_{2-4}$ alkyl substituted by one or two fluorines. In a further embodiment, $R^5$ is $C_{2-4}$ alkyl substituted by two fluorines. In a yet further embodiment, $R^5$ is butyl substituted by two fluorines. In a still yet further embodiment, $R^5$ is 1,1-difluoropropyl or 1,1-difluorobutyl. In one embodiment $R^5$ is difluorobutyl (such as 1,1-difluorobutyl). In one embodiment when X is CH and Y is nitrogen then $R^5$ is difluorobutyl (such as 1,1-difluorobutyl).

Sub-Formulae

In one embodiment the compound of formula (I) is wherein:
X is CH and Y is $CR^9$; X is nitrogen and Y is $CR^9$; X is $CR^9$ and Y is nitrogen; or X and Y are nitrogen;

$R^9$ represents hydrogen or nitrile (in particular hydrogen);
W is either absent or selected from $CR^8R^7$, $CH_2$—O, C=O, $SO_2$, O, $NR^8$ and $CH_2$—$NR^8$; $R^{1a}$, $R^{1b}$, $R^{2a}$, $R^{2b}$, $R^{3a}$, $R^{3b}$, $R^{4a}$ and $R^{4b}$ independently represent hydrogen, $C_{1-4}$ alkyl (such as methyl or isopropyl), halogen (such as fluorine), halo$C_{1-4}$ alkyl (such as monofluoromethyl or trifluoromethyl), hydroxy$C_{1-4}$ alkyl (such as hydroxymethyl), $C_{1-4}$ alkyoxy (such as methoxy), methoxymethyl, carboxyl or nitrile;
or $R^{1a}$ and $R^{1b}$ join together to form cyclopropyl;
or $R^{1a}$ and $R^{3a}$, or $R^{1b}$ and $R^{3b}$ join together to form a $C_{1-4}$ bridged alkyl group (such as ethylene);
or $R^{2a}$ and $R^{3a}$ or $R^{2b}$ and $R^{3b}$ join together to form a $C_{1-4}$ bridged alkyl group (such as methylene);
or $R^{1a}$ and $R^{4a}$ or $R^{1b}$ and $R^{4b}$ join together to form a $C_{1-4}$ bridged alkyl group (such as methylene);
or $R^{2a}$ and $R^{4a}$ or $R^{2b}$ and $R^{4b}$ join together to form a $C_{1-4}$ bridged alkyl group (such as ethylene);
or $R^{2a}/R^{2b}$ join together with the nitrogen atom at W to form a fused heteroaromatic group with 5 or 6 ring members (such as triazolyl) which can be optionally substituted by one or more substituents $R^{10}$;
or when W is absent then $R^{2a}/R^{2b}$ and $R^{4a}/R^{4b}$ can also join together to form a pyridinyl group which can be optionally substituted by one or more substituents $R^{10}$;
or $R^{2a}$ and $R^{2b}$ together represent =O;
or $R^{4a}$ and $R^{4b}$ together represent =O;
provided that except for when X and Y are other than both nitrogen, when W represents $NR^8$:
$R^{4a}$ and $R^{4b}$ do not together represent =O when $R^5$ is 1,1-difluoroethyl and $R^8$ is methyl;
and provided that except for when X and Y are other than both nitrogen, when W represents O:
$R^{1a}$, $R^{1b}$, $R^{2a}$, $R^{2b}$, $R^{3a}$, $R^{3b}$, $R^{4a}$ and $R^{4b}$ are not all hydrogen, or
when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen, or
when $R^{2a}$ and $R^{4a}$ are methyl then $R^{1a}$, $R^{1b}$, $R^{2b}$, $R^{3a}$, $R^{3b}$ and $R^{4b}$ are not all hydrogen, or
$R^{1a}$ or $R^{3b}$ is not methoxymethyl when $R^5$ is 1,1-difluoropropyl;
and provided that except for when X and Y are other than both nitrogen, when W is absent:
$R^{1b}$, $R^{2a}$, $R^{2b}$, $R^{3a}$, $R^{3b}$, $R^{4a}$ and $R^{4b}$ are not all hydrogen, or
when one of $R^{2a}$ or $R^{2b}$ or $R^{4a}$ or $R^{4b}$ is fluorine the remaining $R^{1a}$, $R^{1b}$, $R^{2a}$, $R^{2b}$, $R^{3a}$, $R^{3b}$, $R^{4a}$ and $R^{4b}$ groups are not all hydrogen, or
when $R^{2a}$ and $R^{2b}$, or $R^{4a}$ and $R^{4b}$ join to form =O then the remaining $R^{1a}$, $R^{1b}$, $R^{2a}$, $R^{2b}$, $R^{3a}$, $R^{3b}$, $R^{4a}$ and $R^{4b}$ groups are not all hydrogen, or
$R^{2a}$ and $R^{2b}$, or $R^{4a}$ and $R^{4b}$ are not both fluorine when $R^5$ is 2,4-difluorobenzyl
wherein $R^5$ is as defined in any of the embodiments.

In a further embodiment the compound of formula (I) is wherein:
X is CH and Y is $CR^9$; X is nitrogen and Y is $CR^9$; or X is $CR^9$ and Y is nitrogen;
$R^9$ represents hydrogen or nitrile (in particular hydrogen);
W is either absent or selected from $CR^6R^7$, $CH_2$—O, C=O, $SO_2$, O, $NR^8$ and $CH_2$—$NR^8$;
$R^{1a}$, $R^{1b}$, $R^{2a}$, $R^{2b}$, $R^{3a}$, $R^{3b}$, $R^{4a}$ and $R^{4b}$ independently represent hydrogen, $C_{1-4}$ alkyl (such as methyl or isopropyl), halogen (such as fluorine), halo$C_{1-4}$ alkyl (such as monofluoromethyl or trifluoromethyl), hydroxy$C_{1-4}$ alkyl (such as hydroxymethyl), $C_{1-4}$ alkyoxy (such as methoxy), methoxymethyl, carboxyl or nitrile;

or $R^{1a}$ and $R^{1b}$ join together to form cyclopropyl;

or $R^{1a}$ and $R^{3a}$ or $R^{1b}$ and $R^{3b}$ join together to form a $C_{1-4}$ bridged alkyl group (such as ethylene);

or $R^{2a}$ and $R^{3a}$ or $R^{2b}$ and $R^{3b}$ join together to form a $C_{1-4}$ bridged alkyl group (such as methylene);

or $R^{1a}$ and $R^{4a}$ or $R^{1b}$ and $R^{4b}$ join together to form a $C_{1-4}$ bridged alkyl group (such as methylene);

or $R^{2a}$ and $R^{4a}$ or $R^{2b}$ and $R^{4b}$ join together to form a $C_{1-4}$ bridged alkyl group (such as ethylene);

or $R^{2a}/R^{2b}$ join together with the nitrogen atom at W to form a fused heteroaromatic group with 5 or 6 ring members (such as triazolyl) which can be optionally substituted by one or more substituents $R^{10}$;

or when W is absent then $R^{2a}/R^{2b}$ and $R^{4a}/R^{4b}$ can also join together to form a pyridinyl group which can be optionally substituted by one or more substituents $R^{10}$;

or $R^{2a}$ and $R^{2b}$ together represent =O;

or $R^{4a}$ and $R^{4b}$ together represent =O;

provided that except for when X and Y are other than both nitrogen, when W represents $NR^8$:

$R^{4a}$ and $R^{4b}$ do not together represent =O when $R^5$ is 1,1-difluoroethyl and $R^8$ is methyl;

and provided that except for when X and Y are other than both nitrogen, when W represents O:

$R^{1a}$, $R^{1b}$, $R^{2a}$, $R^{2b}$, $R^{3a}$, $R^{3b}$, $R^{4a}$ and $R^{4b}$ are not all hydrogen, or when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen, or when $R^{2a}$ and $R^{4a}$ are methyl then $R^{1a}$, $R^{2b}$, $R^{3a}$, $R^{3b}$ and $R^{4b}$ are not all hydrogen, or $R^{1a}$ or $R^{3b}$ is not methoxymethyl when $R^5$ is 1,1-difluoropropyl;

and provided that except for when X and Y are other than both nitrogen, when W is absent:

$R^{1a}$, $R^{1b}$, $R^{2a}$, $R^{2b}$, $R^{3a}$, $R^{3b}$, $R^{4a}$ and $R^{4b}$ are not all hydrogen, or when one of $R^{2a}$ or $R^{2b}$ or $R^{4a}$ or $R^{4b}$ is fluorine the remaining $R^{1a}$, $R^{1b}$, $R^{2a}$, $R^{2b}$, $R^{3a}$, $R^{3b}$, $R^{4a}$ and $R^{4b}$ groups are not all hydrogen, or when $R^{2a}$ and $R^{2b}$, or $R^{4a}$ and $R^{4b}$ join to form =O then the remaining $R^{1a}$, $R^{1b}$, $R^{2a}$, $R^{2b}$, $R^{3a}$, $R^{3b}$, $R^{4a}$ and $R^{4b}$ groups are not all hydrogen, or $R^{2a}$ and $R^{2b}$, or $R^{4a}$ and $R^{4b}$ are not both fluorine when $R^5$ is 2,4-difluorobenzyl.

In one embodiment, the compound of formula (I) is a compound of formula (Ia):

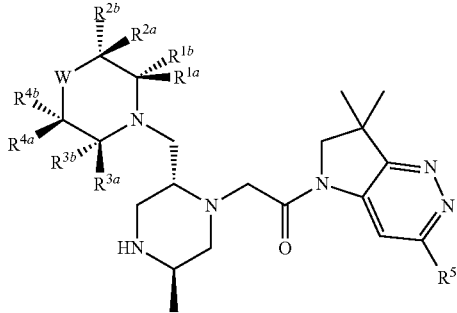

(Ia)

or tautomeric or stereochemically isomeric forms, N-oxides, pharmaceutically acceptable salts or the solvates thereof; wherein $R^{1a}$, $R^{1b}$, $R^{2a}$, $R^{2b}$, $R^{3a}$, $R^{3b}$, $R^{4a}$, $R^{4b}$, W and $R^5$ are as defined in any of the embodiments.

In one embodiment, the compound of formula (I) is a compound of formula (Ia) wherein: W is either absent or selected from $CR^6R^7$, $CH_2$—$CH_2$, $CH_2$—O, O—$CH_2$, C=O, $SO_2$, O, $NR^8$, $CH_2$—$NR^8$ and $NR^8$—$CH_2$;

when W is $CR^6R^7$, $CH_2$—$CH_2$, $CH_2$—O, O—$CH_2$, C=O, $SO_2$, $CH_2$—$NR^8$, or $NR^8$—$CH_2$, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, when W is $NR^8$, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, or $R^{2a/2b}$ or $R^{4a/4b}$ can join together with the nitrogen atom at W to form a fused heterocyclic group with 5 or 6 ring members which can be optionally substituted by one or more substituents $R^{10}$, when W is O then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, when W is absent then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, or $R^{2a/2b}$ and $R^{4a/4b}$ can join together to form a fused phenyl or pyridinyl group which can be optionally substituted by one or more substituents $R^{10}$, $R^5$ is selected from: benzyl optionally substituted on the phenyl group by one or two substituents selected from fluorine and nitrile, and optionally substituted on the methylene by hydroxyl; and $C_{2-4}$ alkyl substituted by one or two substituents selected from fluorine and hydroxyl;

$R^6$ and $R^7$ are independently selected from hydrogen, hydroxyl and fluorine;

$R^8$ is selected from hydrogen, $C_{1-4}$ alkyl, —$SO_2$—$C_{1-4}$ alkyl, —$SO_2$—$NH(C_{1-4}$ alkyl), —$SO_2$—$N(C_{1-4}$ alkyl)$_2$, —C(=O)—NH—$SO_2$—$C_{1-4}$ alkyl, —C(=O)—NH—$SO_2$-phenyl, —C(=O)—$N(C_{1-4}$ alkyl)$_2$, pyrimidinyl, —C(=O)-phenyl, —C(=O)—$C_{3-6}$ cycloalkyl and —C(=O)—$C_{1-4}$ alkyl, wherein the alkyl or cyclic groups can be optionally substituted by one or more $R^{10}$;

$R^{10}$ is independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile.

In one embodiment, the compound of formula (I) is a compound of formula (Ia) wherein: W is either absent or selected from $CR^6R^7$, $CH_2$—$CH_2$, $CH_2$—O, O—$CH_2$, C=O, $SO_2$, O, $NW^8$, $CH_2$—$NR^8$ and $NR^8$—$CH_2$;

$R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, or when W is $NW^8$, then $R^{2a/2b}$ or $R^{4a/4b}$ can join together with the nitrogen atom at W to form a fused heterocyclic group with 5 or 6 ring members which can be optionally substituted by one or more substituents $R^{10}$, or when W is absent then $R^{2a/2b}$ and $R^{4a/4b}$ can join together to form a fused phenyl or pyridinyl group which can be optionally substituted by one or more substituents $R^{10}$, $R^5$ is selected from: benzyl optionally substituted on the phenyl group by one or two substituents selected from fluorine and nitrile, and optionally substituted on the methylene by hydroxyl; and $C_{2-4}$ alkyl substituted by one or two substituents selected from fluorine and hydroxyl;

$R^6$ and $R^7$ are independently selected from hydrogen, hydroxyl and fluorine;

$R^8$ is selected from hydrogen, $C_{1-4}$ alkyl, —$SO_2$—$C_{1-4}$ alkyl, —$SO_2$—$NH(C_{1-4}$ alkyl), —$SO_2$—$N(C_{1-4}$ alkyl)$_2$, —C(=O)—NH—$SO_2$—$C_{1-4}$ alkyl, —C(=O)—NH—$SO_2$-phenyl, —C(=O)—$N(C_{1-4}$ alkyl)$_2$, pyrimidinyl, —C(=O)-phenyl, —C(=O)—$C_{3-6}$ cycloalkyl and —C(=O)—$C_{1-4}$ alkyl, wherein the alkyl or cyclic groups can be optionally substituted by one or more $R^{10}$;

$R^{10}$ is independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile.

In one embodiment of the compounds of formula (Ia), W is either absent or selected from $CR^6R^7$, $CH_2$—O, C=O, $SO_2$, O, $NR^8$ and $CH_2$—$NR^8$. In one embodiment of the compounds of formula (Ia), W is absent, O, or $NR^8$. In one embodiment of the compounds of formula (Ia) W represents O, or $NR^8$.

In one embodiment of the compounds of formula (Ia), $R^{1a}$, $R^{1b}$, $R^{2a}$, $R^{2b}$, $R^{3a}$, $R^{3b}$, $R^{4a}$ and $R^{4b}$ independently represent hydrogen, $C_{1-4}$ alkyl (such as methyl or isopropyl), halogen (such as fluorine), halo$C_{1-4}$ alkyl (such as monofluoromethyl or trifluoromethyl), hydroxy$C_{1-4}$ alkyl (such as hydroxymethyl), $C_{1-4}$ alkyoxy (such as methoxy), methoxymethyl, carboxyl or nitrile;

or $R^{1a}$ and $R^{1b}$ join together to form cyclopropyl;

or $R^{1a}$ and $R^{3a}$, or $R^{1b}$ and $R^{3b}$ join together to form a $C_{1-4}$ bridged alkyl group (such as ethylene);

or $R^{2a}$ and $R^{3a}$ or $R^{2b}$ and $R^{3b}$ join together to form a $C_{1-4}$ bridged alkyl group (such as methylene);

or $R^{3a}$ and $R^{4a}$ or $R^{1b}$ and $R^{4b}$ join together to form a $C_{1-4}$ bridged alkyl group (such as methylene);

or $R^{2a}$ and $R^{4a}$ or $R^{2b}$ and $R^{4b}$ join together to form a $C_{1-4}$ bridged alkyl group (such as ethylene);

or $R^{2a}/R^{2b}$ join together with the nitrogen atom at W to form a fused heteroaromatic group with 5 or 6 ring members (such as triazolyl) which can be optionally substituted by one or more substituents $R^{10}$;

or when W is absent then $R^{2a}/R^{2b}$ and $R^{4a}/R^{4b}$ can also join together to form a pyridinyl group which can be optionally substituted by one or more substituents $R^{10}$;

or $R^{2a}$ and $R^{2b}$ together represent =O;

or $R^{4a}$ and $R^{4b}$ together represent =O.

In a further embodiment of the compounds of formula (Ia), $R^{2a}$ and $R^{4a}$ or $R^{2b}$ and $R^{4b}$ join together to form a $C_{1-4}$ bridged alkyl group (such as ethylene).

In one embodiment of the compounds of formula (Ia), W represents O, $R^{1a}$ is methyl, and $R^{3b}$ is methyl. In another embodiment, W is O, $R^{3a}$ and $R^{3b}$ are methyl, and $R^{1b}$, $R^{2a}$, $R^{2b}$, $R^{1a}$, $R^{4a}$ and $R^{4b}$ are hydrogen.

In one embodiment of the compounds of formula (Ia), W represents O, $R^{4b}$ is hydroxymethyl. In another embodiment, $R^{4b}$ is hydroxymethyl and $R^{1a}$ is methyl. In yet another embodiment, $R^{4b}$ is hydroxymethyl, $R^{1a}$ is methyl and $R^{1b}$, $R^{2a}$, $R^{2b}$, $R^{3a}$, $R^{3b}$ and $R^{4a}$ are hydrogen.

In one embodiment of the compounds of formula (Ia), W represents $NR^8$ and $R^{2a}$ and $R^{2b}$ or $R^{4a}$ and $R^{4b}$ together represent =O.

In one embodiment of the compounds of formula (Ia), W represents $CR^6R^7$ and $R^6$ and $R^7$ both represent hydrogen, fluorine or one represents hydrogen and the other represents hydroxyl.

In one embodiment of the compounds of formula (Ia), $R^8$ represents hydrogen, $C_{1-4}$ alkyl (such as methyl), —$SO_2$—$C_{1-4}$ alkyl (such as $SO_2Me$), —C(=O)—$N(C_{1-4}$ alkyl)$_2$ (such as C(=O)—N(Me)$_2$), pyrimidinyl, —C(=O)-phenyl or —C(=O)—$C_{1-4}$ alkyl (such as C(=O)—$CH_3$).

In one embodiment of the compounds of formula (Ia), $R^5$ is benzyl optionally substituted on the phenyl group by one or two fluorines (such as 4-fluorobenzyl or 2,4-difluorobenzyl) or one fluorine and one nitrile (such as 2-cyano-4-fluorobenzyl), wherein the methylene is optionally substituted by a hydroxyl group (e.g. C(H)(OH)-4-fluorophenyl or —C(H)(OH)-2,4-difluorophenyl).

In an alternative embodiment of the compounds of formula (Ia), $R^5$ is $C_{2-4}$ alkyl substituted by one or two fluorines, such as 1,1-difluoropropyl or 1,1-difluorobutyl, in particular 1,1-difluorobutyl.

In one embodiment, the compound of formula (I) is a compound of formula (Ib):

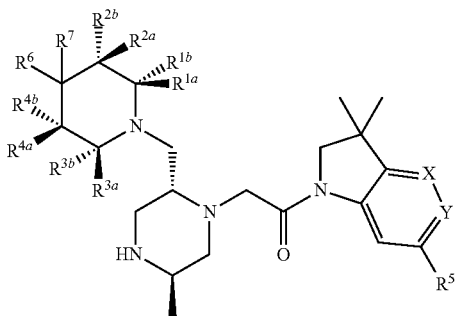

(Ib)

or tautomeric or stereochemically isomeric forms, N-oxides, pharmaceutically acceptable salts or the solvates thereof; wherein $R^{1a}$, $R^{1b}$, $R^{2a}$, $R^{2b}$, $R^{3a}$, $R^{3b}$, $R^{4a}$, $R^{4b}$, $R^6$, $R^7$, X, Y and $R^5$ are as herein defined or in any of the embodiments.

In one embodiment, the compound of formula (I) is a compound of formula (Ib) wherein X is CH and Y is $CR^9$; X is nitrogen and Y is $CR^9$; or X is $CR^9$ and Y is nitrogen, or X and Y are nitrogen;

$R^9$ represents hydrogen or nitrile (such as hydrogen);

$R^{1a}$ and $R^{1b}$ both represent hydrogen or one represents hydrogen and the other represents halo$C_{1-4}$ alkyl (such as trifluoromethyl);

$R^{2a}$ and $R^{2b}$ both represent hydrogen or one represents hydrogen and the other represents halogen (such as fluorine);

$R^{3a}$ and $R^{3b}$ both represent hydrogen;

$R^{4a}$ and $R^{4b}$ both represent hydrogen or halogen (such as fluorine);

$R^6$ and $R^7$ both represent hydrogen, fluorine or one represents hydrogen and the other represents hydroxyl;

$R^5$ is benzyl optionally substituted on the phenyl group by one or two fluorines (such as 4-fluorobenzyl or 2,4-difluorobenzyl) or one fluorine and one nitrile (such as 2-cyano-4-fluorobenzyl), wherein the methylene is optionally substituted by a hydroxyl group (e.g. C(H)(OH)-4-fluorophenyl or —C(H)(OH)-2,4-difluorophenyl) or $R^5$ is $C_{2-4}$ alkyl substituted by one or two fluorines, such as 1,1-difluoropropyl or 1,1-difluorobutyl.

In one embodiment, the compound of formula (I) is a compound of formula (Ic):

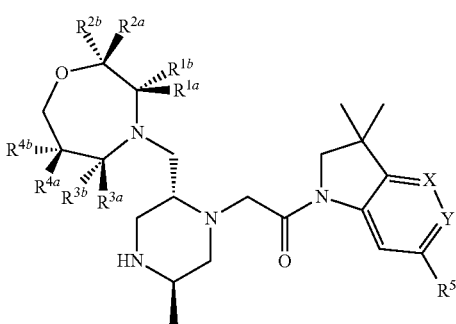

(Ic)

or tautomeric or stereochemically isomeric forms, N-oxides, pharmaceutically acceptable salts or the solvates thereof; wherein $R^{1a}$, $R^{1b}$, $R^{2a}$, $R^{2b}$, $R^{3a}$, $R^{3b}$, $R^{4a}$, $R^{4b}$, X, Y and $R^5$ are as herein defined or in any of the embodiments.

In one embodiment the compound of formula (I) is a compound of formula (Ic) wherein X is CH and Y is $CR^9$; X is nitrogen and Y is $CR^9$; or X is $CR^9$ and Y is nitrogen, or X and Y are nitrogen;

$R^9$ represents hydrogen or nitrile (such as hydrogen);

$R^{1a}$ and $R^{1b}$ both represent hydrogen;

$R^{2a}$ and $R^{2b}$ both represent hydrogen;

$R^{3a}$ and $R^{3b}$ both represent hydrogen;

$R^{4a}$ and $R^{4b}$ both represent halogen (such as fluorine); and $R^5$ is benzyl optionally substituted on the phenyl group by one or two fluorines (such as 4-fluorobenzyl or 2,4-difluorobenzyl) or one fluorine and one nitrile (such as 2-cyano-4-fluorobenzyl), wherein the methylene is optionally substituted by a hydroxyl group (e.g. C(H)(OH)-4-fluorophenyl or —C(H)(OH)-2,4-difluorophenyl) or $R^5$ is $C_{2-4}$ alkyl substituted by one or two fluorines, such as 1,1-difluoropropyl or 1,1-difluorobutyl.

In one embodiment, the compound of formula (I) is a compound of formula (Id):

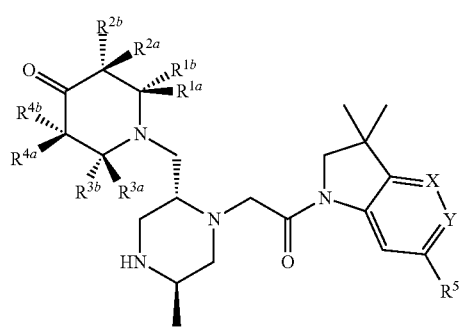

(Id)

or tautomeric or stereochemically isomeric forms, N-oxides, pharmaceutically acceptable salts or the solvates thereof;

wherein $R^{1a}$, $R^{2a}$, $R^{2b}$, $R^{3a}$, $R^{3b}$, $R^{4a}$, $R^{4b}$, X, Y and $R^5$ are as herein defined or in any of the embodiments.

In one embodiment, the compound of formula (I) is a compound of formula (Id) wherein X is CH and Y is $CR^9$; X is nitrogen and Y is $CR^9$; or X is $CR^9$ and Y is nitrogen, or X and Y are nitrogen;

$R^9$ represents hydrogen or nitrile (such as hydrogen);

one of $R^{1a}$ and $R^{1b}$ represents hydrogen and the other represents $C_{1-4}$ alkyl (such as methyl);

$R^{2a}$ and $R^{2b}$ both represent hydrogen;

$R^{3a}$ and $R^{3b}$ both represent hydrogen;

$R^{4a}$ and $R^{4b}$ both represent hydrogen; and $R^5$ is benzyl optionally substituted on the phenyl group by one or two fluorines (such as 4-fluorobenzyl or 2,4-difluorobenzyl) or one fluorine and one nitrile (such as 2-cyano-4-fluorobenzyl), wherein the methylene is optionally substituted by a hydroxyl group (e.g. C(H)(OH)-4-fluorophenyl or —C(H)(OH)-2,4-difluorophenyl) or $R^5$ is $C_{2-4}$ alkyl substituted by one or two fluorines, such as 1,1-difluoropropyl or 1,1-difluorobutyl.

In one embodiment, the compound of formula (I) is a compound of formula (Ie):

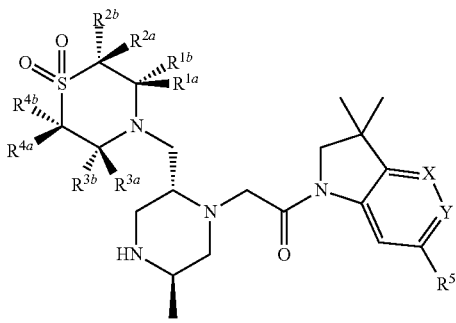

(Ie)

or tautomeric or stereochemically isomeric forms, N-oxides, pharmaceutically acceptable salts or the solvates thereof; wherein $R^{1a}$, $R^{1b}$, $R^{2a}$, $R^{2b}$, $R^{3a}$, $R^{3b}$, $R^{4a}$, $R^{4b}$, X, Y and $R^5$ are as herein defined or in any of the embodiments.

In one embodiment, the compound of formula (I) is a compound of formula (Ie) wherein X is CH and Y is $CR^9$; X is nitrogen and Y is $CR^9$; or X is $CR^9$ and Y is nitrogen, or X and Y are nitrogen;

$R^9$ represents hydrogen or nitrile (such as hydrogen);
$R^{2a}$ and $R^{2b}$ both represent hydrogen;
$R^{3a}$ and $R^{3b}$ both represent hydrogen;
$R^{4a}$ and $R^{4b}$ both represent hydrogen;
$R^5$ is benzyl optionally substituted on the phenyl group by one or two fluorines (such as 4-fluorobenzyl or 2,4-difluorobenzyl) or one fluorine and one nitrile (such as 2-cyano-4-fluorobenzyl), wherein the methylene is optionally substituted by a hydroxyl group (e.g. C(H)(OH)-4-fluorophenyl —C(H)(OH)-2,4-difluorophenyl) or $R^5$ is $C_{2-4}$ alkyl substituted by one or two fluorines, such as 1,1-difluoropropyl or 1,1-difluorobutyl.

In one embodiment, the compound of formula (I) is a compound of formula (If):

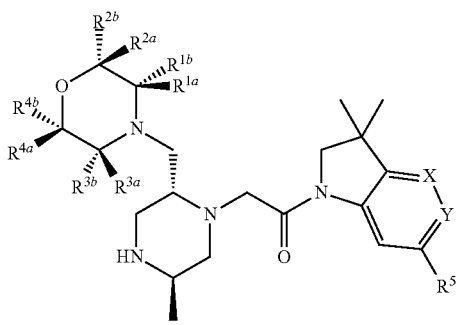

(If)

or tautomeric or stereochemically isomeric forms, N-oxides, pharmaceutically acceptable salts or the solvates thereof; wherein $R^{1a}$, $R^{2a}$, $R^{2b}$, $R^{3a}$, $R^{3b}$, $R^{4a}$, $R^{4b}$, X, Y and $R^5$ are as herein defined or in any of the embodiments;
provided that except for when X and Y are other than both nitrogen:
  $R^{1a}$, $R^{1b}$, $R^{2a}$, $R^{2b}$, $R^{3a}$, $R^{3b}$, $R^{4a}$ and $R^{4b}$ are not all hydrogen, or
  when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen, or
  when $R^{2a}$ and $R^{4a}$ are methyl then $R^{1a}$, $R^{1b}$, $R^{2b}$, $R^{3a}$, $R^{3b}$ and $R^{4b}$ are not all hydrogen, or $R^{1a}$ or $R^{3b}$ is not methoxymethyl when $R^5$ is 1,1-difluoropropyl.

In one embodiment, the compound of formula (I) is a compound of formula (If) wherein X is CH and Y is $CR^9$; X is nitrogen and Y is $CR^9$; or X is $CR^9$ and Y is nitrogen, or X and Y are nitrogen;
$R^9$ represents hydrogen or nitrile (such as hydrogen);
$R^{1a}$ and $R^{1b}$ both represent hydrogen or $C_{1-4}$ alkyl (such as methyl) or one represents hydrogen and the other represents $C_{1-4}$ alkyl (such as methyl or isopropyl), hydroxy$C_{1-4}$ alkyl (such as hydroxymethyl), halo$C_{1-4}$ alkyl (such as monofluoromethyl or trifluoromethyl) or methoxymethyl, or one represents $C_{1-4}$ alkyl (such as methyl) and the other represents hydroxy$C_{1-4}$ alkyl (such as hydroxymethyl) or carboxyl;
$R^{2a}$ and $R^{2b}$ both represent hydrogen or $C_{1-4}$ alkyl (such as methyl) or one represents hydrogen and the other represents nitrile;
$R^{3a}$ and $R^{3b}$ both represent hydrogen or one represents hydrogen and the other represents $C_{1-4}$ alkyl (such as methyl) or hydroxy$C_{1-4}$ alkyl (such as hydroxymethyl) or one represents $C_{1-4}$ alkyl (such as methyl) and the other represents hydroxy$C_{1-4}$ alkyl (such as hydroxymethyl);
$R^{4a}$ and $R^{4b}$ both represent hydrogen or one represents hydrogen and the other represents $C_{1-4}$ alkyl (such as methyl);
or $R^{1a}$ and $R^{1b}$ join together to form cyclopropyl;
or $R^{1a}$ and $R^{3a}$ or $R^{1b}$ and $R^{3b}$ join together to form a $C_{1-4}$ bridged alkyl group (such as ethylene);
or $R^{2a}$ and $R^{3a}$ or $R^{2b}$ and $R^{3b}$ join together to form a $C_{1-4}$ bridged alkyl group (such as methylene);
or $R^{3a}$ and $R^{4a}$ or $R^{1b}$ and $R^{4b}$ join together to form a $C_{1-4}$ bridged alkyl group (such as methylene);
or $R^{2a}$ and $R^{4a}$ or $R^{2b}$ and $R^{4b}$ join together to form a $C_{1-4}$ bridged alkyl group (such as ethylene) provided that except for when X and Y are other than both nitrogen:
  $R^{1a}$, $R^{1b}$, $R^{2a}$, $R^{2b}$, $R^{3a}$, $R^{3b}$, $R^{4a}$ and $R^{4b}$ are not all hydrogen, or
  when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3b}$, $R^{4a}$ and $R^{4b}$ groups are not all hydrogen; and
$R^5$ is benzyl optionally substituted on the phenyl group by one or two fluorines (such as 4-fluorobenzyl or 2,4-difluorobenzyl) or one fluorine and one nitrile (such as 2-cyano-4-fluorobenzyl), wherein the methylene is optionally substituted by a hydroxyl group (such as C(H)(OH)-4-fluorophenyl or —C(H)(OH)-2,4-difluorophenyl) or $R^5$ is $C_{2-4}$ alkyl substituted by one or two fluorines, such as 1,1-difluoropropyl or 1,1-difluorobutyl.

In one embodiment, the compound of formula (I) is a compound of formula (If) wherein: X is CH and Y is $CR^9$; X is nitrogen and Y is $CR^9$; or X is $CR^9$ and Y is nitrogen, or X and Y are nitrogen;
$R^9$ represents hydrogen or nitrile (such as hydrogen);
$R^{1a}$ and $R^{1b}$ both represent hydrogen or $C_{1-4}$ alkyl (such as methyl) or one represents hydrogen and the other represents $C_{1-4}$ alkyl (such as methyl or isopropyl), hydroxy$C_{1-4}$ alkyl (such as hydroxymethyl), halo$C_{1-4}$ alkyl (such as monofluoromethyl or trifluoromethyl) or methoxymethyl, or one represents $C_{1-4}$ alkyl (such as methyl) and the other represents hydroxy$C_{1-4}$ alkyl (such as hydroxymethyl), methoxymethyl or carboxyl;
$R^{2a}$ and $R^{2b}$ both represent hydrogen or $C_{1-4}$ alkyl (such as methyl) or one represents hydrogen and the other represents nitrile;
$R^{3a}$ and $R^{3b}$ both represent hydrogen or one represents hydrogen and the other represents $C_{1-4}$ alkyl (such as methyl) or hydroxyC$_{1-4}$ alkyl (such as hydroxymethyl) or one represents C$_{1-4}$ alkyl (such as methyl) and the other represents hydroxyC$_{1-4}$ alkyl (such as hydroxymethyl);

R$^{4a}$ and R$^{4b}$ both represent hydrogen or one represents hydrogen and the other represents C$_{1-4}$ alkyl (such as methyl);

or R$^{1a}$ and R$^{1b}$ join together to form cyclopropyl;

or R$^{1a}$ and R$^{3a}$ or R$^{1b}$ and R$^{3b}$ join together to form a C$_{1-4}$ bridged alkyl group (such as ethylene);

or R$^{2a}$ and R$^{3a}$ or R$^{2b}$ and R$^{3b}$ join together to form a C$_{1-4}$ bridged alkyl group (such as methylene);

or R$^{3a}$ and R$^{4a}$ or R$^{1b}$ and R$^{4b}$ join together to form a C$_{1-4}$ bridged alkyl group (such as methylene);

or R$^{2a}$ and R$^{4a}$ or R$^{2b}$ and R$^{4b}$ join together to form a C$_{1-4}$ bridged alkyl group (such as ethylene) provided that except for when X and Y are other than both nitrogen:

R$^{1a}$, R$^{1b}$, R$^{2a}$, R$^{2b}$, R$^{3a}$, R$^{3b}$, R$^{4a}$ and R$^{4b}$ are not all hydrogen, or when one of R$^{1a}$ or R$^{1b}$ or R$^{3a}$ or R$^{3b}$ is methyl or ethyl the remaining R$^{1a}$, R$^{1b}$, R$^{2a}$, R$^{2b}$, R$^{3a}$, R$^{3b}$, R$^{4a}$ and R$^{4b}$ groups are not all hydrogen; and R$^5$ is benzyl optionally substituted on the phenyl group by one or two fluorines (such as 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl or 3,4-difluorobenzyl) or one fluorine and one nitrile (such as 2-cyano-4-fluorobenzyl), wherein the methylene is optionally substituted by a hydroxyl group (such as C(H)(OH)-2-fluorophenyl, C(H)(OH)-3-fluorophenyl, C(H)(OH)-4-fluorophenyl, —C(H)(OH)-2,3-difluorophenyl, —C(H)(OH)-2,4-difluorophenyl or —C(H)(OH)-3,4-difluorophenyl) or R$^5$ is C$_{2-4}$ alkyl substituted by a hydroxyl group (such as 1-hydroxybutyl) or one or two fluorines (such as 1,1-difluoropropyl or 1,1-difluorobutyl).

In one embodiment, the compound of formula (I) is a compound of formula (If) wherein R$^{1a}$ and R$^{3b}$ are methyl. In one embodiment, the compound of formula (I) is a compound of formula (If) wherein R$^{1a}$ and R$^{3b}$ are methyl, and R$^{1b}$, R$^{2a}$, R$^{2b}$, R$^{3a}$, R$^{4a}$ and R$^{4b}$ are hydrogen. In one embodiment, the compound of formula (I) is a compound of formula (If) wherein R$^{4b}$ is hydroxymethyl, R$^{1a}$ is methyl and R$^{1b}$, R$^{2a}$, R$^{2b}$, R$^{3a}$, R$^{3b}$ and R$^{4a}$ are hydrogen.

In one embodiment, the compound of formula (I) is a compound of formula (If) wherein R$^{3a}$ is hydroxymethyl. In another embodiment, R$^{3a}$ is hydroxymethyl, R$^{3b}$ is methyl, and R$^{1a}$, R$^{1b}$, R$^{2a}$, R$^{2b}$, R$^{4a}$ and R$^{4b}$ are hydrogen.

In one embodiment, the compound of formula (I) is a compound of formula (Ig):

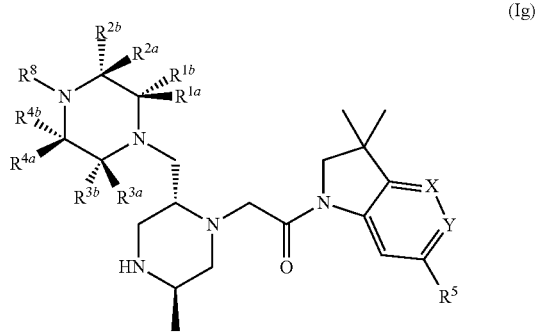

(Ig)

or tautomeric or stereochemically isomeric forms, N-oxides, pharmaceutically acceptable salts or the solvates thereof;

wherein RIG, R$^{1b}$, R$^{2a}$, R$^{2b}$, R$^{3a}$, R$^{3b}$, R$^{4a}$, R$^{4b}$, X, Y, R$^5$ and R$^8$ are as herein defined or in any of the embodiments, provided that except for when X and Y are other than both nitrogen, R$^{4a}$ and R$^{4b}$ do not together represent ═O when R$^5$ is 1,1-difluoroethyl and R$^8$ is methyl.

In one embodiment, the compound of formula (I) is a compound of formula (Ig) wherein X is CH and Y is CR$^9$; X is nitrogen and Y is CR$^9$; or X is CR$^9$ and Y is nitrogen, or X and Y are nitrogen;

R$^9$ represents hydrogen or nitrile (such as hydrogen);

R$^{1a}$ and R$^{1b}$ both represent hydrogen or one represents hydrogen and the other represents C$_{1-4}$ alkyl (such as methyl);

R$^{2a}$ and R$^{2b}$ both represent hydrogen or one represents hydrogen and the other represents C$_{1-4}$ alkyl (such as methyl) or R$^{2a}$ and R$^{2b}$ together represent ═O;

R$^{3a}$ and R$^{3b}$ both represent hydrogen or one represents hydrogen and the other represents C$_{1-4}$ alkyl (such as methyl);

R$^{4a}$ and R$^{4b}$ both represent hydrogen or one represents hydrogen and the other represents C$_{1-4}$ alkyl (such as methyl) or R$^{4a}$ and R$^{4b}$ together represent ═O provided that except for when X and Y are other than both nitrogen, R$^{4a}$ and R$^{4b}$ do not together represent ═O when R$^5$ is 1,1-difluoroethyl and R$^8$ is methyl;

or R$^{2a}$/R$^{2b}$ join together with the nitrogen atom at W to form a fused heteroaromatic group with 5 or 6 ring members (such as triazolyl) which can be optionally substituted by one or more substituents R$^{10}$;

R$^8$ represents hydrogen, C$_{1-4}$ alkyl (such as methyl), —SO$_2$—C$_{1-4}$ alkyl (such as —SO$_2$Me), —C(═O)—N(C$_{1-4}$ alkyl)$_2$ (such as C(═O)—N(Me)$_2$), pyrimidinyl, —C(═O)-phenyl or —C(═O)—C$_{1-4}$ alkyl (such as C(═O)—CH$_3$); and R$^5$ is benzyl optionally substituted on the phenyl group by one or two fluorines (such as 4-fluorobenzyl or 2,4-difluorobenzyl) or one fluorine and one nitrile (such as 2-cyano-4-fluorobenzyl), wherein the methylene is optionally substituted by a hydroxyl group (e.g. C(H)(OH)-4-fluorophenyl or —C(H)(OH)-2,4-difluorophenyl) or R$^5$ is C$_{2-4}$ alkyl substituted by one or two fluorines, such as 1,1-difluoropropyl or 1,1-difluorobutyl.

In one embodiment, the compound of formula (I) is a compound of formula (Ig) wherein R$^8$ is —C(═O)—C$_{1-4}$ alkyl (such as C(═O)—CH$_3$). In another embodiment, R$^8$ is —C(═O)—C$_{1-4}$ alkyl (such as C(═O)—CH$_3$), R$^{3b}$ is methyl and R$^{1a}$, R$^{1b}$, R$^{2a}$, R$^{2b}$, R$^{3a}$, R$^{4a}$ and R$^{4b}$ are hydrogen.

In one embodiment, the compound of formula (I) is a compound of formula (Ig) wherein R$^8$ is —C(═O)—C$_{1-4}$ alkyl (such as C(═O)—CH$_3$), R$^{1a}$ and R$^{3b}$ are methyl, and R$^{1b}$, R$^{2a}$, R$^{2b}$, R$^{3a}$, R$^{4a}$ and R$^{4b}$ are hydrogen.

In one embodiment, the compound of formula (I) is a compound of formula (Ig) wherein R$^8$ is —C(═O)—C$_{1-4}$ alkyl (such as C(═O)—CH$_3$), R$^{1a}$ and R$^{3a}$ are methyl, and R$^{1b}$, R$^{2a}$, R$^{2b}$, R$^{3b}$, R$^{4a}$ and R$^{4b}$ are hydrogen.

In one embodiment, the compound of formula (I) is a compound of formula (Ih):

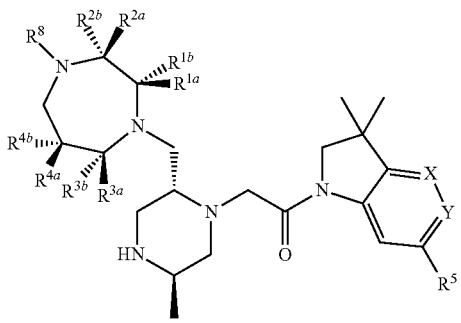

(Ih)

or tautomeric or stereochemically isomeric forms, N-oxides, pharmaceutically acceptable salts or the solvates thereof; wherein $R^{1a}$, $R^{1b}$, $R^{2a}$, $R^{2b}$, $R^{3a}$, $R^{3b}$, $R^{4a}$, $R^5$ and $R^8$ are as herein defined or in any of the embodiments.

In one embodiment, the compound of formula (I) is a compound of formula (Ih) wherein X is CH and Y is $CR^9$; X is nitrogen and Y is $CR^9$; or X is $CR^9$ and Y is nitrogen, or X and Y are nitrogen;

$R^9$ represents hydrogen or nitrile (such as hydrogen);
$R^{1a}$ and $R^{1b}$ both represent hydrogen;
$R^{1a}$ and $R^{2b}$ together represent C=O;
$R^{3a}$ and $R^{3b}$ both represent hydrogen;
$R^{4a}$ and $R^{4b}$ both represent hydrogen;
$R^8$ represents hydrogen; and
$R^5$ is benzyl optionally substituted on the phenyl group by one or two fluorines (such as 4-fluorobenzyl or 2,4-difluorobenzyl) or one fluorine and one nitrile (such as 2-cyano-4-fluorobenzyl), wherein the methylene is optionally substituted by a hydroxyl group (e.g C(H)(OH)-4-fluorophenyl or —C(H)(OH)-2,4-difluorophenyl) or $R^5$ is $C_{2-4}$ alkyl substituted by one or two fluorines, such as 1,1-difluoropropyl or 1,1-difluorobutyl.

In one embodiment, the compound of formula (I) is a compound of formula (Ii):

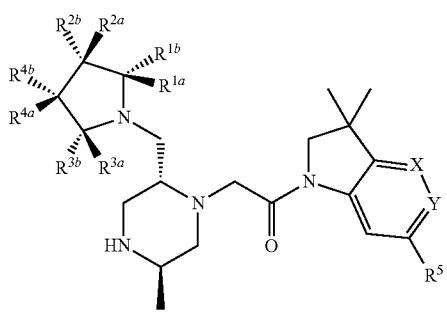

(Ii)

or tautomeric or stereochemically isomeric forms, N-oxides, pharmaceutically acceptable salts or the solvates thereof; wherein $R^{1a}$, $R^{1b}$, $R^{2a}$, $R^{2b}$, $R^{3a}$, $R^{3b}$, $R^{4a}$, $R^{4b}$, X, Y and $R^5$ are as herein defined or in any of the embodiments; provided that except for when X and Y are other than both nitrogen:

$R^{1a}$, $R^{1b}$, $R^{2a}$, $R^{2b}$, $R^{3a}$, $R^{3b}$, $R^{4a}$ and $R^{4b}$ are not all hydrogen, or when one of $R^{2a}$ or $R^{2b}$ or $R^{4a}$ or $R^{4b}$ is fluorine the remaining $R^{1a}$, $R^{1b}$, $R^{2a}$, $R^{2b}$, $R^{3a}$, $R^{3b}$, $R^{4a}$ and $R^{4b}$ groups are not all hydrogen, or when $R^{2a}$ and $R^{2b}$, or $R^{4a}$ and $R^{4b}$ join to form =O then the remaining $R^{1a}$, $R^{1b}$, $R^{2a}$, $R^{2b}$, $R^{3a}$, $R^{3b}$, $R^{4a}$ and $R^{4b}$ groups are not all hydrogen, or $R^{2a}$ and $R^{2b}$, or $R^{4a}$ and $R^{4b}$ are not both fluorine when $R^5$ is 2,4-difluorobenzyl.

In one embodiment, the compound of formula (I) is a compound of formula (Ii) wherein X is CH and Y is $CR^9$; X is nitrogen and Y is $CR^9$; or X is $CR^9$ and Y is nitrogen, or X and Y are nitrogen;

$R^9$ represents hydrogen or nitrile (such as hydrogen);
$R^{1a}$ and $R^{1b}$ both represent hydrogen or one represents hydrogen and the other represents hydroxy$C_{1-4}$ alkyl (such as hydroxymethyl) or halo$C_{1-4}$ alkyl (such as monofluoromethyl or trifluoromethyl);
$R^{2a}$ and $R^{2b}$ both represent hydrogen or halogen (such as fluorine) or one represents hydrogen and the other represents halogen (such as fluorine);
$R^{3a}$ and $R^{3b}$ both represent hydrogen;
$R^{4a}$ and $R^{4b}$ both represent hydrogen or one represents hydrogen and the other represents $C_{1-4}$ alkyoxy (such as methoxy);
or $R^{2a}/R^{2b}$ and $R^{4a}/R^{4b}$ join together to form a pyridinyl group which can be optionally substituted by one or more substituents $R^{10}$; provided that except for when X and Y are other than both nitrogen:

$R^{1a}$, $R^{1b}$, $R^{2a}$, $R^{2b}$, $R^{3a}$, $R^{3b}$, $R^{4a}$ and $R^{4b}$ are not all hydrogen, or when one of $R^{2a}$ or $R^{2b}$ or $R^{4a}$ or $R^{4b}$ is fluorine the remaining $R^{1a}$, $R^{1b}$, $R^{2a}$, $R^{2b}$, $R^{3a}$, $R^{3b}$, $R^{4a}$ and $R^{4b}$ groups are not all hydrogen, or $R^{2a}$ and $R^{2b}$, or $R^{4a}$ and $R^{4b}$ are not both fluorine when $R^5$ is 2,4-difluorobenzyl; and $R^5$ is benzyl optionally substituted on the phenyl group by one or two fluorines (such as 4-fluorobenzyl or 2,4-difluorobenzyl) or one fluorine and one nitrile (such as 2-cyano-4-fluorobenzyl), wherein the methylene is optionally substituted by a hydroxyl group (e.g. C(H)(OH)-4-fluorophenyl or —C(H)(OH)-2,4-difluorophenyl) or $R^5$ is $C_{2-4}$ alkyl substituted by one or two fluorines, such as 1,1-difluoropropyl or 1,1-difluorobutyl.

In one embodiment, the compound of formula (I) is a compound of formula (Ij):

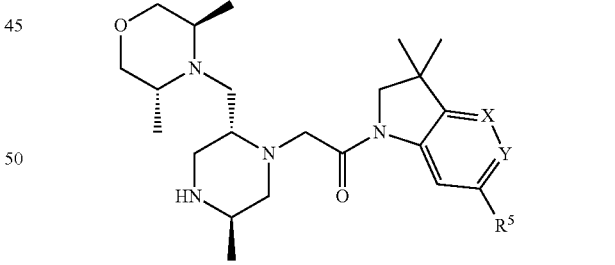

(Ij)

or tautomeric or stereochemically isomeric forms, N-oxides, pharmaceutically acceptable salts or the solvates thereof; wherein X, Y and $R^5$ are as herein defined or in any of the embodiments.

In one embodiment the compound of formula (I) is a compound of formula (Ij) wherein X is nitrogen and Y is $CR^9$ (e.g. CH).

In one embodiment, X is nitrogen and Y is CH and the compound of formula (Ij) is an N-oxide (e.g. X represents $N^+$—$O^-$).

In one embodiment, the compound of formula (I) is a compound of formula (Ik):

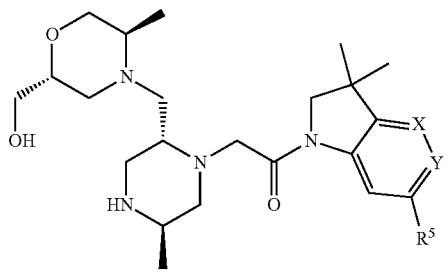
(Ik)

or tautomeric or stereochemically isomeric forms, N-oxides, pharmaceutically acceptable salts or the solvates thereof; wherein X, Y and $R^5$ are as herein defined or in any of the embodiments.

In one embodiment the compound of formula (I) is a compound of formula (Ik) wherein X is nitrogen and Y is $CR^9$ (e.g. CH).

In one embodiment, the compound of formula (I) is a compound of formula (Ib), (Ic), (Id), (Ie), (If), (Ig), (Ih), (Ij) or (Ik) wherein X is nitrogen and Y is $CR^9$ (such as CH). In one embodiment, the compound of formula (I) is a compound of formula (Ib), (Ic), (Id), (Ie), (If), (Ig), (Ih), (Ij) or (Ik) wherein Y is $CR^9$ represents C—CN.

In one embodiment, the compound of formula (I) is a compound of formula (Ib), (Ic), (Id), (Ie), (If), (Ig), (Ih), (Ij) or (Ik) wherein X is nitrogen and Y is $CR^9$ (such as CH). In one embodiment, the compound of formula (I) is a compound of formula (Ib), (Ic), (Id), (Ie), (If), (Ig), (Ih), (Ij) or (Ik) wherein Y is $CR^9$ represents C—CN.

In one embodiment, the compound of formula (I) is a compound of formula (Ib), (Ic), (Id), (Ie), (If), (Ig), (Ih), (Ij) or (Ik) wherein X is $CR^9$ (such as CH) and Y is nitrogen.

In one embodiment, the compound of formula (I) is a compound of formula (Ib), (Ic), (Id), (Ie), (If), (Ig), (Ih), (Ii), (Ij) or (Ik) wherein X is nitrogen and Y is CH.

In one embodiment, the compound of formula (I) is a compound of formula (Ib), (Ic), (Id), (Ie), (If), (Ig), (Ih), (Ii), (Ij) or (Ik) wherein X is $CR^9$ (such as CH) and Y is nitrogen.

In one embodiment, the compound of formula (I) is a compound of formula (Ib), (Ic), (Id), (Ie), (If), (Ig), (Ih), (Ii), (Ij) or (Ik) wherein X and Y are nitrogen.

In one embodiment, the compound of formula (I) is a compound of formula (Ib), (Ic), (Id), (Ie), (If), (Ig), (Ih), (Ii), (Ij) or (Ik) wherein X and Y are nitrogen.

In one embodiment, the compound of formula (I) is a compound of formula (Ia), (Ib), (Ic), (Id), (Ie), (If), (Ig), (Ih), (Ii), (Ij) or (Ik) wherein $R^5$ is benzyl optionally substituted on the phenyl group by one or two fluorines (such as 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl or 3,4-difluorobenzyl) or $R^5$ is $C_{2-4}$ alkyl substituted by a hydroxyl group (such as 1-hydroxybutyl) or one or two fluorines (such as 1,1-difluoropropyl or 1,1-difluorobutyl e.g. 1,1-difluorobutyl).

In one embodiment, the compound of formula (I) is a compound of formula (Ia), (Ib), (Ic), (Id), (Ie), (If), (Ig), (Ih), (Ii), (Ij) or (Ik) wherein $R^5$ is benzyl optionally substituted on the phenyl group by one or two fluorines (such as 4-fluorobenzyl or 2,4-difluorobenzyl) or $R^5$ is $C_{2-4}$ alkyl substituted by one or two fluorines, such as 1,1-difluoropropyl or 1,1-difluorobutyl e.g. 1,1-difluorobutyl.

In one embodiment, the compound of formula (I) is a compound of formula (Ia), (Ib), (Ic), (Id), (Ie), (If), (Ig), (Ih), (Ii), (Ij) or (Ik) wherein $R^5$ is benzyl optionally substituted on the phenyl group by one or two fluorine substituents (such as unsubstituted benzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl or 3,4-difluorobenzyl) or one fluorine and one nitrile (such as 2-cyano-4-fluorobenzyl), wherein the methylene is optionally substituted by a hydroxyl group (e.g. C(H)(OH)benzyl, C(H)(OH)-2-fluorophenyl, C(H)(OH)-3-fluorophenyl, C(H)(OH)-4-fluorophenyl, —C(H)(OH)-2,3-difluorophenyl, —C(H)(OH)-2,4-difluorophenyl, —C(H)(OH)-2,5-difluorophenyl, —C(H)(OH)-2,6-difluorophenyl or —C(H)(OH)-3,4-difluorophenyl) or $R^5$ is $C_{2-4}$ alkyl substituted by one or two fluorines or hydroxyl, such as 1-hydroxybutyl, 1,1-difluoropropyl or 1,1-difluorobutyl, in particular 1,1-difluorobutyl.

In one embodiment, the compound of formula (I) is a compound of formula (Ia), (Ib), (Ic), (Id), (Ie), (If), (Ig), (Ih), (Ii), (Ij) or (Ik) wherein $R^5$ is CH(OH)-phenyl where the phenyl group is optionally substituted with one or two substituents selected from fluorine or hydroxyl (such as fluorine.

In one embodiment, the compound of formula (I) is a compound of formula (Ia), (Ib), (Ic), (Id), (Ie), (If), (Ig), (Ih), (Ii), (Ij) or (Ik) wherein $R^5$ is $C_{2-4}$ alkyl substituted by one or two substituents selected from fluorine and hydroxyl. In one embodiment, $R^5$ is $C_{2-4}$ alkyl substituted by one hydroxyl (such as 1-hydroxybutyl).

In one embodiment, the compound of formula (I) is a compound of formula (Ia), (Ib), (Ic), (Id), (Ie), (If), (Ig), (Ih), (Ii), (Ij) or (Ik) wherein $R^5$ is $C_{2-4}$ alkyl substituted by one or two substituents selected from fluorine and hydroxyl. In one embodiment, $R^5$ is $C_{2-4}$ alkyl substituted by one hydroxyl (such as 1-hydroxybutyl).

In one embodiment, the compound of formula (I) is a compound of formula (Ia), (Ib), (Ic), (Id), (Ie), (If), (Ig), (Ih), (Ii), (Ij) or (Ik) wherein $R^5$ is $C_{2-4}$ alkyl substituted by one or two fluorines, such as 1,1-difluoropropyl or 1,1-difluorobutyl e.g. 1,1-difluorobutyl.

In one embodiment, the invention provides a compound of formula (I) which comprises a compound of Examples 1-121 or a tautomeric or stereochemically isomeric form, N-oxide, pharmaceutically acceptable salt or the solvate thereof. In one embodiment, the invention provides a compound of formula (I) which comprises a compound of Examples 1-120 or a tautomeric or stereochemically isomeric form, N-oxide, pharmaceutically acceptable salt or the solvate thereof. In one embodiment, the invention provides a compound of formula (I) which comprises a compound of Examples 1-121 (in particular Examples 1 to 63, 66-69, 71, 76, 87-88, 90 and 92-121) or a tautomeric or stereochemically isomeric form, N-oxide, pharmaceutically acceptable salt or the solvate thereof. In one embodiment, the invention provides a compound of formula (I) which comprises a compound of Examples 1-91 (in particular Examples 1-63) or a tautomeric or stereochemically isomeric form, N-oxide, pharmaceutically acceptable salt or the solvate thereof. In one embodiment, the invention provides a compound of formula (I) which comprises a compound of Example 121 or a tautomeric or stereochemically isomeric form, pharmaceutically acceptable salt or the solvate thereof.

In another embodiment, the invention provides a compound of formula (I) which comprises a compound of Examples 64-91 or a tautomeric or stereochemically isomeric form, N-oxide, pharmaceutically acceptable salt or the solvate thereof.

In one embodiment, the invention provides a compound of formula (I) which is a compound of Examples 1-121 (in particular Examples 1 to 63, 66-69, 71, 76, 87-88, 90 and 92-121) or a tautomeric or stereochemically isomeric form, N-oxide, pharmaceutically acceptable salt or the solvate thereof. In one embodiment, the invention provides a compound of formula (I) which is a compound of Examples 1-91 (in particular Examples 1-63) or a tautomeric or stereochemically isomeric form, N-oxide, pharmaceutically acceptable salt or the solvate thereof.

In one embodiment, the invention provides a compound of formula (I) which is the free base of a compound of Examples 1-121 (in particular Examples 1 to 63, 66-69, 71, 76, 87-88, 90 and 92-121) or a tautomeric or stereochemically isomeric form, N-oxide, pharmaceutically acceptable salt or the solvate thereof. In one embodiment, the invention provides a compound of formula (I) which is the free base of a compound of Examples 1-91 (in particular Examples 1-63) or a tautomeric or stereochemically isomeric form, N-oxide, pharmaceutically acceptable salt or the solvate thereof.

In one embodiment, the invention provides a compound of formula (I) which is the free base of a compound of Example 15 or a tautomeric or stereochemically isomeric form, N-oxide, pharmaceutically acceptable salt or the solvate thereof.

In one embodiment, the invention provides a compound of formula (I) which is the free base of a compound of Example 107 or a tautomeric or stereochemically isomeric form, N-oxide, pharmaceutically acceptable salt or the solvate thereof.

In one embodiment, the invention provides a compound of formula (I) which is the free base of a compound of Example 111 or a tautomeric or stereochemically isomeric form, N-oxide, pharmaceutically acceptable salt or the solvate thereof.

In one embodiment the invention provides (S)-1-{6-[(2,4-difluorophenyl)(hydroxy)methyl]-3,3-dimethyl-1H,2H,3H-pyrrolo[3,2-b]pyridin-1-yl}-2-[(2R,5R)-2-{[(3R,5R)-3,5-dimethylmorpholin-4-yl]methyl}-5-methylpiperazin-1-yl]ethan-1-one dihydrochloride.

In one embodiment the invention provides (R)-1-{6-[(2,4-difluorophenyl)(hydroxy)methyl]-3,3-dimethyl-1H,2H,3H-pyrrolo[3,2-b]pyridin-1-yl}-2-[(2R,5R)-2-{[(3R,5R)-3,5-dimethylmorpholin-4-yl]methyl}-5-methylpiperazin-1-yl]ethan-1-one dihydrochloride.

In one embodiment the invention provides 2-[(2R,5R)-2-{[(3R,5R)-3,5-dimethylmorpholin-4-yl]methyl}-5-methylpiperazin-1-yl]-1-{6-[(R)-(2-fluorophenyl)-(hydroxy)methyl]-3,3-dimethyl-1H,2H,3H-pyrrolo[3,2-b]pyridin-1-yl}ethan-1-one dihydrochloride.

In an alternative embodiment the invention provides 2-[(2R,5R)-2-{[(3R,5R)-3,5-dimethylmorpholin-4-yl]methyl}-5-methylpiperazin-1-yl]-1-{6-[(S)-(2-fluorophenyl)-(hydroxy)methyl]-3,3-dimethyl-1H,2H,3H-pyrrolo[3,2-b]pyridin-1-yl}ethan-1-one dihydrochloride.

In one embodiment, the invention provides 1-{6-[(4-fluorophenyl)methyl]-3,3-dimethyl-2,3-dihydro-1H-indol-1-yl}-2-[(2R,5R)-5-methyl-2-{[(3R)-3-methylmorpholin-4-yl]methyl}piperazin-1-yl]ethan-1-one or a tautomeric or stereochemically isomeric form, N-oxide, pharmaceutically acceptable salt or the solvate thereof. In a further embodiment, the invention provides 1-{6-[(4-fluorophenyl)methyl]-3,3-dimethyl-2,3-dihydro-1H-indol-1-yl}-2-[(2R,5R)-5-methyl-2-{[(3R)-3-methylmorpholin-4-yl]methyl}piperazin-1-yl]ethan-1-one dihydrochloride (E45).

The preparation of the compound of E45 is described herein as a Reference Example (Ref. Eg.).

For the avoidance of doubt, it is to be understood that each general and specific preference, embodiment and example for one substituent may be combined with each general and specific preference, embodiment and example for one or more, preferably, all other substituents as defined herein and that all such embodiments are embraced by this application.

Salts, Solvates, Tautomers, Isomers, N-Oxides, Esters, Prodrugs and Isotopes

A reference to a compound of the formula (I) and subgroups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof.

Salts

Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetannidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (I) and sub-groups and examples thereof as described herein in the form of a salt in a concentration of greater than 10 mg/ml, typically greater than 15 mg/ml and preferably greater than 20 mg/ml.

N-Oxides

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

One particular example of an N-oxide compound is the compound of Example 121 which is the N-oxide derivative of Example 15.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I), ring E can exist in two tautomeric forms as illustrated below. For simplicity, the general formula (I) illustrates one form A but the formula is to be taken as embracing both tautomeric forms.

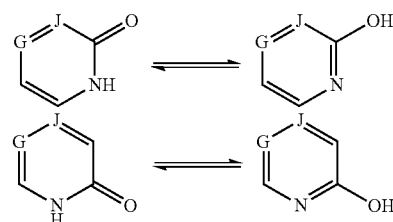

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

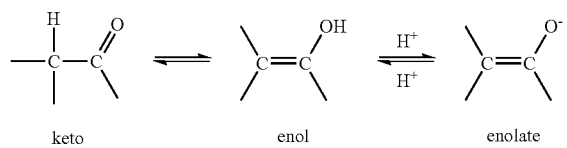

keto        enol        enolate

Stereoisomers

Unless otherwise mentioned or indicated, the chemical designation of compounds denotes the mixture of all possible stereochemically isomeric forms.

Stereocentres are illustrated in the usual fashion, using 'hashed' or 'wedged' lines. e.g.

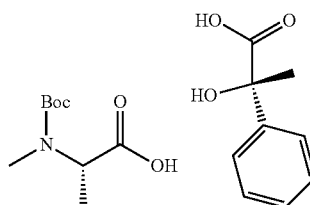

Boc-N-Methyl alanine (S)-(+)-2-hydroxy-2-phenyl-propionic acid

Where a compound is described as a mixture of two diastereoisomers/epimers, the configuration of the stereocentre is not specified and is represented by straight lines.

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally enantiomeric separation can be achieved by covalently linking a enantiomerically pure chiral auxiliary onto the compound and then performing diastereoisomer separation using conventional methods such as chromatography. This is then followed by cleavage of the aforementioned covalent linkage to generate the appropriate enantiomerically pure product.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^{2}$H (D) and $^{3}$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$C, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$O $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formula (I) bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-12}$ heterocyclyl group, or a $C_{5-12}$ aryl group, preferably a $C_{1-6}$ alkyl group. Particular examples of ester groups include, but are not limited to —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-6}$ alkyl group, a $C_{3-12}$ heterocyclyl group, or a $C_{5-12}$ aryl group, preferably a $C_{1-6}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph. Examples of phosphate esters are those derived from phosphoric acid.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group.

Solvates and Crystalline Forms

Also encompassed by formula (I) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described above, can be used to establish whether solvates had formed.

Furthermore, the compounds of the present invention may have one or more polymorph or amorphous crystalline forms and as such are intended to be included in the scope of the invention.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodrugs

Also encompassed by formula (I) are any pro-drugs of the compounds of the formula (I). By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl (e.g., -Me, -Et, -nPr, -iPr, -nBu, -sBu, -iBu, -tBu); $C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methypethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxyl)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (I) does not include pro-drugs of the compounds of the formula (I) within its scope.

Advantages of Compounds of the Invention

The compounds of the formula (I) may have a number of advantages over prior art compounds.

Compounds of the invention may have particular advantage in one or more of the following aspects:
  (i) Superior selectivity versus the IKr (hERG) cardiac ion channel;
  (ii) Superior metabolic stability;
  (iii) Superior oral bioavailabilty; and
  (iv) Superior in vivo efficacy.

Superior Selectivity Versus the IKr (hERG) Cardiac Ion Channel

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. Nature, 345 (6277):672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. Cell, 81:299-307, and Trudeau, M. C., Warmke, J. W., Ganetzky, B., and Robertson, G. A. (1995). HERG, a Human Inward Rectifier in the Voltage-Gated Potassium Channel Family.

Science, 269:92-95. Therefore, elimination of hERG blocking activity remains an important consideration in the development of any new drug.

It has been found that many compounds of the formula (I) have reduced hERG activity and/or a good separation between IAP activity and hERG activity (greater 'therapeutic window'). One method for measurement of hERG activity is the patch clamp electrophysiology method. Alternative methods for measurement of functional hERG activity include hERG binding assays, which can use commercially available membranes isolated from cells stably expressing the hERG channel or commercially available cell lines expressing the hERG channel.

Many compounds of the formula (I) have improved Cardiac Safety Index (CSI) [CSI=hERG IC50/Cmax(unbound)] (Shultz et al, J. Med. Chem., 2011; Redfern et al, Cardiovasc. Res., 2003). This can be due to an increase in hERG IC50 or a reduction in Cmax required for efficacy (due to better IAP potency and/or PK).

The preferred compounds of formula (I) have reduced hERG ion channel blocking activity. Preferred compounds of the formula (I) have mean IC50 values against hERG that are greater than 30 times, or greater than 40 times, or greater than 50 times the IC50 values of the compounds in cellular proliferation assays. Preferred compounds of the formula (I) have mean IC50 values against hERG that are greater than 5 µM, more particularly greater than 10 µM, and more preferably greater than 15 µM. Some compounds of the invention have mean $IC_{50}$ values against hERG that are greater than 30 µM or display % inhibition representative of such an IC50 at concentrations of 1, 3, 10 or 30 µM. Some compounds of the invention have mean CSI of higher than minimum recommended value (30 fold).

Superior Metabolic Stability

The compounds of the formula (I) may have advantageous ADMET properties for example better metabolic stability (for example as determined with mouse liver microsomes), a better P450 profile and/or beneficial clearance (e.g. low clearance). These features could confer the advantage of having more drug available in the systemic circulation to reach the appropriate site of action to exert its therapeutic effect. Increased drug concentrations to exert pharmacological action in tumours potentially leads to improved efficacy which thereby allows reduced dosages to be administered. Thus, the compounds of formula (I) should exhibit reduced dosage requirements and should be more readily formulated and administered.

Many of the compounds of the formula (I) are advantageous in that they have different susceptibilities to P450 enzymes. For example, the preferred compounds of the formula (I) have $IC_{50}$ values of greater than 10 µM against each of the cytochrome P450 enzymes 1A2, 2C9, 2C19, 3A4 and 2D6 (in particular 3A4). In addition preferably the compounds are not P450 inhibitors nor substrates for P450 (i.e. not turned over by P450).

Superior Oral Bioavailabilty

Potentially the compounds of the invention have physiochemical properties suitable for oral exposure (oral exposure or AUC). In particular, compounds of the formula (I) may exhibit improved oral bioavailability. Oral bioavailability can be defined as the ratio (F) of the plasma exposure of a compound when dosed by the oral route to the plasma exposure of the compound when dosed by the intravenous (i.v.) route, expressed as a percentage.

Compounds having an oral bioavailability (F value) of greater than 30%, more preferably greater than 40%, are particularly advantageous in that they may be adminstered orally rather than, or as well as, by parenteral administration.

Superior In Vivo Efficacy

As a result of increased potency against XIAP and/or cIAP compounds of the invention may have increased in vivo efficacy in cancer cell lines and in vivo models.

Methods for the Preparation of Compounds of Formula (I)

In this section, as in all other sections of this application unless the context indicates otherwise, references to formula (I) also include all other sub-groups and examples thereof as defined herein.

Compounds of the formula (I) can be prepared in accordance with synthetic methods well known to the skilled person.

According to a further aspect of the invention there is provided a process for preparing a compound of formula (I) as hereinbefore defined which comprises:

(a) (i) reacting a compound of formula (II):

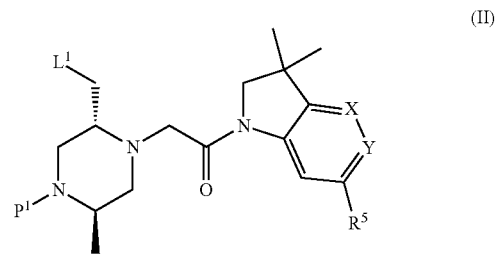

(II)

wherein $R^5$, X and Y are as defined hereinbefore for compounds of formula (I), $L^1$ represents a suitable leaving group, such as a halogen atom (e.g. chlorine) and $P^1$ represents hydrogen or a suitable protecting group such as a tert-butyloxycarbonyl (tBoc) group, with a compound of formula (III):

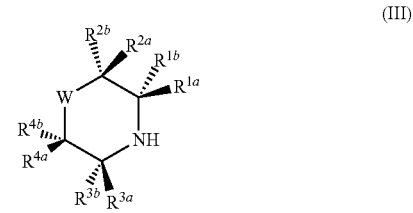

(III)

or an optionally protected derivative thereof; wherein $R^{1a}$, $R^{1b}$, $R^{2a}$, $R^{2b}$, $R^{3a}$, $R^{3b}$, $R^{4a}$, $R^{4b}$ and W are as defined hereinbefore for compounds of formula (I), followed by a deprotection reaction suitable to remove the $P^1$ protecting group and any other protecting groups as necessary; or (ii) reacting a compound of formula (IV):

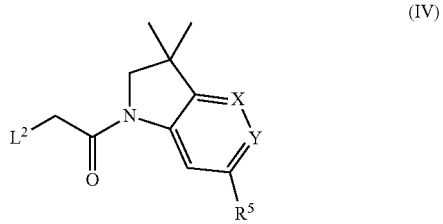

wherein X, Y and $R^5$ are as defined hereinbefore for compounds of formula (I), and $L^2$ represents a suitable leaving group such as halogen (e.g. chlorine), with a compound of formula (V):

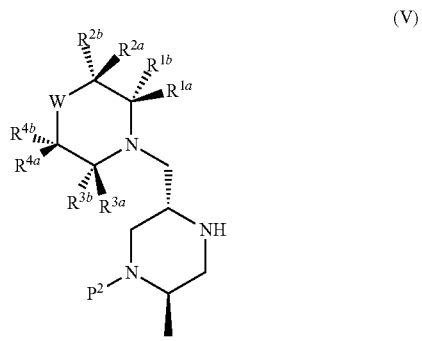

or an optionally protected derivative thereof; wherein $R^{1a}$, $R^{1b}$, $R^{2a}$, $R^{2b}$, $R^{3a}$, $R^{3b}$, $R^{4a}$, $R^{4b}$ and W are as defined hereinbefore for compounds of formula (I) and $P^2$ represents hydrogen or a suitable protecting group such as a tert-butyloxycarbonyl (tBoc) group, followed by a deprotection reaction suitable to remove the $P^2$ protecting group and any other protecting groups as necessary; and/or
(b) deprotection of a protected derivative of a compound of formula (I); and/or
(c) interconversion of a compound of formula (I) or protected derivative thereof to a further compound of formula (I) or protected derivative thereof; and
(d) optional formation of a pharmaceutically acceptable salt of a compound of formula (I).

Process (a)(i) typically comprises reacting a compound of formula (II) with a compound of formula (III), optionally in the presence of a suitable additive such as potassium iodide and a suitable base such as potassium carbonate in a suitable solvent such as acetonitrile. Such a process may be carried out at ambient temperature or at elevated temperature, e.g. 70° C.

Process (a)(ii) typically comprises reacting a compound of formula (IV) with a compound of formula (V), optionally in the presence of a suitable additive such as potassium iodide and a suitable base such as potassium carbonate in a suitable solvent such as acetonitrile.

Process (b) typically comprises any suitable deprotection reaction, the conditions of which will depend upon the nature of the protecting group. When the protecting group represents tBoc, such a deprotection reaction will typically comprise the use of a suitable acid in a suitable solvent. For example, the acid may suitably comprise trifluoroacetic acid or hydrogen chloride and the solvent may suitably comprise dichloromethane ethyl acetate, 1,4-dioxane, methanol or water. Optionally a mixture of solvents may be used, for example aqueous methanol or ethyl acetate/1,4-dioxane.

Process (b) may be carried out in accordance with the procedures described herein as Preparation of Compounds of Formula (I), Method 1.

It will be appreciated that, when the protecting group represents tBoc, deprotection using a suitable acid as described above may generate a compound of formula (I) as a pharmaceutically acceptable salt, which may be isolated directly. Alternatively, the compound of formula (I) may be isolated as the free base using methods well known in the art and thereafter optionally converted to a pharmaceutically acceptable salt according to process (d).

Process (c) typically comprises interconversion procedures known by one skilled in the art. For example, in compounds of formula (I), a first substituent may be converted by methods known by one skilled in the art into a second, alternative substituent. A wide range of well known functional group interconversions are known by a person skilled in the art for converting a precursor comound to a compound of formula I and are described in *Advanced Organic Chemistry* by Jerry March, 4th Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of Organo Palladium Chemistry for Organic Synthesis [Volume 1, Edited by Ei-ichi Negishi, Wiley, ISBN 0-471-31506-0].

Process (d) may be carried out by treatment of a compound of formula (I) in the free base form, dissolved in a suitable solvent, with a stoichiometric amount or an excess of a pharmaceutically acceptable organic or inorganic acid, then isolation of the resulting salt by methods well known in the art, e.g. evaporation of solvent or crystallisation.

If appropriate, the reactions previously described in processes (a), (b) and (c) are followed or preceded by one or more reactions known to the skilled of the art and are performed in an appropriate order to achieve the requisite substitutions on $R^{1a}$, $R^{1b}$, $R^{2a}$, $R^{2b}$, $R^{3a}$, $R^{3b}$, $R^{4a}$, $R^{4b}$ and $R^5$ defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation and arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups, S-oxidation,
N-oxidation,
salification.

Compounds of formula (II) may be prepared from compounds of formula (IV) in accordance with the following Scheme 1:

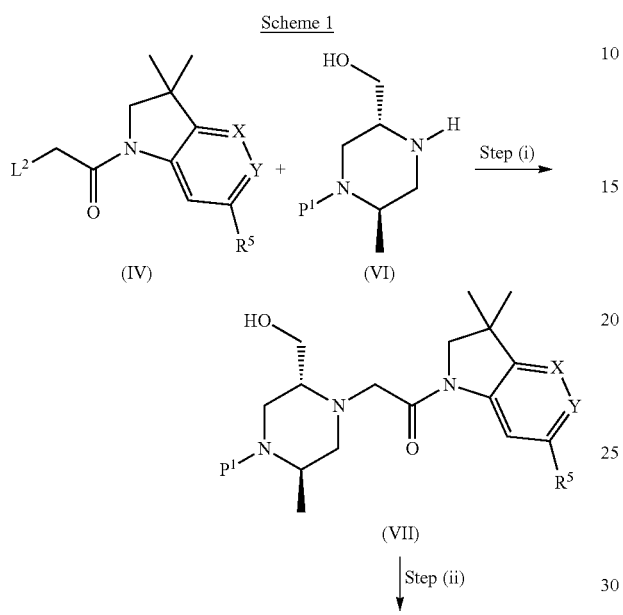

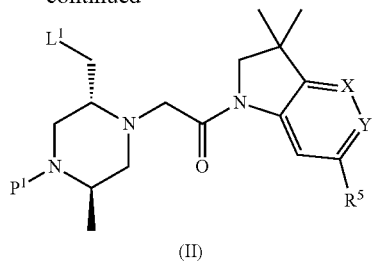

wherein X, Y, $R^5$, $L^1$, $L^2$ and $P^1$ are as defined hereinbefore.

Step (i) of Scheme 1 typically comprises reacting the compounds of formulae (IV) and (VI), optionally in the presence of a suitable additive such as potassium iodide and a suitable base such as potassium carbonate in a suitable solvent such as acetonitrile. An example of such a reaction is shown herein in Preparation 18.

When $L^1$ represents chlorine, step (ii) of Scheme 1 typically comprises reacting the compound of formula (VII) with a reagent capable of converting a hydroxyl group into a good leaving group, e.g. methylsulfonyl chloride, in the presence of a base such as triethylamine. An example of such a reaction is shown herein in Preparation 19.

Compounds of formula (IV) may be prepared in accordance with the following Scheme 2:

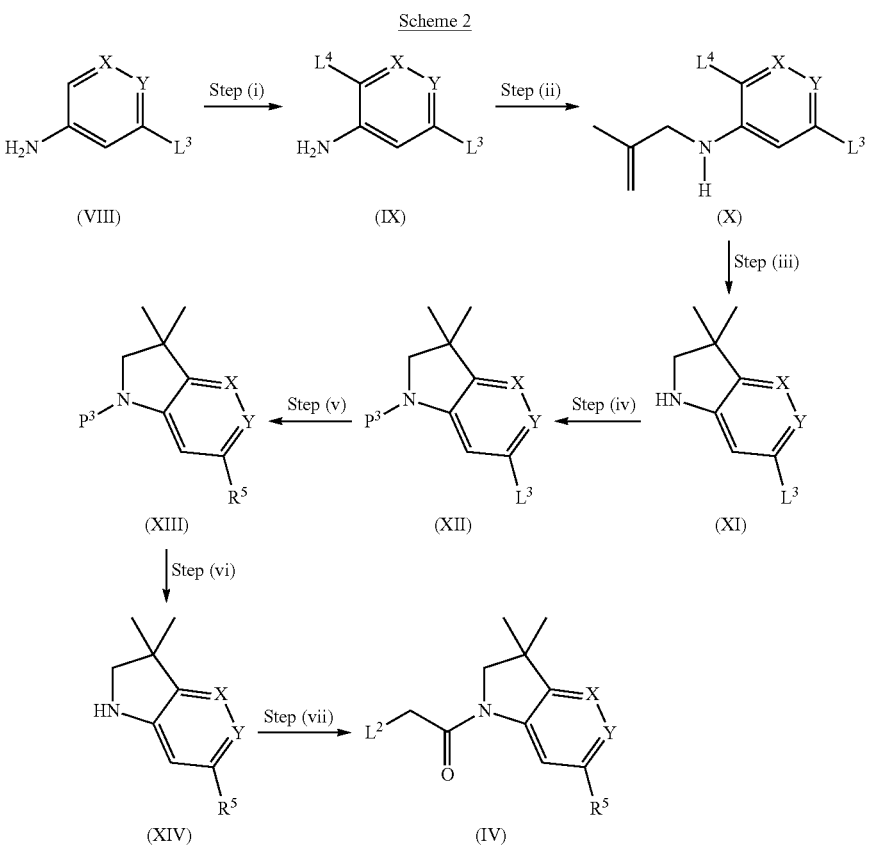

wherein X, Y and $R^5$ are as defined hereinbefore for compounds of formula (IV), $L^3$ and $L^4$ represent suitable leaving groups, such as a halogen atom, wherein $L^3$ and $L^4$ are chosen such that they have differential reactivity (for example $L^3$ represents bromine and $L^4$ represents iodine) and $P^3$ represents a suitable protecting group, such as a tert-butyloxycarbonyl (tBoc) group.

When $L^3$ represents bromine and $L^4$ represents iodine, step (i) of Scheme 2 typically comprises reacting a compound of formula (VIII) with an iodinating agent such as N-iodosuccinimide. An example of such a reaction is shown herein in Preparation 11.

Step (ii) of Scheme 2 typically comprises reacting the compound of formula (IX) with 3-bromo-2-methylprop-1-ene in the presence of a base such as potassium tert-butoxide. An example of such a reaction is shown herein in Preparation 12.

Step (iii) of Scheme 2 typically comprises cyclisation of the compound of formula (X) using a transition metal catalyst such as a palladium salt in the presence of base in a suitable solvent system. Suitable conditions for such a process may involve the use of tetrabutylammonium chloride, sodium formate, palladium acetate, triethylamine, water and dimethyl sulfoxide. An example of such a reaction is shown herein in Preparation 13.

When $P^3$ represents tBoc, step (iv) of Scheme 2 typically comprises reacting the compound of formula (XI) with di-tert-butyldicarbonate in a suitable solvent such as THF in the presence of a base such as potassium tert-butoxide. An example of such a reaction is shown herein in Preparation 14.

Step (v) of Scheme 2 typically comprises reacting the compound of formula (XII) with a compound of formula $R^5$-M, wherein $R^5$ is as defined hereinbefore and M represents the residue of an organometallic species such that $R^5$-M represents a nucleophilic organometallic reagent such as an organozinc halide. An example of such a reaction is shown herein in Preparation 15. Alternatively, where $L^3$ represents a halogen such as bromine, the compound (XII) may be metallated using a suitable organometallic reagent such as butyllithium, ideally at low temperature in an inert solvent such as THF, and the resulting anion quenched with a suitable electrophile, for example a Weinreb amide such as N-methoxy-N-methylpropionamide or an aldehyde such as 4-fluorobenzaldehyde, followed by functional group interconversion as appropriate. Examples of such reactions are shown in Preparations 35 and 56 respectively.

Step (vi) of Scheme 2 typically comprises a deprotection reaction of the compound of formula (XIII). For example, when $P^3$ represent tBoc, step (vi) typically comprises treatment with hydrochloric acid. An example of such a reaction is shown herein in Preparation 16.

When $L^2$ represents a halogen such as chlorine, step (vii) of Scheme 2 typically comprises reacting the compound of formula (XIV) with a haloacetyl halide such as chloroacetyl chloride in an inert solvent such as acetonitrile. An example of such a reaction is shown herein in Preparation 17.

In the compounds (XIII) and/or (XIV), functional group interconversions may optionally be carried out, for example to modify the group $R^5$. Examples of such transformations are shown in Preparations 36 and 38-40.

Compounds of formula (V), or optionally protected derivatives thereof, may be prepared in accordance with the following Scheme 3:

Scheme 3

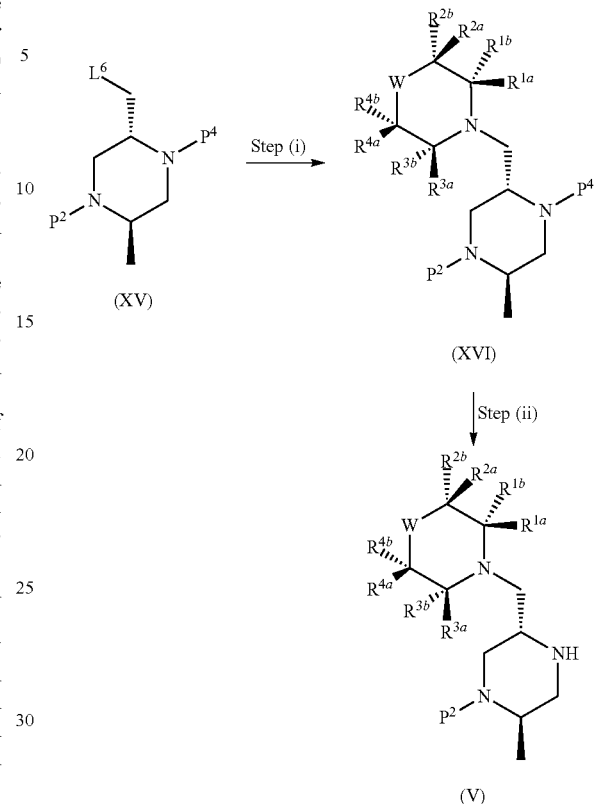

wherein RIG, $R^{1b}$, $R^{2a}$, $R^{2b}$, $R^{3a}$, $R^{3b}$, $R^{4a}$, $R^{4b}$, W and $P^2$ are as defined hereinbefore for compounds of formula (V), $L^6$ represents a suitable leaving group such as a halogen atom (e.g. chlorine) and $P^4$ represents a suitable protecting group, such as benzyl.

Step (i) of Scheme 3 typically comprises reacting a compound of formula (XV) with a compound of formula (III), or an optionally protected derivative thereof, as hereinbefore defined. The reaction typically comprises the use of a base such as potassium carbonate in the presence of a suitable solvent, such as acetonitrile. An example of such a reaction is shown herein in Preparation 21.

Step (ii) of Scheme 3 typically comprises a deprotection reaction. For example, when $P^4$ represents benzyl, step (ii) typically comprises hydrogenation of the compound of formula (XVI) in the presence of a suitable catalyst such as palladium on carbon in a suitable solvent system such as acetic acid and ethanol. An example of such a reaction is shown herein in Preparation 22.

Alternatively, compounds of formula (XI) and (XIV) wherein X and Y independently represent CH and $CR^9$ may be prepared by reaction of a compound of formula (XVII):

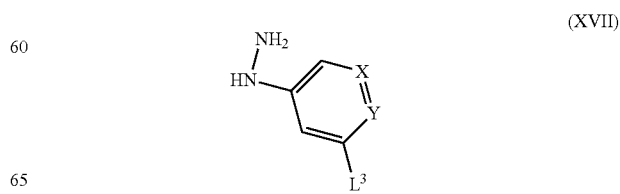

(XVII)

wherein R⁹ and L³ are as defined above, with a compound of formula Me₂CHCHO, to form a hydrazone, then subsequent cyclisation to form the desired substituted indoline. Such a process is typically accomplished using acidic conditions, for example using acetic acid as solvent or using an appropriate acid in an inert solvent such as toluene. It will be appreciated that, for certain combinations of X and Y, this sequence will result in production of a mixture of regioisomers and that separation of these may be carried out by standard methods known by one skilled in the art e.g. column chromatography. Such a separation may be facilitated by N-acylation of the product from this process e.g. using chloroacetyl chloride or N-protection using, for example a tBoc protecting group after which the compound of formula (XIV) may optionally be re-generated by deprotection using standard conditions, e.g. for a tBoc protected compound, treatment with an appropriate acid such as HCl.

Alternatively, compounds of formula (XI) as defined above wherein X is N and Y is CH may be prepared in accordance with the following Scheme 4:

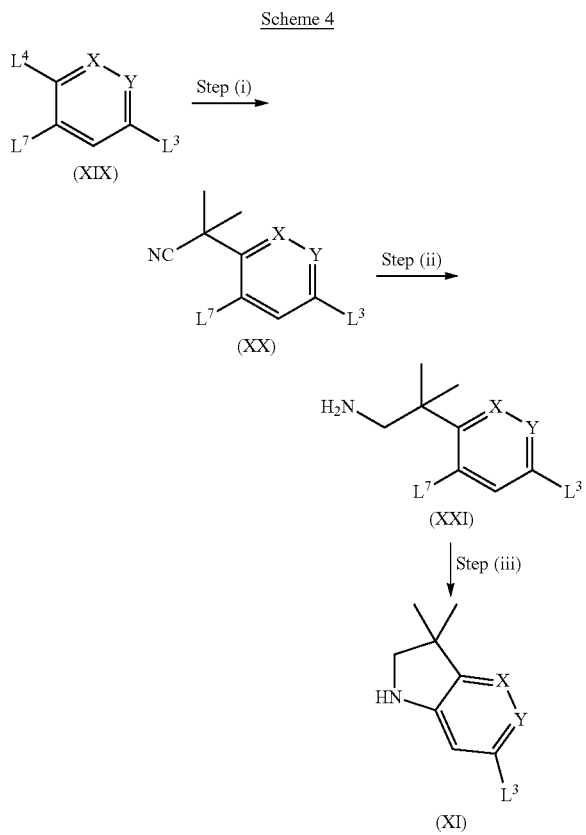

wherein L³ and L⁴ are as defined above and L⁷ represents a suitable leaving group such as fluorine. Step (i) may be carried out by reaction with isobutyronitrile in the presence of a suitable base such as sodium bis(trimethylsilyl)amide in an appropriate solvent such as tetrahydrofuran. Step (ii) may be effected using a suitable reducing agent such as borane in a compatible solvent such as tetrahydrofuran. Cyclisation according to step (iii) may be carried out at elevated temperature in the presence of a suitable base such as potassium carbonate in an appropriate high boiling solvent such as 1-methyl-2-pyrrolidinone.

Alternatively compounds of formula (I) can be synthesised by reacting a compound of formula (XVIII):

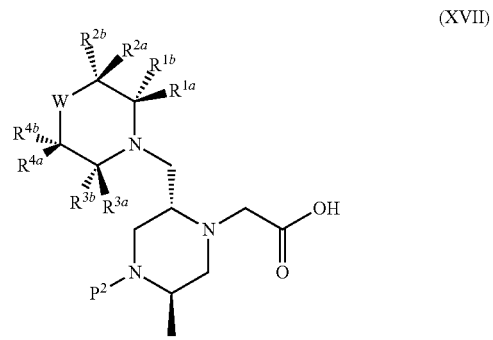

or an optionally protected derivative thereof, wherein $R^{1a}$, $R^{1b}$, $R^{2a}$, $R^{2b}$, $R^{3a}$, $R^{3b}$, $R^{4a}$, $R^{4b}$ and W are as defined hereinbefore for compounds of formula (I) and $P^2$ represents a suitable protecting group such as a tert-butyloxycarbonyl (tBoc) group, with a compound of formula (XIV) as defined hereinbefore followed by a deprotection reaction suitable to remove the protecting group $P^2$ and any additional protecting groups.

This reaction typically comprises reacting a compound of formula (XVIII) with a compound of formula (XIV) in a suitable solvent and at a suitable temperature e.g. ambient temperature, in the presence of a suitable base and a reagent capable of activating the carboxylic acid group present in the compound of formula (XVIII). A suitable solvent should be inert toward the reagents used, for example dichloromethane. Examples of suitable bases are triethylamine and N,N-diisopropylethylamine (DIPEA). Examples of suitable activating reagents are bromo-tris-pyrrolidino-phosphonium hexofluorophosphate (PyBrop), O-benzotriazole-N,N,N',N'-tetramethyl-uronium-hexafluoro-phosphate (HBTU), 1,1'-carbonyldiimidazole, 1-ethyl-3-(3'-dimethylaminopropyl)-carbodiimide hydrochloride (EDC) and 2-(7-aza-1H-benzotriazole-1-yl)-1,1,3,3-tetramethyluronium hexafluorophosphate) (HATU). This process may optionally be carried out in the presence of a catalytic or stoichiometric amount of a suitable co-activating reagent such as 1-hydroxybenzotriazole (HOBt) or 1-hydroxyazabenzotriazole (HOAt).

Compounds of formula (XVIII) or optionally protected derivatives thereof may be prepared from compounds of formula (V) or optionally protected derivatives thereof as defined above by methods well known in the art, for example by reaction with an ester of a monohaloacetic acid such as benzyl bromoacetate in the presence of a suitable base such as potassium carbonate in a suitable solvent such as acetonitrile; and subsequent ester hydrolysis (or optionally hydrogenolysis in the case of a benzyl ester).

It will be appreciated that certain compounds e.g. compounds of formulae (I), (III), (V), (VI), (XIV), (XVI) and (XVIII) can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid; or enantiomer separation of a diastereomeric derivative formed by covalently linking a enantiomerically pure chiral auxiliary onto the compound, followed by separation using conventional methods such as chiral chromatography. The aforementioned covalent linkage is then cleaved to generate the appropriate enantiomerically pure product.

The required intermediates, for example compounds of formula (III), (VI), (VIII), $R^5$-M, (XV) and (XIX) are either commercially available, known in the literature, prepared by methods analogous to those in the literature or prepared by methods analogous to those described in the example experimental procedures below. Other compounds may be prepared by functional group interconversion of the groups $R^{1a}$, $R^{1b}$, $R^{2a}$, $R^{2b}$, $R^{3a}$, $R^{3b}$, $R^{4a}$, $R^{4b}$ and $R^5$ using methods well known in the art.

In a further embodiment the invention provides a novel intermediate. In one embodiment the invention provides a novel intermediate of formula (II) or (IV) or (V) or (VII) or (XVI).

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

In particular the groups $R^{1a}$, $R^{1b}$, $R^{2a}$, $R^{2b}$, $R^{3a}$, $R^{3b}$, $R^{4a}$, $R^{4b}$ may be synthesised in protected forms and the protecting groups removed to generate a compound of formula (I).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHOO—OC(CH$_3$)$_3$, —NH-Boc); a 2-biphenyl-2-propyl carbamate (—NHOO—OC(CH$_3$)$_2$C$_6$H$_4$C$_6$H$_5$, —NH-Bpoc), as a 9-fluorenylmethyl carbamate (—NH—Fmoc), as a 6-nitroveratryl carbamate (—NH—Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH—Psec).

For example, in compounds of formula II contains an amino group, the amino group can be protected by means of a protecting group as hereinbefore defined, one preferred group being the tert-butyloxycarbonyl (Boc) group while the additional funactionalisation is introduced. Where no subsequent modification of the amino group is required, the protecting group can be carried through the reaction sequence to give an N-protected form of a compound of the formula (I) which can then be de-protected by standard methods (e.g. treatment with acid in the case of the Boc group) to give the compound of formula (I).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an $C_{1-7}$ alkyl ester (e.g., a methyl ester; a t-butyl ester); a $C_{1-7}$ haloalkyl ester (e.g., a $C_{1-7}$ trihaloalkyl ester); a alkylsilyl-$C_{1-7}$ alkyl ester; or a $C_{5-20}$ aryl-$C_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9. An example of such a system for purifying compounds via preparative LC-MS is described below in the Examples section of this application (under the heading "Mass Directed Purification LC-MS System").

Methods of recrystallisation of compounds of formula (I) and salt thereof can be carried out by methods well known to the skilled person see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes an heating step under vacuum for example using a cold finger, and crystallization from melt (Crystallization Technology Handbook 2nd Edition, edited by A. Mersmann, 2001).

Biological Effects

The compounds of the invention, subgroups and examples thereof, are antagonists of inhibitor of apoptosis protein (IAP), and which may be useful in preventing or treating disease states or conditions described herein. In addition the compounds of the invention, and subgroups thereof, will be useful in preventing or treating diseases or condition mediated by IAP. References to the preventing or prophylaxis or treatment of a disease state or condition such as cancer include within their scope alleviating or reducing the incidence of cancer.

Thus, for example, it is envisaged that the compounds of the invention will be useful in alleviating or reducing the incidence of cancer.

The compounds of the present invention may be useful for the treatment of the adult population. The compounds of the present invention may be useful for the treatment of the pediatric population.

More particularly, the compounds of the formula (I) and sub-groups thereof are antagonists of IAP. For example, compounds of the invention have affinity against XIAP, cIAP1 and/or cIAP2, and in particular an IAP selected from XIAP and cIAP1.

Preferred compounds are compounds that have affinity for one or more IAP selected from XIAP, cIAP1 and cIAP2. Preferred compounds of the invention are those having IC50 values of less than 0.1 μM.

The antagonist compounds of formula (I) are capable of binding to IAP and exhibiting potency for IAP. In one embodiment the antagonist compounds of formula (I) exhibit selectivity for one or more IAP over other IAP family members, and may be capable of binding to and/or exhibiting affinity for XIAP and/or cIAP in preference to binding to and/or exhibiting affinity for other of the IAP family members.

In addition many of the compounds of the invention exhibit selectivity for the XIAP compared to cIAP or vice versa, selectivity for the cIAP compared to XIAP (in particular cIAP1), and such compounds represent one embodiment of the invention. In particular compounds of the invention may have at least 10 times greater affinity against one or more IAP family member in particular XIAP, cIAP1 and/or cIAP2 than other IAP family members. This can be determined using the methods described herein. In a further embodiment compounds of the invention may have equivalent affinity for XIAP, cIAP1 and/or cIAP2, in particular equivalent affinity (i.e. less than 10-fold difference in affinity) for XIAP and cIAP1.

Activity against XIAP and cIAP1 may be particularly advantageous. Antagonising XIAP and cIAP1 with equipotency should enable triggering of apoptosis via activation of caspase-8 and the switch away from pro-survival NF-kappaB signalling towards apoptosis; and potent antagonism of XIAP will ensure that apoptosis is achieved before any inherent resistance mechanism is upregulated to block the process. On depletion of cIAP1 via autoubiquitination and proteasomal degradation there is a temporary upregulation of NF-kappaB signalling that is responsible for expression of TNF-alpha in sensitive cell lines—this is also responsible for upregulation of anti-apoptotic factors such as cIAP2 and c-FLIP. Hence the need for potent XIAP antagonism to potentiate effector caspase activation and cell death, rather than allowing cIAP2-mediated resistance to build up. It is generally believed that toxicities that arise on dosing these compounds in vivo will arise from the temporary induction of NFkappaB signalling and resultant upregulation of pro-inflammatory cytokines, which is mediated solely by cIAP1/2 antagonism. Therefore dual potency should enable a therapeutic window to be achieved before dose-limiting toxicities are encountered.

IAP function in controlling programmed cell death has also been implicated in many diseases, including disorders associated with cell accumulation (e.g. cancer, autoimmune disorders, inflammation and restenosis), disorders where excessive apoptosis results in cell loss (e.g. stroke, heart failure, neurodegeneration such as Alzheimers' disease, Parkinson's disease, Huntington's disease, amyotrophic lateral sclerosis, AIDS, ischemia (stroke, myocardial infarction) and osteoporosis or treating autoimmune diseases such as multiple sclerosis (MS).

Therefore, it is also envisaged that the compounds of the invention may be useful in treating other conditions such as inflammation, hepatitis, ulcerative colitis, gastritis, autoimmunity, inflammation, restenosis, stroke, heart failure, neurodegenerative conditions such as Alzheimers' disease, Parkinson's disease, Huntington's disease, myotonic dystrophy, and amyotrophic lateral sclerosis, AIDS, ischemia such as traumatic brain injury, spinal cord injury, cerebral ischemia, cerebral ischemia/reperfusion (I/R) injury, acute and chronic CNS injury ischemia, stroke or myocardial infarction, degenerative diseases of the musculoskeletal system such as osteoporosis, autoimmune diseases such as multiple sclerosis (MS) and Type I diabetes, and eye diseases such as retinal degeneration which result from loss of control of programmed cell death.

As a consequence of their affinity for IAP, the compounds will be useful in providing a means of controlling programmed cell death. It is therefore anticipated that the compounds may prove useful in treating or preventing proliferative disorders such as cancers. In addition, the compounds of the invention may be useful in the treatment of diseases in which there is a disorder associated with cell accumulation or where excessive apoptosis results in cell loss.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Growth of cells is a closely controlled function. Cancer, a condition of abnormal cell growth, results when cells replicate in an uncontrolled manner (increasing in number), uncontrollably grow (getting larger) and/or experience reduced cell death by apoptosis (programmed cell death), necrosis, or annoikis. In one embodiment abnormal cell growth is selected from uncontrolled cell proliferation, excessive cell growth or reduced programmed cell death. In particular, the condition or disease of abnormal cell growth is a cancer. Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

In one embodiment the haematological malignancies is leukaemia. In another embodiment the haematological malignancies is lymphoma.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis. In particular, the compounds of the invention may be useful in the treatment of metastasis and metastatic cancers.

Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body.

Particular cancers include hepatocellular carcinoma, melanoma, oesophageal, renal, colon, colorectal, lung e.g. mesothelioma or lung adenocarcinoma, breast, bladder, gastrointestinal, ovarian and prostate cancers.

Particular cancers include renal, melanoma, colon, lung, breast, ovarian and prostate cancers. In one embodiment the cancer is selected from melanoma, colon, breast and ovarian. In one embodiment the cancer is melanoma. In one embodiment the cancer is infammatory breast cancer.

A further aspect of the invention includes a compound of the invention for use in the prophylaxis or treatment of cancer in a patient selected from a sub-population possessing cancers with a high inflammatory component. Such cancers are also known as "inflammatory phenotype" and include tumours with elevated cytokine signalling (e.g. TNF). In one embodiment the cancer is an inflammatory tumour, for example, melanoma, colon, breast and ovarian, in particular, melanoma.

In one embodiment the disease to be treated is leukaemia, such as acute and chronic leukaemias, acute myeloid leukaemia (AML), and chronic lymphocytic leukaemia (CLL). In one embodiment the leukaemia is refractory DLBCL.

In one embodiment the cancer is mesothelioma including malignant peritoneal mesothelioma or malignant pleural mesothelioma.

Certain cancers are resistant to treatment with particular drugs. This can be due to the type of the tumour (most common epithelial malignancies are inherently chemoresistant) or resistance can arise spontaneously as the disease progresses or as a result of treatment. In this regard, references to mesothelioma includes mesothelioma with resistance towards topoisomerase poisons, alkylating agents, antitubulines, antifolates, platinum compounds and radiation therapy, in particular cisplatin-resistant mesothelioma. Similarly references to multiple myeloma includes bortezomib-sensitive multiple myeloma or refractory multiple myeloma and references to chronic myelogenous leukemia includes imitanib-sensitive chronic myelogenous leukemia and refractory chronic myelogenous leukemia.

The cancers may be cancers which are sensitive to antagonism of any one or more IAP selected from XIAP, cIAP1, cIAP2, NAIP, ILP2, ML-IAP, survivin and BRUCE, more preferably XIAP, cIAP1, cIAP2, ML-IAP, most preferably XIAP.

It is further envisaged that the compounds of the invention, and in particular those compounds having IAP affinity will be particularly useful in the treatment or prevention of cancers of a type associated with or characterised by the presence of elevated levels of IAP or amplification of 11q22 for example the cancers referred to in this context in the introductory section of this application.

Elevated levels of IAP due to overexpression of IAP is found in many cancers and is associated with a poor prognosis. In addition, cancers with the 11q22 amplification may also be sensitive to an IAP antagonist. The elevated levels of IAP and amplification of 11q22 can be identified by the techniques outlined herein. Whether a particular cancer is one which is sensitive to IAP function, may be determined by a method as set out in the section headed "Methods of Diagnosis".

A further aspect provides the use of a compound for the manufacture of a medicament for the treatment of a disease or condition as described herein, in particular cancer.

The compounds may also be useful in the treatment of tumour growth, pathogenesis, resistance to chemo- and radio-therapy by sensitising cells to chemotherapy and as an anti-metastatic agent.

Therapeutic anticancer interventions of all types necessarily increase the stresses imposed on the target tumour cells. In mitigating the deleterious effects of such stresses, IAPs are directly implicated in resisting the effects of cancer drugs and treatment regimens. Thus, antagonists of IAP represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

As a consequence of their affinity for IAP, the compounds will be useful in providing a means of controlling programmed cell death. Therefore, it is also envisaged that the compounds of the invention may be useful in treating other conditions such as inflammatory disorders such as hepatitis, ulcerative colitis, and gastritis; neurodegenerative conditions such as Alzheimers' disease, Parkinson's disease, Huntington's disease, myotonic dystrophy, and amyotrophic lateral sclerosis; AIDS, ischemia such as restenosis, traumatic brain injury, spinal cord injury, cerebral ischemia, cerebral ischemia/reperfusion (I/R) injury, acute and chronic CNS injury ischemia, stroke or myocardial infarction; degenerative diseases of the musculoskeletal system such as osteoporosis; autoimmune diseases such as multiple sclerosis (MS) and Type I diabetes, and eye diseases such as retinal degeneration.

The affinity of the compounds of the invention as antagonists of IAP can be measured using the biological and biophysical assays set forth in the examples herein and the level of affinity exhibited by a given compound can be defined in terms of the 1050 value. Preferred compounds of the present invention are compounds having an 1050 value of less than 1 µM, more preferably less than 0.1 µM.

In one embodiment the invention provides a compound for use in the treatment of a disease or condition which is mediated by IAP (e.g. XIAP and/or cIAP e.g. cIAP1). In a further embodiment the invention provides a compound for use in the treatment of a disease or condition which overexpresses IAP (e.g. XIAP and/or cIAP e.g. cIAP1).

In one embodiment the invention provides a compound for use in the treatment of a disease or condition which is mediated by IAP, wherein the compound is an antagonist of IAP having an 1050 of less than 50 µM in at least one assay (e.g. a displacement binding) against an IAP. In particular the IAP is XIAP, cIAP1 and/or cIAP2. In a further embodiment the disease or condition which is mediated by IAP is a cancer which is characterised by overexpression of at least one IAP and/or amplication of 11q22.

In one embodiment the invention provides a compound for use in the treatment of a disease or condition which is mediated by IAP, wherein the compound has an 1050 of less than 10 µM against at least one IAP in an assay (e.g. displacement binding) against IAP.

A further aspect provides the use of a compound for the manufacture of a medicament for the treatment of a disease or condition which is mediated by IAP, wherein the compound is an antagonist of IAP having an $IC_{50}$ of less than 50 µM against at least one IAP in an assay (e.g. a displacement binding).

Methods of Diagnosis

Prior to administration of a compound of the formula (I), a patient may be screened to determine whether a disease or condition from which the patient is or may be suffering is one which would be susceptible to treatment with a compound having affinity for IAP. The term 'patient' includes human and veterinary subjects.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of IAP or to sensitisation of a pathway to normal IAP function or to upregulation of a biochemical pathway downstream of IAP activation.

Examples of such abnormalities that result in activation or sensitisation of the IAP, loss of, or inhibition of apoptotic pathways, up-regulation of the receptors or ligands, cytogenetic aberrations or presence of mutant variants of the receptors or ligands. Tumours with up-regulation of IAP, in particular over-expression of IAP, may be particularly sensitive to IAP antagonists. For example, overexpression of XIAP and cIAP has been identified in a range of cancers as discussion in the Background section.

Amplification of chromosome 11q22 has been detected in cell lines and primary tumours from squamous cell carcinomas of the esophagus (Imoto et al., 2001) and cervix (Imoto et al., 2002) as well as in primary lung cancers/cell lines (Dai et al., 2003). Immunohistochemistry and western blot analysis have identified cIAP1 and cIAP2 as potential oncogenes in this region as both are overexpressed in cancers in which this rare amplification arises.

The term up-regulation includes elevated expression or over-expression, including gene amplification (i.e. multiple gene copies), cytogenetic aberration and increased expression by a transcriptional effect. Thus, the patient may be subjected to a diagnostic test to detect a marker characteristic of up-regulation of IAP. The term diagnosis includes screening. By marker we include genetic markers including, for example, the measurement of DNA composition to identify presence of mutations of IAP or 11q22 amplification. The term marker also includes markers which are characteristic of up regulation of IAP, including protein levels, protein state and mRNA levels of the aforementioned proteins.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal spears, skin biopsy or urine.

Methods of identification and analysis of cytogenetic aberration, genetic amplification, mutations and up-regulation of proteins are known to a person skilled in the art. Screening methods could include, but are not limited to, standard methods such as reverse-transcriptase polymerase chain reaction (RT-PCR) or in situ hybridization such as fluorescence in situ hybridization (FISH).

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in situ hybridisation technique for assessing mRNA expression would be fluorescence in situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), BMC Cancer, 3:3). Briefly, the protocol is as follows: double-stranded cDNA is synthesized from total RNA using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of IAP, detection of IAP variants or mutants, or detection of 11q22 amplification could be applicable in the present case.

Abnormal levels of proteins such as IAP can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured.

Alternative methods for the measurement of the over expression or elevation of IAPs including the isoforms thereof, include the measurement of microvessel density. This can for example be measured using methods described by Orre and Rogers (Int J Cancer (1999), 84(2), 101-8). Assay methods also include the use of markers.

Therefore all of these techniques could also be used to identify tumours particularly suitable for treatment with the compounds of the invention.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having affinity for IAP (i.e. an IAP antagonist).

Another aspect of the invention includes a compound of the invention for use in the prophylaxis or treatment of cancer in a patient selected from a sub-population possessing overexpression of one or more of the IAP family members (e.g. cIAP and/or XIAP).

Another aspect of the invention includes a compound of the invention for use in the prophylaxis or treatment of cancer in a patient selected as possessing a cytogenetic abherration that results in overexpression of IAPs, for example, a patient selected as possessing the 11q22 amplification.

MRI determination of vessel normalization (e.g. using MRI gradient echo, spin echo, and contrast enhancement to measure blood volume, relative vessel size, and vascular permeability) in combination with circulating biomarkers may also be used to identify for treatment with a compound of the invention.

Thus a further aspect of the invention is a method for the diagnosis and treatment of a disease state or condition mediated by a IAP, which method comprises (i) screening a patient to determine whether a disease or condition from which the patient is or may be suffering is one which would be susceptible to treatment with a compound having affinity for IAP; and (ii) where it is indicated that the disease or condition from which the patient is thus susceptible, thereafter administering to the patient a compound of formula (I) and sub-groups or examples thereof as defined herein.

Pharmaceutical Formulations

While it is possible for the active compound to be administered alone, it is preferable to present it as a pharmaceutical composition (e.g. formulation).

Thus, the present invention further provides pharmaceutical compositions, as defined above, and methods of making a pharmaceutical composition comprising (e.g admixing) at least one compound of formula (I) (and sub-groups thereof as defined herein), together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract. Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. Aug. 1, 2006 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by IAP. Thus, according to a further aspect of the invention there is provided a method of treating a disease state or condition mediated by IAP, such as an XIAP and/or cIAP which comprises administering to a subject in need thereof a compound of formula (I) as described herein. According to a further aspect of the invention there is provided a method of treating a disease state or condition which overexpresses IAP, such as an XIAP and/or cIAP which comprises administering to a subject in need thereof a compound of formula (I) as described herein. Examples of such disease states and conditions are set out above, and in particular include cancer.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

It has been discovered that IAP antagonists can be used as a single agent or in combination with other anticancer agents. For example, it may be beneficial to combine an antagonist that induces apoptosis with another agent which acts via a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formula (I) include but are not limited to:
Topoisomerase I inhibitors;
Antimetabolites;
Tubulin targeting agents;
DNA binder and topoisomerase II inhibitors;
Alkylating Agents;
Monoclonal Antibodies;
Anti-Hormones;
Signal Transduction Inhibitors;
Proteasome Inhibitors;
DNA methyl transferases;
Cytokines and retinoids;
Chromatin targeted therapies;
Radiotherapy; and
Other therapeutic or prophylactic agents.

Particular examples of anti-cancer agents or adjuvants (or salts thereof), include but are not limited to any of the agents selected from groups (i)-(xlvii), and optionally group (xlvii), below:
(i) Platinum compounds, for example cisplatin (optionally combined with amifostine), carboplatin or oxaliplatin;
(ii) Taxane compounds, for example paclitaxel, paclitaxel protein bound particles (Abraxane™), docetaxel, cabazitaxel or larotaxel;
(iii) Topoisomerase I inhibitors, for example camptothecin compounds, for example camptothecin, irinotecan (CPT11), SN-38, or topotecan;
(iv) Topoisomerase II inhibitors, for example anti-tumour epipodophyllotoxins or podophyllotoxin derivatives for example etoposide, or teniposide;
(v) Vinca alkaloids, for example vinblastine, vincristine, liposomal vincristine (Onco-TCS), vinorelbine, vindesine, vinflunine or vinvesir;
(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;
(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);
(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);
(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;
(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;
(xi) DNA methyl transferase inhibitors, for example temozolomide, azacytidine or decitabine;
(xii) Antifolates, for example methotrexate, pemetrexed disodium, or raltitrexed;
(xiii) Cytotoxic antibiotics, for example antinomycin D, bleomycin, mitomycin C, dactinomycin, carminomycin, daunomycin, levamisole, plicamycin, or mithramycin;
(xiv) Tubulin-binding agents, for example combrestatin, colchicines or nocodazole;
(xv) Signal Transduction inhibitors such as Kinase inhibitors (e.g. EGFR (epithelial growth factor receptor) inhibitors, VEGFR (vascular endothelial growth factor receptor) inhibitors, PDGFR (platelet-derived growth factor receptor) inhibitors, MTKI (multi target kinase inhibitors), Raf inhibitors, mTOR inhibitors for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), or vennurafenib (PLX4032/RG7204);
(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;
(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, PD332991, ZK-304709, or AZD-5438;
(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);
(xix) Hsp90 inhibitors for example AT13387, herbimycin, geldanamycin (GA), 17-allylamino-17-desnnethoxygel-danannycin (17-AAG) e.g. NSC-330507, Kos-953 and CNF-1010, 17-dimethylaminoethylamino-17-dennethoxygeldanannycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112) or IPI-504;
(xx) Monoclonal Antibodies (unconjugated or conjugated to radioisotopes, toxins or other agents), antibody derivatives and related agents, such as anti-CD, anti-VEGFR, anti-HER$^2$ or anti-EGFR antibodies, for example rituximab (CD20), ofatumumab (CD20), ibritumomab tiuxetan (CD20), GA101 (CD20), tositumomab (CD20), epratuzumab (CD22), lintuzunnab (CD33), gemtuzumab ozogamicin (CD33), alemtuzumab (CD52), galiximab (CD80), trastuzumab (HER2 antibody), pertuzunnab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), ipilimumab (CTLA4), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17, 20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin;

(xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;

(xxxii) Proteasome Inhibitors for example bortezomib, carfilzomib, CEP-18770, MLN-9708, or ONX-0912;

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositunnonnab;

(xxxvi) Telomerase inhibitors for example telomestatin;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, INO-1001, AG-014699, or ONO-2231;

(xlvi) Agonists of Death receptor (e.g. TNF-related apoptosis inducing ligand (TRAIL) receptor), such as mapatumumab (formerly HGS-ETR$^1$), conatumumab (formerly AMG 655), PRO95780, lexatumumab, dulanermin, CS-1008, apomab or recombinant TRAIL ligands such as recombinant Human TRAIL/Apo2 Ligand;

(xlvii) Prophylactic agents (adjuncts); i.e. agents that reduce or alleviate some of the side effects associated with chemotherapy agents, for example anti-emetic agents, agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim), agents that inhibit bone resorption such as denosumab or bisphosphonates e.g. zoledronate, zoledronic acid, pamidronate and ibandronate, agents that suppress inflammatory responses such as dexamethasone, prednisone, and prednisolone, agents used to reduce blood levels of growth hormone and IGF-I (and other hormones) in patients with acromegaly or other rare hormone-producing tumours, such as synthetic forms of the hormone somatostatin e.g. octreotide acetate, antidote to drugs that decrease levels of folic acid such as leucovorin, or folinic acid, agents for pain e.g. opiates such as morphine, diamorphine and fentanyl, non-steroidal anti-inflammatory drugs (NSAID) such as COX-2 inhibitors for example celecoxib, etoricoxib and lumiracoxib, agents for mucositis e.g. palifermin, agents for the treatment of side-effects including anorexia, cachexia, oedema or thromoembolic episodes, such as megestrol acetate.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

Where the compound of the formula (I) is administered in combination therapy with one, two, three, four or more other therapeutic agents (preferably one or two, more preferably one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

For use in combination therapy with another chemotherapeutic agent, the compound of the formula (I) and one, two, three, four or more other therapeutic agents can be, for example, formulated together in a dosage form containing two, three, four or more therapeutic agents i.e. in a unitary pharmaceutical composition containing all components. In an alternative embodiment, the individual therapeutic agents may be formulated separately and presented together in the form of a kit, optionally with instructions for their use.

In one embodiment is provided a combination of a compound of formula (I) with one or more (e.g. 1 or 2) other therapeutic agents (e.g. anticancer agents as described above).

In another embodiment is provided a compound of formula (I) in combination with one or more (e.g. 1 or 2) other therapeutic agents (e.g. anticancer agents) for use in therapy, such as in the prophylaxis or treatment of cancer.

In one embodiment the pharmaceutical composition comprises a compound of formula (I) together with a pharmaceutically acceptable carrier and optionally one or more therapeutic agent(s).

In another embodiment the invention relates to the use of a combination according to the invention in the manufacture of a pharmaceutical composition for inhibiting the growth of tumour cells.

In a further embodiment the invention relates to a product containing a compound of formula (I) and one or more anticancer agent, as a combined preparation for simultaneous, separate or sequential use in the treatment of patients suffering from cancer.

Examples

The invention will now be illustrated, but not limited, by reference to the specific embodiments described in the following examples. Compounds are named using an automated naming package such as AutoNom (MDL) or are as named by the chemical supplier.

The following synthetic procedures are provided for illustration of the methods used; for a given preparation or step the precursor used may not necessarily derive from the individual batch synthesised according to the step in the description given. In the examples, the following abbreviations are used.

AcOH acetic acid
Boc tert-butyloxycarbonyl
Boc-Abu-OH (S)-2-(Boc-amino)butyric acid
BuLi butyllithium
CDI 1,1-carbonyldiinnidazole
DAST Diethylaminosulfur trifluoride
DCM dichloromethane
DIPEA N-ethyl-N-(1-methylethyl)-2-propylamine
DMC dimethyl carbonate
DMF N,N-dimethylformamide
DMSO dimethyl sulfoxide
EDC 1-ethyl-3-(3'-dimethylaminopropyl)-carbodiimide hydrochloride
$Et_3N$ triethylamine
EtOAc ethyl acetate
EtOH ethanol
$Et_2O$ diethyl ether
HATU 2-(7-aza-1H-benzotriazole-1-yl)-1,1,3,3-tetramethyluronium hexafluorophosphate)
HBTU O-benzotriazole-N,N,N',N'-tetramethyl-uronium-hexafluoro-phosphate
HCl hydrochloric acid
HOAc acetic acid
HOAt 1-hydroxyazabenzotriazole
HOBt 1-hydroxybenzotriazole
HPLC high pressure liquid chromatography
IPA isopropyl alcohol
KHMDS potassium hexamethyldisilazide
LiHMDS lithium bis(trimethylsilyl)amide
MeCN acetonitrile
MeOH methanol
mins. minutes
MS mass spectrometry
$NaBH(OAc)_3$ sodium triacetoxyborohydride
NaOtBu potassium tert-butoxide
NMP N-methyl-2-pyrrolidinone
NMR nuclear magnetic resonance spectroscopy
$Pd_2(dba)_3$ tris(dibenzylideneacetone)dipalladium (o)
$Pd(OAc)_2$ palladium (2) acetate
$Pd(PPh_3)_4$ tetrakis(triphenylphosphine)palladium (O)

petrol petroleum ether fraction with boiling point range 40-60° C.
PyBrop bromo-tris-pyrrolidino-phosphonium hexafluorophosphate
RT room temperature
$SiO_2$ silica
TBABr tetrabutylammonium bromide
TBAF tetrabutylammonium fluoride
TBTU N,N,N',N'-tetramethyl-O-(benzotriazol-1-yl)uronium tetrafluoroborate
TEA triethylamine
TFA trifluoroacetic acid
THF tetrahydrofuran
TMEDA N,N,N,N-tetramethylethylenediannine
NMR Data: Unless indicated, $^1$H NMR spectra were recorded at 25° C. on a Bruker Avance I spectrometer operating at 400 MHz. The data were processed and analysed using Topspin 2.1 software. For NMR data, where the number of protons assigned is less than the theoretical number of protons in the molecule, it is assumed that the apparently missing signal(s) is/are obscured by solvent and/or water peaks. In addition, where spectra were obtained in protic NMR solvents, exchange of NH and/or OH protons with solvent occurs and hence such signals are normally not observed.

IR Data: IR Spectra were recorded using Bruker Alpha P IR spectrometer.

Analytical and Preparative LC-MS Systems
Analytical LC-MS System and Method Description In the following examples, compounds were characterised by mass spectroscopy using the systems and operating conditions set out below. Where atoms with different isotopes are present and a single mass quoted, the mass quoted for the compound is the monoisotopic mass (i.e. $^{35}$Cl; $^{79}$Br etc.).

Waters Platform LC-MS System:
  HPLC System: Waters 2795
  Mass Spec Detector: Micromass Platform LC
  PDA Detector: Waters 2996 PDA
  Platform MS Conditions:
  Capillary voltage: 3.6 kV (3.40 kV on ES negative)
  Cone voltage: 30 V
  Source Temperature: 120° C.
  Scan Range: 125-800 amu
  Ionisation Mode: ElectroSpray Positive or
  ElectroSpray Negative or
  ElectroSpray Positive & Negative
Waters Fractionlynx LC-MS System:
  HPLC System: 2767 autosampler—2525 binary gradient pump
  Mass Spec Detector: Waters ZQ
  PDA Detector: Waters 2996 PDA
  Fractionlynx MS Conditions:
  Capillary voltage: 3.5 kV (3.25 kV on ES negative)
  Cone voltage: 40 V (25 V on ES negative)
  Source Temperature: 120° C.
  Scan Range: 125-800 amu
  Ionisation Mode: ElectroSpray Positive or
  ElectroSpray Negative or
  ElectroSpray Positive & Negative
Agilent 1200SL-6140 LC-MS System—RAPID:
  HPLC System: Agilent 1200 series SL
  Mass Spec Detector: Agilent 6140 single quadrupole
  Second Detector: Agilent 1200 MWD SL
  Agilent MS Conditions:
  Capillary voltage: 4000V on ES pos (3500V on ES Neg)
  Fragmentor/Gain: 100
  Gain: 1
  Drying gas flow: 7.0 L/min
  Gas Temperature: 345° C.
  Nebuliser Pressure: 35 psig
  Scan Range: 125-800 amu
  Ionisation Mode: ElectroSpray Positive-Negative switching Preparative LC-MS System and Method Description Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Several systems for purifying compounds via preparative LC-MS are described below although a person skilled in the art will appreciate that alternative systems and methods to those described could be used. From the information provided herein, or employing alternative chromatographic systems, a person skilled in the art could purify the compounds described herein by preparative LC-MS.

Waters Fractionlynx System:
  Hardware:
  2767 Dual Loop Autosampler/Fraction Collector
  2525 preparative pump
  CFO (column fluidic organiser) for column selection
  RMA (Waters reagent manager) as make up pump
  Waters ZQ Mass Spectrometer
  Waters 2996 Photo Diode Array detector
  Waters ZQ Mass Spectrometer
  Waters MS Running Conditions:
  Capillary voltage: 3.5 kV (3.2 kV on ES Negative)
  Cone voltage: 25 V
  Source Temperature: 120° C.
  Scan Range: 125-800 amu
  Ionisation Mode: ElectroSpray Positive or
  ElectroSpray Negative
Agilent 1100 LC-MS Preparative System:
  Hardware:
  Autosampler: 1100 series "prepALS"
  Pump: 1100 series "PrepPump" for preparative flow gradient and 1100 series
  "QuatPump" for pumping modifier in prep flow
  UV detector: 1100 series "MWD" Multi Wavelength Detector
  MS detector: 1100 series "LC-MSD VL"
  Fraction Collector: 2×"Prep-FC"
  Make Up pump: "Waters RMA"
  Agilent Active Splitter
  Agilent MS Running Conditions:
  Capillary voltage: 4000 V (3500 V on ES Negative)
  Fragmentor/Gain: 150/1

Drying gas flow: 12.0 L/min
Gas Temperature: 350° C.
Nebuliser Pressure: 50 psig
Scan Range: 125-800 amu
Ionisation Mode: ElectroSpray Positive or ElectroSpray Negative
Columns:
A range of commercially available columns both achiral and chiral—may be used such that, in conjunction with the changes in mobile phase, organic modifier and pH, they enabled the greatest cover in terms of a broad range of selectivity. All columns were used in accordance with the manufacturers recommended operating conditions. Typically 5 micron particle sized columns were used where available. For example, columns from Waters (including but not limited to XBridge™ Prep OBD™ C18 and Phenyl, Atlantis® Prep T3 OBD™ and Sunfire™ Prep OBD C18 5 μm 19×100 mm), Phenomenex (including but not limited to Synergy MAX-RP and LUX™ Cellulose-2), Astec (Chirobiotic™ columns including but not limited to V, V2 and T2) and Diacel® (including but not limited to Chiralpak® AD-H) were available for screening.
Eluents:
Mobile phase eluent was chosen in conjunction with column manufacturers recommended stationary phase limitations in order to optimise a columns separation performance.
Methods:
Achiral Preparative Chromatography
The compound examples described have undergone HPLC purification, where indicated, using methods developed following recommendations as described in Snyder L. R., Dolan J. W., High-Performance Gradient Elution The Practical Application of the Linear-Solvent-Strength Model, Wiley, Hoboken, 2007.
Chiral Preparative Chromatography
Preparative separations using Chiral Stationary Phases (CSPs) are the natural technique to apply to the resolution of enantiomeric mixtures. Equally, it can be applied to the separation of diastereomers and achiral molecules. Methods are well known in the art for optimising preparative chiral separations on CSPs and then using them to purify compounds. Such methods are described in Beesley T. E., Scott R. P. W.; Chiral Chromatography; Wiley, Chichester, 1998.

Preparation 1: (R)-2-((S)-2-Benzyloxycarbonylamino-3-hydroxy-propionyl-amino)-propionic acid methyl ester Diisopropylethylamine (375 mL) was added dropwise to a cooled mixture of (R)-2-amino-propionic acid methyl ester hydrochloride (100 g, 0.716 mol), EDC (165 g, 0.86 mol), carbobenzyloxy-L-serine (171.4 g, 0.716 mol) and DCM (3.6 L). The resulting mixture was stirred under nitrogen at ambient temperature for 16 h. After removing solvent in vacuo at 40° C., the residue was diluted with saturated sodium carbonate (1 L), water (1 L) and extracted with EtOAc (2 L, 2×1 L). The combined organic phases were washed with 2 M hydrochloric acid (1 L), saturated brine solution (1 L), dried over magnesium sulfate and concentrated in vacuo at 40° C., to give the title compound (172 g) as a colourless solid. $^1$H NMR (Me-d3-OD): 7.44-7.28 (6H, m), 5.13 (2H, s), 4.46 (1H, d), 4.43 (1H, d), 4.25 (1H, t), 3.82-3.68 (5H, m), 1.39 (3H, d).

Preparation 2: (3S,6R)-3-Hydroxymethyl-6-methyl-piperazine-2,5-dione

To (R)-2-((S)-2-benzyloxycarbonylamino-3-hydroxy-propionylamino)-propionic acid methyl ester (172 g, 0.53 mol) was added 10% Pd/C (8.6 g), MeOH (530 mL) and cyclohexene (344 mL) under nitrogen. The mixture was heated to reflux for 17 h. MeOH (500 mL) was added and the reflux continued for 1 h. The hot reaction mixture was filtered through a pad of celite, cake washing with hot MeOH (2×500 mL). The combined filtrates were concentrated. The resulting solid was slurried in 2-butanone (400 mL) and petrol (400 mL) was added gradually over 10 min. After stirring for 30 min, the solids were filtered, cake washed with 2:1 petrol/2-butanone (300 mL). The filter cake was dried in vacuo at 40° C., to give the title compound (68.3 g) as an off white solid. $^1$H NMR (DMSO-d6): 8.08 (1H, s), 7.90 (1H, s), 5.11 (1H, t), 3.92 (1H, q), 3.80-3.71 (1H, m), 3.71-3.60 (1H, m), 3.58-3.47 (1H, m), 1.24 (3H, d).

Preparation 3: ((2R,5R)-5-Methyl-piperazin-2-yl)-methanol hydrochloride

To (3S,6R)-3-hydroxymethyl-6-methyl-piperazine-2,5-dione (34 g, 0.215 mol) was added a solution of borane in THF (1 M, 1.6 L, 1.6 mol) and the mixture was heated to 70° C. for 18 h. The solution was cooled in ice, then MeOH (425 mL) was gradually added, followed by 5 M hydrochloric acid (113 mL). The mixture was heated to 70° C. for 2 h and then cooled to ambient temperature. The resulting solid was filtered, cake washed with THF (200 mL) and dried in vacuo at 40° C., to give the title compound (39.3 g) as a colourless solid. $^1$H NMR (DMSO-d6): 9.79 (3H, s), 5.59 (1H, s), 3.76-3.40 (5H, m), 3.19-2.94 (2H, m), 1.28 (3H, d).

Preparation 4: (2R,5R)-5-Hydroxymethyl-2-methyl-piperazine-1-carboxylic acid tert-butyl ester To ((2R,5R)-5-methyl-piperazin-2-yl)-methanol hydrochloride (20 g, 119 mmol) in MeOH (96 mL) at 0° C. (ice bath) was added triethylamine (48.7 mL, 357 mmol). tert-Butyl dicarbonate (61 g, 280 mmol) in MeOH (145 mL) was added over 30 min. The reaction temperature was maintained at <10° C. for 1 h, warmed to ambient temperature over 1 h and then heated to 50° C. for 18 h. The reaction was concentrated and the residue dissolved in ethanol (397 mL). A solution of NaOH (23.8 g, 595 mmol) in water (397 mL) was added and the reaction heated to 100° C. for 18 h, then cooled to ambient temperature. Mixture was neutralised with 1M HCl (~300 mL) to pH 9 (using a pH meter), then extracted with chloroform (3×700 mL), dried over sodium sulfate, filtered and concentrated. The residue was redissolved in MeOH and concentrated, then dried in vacuo at 40° C., to give the title compound (21 g, 75%) as a colourless solid. $^1$H NMR (Me-d3-OD): 4.20-4.07 (1H, m), 3.79 (1H, dd), 3.71-3.58 (2H, m), 3.54 (1H, dd), 3.24 (1H, dd), 3.18-3.01 (1H, m), 3.01-2.89 (1H, m), 2.55 (1H, dd), 1.48 (9H, s), 1.25 (3H, s).

Preparation 5: (2R,5R)-4-Benzyl-5-hydroxymethyl-2-methyl-piperazine-1-carboxylic acid tert-butyl ester

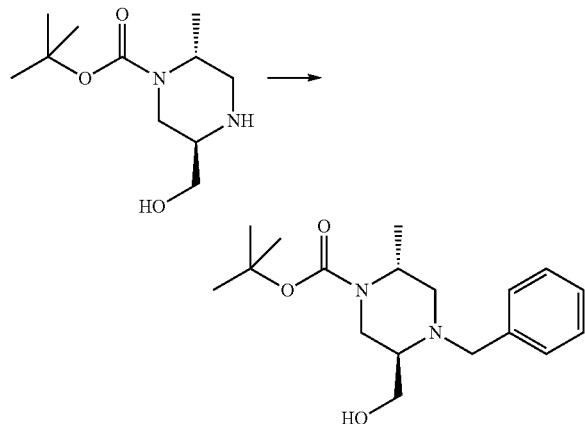

A mixture of (2R,5R)-5-hydroxymethyl-2-methyl-piperazine-1-carboxylic acid tert-butyl ester (3.48 g, 15.1 mmol), benzaldehyde (1.76 g, 16.6 mmol), sodium triacetoxyborohydride (3.84 g, 18.1 mmol) and 1,2-dichloroethane (30 mL) was stirred at 20° C. for 18 h, then partitioned between saturated aqueous NaHCO$_3$ (150 mL) and DCM (3×50 mL). Combined organic extracts were dried (Na$_2$SO$_4$) then evaporated in vacuo to give an oil. Chromatography (SiO$_2$, 0-30% EtOAc in petrol) gave the title compound (4.588 g, 74%) as a colourless solid. MS: [M+H]$^+$=321.

Preparation 6: (2R,5R)-4-Benzyl-5-chloromethyl-2-methyl-piperazine-1-carboxylic acid tert-butyl ester Methanesulfonyl chloride (570 μL, 7.35 mmol) was added to a solution of (2R,5R)-4-benzyl-5-hydroxymethyl-2-methyl-piperazine-1-carboxylic acid tert-butyl ester (1.9 g, 6.12 mmol) containing TEA (2.6 mL, 18.4 mmol) in DCM (30 mL) at 0° C. The solution was stirred at room temperature for 18 h. The reaction was partitioned between aqueous NH$_4$Cl and DCM. The organic phase was collected, dried over MgSO$_4$, filtered and concentrated in vacuo. Chromatography (30% EtOAc in petrol) gave the title compound (1.6 g) as a white solid. MS: [M+H]$^+$=339.

Preparation 7: 2-Chloro-5-iodo-pyridin-4-ylamine

N-Iodosuccinimide (24.75 g, 110.0 mmol) was added to a solution of 2-chloro-pyridin-4-ylamine (12.85 g, 100.0 mmol) in acetonitrile (400 mL) and the mixture stirred and held at reflux overnight. Upon cooling to room temperature the solvent was removed in vacuo and residue partitioned between EtOAc (250 mL), saturated sodium thiosulfate (100 mL) and water (250 mL). The organic layer was separated, washed with water (2×250 mL), separated and the solvent removed in vacuo to afford an orange oil that was subjected to column chromatography on silica. Gradient elution with 30-50% EtOAc in petrol afforded a pale orange solid that was rinsed with 25% EtOAc in petrol (80 mL). Solids were collected by filtration and sucked dry to afford the title compound (7.32 g) as an off-white solid. The mother liquors were concentrated to dryness in vacuo and the residues subjected to column chromatography on silica. Elution with 30-50% EtOAc in petrol afforded further pure material (1.90 g). Combined yield: (9.22 g, 36%) $^1$H NMR (DMSO-d6) 8.20 (1H, s), 6.64 (1H, s), 6.50 (2H, br s). MS: [M+H]$^+$ 255.

Preparation 8: (2-Chloro-5-iodo-pyridin-4-yl)-(2-methyl-allyl)-amine

Potassium tert-butoxide (4.56 g, 40.73 mmol) was added to a stirred solution of 2-chloro-5-iodo-pyridin-4-ylamine (8.62 g, 33.94 mmol) in anhydrous THF (140 mL) and the mixture was stirred at room temperature for 0.25 h. 3-Bromo-2-methyl-prop-1-ene (5.51 g, 40.73 mmol) was added and the mixture was stirred at room temperature overnight. The solvent was removed in vacuo and the residues partitioned between DCM (100 mL) and water (100 mL). The organic layer was separated, the solvent removed in vacuo and the residues subjected to column chromatography on silica. Gradient elution with 5-20% EtOAc in petrol afforded the title compound (7.93 g, 76%) as a pale yellow oil. $^1$H NMR (DMSO-d6) 8.24 (1H, s), 6.50 (1H, br t), 6.39 (1H, s), 4.84 (1H, d), 4.73 (1H, d), 3.83 (2H, d), 1.70 (3H, s). MS: [M+H]$^+$ 309.

Preparation 9: 6-Chloro-3,3-dimethyl-2,3-dihydro-1H-pyrrolo[3,2-c]pyridine

Palladium (II) acetate (300 mg, 1.34 mmol), sodium formate (2.40 g, 30.53 mmol), tetra-n-butyl-ammonium chloride (8.48 g, 30.53 mmol) and triethylamine (10.6 mL, 76.32 mmol) were added to a solution of (2-chloro-5-iodo-pyridin-4-yl)-(2-methyl-allyl)-amine (7.85 g, 25.44 mmol) in toluene (200 mL) and water (10 mL) and the mixture was stirred and held at 100° C. under a nitrogen atmosphere overnight. The mixture was filtered whilst hot and the solids rinsed with toluene (50 mL), water (50 mL) and EtOAc (50 mL). The organic solvent was removed in vacuo, the aqueous residues were diluted with water (100 mL) and extracted with EtOAc (2×200 mL). The organic layer was separated, the solvent was removed in vacuo and the residues subjected to column chromatography on silica. Elution with 30-100% EtOAc in petrol afforded the title compound (4.12 g, 89%) as a colourless solid. $^1$H NMR (DMSO-d6) 7.72 (1H, s), 6.75 (1H, br s), 6.33 (1H, s), 3.32 (2H, d), 1.25 (6H, s). MS: [M+H]$^+$ 183.

Preparation 10: 6-Chloro-3,3-dimethyl-2,3-dihydro-pyrrolo[3,2-c]pyridine-1-carboxylic acid tert-butyl ester To a solution of 6-chloro-3,3-dimethyl-2,3-dihydro-1H-pyrrolo[3,2-c]pyridine (1.3 g, 7.4 mmol) in THF (20 mL) were added tert-butyl dicarbonate (4.1 g, 18.6 mmol) and dimethyl-pyridin-4-yl-amine (2.22 g, 18.6 mmol) and the solution was stirred for 2 h. Water (60 mL) was added and the product was extracted with EtOAc. The organic phase was washed with brine, dried (MgSO$_4$), filtered and evaporated. Chromatography (SiO$_2$, eluted with petrol EtOAc 0-40%) gave the title compound (1.04 g). $^1$H NMR (Me-d3-OD): 8.04 (1H, s), 7.60 (1H, s), 3.81 (2H, s), 1.59 (9H, s), 1.40 (6H, s). MS: [M+H]$^+$=283.

Alternative procedure: Potassium tert-butoxide (600 mg, 5.36 mmol) was added to a stirred solution of 6-chloro-3,3-dimethyl-2,3-dihydro-1H-pyrrolo[3,2-c]pyridine (800 mg, 4.38 mmol) in anhydrous THF (15 mL) and was stirred at room temperature for 10 minutes. A solution of di-tert-butyl dicarbonate (1.07 g, 4.89 mmol) in anhydrous THF (15 mL) was added and the mixture was stirred at room temperature overnight. The organic solvent was removed in vacuo, the aqueous residues were diluted with water (100 mL) and extracted with EtOAc (2×200 mL). The organic layers were combined and the solvent was removed in vacuo to afford the title compound (1.19 g, 96%), NMR data consistent with those previously obtained.

Preparation 11: 5-Bromo-2-iodo-pyridin-3-ylamine

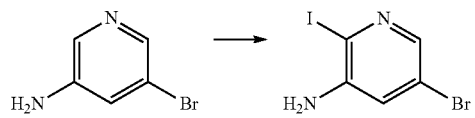 [SMILES: Nc1cncc(Br)c1 ; Nc1cc(Br)cnc1I]

3-Amino-5-bromopyridine (13.8 g, 79.8 mmol) was dissolved in acetic acid (440 mL) and placed under a nitrogen atmosphere. N-Iodosuccinimide (16.15 g, 71.8 mmol) was charged to the reaction which was stirred at room temperature overnight. The reaction was concentrated and the residue partitioned between EtOAc (200 mL) and saturated aqueous sodium hydrogen carbonate (200 mL). The layers were separated and the organic phase was washed with saturated aqueous sodium hydrogen carbonate (200 mL). The aqueous phase was extracted with EtOAc (3×200 mL). The organic extracts were dried over magnesium sulfate, filtered and concentrated. Chromatography (silica; 1.4 Kg packed in 70% DCM:30% heptane, eluting with 70-100% DCM in heptane) gave the title compound (11.5 g). $^1$H NMR (270 MHz, CDCl$_3$): 7.83 (1H, m), 7.04 (1H, m), 4.33 (2H, br s).

Preparation 12: (5-Bromo-2-iodo-pyridin-3-yl)-(2-methyl-allyl)-amine

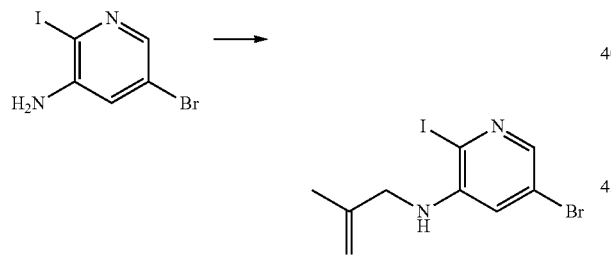

The title compound was prepared following similar methods to those described in Preparation 8, except using 5-bromo-2-iodopyridinyl-3-amine, potassium tert-butoxide (1.1 eq) and 3-bromo-2-methylprop-1-ene (1.1 eq), $^1$H NMR (270 MHz, CDCl$_3$): 7.76 (1H, d), 6.72 (1H, d), 4.92 (2H, m), 4.61 (1H, s), 3.70 (2H, d), 1.69 (3H, s).

Preparation 13: 6-Bromo-3,3-dimethyl-2,3-dihydro-1H-pyrrolo[3,2-b]pyridine

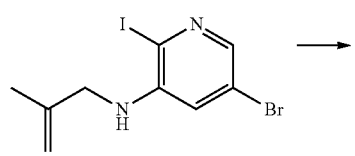

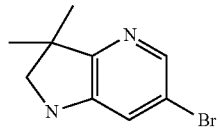

A mixture of (5-bromo-2-iodo-pyridin-3-yl)-(2-methyl-allyl)-amine (10.2 g, 28.9 mmol), tetrabutylammonium chloride (9.64 g, 34.7 mmol), sodium formate (2.36 g, 34.7 mmol), palladium acetate (0.97 g, 4.3 mmol), triethylamine (8.76 g, 86.7 mmol), water (12.1 mL) and dimethyl sulfoxide (255 mL) was stirred at 100° C. under nitrogen for 1 h. The mixture was cooled by the addition of ice (100 g) then was diluted with water (200 mL) with stirring. The mixture was partitioned between water (1 L) and a mixture of toluene (600 mL) and EtOAc (50 mL). The organic phase was washed with water (4×250 mL), dried (Na$_2$SO$_4$) and evaporated in vacuo to give a brown oil. Chromatography (SiO$_2$, gradient elution with 0-100% diethyl ether in 40-60 petroleum ether) gave the title compound (2.84 g) as a yellow solid. MS: [M+H]$^+$=227, 229.

Preparation 14: 6-Bromo-3,3-dimethyl-2,3-dihydro-pyrrolo[3,2-b]pyridine-1-carboxylic acid tert-butyl ester

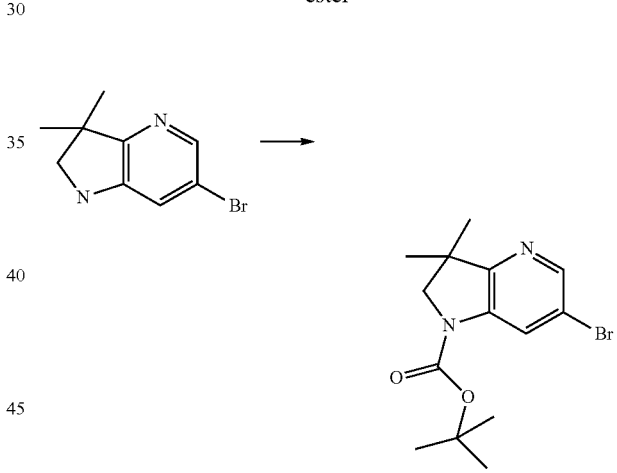

6-Bromo-2,3-dihydro-3,3-dimethyl-1H-pyrrolo[2,3-b]pyridine (2.45 g, 10.8 mmol) was dissolved in THF (44 mL) and placed under a nitrogen atmosphere. Potassium tert-butoxide (1.2 g, 10.8 mmol) was added to the reaction which was stirred at room temperature for 10 minutes. Di-tert-butyldicarbonate (2.73 mL, 11.9 mmol) was charged to the reaction which was stirred for 1 h. An additional charge of di-tert-butyldicarbonate (0.25 mL, 1.0 mmol) was added to the reaction. After a further 45 minutes the reaction was concentrated. The residue was partitioned between water (50 mL) and DCM (50 mL). The layers were separated and the aqueous was extracted with DCM (2×50 mL). The organic extracts were dried over magnesium sulfate, filtered and concentrated. Chromatography (silica; 250 g packed in heptane, eluting with 5% EtOAc:heptane) gave the title compound (2.3 g), MS: [M+H]$^+$=327.

Preparation 15: 6-(4-Fluoro-benzyl)-3,3-dimethyl-2,3-dihydro-pyrrolo[3,2-b]pyridine-1-carboxylic acid tert-butyl ester

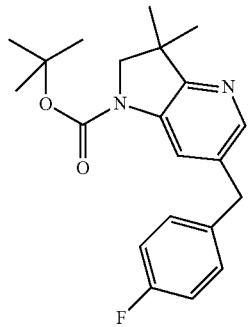 [SMILES: CC(C)(C)OC(=O)N1CC(C)(C)c2ncc(Cc3ccc(F)cc3)cc21]

To a nitrogen-degassed mixture of 6-bromo-3,3-dimethyl-2,3-dihydro-pyrrolo[3,2-b]pyridine-1-carboxylic acid tert-butyl ester (3.27 g, 10.0 mmol), lithium bromide (2.58 g, 30.0 mmol), (1,3-diisopropylimidazol-2-ylidene)(3-chloropyridyl)palladium (II) dichloride (0.136 g, 0.2 mmol), 1-methyl-2-pyrrolidinone (30 mL) and THF (30 mL) was added a solution of 4-fluoro-benzylzinc chloride in THF (0.5 M, 40 mL, 20 mmol) and resulting mixture was stirred at 20° C. for 3 h. The mixture was poured into water (150 mL) and 5% aqueous citric acid (30 mL) and the resulting mixture extracted with Et₂O (3×70 mL). The organic phase was washed with water (100 mL), brine (3×100 mL), dried (MgSO₄) and evaporated in vacuo to give an oil. Chromatography (SiO₂, eluted with petrol EtOAc 0-30%) gave the title compound (3.5 g, 99%) as an oil. MS: [M+H]⁺=357.

Preparation 16: 6-(4-Fluoro-benzyl)-3,3-dimethyl-2,3-dihydro-1H-pyrrolo[3,2-b]pyridine

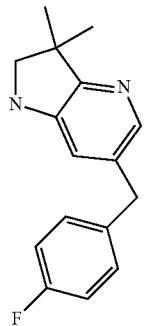 [SMILES: CC1(C)CNc2cc(Cc3ccc(F)cc3)cnc21]

A solution of 6-(4-fluoro-benzyl)-3,3-dimethyl-2,3-dihydro-pyrrolo[3,2-b]pyridine-1-carboxylic acid tert-butyl ester (9.0 g, 25 mmol) in methanol (62.5 mL) was treated with 5 M hydrochloric acid (62.5 mL) and the mixture stirred at 20° C. for 18 h then heated at 50° C. for 2 h. Solvent was evaporated and the residue was partitioned between water (200 mL) and EtOAc (3×). The aqueous phase was slowly poured into saturated aqueous NaHCO₃ and the resulting solid collected by filtration to afford the title compound (3.45 g). 1H NMR (CDCl₃): 7.81 (1H, s), 7.16 (2H, dd), 6.99 (2H, t), 6.58 (1H, d), 3.84 (2H, s), 3.38 (2H, s), 1.36 (6H, s). MS: [M+H]⁺=257. Further title compound (1.5 g) was obtained by aqueous acid extraction of the combined organic extracts and subsequent basification of the combined aqueous extracts.

The following compounds were prepared following methods analogous to those described in Preparations 15 and 16:
6-Benzyl-3,3-dimethyl-2,3-dihydro-1H-pyrrolo[3,2-b]pyridine; MS: [M+H]⁺=239.
6-(4-Fluoro-benzyl)-3,3-dimethyl-2,3-dihydro-1H-pyrrolo[3,2-c]pyridine; MS: [M+H]⁺=257.
6-(2,4-difluoro-benzyl)-3,3-dimethyl-2,3-dihydro-1H-pyrrolo[3,2-c]pyridine; MS: [M+H]⁺=275.
6-(2,4-difluoro-benzyl)-3,3-dimethyl-2,3-dihydro-1H-pyrrolo[3,2-b]pyridine; MS: [M+H]⁺=275
3-(4-Fluoro-benzyl)-7,7-dimethyl-6,7-dihydro-5H-pyrrolo[3,2-c]pyridazine; [M+H]⁺=258.
3-(2,4-Difluoro-benzyl)-7,7-dimethyl-6,7-dihydro-5H-pyrrolo[3,2-c]pyridazine; [M+H]⁺=276.

The following compounds were prepared from the corresponding N-Boc derivatives following a similar procedure to Preparation 16:
(R)-(3,3-Dimethyl-2,3-dihydro-1H-pyrrolo[3,2-b]pyridin-6-yl)-(4-fluoro-phenyl)-methanol; [M+H]⁺=273.
(S)-(3,3-Dimethyl-2,3-dihydro-1H-pyrrolo[3,2-b]pyridin-6-yl)-(4-fluoro-phenyl)-methanol; [M+H]⁺=273.
1-(3,3-Dimethyl-2,3-dihydro-1H-pyrrolo[3,2-c]pyridin-6-yl)-butan-1-ol.
1-(3,3-Dimethyl-2,3-dihydro-1H-pyrrolo[3,2-b]pyridin-6-yl)-butan-1-one; [M+H]⁺=219.

Preparation 17: 2-Chloro-1-[6-(4-fluorobenzyl)-3,3-dimethyl-2,3-dihydro-pyrrolo[3,2-b]pyridin-1-yl]-ethanone hydrochloride

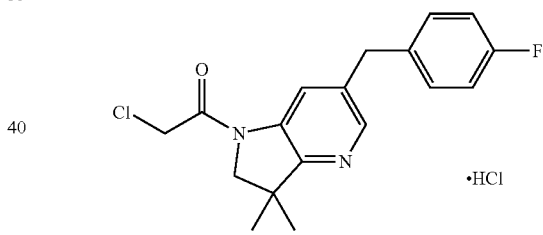

To a stirred suspension of 6-(4-fluoro-benzyl)-3,3-dimethyl-2,3-dihydro-1H-pyrrolo[3,2-b]pyridine (6.68 g, 26 mmol) in acetonitrile (20 mL) at 20° C. was added, steadily over 0.2 h, a solution of chloroacetyl chloride (3.83 g, 2.7 mL, 33.9 mmol) in acetonitrile (10 mL), maintaining the reaction mixture at or below 20° C. using an external ice-methanol bath. A clear solution resulted then, as the internal temperature reached 0° C., a solid began to crystallize from the reaction mixture. Stirring at 20° C. was continued for 1 h then toluene (20 mL) and 40-60 petroleum ether (20 mL) were added slowly and stirring continued for 0.2 h. The resulting colourless solid was collected by filtration to give the title compound (8.0 g, 83%). 1H NMR (Me-d3-OD): 8.81 (1H, s), 8.31 (1H, s), 7.39-7.29 (2H, m), 7.16-7.04 (2H, m), 4.45 (2H, s), 4.19 (4H, s), 1.58 (6H, s). MS: [M+H]⁺=333.

The following compounds were prepared following an analogous procedure to that described in Preparation 17. In some cases, the product was isolated by evaporation of the reaction mixture and toluene azeotrope to remove excess chloroacetyl chloride and product was not further purified or characterised:

17A: 2-Chloro-1-[6-benzyl-3,3-dimethyl-2,3-dihydro-pyrrolo[3,2-b]pyridin-1-yl]-ethanone hydrochloride.

17B: 2-Chloro-1-[6-(4-fluoro-benzyl)-3,3-dimethyl-2,3-dihydro-pyrrolo[3,2-c]pyridin-1-yl]-ethanone hydrochloride; MS: [M+H]$^+$=333.

17C: 2-Chloro-1-[6-(1,1-difluoro-propyl)-3,3-dimethyl-2,3-dihydro-pyrrolo[3,2-b]pyridin-1-yl]-ethanone hydrochloride; MS: [M+H]$^+$=303.

17D: 2-Chloro-1-[6-(1,1-difluoro-butyl)-3,3-dimethyl-2,3-dihydro-pyrrolo[3,2-c]pyridin-1-yl]-ethanone; MS: [M+H]$^+$=317.

17E: 2-Chloro-1-[6-(2,4-difluoro-benzyl)-3,3-dimethyl-2,3-dihydro-pyrrolo[3,2-c]pyridin-1-yl]-ethanone hydrochloride; MS: [M+H]$^+$=351.

17F: 2-Chloro-1-[6-(2,4-difluoro-benzyl)-3,3-dimethyl-2,3-dihydro-pyrrolo[3,2-b]pyridin-1-yl]-ethanone hydrochloride; MS: [M+H]$^+$=351.

17G: 2-Bromo-1-[3-(4-fluoro-benzyl)-7,7-dimethyl-6,7-dihydro-pyrrolo[3,2-c]pyridazin-5-yl]-ethanone hydrochloride (made using bromoacetyl bromide instead of chloroacetyl chloride); [M+H]$^+$=378, 380.

17H: 2-Chloro-1-[3-(2,4-difluoro-benzyl)-7,7-dimethyl-6,7-dihydro-pyrrolo[3,2-c]pyridazin-5-yl]-ethanone, hydrochloride; [M+H]$^+$=352.

17I: 2-Chloro-1-{6-[(2-fluoro-phenyl)-(R or S)-hydroxymethyl]-3,3-dimethyl-2,3-dihydro-pyrrolo[3,2-b]pyridin-1-yl}-ethanone, hydrochloride (from 58J, slower eluting); [M+H]$^+$=349.

17K: (±)-2-Chloro-1-{6-[(4-fluoro-phenyl)-hydroxymethyl]-3,3-dimethyl-2,3-dihydro-pyrrolo[3,2-b]pyridin-1-yl}-ethanone hydrochloride; [M+H]$^+$=365.

17L: 2-Chloro-1-{6-[(4-fluoro-phenyl)-(R)-hydroxymethyl]-3,3-dimethyl-2,3-dihydro-pyrrolo[3,2-b]pyridin-1-yl}-ethanone; [M+H]$^+$=365.

17M: 2-Chloro-1-{6-[(4-fluoro-phenyl)-(S)-hydroxymethyl]-3,3-dimethyl-2,3-dihydro-pyrrolo[3,2-b]pyridin-1-yl}-ethanone; [M+H]$^+$=365.

17N: 2-Chloro-1-[6-(1-hydroxy-butyl)-3,3-dimethyl-2,3-dihydro-pyrrolo[3,2-c]pyridin-1-yl]-ethanone hydrochloride; [M+H]$^+$ 297.

17P: 1-[1-(2-Chloro-acetyl)-3,3-dimethyl-2,3-dihydro-1H-pyrrolo[3,2-b]pyridin-6-yl]-butan-1-one hydrochloride; [M+H]$^+$ 295.

17Q: 2-Chloro-1-{6-[(3-fluoro-phenyl)-(R or S)-hydroxymethyl]-3,3-dimethyl-2,3-dihydro-pyrrolo[3,2-b]pyridin-1-yl}-ethanone, hydrochloride (from 58A, faster eluting).

17R: 2-Chloro-1-{6-[(3-fluoro-phenyl)-(R or S)-hydroxymethyl]-3,3-dimethyl-2,3-dihydro-pyrrolo[3,2-b]pyridin-1-yl}-ethanone, hydrochloride (from 58B, slower eluting).

17S: 2-Chloro-1-{6-[(2,4-difluoro-phenyl)-(R or S)-hydroxy-methyl]-3,3-dimethyl-2,3-dihydro-pyrrolo[3,2-b]pyridin-1-yl}-ethanone, hydrochloride (from 58C, faster eluting).

17T: 2-Chloro-1-{6-[(2,4-difluoro-phenyl)-(R or S)-hydroxy-methyl]-3,3-dimethyl-2,3-dihydro-pyrrolo[3,2-b]pyridin-1-yl}-ethanone, hydrochloride (from 58D, slower eluting).

17U: 2-Chloro-1-{6-[(3,4-difluoro-phenyl)-(R or S)-hydroxy-methyl]-3,3-dimethyl-2,3-dihydro-pyrrolo[3,2-b]pyridin-1-yl}-ethanone, hydrochloride (from 58E, faster eluting).

17W: 2-Chloro-1-{6-[(3,4-difluoro-phenyl)-(R or S)-hydroxy-methyl]-3,3-dimethyl-2,3-dihydro-pyrrolo[3,2-b]pyridin-1-yl}-ethanone, hydrochloride (from 58F, slower eluting).

17X: 2-Chloro-1-{6-[(2,3-difluoro-phenyl)-(R or S)-hydroxy-methyl]-3,3-dimethyl-2,3-dihydro-pyrrolo[3,2-b]pyridin-1-yl}-ethanone, hydrochloride (from 58G, faster eluting).

17Y: 2-Chloro-1-{6-[(2,3-difluoro-phenyl)-(R or S)-hydroxy-methyl]-3,3-dimethyl-2,3-dihydro-pyrrolo[3,2-b]pyridin-1-yl}-ethanone, hydrochloride (from 58H, slower eluting).

17Z: 2-Chloro-1-{6-[(2-fluoro-phenyl)-(R or S)-hydroxy-methyl]-3,3-dimethyl-2,3-dihydro-pyrrolo[3,2-b]pyridin-1-yl}-ethanone, hydrochloride (from 58I, faster eluting); [M+H]$^+$ 349.

17EE: 2-Chloro-1-[(R or S)-6-(hydroxy-phenyl-methyl)-3,3-dimethyl-2,3-dihydro-pyrrolo[3,2-b]pyridin-1-yl]ethanone hydrochloride (from 58O, faster eluting precursor); [M+H]$^+$ 331.

17FF: 2-Chloro-1-[(R or S)-6-(hydroxy-phenyl-methyl)-3,3-dimethyl-2,3-dihydro-pyrrolo[3,2-b]pyridin-1-yl]-ethanone hydrochloride (from 58P, slower eluting precursor); [M+H]$^+$ 331.

17GG: 2-Chloro-1-{(RS)-6-[(2,5-difluoro-phenyl)-hydroxy-methyl]-3,3-dimethyl-2,3-dihydro-pyrrolo[3,2-b]pyridin-1-yl}-ethanone hydrochloride; (from 58Q); M+H]$^+$ 367.

17HH: 2-Chloro-1-{(R or S)-6-[(2,6-difluoro-phenyl)-hydroxy-methyl]-3,3-dimethyl-2,3-dihydro-pyrrolo[3,2-b]pyridin-1-yl}-ethanone hydrochloride; (from 58R, faster eluting precursor); 1H NMR (400 MHz, Me-d3-OD): 8.89 (1H, s), 8.47 (1H, s), 7.51-7.39 (1H, m), 7.04 (2H, t), 6.41 (1H, s), 4.46 (2H, s), 4.22 (2H, s), 1.61 (6H, s).

17II: 2-Chloro-1-{(R or S)-6-[(2,6-difluoro-phenyl)-hydroxy-methyl]-3,3-dimethyl-2,3-dihydro-pyrrolo[3,2-b]pyridin-1-yl}-ethanone hydrochloride; (from 58S, slower eluting precursor); 1H NMR (400 MHz, Me-d3-OD): 8.87 (1H, s), 8.47 (1H, s), 7.50-7.39 (1H, m), 7.04 (2H, t), 6.40 (1H, s), 4.45 (2H, s), 4.21 (2H, s), 1.60 (6H, s).

Preparation 18: (2R,5R)-4-{2-[6-(4-Fluoro-benzyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester Finely ground potassium iodide (7.5 g, 45.26 mmol) was added to a mixture of (2R,5R)-5-hydroxymethyl-2-methyl-piperazine-1-carboxylic acid tert-butyl ester (5.7 g, 24.89 mmol), 2-chloro-1-[6-(4-fluorobenzyl)-3,3-dimethyl-2,3-dihydro-pyrrolo[3,2-b]pyridin-1-yl]-ethanone hydrochloride (8.35 g, 22.63 mmol) potassium carbonate (12.5 g, 90.51 mmol) and acetonitrile (100 mL) under nitrogen. The mixture was stirred at 20° C. overnight. The mixture was partitioned between water (300 mL) and EtOAc (300 mL) and the organic phase was dried and evaporated in vacuo to give the title compound (12.14 g). MS: [M+H]$^+$=527.

Preparation 19: (2R,5R)-5-Chloromethyl-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester Methylsulfonyl chloride (0.76 mL, 10 mmol) was assed to a solution of (2R,5R)-4-{2-[6-(4-fluoro-benzyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester (4.33 g, 8.23 mmol) and triethylamine (3.6 mL, 24.7 mmol) in DCM (50 mL) at 0° C. The solution was allowed to warm to room temperature and stirred under a nitrogen atmosphere overnight. The mixture was partitioned between aqueous ammonium chloride (100 mL) and DCM (100 mL) and the organic phase was dried (Na₂SO₄) and evaporated in vacuo.

Chromatography (SiO₂, eluted with petrol EtOAc 0-70% gradient), gave the title compound (3.44 g, 77%). MS: [M+H]⁺=545.

Preparation 20: (2R,5S)-5-((3R,5R)-3,5-Dimethyl-morpholin-4-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester

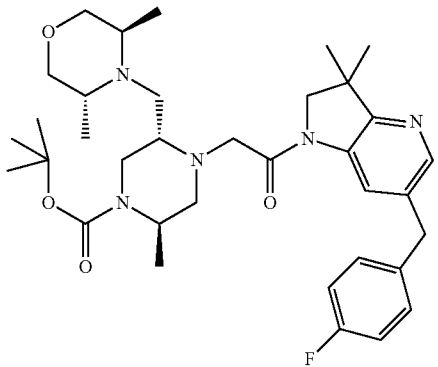 [SMILES: C[C@@H]1CN(CC(=O)N2CC(C)(C)c3ncc(Cc4ccc(F)cc4)cc32)[C@@H](CN2[C@H](C)COC[C@H]2C)CN1C(=O)OC(C)(C)C]

A mixture of (2R,5R)-5-Chloromethyl-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester (0.10 g, 0.18 mmol), (3R,5R)-3,5-dimethyl-morpholine (0.026 g, 0.23 mmol), potassium carbonate (0.10 g, 0.72 mmol), potassium iodide (0.09 g, 0.54 mmol) and acetonitrile (2 mL) was heated at 90° C. for 6 h. Mixture was partitioned between water (30 mL) and DCM (3×20 mL) and the combined organic extracts were dried (Na₂SO₄) and evaporated in vacuo. Chromatography (SiO₂, eluted with petrol EtOAc 0-100% gradient) gave the title compound (0.073 g). MS: [M+H]⁺=624.

Compounds listed below were prepared following an analogous method to that described in Preparation 20:

(2R,5S)-4-{2-[6-(4-Fluoro-benzyl)-3,3-dimethyl-2,3-dihydro-pyrrolo[3,2-b]pyridin-1-yl]-2-oxo-ethyl}-5-((R)-3-methoxymethyl-morpholin-4-ylmethyl)-2-methyl-piperazine-1-carboxylic acid tert-butyl ester; MS: [M+H]⁺=640.

(2R,5S)-4-{2-[6-(4-Fluoro-benzyl)-3,3-dimethyl-2,3-dihydro-pyrrolo[3,2-b]pyridin-1-yl]-2-oxo-ethyl}-5-((R)-3-hydroxymethyl-morpholin-4-ylmethyl)-2-methyl-piperazine-1-carboxylic acid tert-butyl ester; MS: [M+H]⁺=626.

(2R,5S)-5-(3,3-Difluoro-piperidin-1-yl methyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester; MS: [M+H]⁺=630.

(2R,5S)-5-(4,4-Difluoro-piperidin-1-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester; MS: [M+H]⁺=630.

(2R,5S)-5-(3,3-Dimethyl-morpholin-4-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester; MS: [M+H]⁺=624.

(2R,5S)-5-(3,3-Difluoro-pyrrolidin-1-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester; MS: [M+H]⁺=616.

(2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-[(1S,4S)-1-(2-oxa-5-aza-bicyclo[2.2.1]hept-5-yl)methyl]-piperazine-1-carboxylic acid tert-butyl ester; MS: [M+H]⁺=608.

(2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-(2-methyl-4-oxo-piperidin-1-ylmethyl)-piperazine-1-carboxylic acid tert-butyl ester; MS: [M+H]⁺=622.

(2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-(3-methyl-1,1-dioxo-1lambda*6*-thiomorpholin-4-ylmethyl)-piperazine-1-carboxylic acid tert-butyl ester; MS: [M+H]⁺=658.

2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-(7-oxa-4-aza-spiro[2.5]oct-4-ylmethyl)-piperazine-1-carboxylic acid tert-butyl ester; MS: [M+H]⁺=622.

(2R,5S)-5-((2R,5R)-2,5-Dimethyl-morpholin-4-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester; MS: [M+H]⁺=624.

(2R,5S)-4-{2-[6-(4-Fluoro-benzyl)-3,3-dimethyl-2,3-dihydro-pyrrolo[3,2-b]pyridin-1-yl]-2-oxo-ethyl}-5-((S)-2-hydroxymethyl-pyrrolidin-1-ylmethyl)-2-methyl-piperazine-1-carboxylic acid tert-butyl ester; MS: [M+H]⁺=610.

(2R,5S)-4-{2-[6-(4-Fluoro-benzyl)-3,3-dimethyl-2,3-dihydro-pyrrolo[3,2-b]pyridin-1-yl]-2-oxo-ethyl}-5-((R)-3-isopropyl-morpholin-4-ylmethyl)-2-methyl-piperazine-1-carboxylic acid tert-butyl ester; MS: [M+H]⁺=638.

(2R,5S)-4-{2-[6-(4-Fluoro-benzyl)-3,3-dimethyl-2,3-dihydro-pyrrolo[3,2-b]pyridin-1-yl]-2-oxo-ethyl}-5-((R)-3-fluoro-piperidin-1-ylmethyl)-2-methyl-piperazine-1-carboxylic acid tert-butyl ester; prepared from the product of Procedure 29; MS: [M+H]⁺=612.

(2R,5S)-5-((3S,5R)-3,5-Dimethyl-morpholin-4-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester; MS: [M+H]⁺=624.

(2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-(3-oxa-8-aza-bicyclo[3.2.1]oct-8-ylmethyl)-piperazine-1-carboxylic acid tert-butyl ester; MS: [M+H]⁺=622.

(2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-(8-oxa-3-aza-bicyclo[3.2.1]oct-3-ylmethyl)-piperazine-1-carboxylic acid tert-butyl ester; MS: [M+H]⁺=622.

(2R,5S)-4-{2-[6-(4-Fluoro-benzyl)-3,3-dimethyl-2,3-dihydro-pyrrolo[3,2-b]pyridin-1-yl]-2-oxo-ethyl}-5-((S)-3-fluoromethyl-morpholin-4-ylmethyl)-2-methyl-piperazine-1-carboxylic acid tert-butyl ester; MS: [M+H]⁺=628.

(2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-(2-oxa-5-aza-bicyclo[2.2.1]hept-5-ylmethyl)-piperazine-1-carboxylic acid tert-butyl ester; MS: [M+H]⁺=608.

(2R,5S)-5-(5,7-Dihydro-pyrrolo[3,4-b]pyridin-6-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester; MS: [M+H]⁺=629.

tert-Butyl (2R,5S)-5-{[(3R,5S)-4-[(tert-butoxy)carbonyl]-3,5-dimethylpiperazin-1-yl]methyl}-4-(2-{6-[(4-fluorophenyl)methyl]-3,3-di methyl-1H,2H,3H-pyrrolo[3,2-b]pyridin-1-yl}-2-oxoethyl)-2-methylpiperazine-1-carboxylate; MS: [M+H]⁺=723.

tert-Butyl (2R,5S)-4-(2-{6-[(4-fluorophenyl)methyl]-3,3-dimethyl-1H,2H,3H-pyrrolo[3,2-b]pyridin-1-yl}-2-oxoethyl)-5-[(4-hydroxypiperidin-1-yl)methyl]-2-methylpiperazine-1-carboxylate; MS: [M+H]⁺=610.

tert-Butyl (2R,5S)-4-(2-{6-[(4-fluorophenyl)methyl]-3,3-dimethyl-1H,2H,3H-pyrrolo[3,2-b]pyridin-1-yl}-2-oxoethyl)-2-methyl-5-{[2-(trifluoromethyl)piperidin-1-yl]methyl}piperazine-1-carboxylate; [M+H]⁺=662, prepared as diastereomer mixture, separated by flash chromatography.

tert-Butyl (2R,5S)-4-(2-{6-[(4-fluorophenyl)methyl]-3,3-dimethyl-1H,2H,3H-pyrrolo[3,2-b]pyridin-1-yl}-2-oxoethyl)-2-methyl-5-{[3-(trifluoromethyl)morpholin-4-yl]methyl}piperazine-1-carboxylate; [M+H]⁺=664, prepared as diastereomer mixture, separated by flash chromatography.

tert-Butyl (2R,5S)-5-[(6,6-difluoro-1,4-oxazepan-4-yl)methyl]-4-(2-{6-[(4-fluorophenyl)methyl]-3,3-dimethyl-1H,2H,3H-pyrrolo[3,2-b]pyridin-1-yl}-2-oxoethyl)-2-methylpiperazine-1-carboxylate; [M+H]⁺=646.

tert-Butyl (2R,5S)-5-{[(2S)-2-(fluoromethyl)pyrrolidin-1-yl]methyl}-4-(2-{6-[(4-fluorophenyl)methyl]-3,3-dimethyl-1H,2H,3H-pyrrolo[3,2-b]pyridin-1-yl}-2-oxoethyl)-2-methylpiperazine-1-carboxylate; [M+H]⁺=612.

tert-Butyl (2R,5S)-5-[(2-cyanomorpholin-4-yl)methyl]-4-(2-{6-[(4-fluorophenyl)methyl]-3,3-dimethyl-1H,2H,3H-pyrrolo[3,2-b]pyridin-1-yl}-2-oxoethyl)-2-methylpiperazine-1-carboxylate; [M+H]⁺=621.

tert-Butyl (2R,5S)-4-(2-{6-[(4-fluorophenyl)methyl]-3,3-dimethyl-1H,2H,3H-pyrrolo[3,2-b]pyridin-1-yl}-2-oxoethyl)-2-methyl-5-[(2,2,3-trimethylmorpholin-4-yl)methyl]piperazine-1-carboxylate; [M+H]⁺=638.

tert-Butyl (2R,5S)-5-[(4-acetyl-2-methylpiperazin-1-yl)methyl]-4-(2-{6-[(4-fluorophenyl)methyl]-3,3-dimethyl-1H,2H,3H-pyrrolo[3,2-b]pyridin-1-yl}-2-oxoethyl)-2-methylpiperazine-1-carboxylate; [M+H]⁺=651.

tert-Butyl (2R,5S)-4-(2-{6-[(4-fluorophenyl)methyl]-3,3-dimethyl-1H,2H,3H-pyrrolo[3,2-b]pyridin-1-yl}-2-oxoethyl)-2-methyl-5-{[(2R)-2-methyl-3-oxopiperazin-1-yl]methyl}piperazine-1-carboxylate; [M+H]⁺=623.

tert-Butyl (2R,5S)-4-(2-{6-[(4-fluorophenyl)methyl]-3,3-dimethyl-1H,2H,3H-pyrrolo[3,2-b]pyridin-1-yl}-2-oxoethyl)-2-methyl-5-{[(2S)-2-(trifluoromethyl)pyrrolidin-1-yl]methyl}piperazine-1-carboxylate; 1H NMR (400 MHz, Me-d3-OD): 8.26 (1H, s), 8.07 (1H, s), 7.24 (2H, dd), 7.02 (2H, t), 4.18 (1H, s), 4.13-3.88 (5H, m), 3.79 (1H, d), 3.55 (1H, d), 3.33 (1H, d), 3.30-3.12 (4H, m), 3.07 (1H, s), 2.99-2.73 (1H, m), 2.65 (1H, dd), 2.60-2.34 (2H, m), 2.13-1.96 (1H, m), 1.96-1.70 (3H, m), 1.70-1.44 (9H, m), 1.39 (6H, s), 1.24 (3H, d).

tert-Butyl (2R,5S)-4-(2-{6-[(4-fluorophenyl)methyl]-3,3-dimethyl-1H,2H,3H-pyrrolo[3,2-b]pyridin-1-yl}-2-oxoethyl)-5-{[(3R,5R)-3-(tert-butyldimethylsilyloxymethyl)-5-methylmorpholin-4-yl]methyl}-2-methylpiperazine-1-carboxylate; 1H NMR (400 MHz, CDCl3): 8.25 (1H, s), 8.10 (1H, s), 7.17 (2H, t), 6.98 (2H, t), 4.21 (1H, d), 4.10-3.94 (3H, m), 3.92 (2H, d), 3.88-3.81 (1H, m), 3.71 (1H, dd), 3.54-3.46 (2H, m), 3.46-3.36 (2H, m), 3.31-3.22 (1H, m), 3.13 (1H, d), 3.09-3.01 (1H, m), 2.90-2.76 (2H, m), 2.72 (2H, d), 2.60-2.39 (2H, m), 1.53-1.44 (9H, m), 1.41 (6H, d), 1.23 (3H, d), 1.01 (3H, d), 0.86 (9H, s), 0.03 (6H, d).

tert-Butyl (2R,5S)-4-(2-{6-[(4-fluorophenyl)methyl]-3,3-dimethyl-1H,2H,3H-pyrrolo[3,2-b]pyridin-1-yl}-2-oxoethyl)-2-methyl-5-{[(2R)-2-(trifluoromethyl)pyrrolidin-1-yl]methyl}piperazine-1-carboxylate; 1H NMR (400 MHz, Me-d3-OD): 8.26 (1H, s), 8.07 (1H, s), 7.23 (2H, t), 7.01 (2H, t), 4.24-4.01 (5H, m), 3.95 (2H, s), 3.75-3.59 (1H, m), 3.59-3.38 (1H, m), 3.28-3.04 (4H, m), 2.97 (1H, d), 2.84 (1H, dd), 2.68 (1H, d), 2.52 (1H, d), 2.45-2.28 (1H, m), 2.11-1.95 (1H, m), 1.95-1.70 (3H, m), 1.49-1.43 (9H, m), 1.40 (6H, d), 1.22 (3H, d).

tert-Butyl (2R,5S)-5-{[(3S,4R)-3-fluoro-4-methoxypyrrolidin-1-yl]methyl}-4-(2-{6-[(4-fluorophenyl)methyl]-3,3-dimethyl-1H,2H,3H-pyrrolo[3,2-b]pyridin-1-yl}-2-oxoethyl)-2-methylpiperazine-1-carboxylate and tert-Butyl (2R,5S)-5-{[(3R,4S)-3-fluoro-4-methoxypyrrolidin-1-yl]methyl}-4-(2-{6-[(4-fluorophenyl)methyl]-3,3-dimethyl-1H,2H,3H-pyrrolo[3,2-b]pyridin-1-yl}-2-oxoethyl)-2-methylpiperazine-1-carboxylate; [M+H]⁺=628.

tert-Butyl (2R,5S)-4-(2-{6-[(4-fluorophenyl)methyl]-3,3-dimethyl-1H,2H,3H-pyrrolo[3,2-b]pyridin-1-yl}-2-oxoethyl)-2-methyl-5-{(3-oxopiperazin-1-yl)methyl]piperazine-1-carboxylate; [M+H]⁺=609.

(2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-(3-oxo-[1,4]diazepan-1-ylmethyl)-piperazine-1-carboxylic acid tert-butyl ester; [M+H]⁺=623.

(2R,5S)-4-{2-[6-(4-Fluoro-benzyl)-3,3-dimethyl-2,3-dihydro-pyrrolo[3,2-b]pyridin-1-yl]-2-oxo-ethyl}-5-(3-hydroxymethyl-3-methyl-morpholin-4-ylmethyl)-2-methyl-piperazine-1-carboxylic acid tert-butyl ester; [M+H]⁺=640.

(2R,5S)-5-((2R,5S)-2,5-Dimethyl-3-oxo-piperazin-1-yl methyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester, 70:30 mixture with a diastereoisomer; [M+H]⁺=637.

(2R,5S)-4-{2-[6-(4-Fluoro-benzyl)-3,3-dimethyl-2,3-dihydro-pyrrolo[3,2-b]pyridin-1-yl]-2-oxo-ethyl}-5-((S)-3-hydroxymethyl-3-methyl-morpholin-4-ylmethyl)-2-methyl-piperazine-1-carboxylic acid tert-butyl ester (Diastereomeric mixture separated by chromatography); [M+H]⁺=640.

(2R,5S)-4-{2-[6-(4-Fluoro-benzyl)-3,3-dimethyl-2,3-dihydro-pyrrolo[3,2-b]pyridin-1-yl]-2-oxo-ethyl}-5-((R)-3-hydroxymethyl-3-methyl-morpholin-4-ylmethyl)-2-methyl-piperazine-1-carboxylic acid tert-butyl ester (Diastereomeric mixture separated by chromatography); [M+H]⁺=640.

(2R,5S)-5-((R)-4-Acetyl-2-methyl-piperazin-1-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester; [M+H]⁺=651.

(2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-((R)-2-methyl-4-pyrimidin-2-yl-piperazin-1-ylmethyl)-piperazine-1-carboxylic acid tert-butyl ester; [M+H]⁺=687.

4-{[(2S,5R)-4-[(tert-Butoxy)carbonyl]-1-(2-{6-[(2,4-difluorophenyl)methyl]-3,3-dimethyl-1H,2H,3H-pyrrolo[3,2-b]pyridin-1-yl}-2-oxoethyl)-5-methylpiperazin-2-yl]methyl}-3-methylmorpholine-3-carboxylic acid; [M+H]⁺=654.

(2R,5S)-5-(5,6-Dihydro-8H-[1,2,4]triazolo[4,3-a]pyrazin-7-ylmethyl)-4-{2-[6-(4-fluoro-benzyl)-3,3-dimethyl-2,3- dihydro-pyrrolo[3,2-b]pyridin-1-yl]-2-oxo-ethyl}-2-methyl-piperazine-1-carboxylic acid tert-butyl ester; [M+H]⁺ 633.

Preparation 21: (2R,5S)-4-Benzyl-5-((3R,5R)-3,5-dimethyl-morpholin-4-ylmethyl)-2-methyl-piperazine-1-carboxylic acid tert-butyl ester

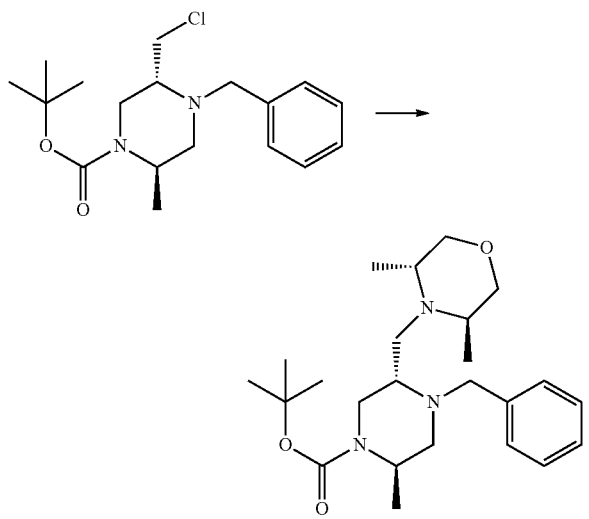

K₂CO₃ (2.7 g, 19.5 mmol) and KI (1.83 g, 11.05 mmol) were added to a solution of (2R,5R)-4-benzyl-5-chloromethyl-2-methyl-piperazine-1-carboxylic acid tert-butyl ester (2.2 g, 6.5 mmol) in acetonitrile (30 mL) followed by (3R,5R)-3,5-dimethyl-morpholine (0.80 g, 7.0 mmol). The reaction was stirred at 70° C. for 18 h. The solid was then removed by filtration and the solvent removed in vacuo. The residue was partitioned between water and dichloromethane. The organic phase was dried, filtered and the solvent evaporated. The crude material was purified by chromatography on silica (0-40% EtOAc in Petrol) to give the title compound (2.56 g, 94%) as a white solid. MS: [M+H]⁺=418.

Preparation 22: (2R,5S)-5-((3R,5R)-3,5-Dimethyl-morpholin-4-ylmethyl)-2-methyl-piperazine-1-carboxylic acid tert-butyl ester

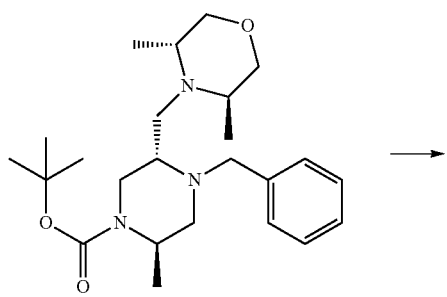

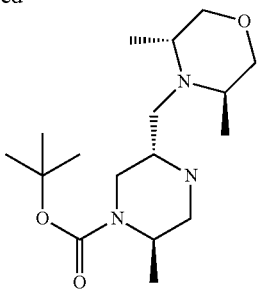

Pd/C (1.6 g) and acetic acid (10 mL) were added to a solution of (2R,5S)-4-benzyl-5-((3R,5R)-3,5-dimethyl-morpholin-4-ylmethyl)-2-methyl-piperazine-1-carboxylic acid tert-butyl ester (2.5 g, 6.0 mmol) in EtOH (70 mL). The mixture was stirred under H₂ (1 atmosphere) at room temperature for 3 h. The reaction mixture was then filtered through a pad of Celite to remove the catalyst and the solvent was removed in vacuo. The crude material was partitioned between saturated aqueous NaHCO₃ and DCM and the product extracted with DCM (3×). The organic phase was dried over MgSO₄, filtered and concentrated in vacuo to give the title compound (1.53 g, 78%) as a pale yellow oil. 1H NMR (400 MHz, CDCl3): 4.16 (1H, s), 3.79-3.59 (3H, m), 3.44-3.19 (3H, m), 3.08 (1H, dd), 2.99-2.69 (4H, m), 2.52 (1H, dd), 2.29 (1H, dd), 1.47 (9H, s), 1.27 (3H, d), 1.00 (6H, d).

The following compounds were prepared in an analogous method to that shown in Preparations 21 and 22:

22A: 2-Methyl-(2R,5S)-5-((3R)-3-methyl-morpholin-4-ylmethyl)-2-methyl-piperazine-1-carboxylic acid tert-butyl ester.

22B: tert-Butyl (2R,5S)-5-{[(2R)-4-acetyl-2-methylpiperazin-1-yl]methyl}-2-methylpiperazine-1-carboxylate; [M+H]⁺=355.

22C: tert-Butyl (2R,5S)-5-{[3-(hydroxymethyl)-3-methyl-morpholin-4-yl]methyl}-2-methylpiperazine-1-carboxylate; [M+H]⁺=344.

22D: (2R,5S)-5-((R)-3-Methoxymethyl-morpholin-4-ylmethyl)-2-methyl-piperazine-1-carboxylic acid tert-butyl ester; [M+H]⁺=344.

22E: (2R,5S)-5-(3-Hydroxymethyl-3-methyl-morpholin-4-ylmethyl)-2-methyl-piperazine-1-carboxylic acid tert-butyl ester.

22F: (2R,5S)-5-((2S,6R)-4-Acetyl-2,6-dimethyl-piperazin-1-ylmethyl)-2-methyl-piperazine-1-carboxylic acid tert-butyl ester; ¹H NMR (400 MHz, CDCl3): 4.15-4.05 (2H, m), 3.72 (1H, d), 3.57-3.39 (1H, m), 3.39-3.16 (1H, m), 3.16-2.91 (3H, m), 2.91-2.70 (2H, m), 2.66-2.50 (4H, m), 2.09 (3H, s), 1.48-1.45 (9H, m), 1.27-1.23 (3H, m), 1.16-1.08 (6H, m). [Prepared from 1-((3S,5R)-3,5-Dimethyl-piperazin-1-yl)ethanone, see Tetrahedron Letters (1997), 38(21), 3751-3754].

22G: (2R,5S)-5-(3-Methoxymethyl-3-methyl-morpholin-4-ylmethyl)-2-methyl-piperazine-1-carboxylic acid tert-butyl ester; 1H NMR (400 MHz, CDCl3): 4.16 (1.1H, s), 4.08-3.52 (4.9H, m), 3.51-3.16 (6.8H, m), 3.16-3.00 (1.1H, m), 2.99-2.81 (1.5H, m), 2.81-2.46 (3.6H, m), 2.46-2.23 (1.1;H, m), 2.23-1.58 (1.6H, m), 1.49 (9.0H, d), 1.28 (2.9H, t), 1.25-1.21 (0.7H, m), 1.04 (2.8H, d) [mixture of diastereomers].

Preparation 23: (2R,5S)-4-[2-(6-Benzyl-3,3-dimethyl-2,3-dihydro-pyrrolo[3,2-b]pyridin-1-yl)-2-oxoethyl]-5-((3R,5R)-3,5-dimethyl-morpholin-4-ylmethyl)-2-methyl-piperazine-1-carboxylic acid tert-butyl ester

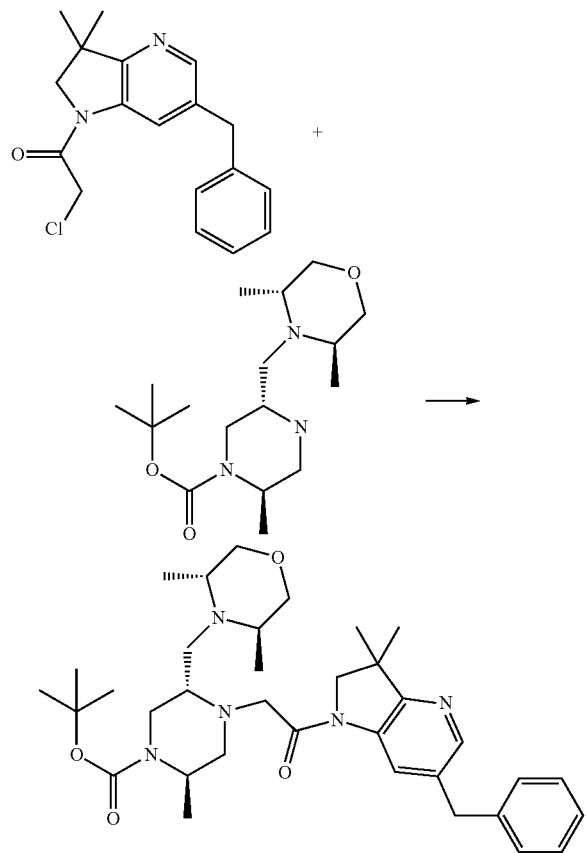

A mixture of 1-(6-benzyl-3,3-dimethyl-2,3-dihydro-pyrrolo[3,2-b]pyridin-1-yl)-2-chloro-ethanone hydrochloride (0.157 g, 0.45 mmol), (2R,5S)-5-((3R,5R)-3,5-dimethyl-morpholin-4-ylmethyl)-2-methyl-piperazine-1-carboxylic acid tert-butyl ester (0.164 g, 0.5 mmol), potassium carbonate (0.276 g, 2.0 mmol) and finely ground potassium iodide (0.166 g, 1.0 mmol) in acetonitrile (3 mL) was stirred at 20° C. for 18 h. Water (20 mL) was added and the mixture was extracted with DCM (20 mL). The organic phase was dried (MgSO$_4$) and evaporated in vacuo. The crude material was purified by chromatography on silica (0-100% EtOAc in Petrol) to give the title compound (0.203 g, 75%) as a white semi-solid. MS: [M+H]$^+$=606.

Compounds listed below were prepared in an analogous manner to that of Preparation 23:

(2R,5S)-4-{2-[6-(1,1-Difluoro-propyl)-3,3-di methyl-2,3-dihydro-pyrrolo[3,2-b]pyridin-1-yl]-2-oxo-ethyl}-5-((3R,5R)-3,5-dimethyl-morpholin-4-ylmethyl)-2-methyl-piperazine-1-carboxylic acid tert-butyl ester; [M+H]$^+$=594.

(2R,5S)-4-{2-[6-(1,1-Difluoro-butyl)-3,3-dimethyl-2,3-dihydro-pyrrolo[3,2-c]pyridin-1-yl]-2-oxo-ethyl}-5-((3R,5R)-3,5-dimethyl-morpholin-4-ylmethyl)-2-methyl-piperazine-1-carboxylic acid tert-butyl ester; [M+H]$^+$=608.

tert-Butyl (2R,5S)-4-(2-{6-[(2,4-difluorophenyl)methyl]-3,3-dimethyl-1H,2H,3H-pyrrolo[3,2-b]pyridin-1-yl}-2-oxoethyl)-5-{[(3R,5R)-3,5-di methyl morpholin-4-yl]methyl}-2-methylpiperazine-1-carboxylate; [M+H]$^+$=642.

tert-Butyl (2R,5S)-5-{[(3R,5R)-3,5-di methyl morpholin-4-yl]methyl}-4-(2-{6-[(4-fluorophenyl)methyl]-3,3-dimethyl-1H,2H,3H-pyrrolo[3,2-c]pyridin-1-yl}-2-oxoethyl)-2-methylpiperazine-1-carboxylate; [M+H]$^+$=624.

tert-Butyl (2R,5S)-5-{[(2R)-4-acetyl-2-methylpiperazin-1-yl]methyl}-4-(2-{6-[(4-fluorophenyl)methyl]-3,3-dimethyl-1H,2H,3H-pyrrolo[3,2-c]pyridin-1-yl}-2-oxoethyl)-2-methylpiperazine-1-carboxylate; [M+H]$^+$=651.

tert-Butyl (2R,5S)-4-(2-{6-[(2,4-difluorophenyl)methyl]-3,3-dimethyl-1H,2H,3H-pyrrolo[3,2-b]pyridin-1-yl}-2-oxoethyl)-5-{[3-(hydroxymethyl)-3-methylmorpholin-4-yl]methyl}-2-methylpiperazine-1-carboxylate; [M+H]$^+$=658.

tert-Butyl (2R,5S)-5-{[(2R)-4-acetyl-2-methylpiperazin-1-yl]methyl}-4-{2-[6-(1,1-difluorobutyl)-3,3-dimethyl-1H,2H,3H-pyrrolo[3,2-c]pyridin-1-yl]-2-oxoethyl}-2-methylpiperazine-1-carboxylate; [M+H]$^+$=635.

tert-Butyl (2R,5S)-4-(2-{6-[(4-fluorophenyl)methyl]-3,3-dimethyl-1H,2H,3H-pyrrolo[3,2-c]pyridin-1-yl}-2-oxoethyl)-5-{[3-(hydroxymethyl)-3-methylmorpholin-4-yl]methyl}-2-methylpiperazine-1-carboxylate; [M+H]$^+$=640.

tert-Butyl (2R,5S)-4-(2-{6-[(2,4-difluorophenyl)methyl]-3,3-dimethyl-1H,2H,3H-pyrrolo[3,2-c]pyridin-1-yl}-2-oxoethyl)-5-{[(3R,5R)-3,5-dimethylmorpholin-4-yl]methyl}-2-methylpiperazine-1-carboxylate; [M+H]$^+$=642.

(2R,5S)-4-{2-[6-(2,4-Difluoro-benzyl)-3,3-dimethyl-2,3-dihydro-pyrrolo[3,2-c]pyridin-1-yl]-2-oxo-ethyl}-5-((S)-3-hydroxymethyl-3-methyl-morpholin-4-ylmethyl)-2-methyl-piperazine-1-carboxylic acid tert-butyl ester; [M+H]$^+$=658.

(2R,5S)-4-{2-[6-(1,1-Difluoro-butyl)-3,3-dimethyl-2,3-dihydro-pyrrolo[3,2-c]pyridin-1-yl]-2-oxo-ethyl}-5-((S)-3-hydroxymethyl-3-methyl-morpholin-4-ylmethyl)-2-methyl-piperazine-1-carboxylic acid tert-butyl ester; [M+H]$^+$=624.

(2R,5S)-4-{2-[6-(4-Fluoro-benzyl)-3,3-dimethyl-2,3-dihydro-pyrrolo[3,2-c]pyridin-1-yl]-2-oxo-ethyl}-5-((R)-3-methoxymethyl-morpholin-4-ylmethyl)-2-methyl-piperazine-1-carboxylic acid tert-butyl ester; [M+H]$^+$=640.

(2R,5S)-5-((3R,5R)-3,5-Dimethyl-morpholin-4-ylmethyl)-4-{2-[3-(4-fluoro-benzyl)-7,7-dimethyl-6,7-dihydro-pyrrolo[3,2-c]pyridazin-5-yl]-2-oxo-ethyl}-2-methyl-piperazine-1-carboxylic acid tert-butyl ester; [M+H]$^+$=625.

(2R,5S)-5-((3R,5R)-3,5-Dimethyl-morpholin-4-ylmethyl)-4-(2-{6-[(2-fluoro-phenyl)-(R or S)-hydroxy-methyl]-3,3-dimethyl-2,3-dihydro-pyrrolo[3,2-b]pyridin-1-yl}-2-oxo-ethyl)-2-methyl-piperazine-1-carboxylic acid tert-butyl ester (from slower eluting precursor); [M+H]$^+$=640.

(±)-(2R,5S)-5-((3R,5R)-3,5-Dimethyl-morpholin-4-ylmethyl)-4-(2-{6-[(4-fluoro-phenyl)-hydroxy-methyl]-3,3-dimethyl-2,3-dihydro-pyrrolo[3,2-b]pyridin-1-yl}-2-oxo-ethyl)-2-methyl-piperazine-1-carboxylic acid tert-butyl ester; [M+H]$^+$=640.

(2R,5S)-5-((3R,5R)-3,5-Dimethyl-morpholin-4-ylmethyl)-4-(2-{6-[(4-fluoro-phenyl)-(R)-hydroxy-methyl]-3,3-dimethyl-2,3-dihydro-pyrrolo[3,2-b]pyridin-1-yl}-2oxo-ethyl)-2-methyl-piperazine-1-carboxylic acid tert-butyl ester; [M+H]$^+$=640.

(2R,5S)-5-((3R,5R)-3,5-Dimethyl-morpholin-4-ylmethyl)-4-(2-{6-[(4-fluoro-phenyl)-(S)-hydroxy-methyl]-3,3-di methyl-2,3-dihydro-pyrrolo[3,2-b]pyridin-1-yl}-2-oxo-ethyl)-2-methyl-piperazine-1-carboxylic acid tert-butyl ester; [M+H]$^+$=640.

(2R,5S)-4-{2-[3-(2,4-Difluoro-benzyl)-7,7-dimethyl-6,7-dihydro-pyrrolo[3,2-c]pyridazin-5-yl]-2-oxo-ethyl}-5-((3R,5R)-3,5-dimethyl-morpholin-4-ylmethyl)-2-methyl-piperazine-1-carboxylic acid tert-butyl ester; [M+H]$^+$=643.

(2R,5S)-5-((3R,5R)-3,5-Dimethyl-morpholin-4-ylmethyl)-4-{2-[6-(1-hydroxy-butyl)-3,3-dimethyl-2,3-dihydro-pyrrolo[3,2-c]pyridin-1-yl]-2-oxo-ethyl}-2-methyl-piperazine-1-carboxylic acid tert-butyl ester; [M+H]$^+$=631 ($CO_2H$ adduct).

(2R,5S)-5-((2S,6R)-4-Acetyl-2,6-dimethyl-piperazin-1-ylmethyl)-4-{2-[6-(1,1-difluoro-butyl)-3,3-dimethyl-2,3-dihydro-pyrrolo[3,2-c]pyridin-1-yl]-2-oxo-ethyl}-2-methyl-piperazine-1-carboxylic acid tert-butyl ester; [M+H]$^+$=649.

(2R,5S)-4-{2-[6-(2,4-Difluoro-benzyl)-3,3-dimethyl-2,3-dihydro-pyrrolo[3,2-c]pyridin-1-yl]-2-oxo-ethyl}-5-(3-methoxymethyl-3-methyl-morpholin-4-ylmethyl)-2-methyl-piperazine-1-carboxylic acid tert-butyl ester; [M+H]$^+$=672.

(2R,5S)-4-{2-[6-(4-Fluoro-benzyl)-3,3-dimethyl-2,3-dihydro-pyrrolo[3,2-c]pyridin-1-yl]-2-oxo-ethyl}-5-(3-methoxymethyl-3-methyl-morpholin-4-ylmethyl)-2-methyl-piperazine-1-carboxylic acid tert-butyl ester; [M+H]$^+$=672.

(2R,5S)-4-[2-(6-Butyryl-3,3-dimethyl-2,3-dihydro-pyrrolo[3,2-b]pyridin-1-yl)-2-oxo-ethyl]-5-((3R,5R)-3,5-dimethyl-morpholin-4-ylmethyl)-2-methyl-piperazine-1-carboxylic acid tert-butyl ester; [M+H]$^+$=586. From reaction of the products of preparations 17P and 22.

(2R,5S)-4-(2-{6-[((R or S)-2,4-Difluoro-phenylhydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from slower eluting precursor); [M+H]$^+$=658.

(2R,5S)-4-(2-{6-[((R or S)-2,4-Difluoro-phenylhydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from faster eluting precursor); [M+H]$^+$=658.

(2R,5S)-4-(2-{6-[((R or S)-3-Fluoro-phenylyhydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from slower eluting precursor); [M+H]$^+$=640.

(2R,5S)-4-(2-{6-[((R or S)-3-Fluoro-phenylyhydroxy-methyl]-3,3-dimethyl-2,3-dihydro-pyrrolo[3,2-b]pyridin-1-yl}-2-oxo-ethyl)-5-((3R,5R)-3,5-di methyl-morpholin-4-ylmethyl)-2-methyl-piperazine-1-carboxylic acid tert-butyl ester (from faster eluting precursor); [M+H]$^+$=640.

(2R,5S)-4-(2-{6-[((R or S)-2-Fluoro-phenylyhydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from slower eluting precursor); [M+H]$^+$=640.

(2R,5S)-4-(2-{6-[((R or S)-2-Fluoro-phenylyhydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from faster eluting precursor); [M+H]$^+$=640.

(2R,5S)-4-(2-{6-[((R or S)-3,4-Difluoro-phenyl)-hydroxy-methyl]-3,3-dimethyl-2,3-dihydro-pyrrolo[3,2-b]pyridin-1-yl}-2-oxo-ethyl)-5-((3R,5R)-3,5-di methyl-morpholin-4-ylmethyl)-2-methyl-piperazine-1-carboxylic acid tert-butyl ester (from slower eluting precursor); [M+H]$^+$=658.

(2R,5S)-4-(2-{6-[((R or S)-3,4-Difluoro-phenyl)-hydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from faster eluting precursor); [M+H]$^+$=658.

(2R,5S)-4-(2-{6-[((R or S)-2,3-Difluoro-phenyl)-hydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from slower eluting precursor); [M+H]$^+$=658.

(2R,5S)-4-(2-{6-[((R or S)-2,3-Difluoro-phenyl)-hydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from faster eluting precursor); [M+H]$^+$=658.

(2R,5S)-5-((3R,5R)-3,5-Dimethyl-morpholin-4-ylmethyl)-4-{2-[(R or S)-6-(hydroxy-phenyl-methyl)-3,3-dimethyl-2,3-dihydro-pyrrolo[3,2-b]pyridin-1-yl]-2-oxo-ethyl}-2-methyl-piperazine-1-carboxylic acid tert-butyl ester (from faster eluting precursor); [M+H]$^+$=622.

(2R,5S)-5-((3R,5R)-3,5-Dimethyl-morpholin-4-ylmethyl)-4-{2-[(R or S)-6-(hydroxy-phenyl-methyl)-3,3-dimethyl-2,3-dihydro-pyrrolo[3,2-b]pyridin-1-yl]-2-oxo-ethyl}-2-methyl-piperazine-1-carboxylic acid tert-butyl ester (from slower eluting precursor); [M+H]$^+$=622.

(2R,5S)-4-(2-{(R or S)-6-[(2,5-Difluoro-phenyl)-hydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from 17GG, separation of diastereomer mixture using Lux-2 column eluting with heptane ethanol 75:25+0.2% diethylamine; faster eluting); [M+H]$^+$=658.

(2R,5S)-4-(2-{(R or S)-6-[(2,5-Difluoro-phenyl)-hydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from 17GG, separation of diastereomer mixture using Lux-2 column eluting with heptane ethanol 75:25+0.2% diethylamine; slower eluting); [M+H]$^+$=658.

(2R,5S)-4-(2-{(R or S)-6-[(2,6-Difluoro-phenyl)-hydroxy-methyl]-3,3-dimethyl-2,3-dihydro-pyrrolo[3,2-b]pyridin-1-yl}-2-oxo-ethyl)-5-((3R,5R)-3,5-dimethyl-morpholin-4-ylmethyl)-2-methyl-piperazine-1-carboxylic acid tert-butyl ester (from faster eluting precursor); [M+H]$^+$=658.

(2R,5S)-4-(2-{(R or S)-6-[(2,6-Difluoro-phenyl)-hydroxy-methyl]-3,3-dimethyl-2,3-dihydro-pyrrolo[3,2-b]pyridin-1-yl}-2-oxo-ethyl)-5-((3R,5R)-3,5-di methyl-morpholin-4-ylmethyl)-2-methyl-piperazine-1-carboxylic acid tert-butyl ester (from slower eluting precursor); [M+H]$^+$=658.

tert-Butyl (2R,5S)-5-{[(3R,5R)-3,5-di methyl morpholin-4-yl]methyl}-4-(2-{6-[(4-fluorophenyl)methyl]-3,3-dimethyl-1H,2H,3H-pyrrolo[3,2-b]pyridin-1-yl}-2-oxo-ethyl)-2-methylpiperazine-1-carboxylate-4-oxide; [M+H] 640.

Preparation 24: 2-Methyl-piperidin-4-one hydrochloride

2-Methyl-4-oxo-piperidine-1-carboxylic acid tert-butyl ester (1 g, 4.7 mmol) was dissolved in EtOAc (10 mL); to this was added 4 M HCl in 1,4-dioxane (10 mL). The sample was stirred at room temperature overnight and then evaporated to give the title compound. MS: [M+H]$^+$=114.

Preparation 25: (3S,5R)-3-((tert-Butyldimethylsilyloxy)methyl)-5-methyl-morpholine Prepared in an analogous manner to that described in Org. Biomol. Chem., 2011, 9, 7365.

Preparation 26: 6,6-Difluoro-[1,4]oxazepane-4-carboxylic acid tert-butyl ester 6-Oxo-[1,4]oxazepane-4-carboxylic acid tert-butyl ester (901 mg, 4.19 mol) was dissolved in DCM (21.76 mL) and cooled in ice. Diethylaminosulfur trifluoride (4.60 mL, 34.8 mmol) was added and the reaction stirred overnight (18 h). The reaction was poured into saturated aqueous sodium bicarbonate and stirred for 5 min. The solution was extracted with dichloromethane dried over sodium sulfate and concentrated. The crude product was purified by column chromatography on silica gel (gradient elution, 0-30%, ethyl acetate in petrol), to give the title compound (1.0 g). 1H NMR (400 MHz, CDCl3): 7.29 (1H, s), 4.26-3.74 (6H, m), 3.62 (2H, s), 1.50 (9H, s).

Preparation 27: 6,6-Difluoro-[1,4]oxazepane 6,6-Difluoro-[1,4]oxazepane-4-carboxylic acid tert-butyl ester (1.0 g, 4.22 mmol) was dissolved in 50% TFA/DCM (4.0 ml). The reaction was stirred overnight (18 h) and concentrated. The residue was dissolved in methanol and loaded onto an NH2 ion exchange column eluting with methanol to release the amine, to give the title compound (402 mg). 1H NMR (400 MHz, CDCl3): 4.10 (2H, t), 4.00 (2H, t), 3.52 (2H, t), 3.35-3.24 (2H, m).

Preparation 28: (R)-1-Benzyl-3-fluoro-piperidine and (S)-1-benzyl-2-fluoromethyl-pyrrolidine

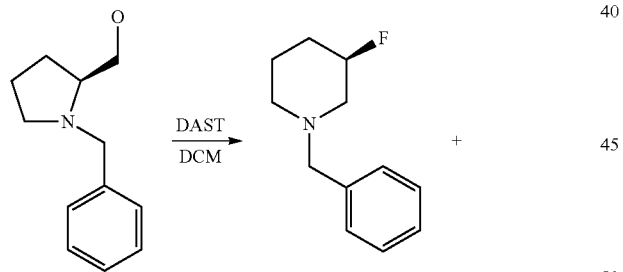

To a stirred solution of ((S)-1-benzyl-pyrrolidin-2-yl)-methanol (1.9 g, 10 mmol) in DCM (20 mL) was added diethylamino-sulfur trifluoride (DAST) (2.5 mL, 19.0 mmol) at −78° C. The reaction mixture was stirred at this temperature for 1 h, left to warm to room temperature and stirred for 2 h. The reaction mixture was poured on ice cooled saturated NaHCO3 solution, extracted with DCM. The organic phase was dried, filtered, the filtrate evaporated. The crude material was purified by chromatography on silica (0-30% EtOAc in Petrol) to give the mixture of the title compounds (0.89 g, 46%) as an oil. MS: [M+H]+=194. 19F NMR: −181, −220.

Preparation 29: (R)-3-Fluoro-piperidine and (S)-2-fluoromethyl-pyrrolidine hydrochloride

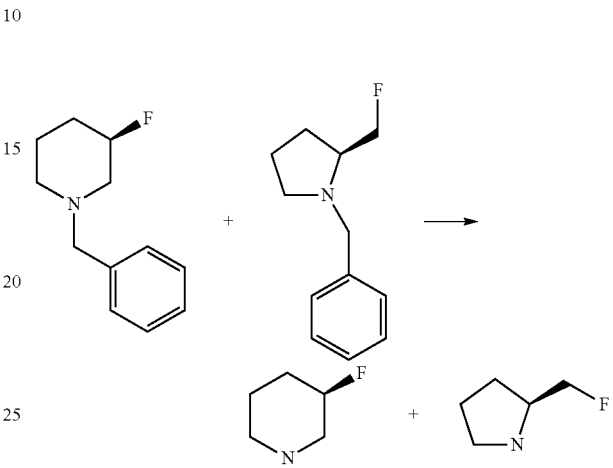

1-Chloroethyl chloroformate (0.55 mL, 5.1 mmol) was added to the above-obtained mixture of (R)-1-benzyl-3-fluoropiperidine and (S)-1-benzyl-2-fluoromethylpyrrolidine and (0.88 g, 4.56 mmol) in DCM (30 mL). The resultant mixture was refluxed for 2 hours, followed by cooling in air. The reaction solvent was removed under reduced pressure. The residue was dissolved in methanol (15 mL). The resultant mixture was refluxed for 1.5 hours, followed by cooling in air. The reaction solvent was removed under reduced pressure. Diethyl ether was added to the resultant mixture. The precipitate was collected by filtration, and then dried, to thereby give a 1:2 mixture of (S)-fluoromethylpyrrolidine hydrochloride and (3R)-fluoropiperidine hydrochloride (0.495 g, 79%). 1H-NMR (400 MHz, DMSO-d6) consistent as reported in EP1621537.

Preparation 30: 6-Oxa-3-aza-bicyclo[3.1.0]hexane-3-carboxylic acid benzyl ester

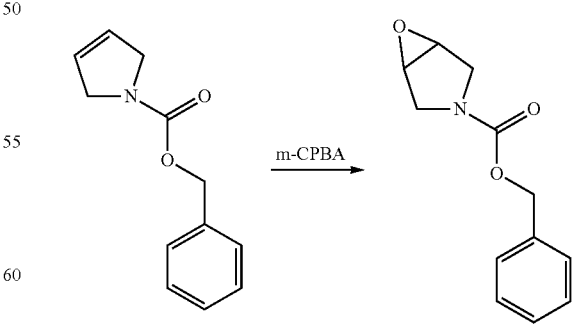

A mixture of commercially available 2,5-dihydro-pyrrole-1-carboxylic acid benzyl ester (5.0 g, 24.6 mmol) and m-CPBA (77%, 11.1 g, 50 mmol) in chloroform (100 mL) was stirred at 45° C. overnight. The reaction mixture was diluted with DCM (100 mL) and washed sequentially with sat. aq. Na₂S₂O₃, and 1N NaOH. The organic layer was dried with anhydrous MgSO₄ and then concentrated. The crude material was purified by chromatography on silica (20-70% EtOAc in Petrol) to give the title compound (4.65 g, 86%) as an oil. MS: [M+H]⁺=220.

Preparation 31:
trans-3-Hydroxy-4-methoxy-pyrrolidine-1-carboxylic acid benzyl ester

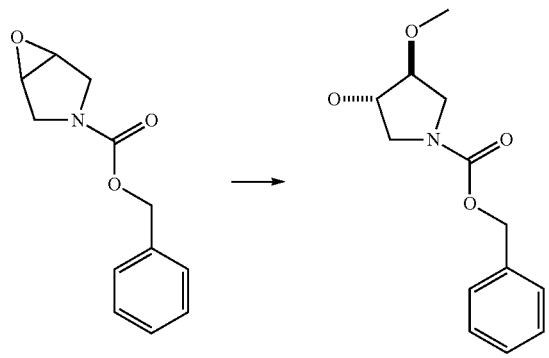 [SMILES: O=C(OCc1ccccc1)N1CC2OC2C1 ; CO[C@H]1CN(C(=O)OCc2ccccc2)C[C@@H]1O]

To a solution of LiOMe (0.97 g, 25.5 mmol) in MeOH (15 mL) was added 6-oxa-3-aza-bicyclo[3.1.0]hexane-3-carboxylic acid benzyl ester (1.11 g, 5.1 mmol) and the reaction mixture was stirred at room temperature for 3 days. After neutralization with AcOH under ice-cooling the solvent was evaporated, the residue was dissolved in DCM and washed with water. The organic layer was dried over MgSO₄ and concentrated. The crude material was purified by chromatography on silica (0-100% EtOAc in Petrol) to give the title compound (1.01 g, 79%). MS: [M+H]⁺=252.

Preparation 32:
cis-3-Fluoro-4-methoxy-pyrrolidine-1-carboxylic acid benzyl ester

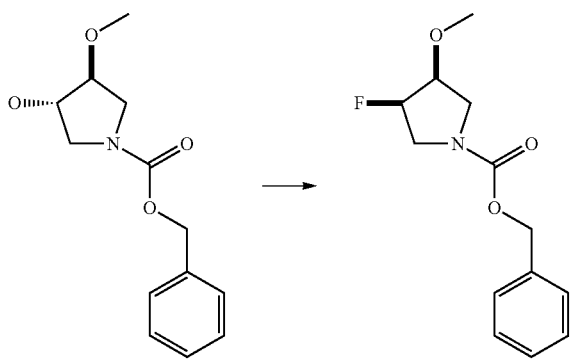 [SMILES: CO[C@H]1CN(C(=O)OCc2ccccc2)C[C@@H]1O ; CO[C@H]1CN(C(=O)OCc2ccccc2)C[C@H]1F]

To a stirred solution of trans-3-hydroxy-4-methoxy-pyrrolidine-1-carboxylic acid benzyl ester (194 mg, 0.77 mmol) in DCM (5 mL) was added diethylamino-sulfur trifluoride (DAST) (0.2 mL, 1.55 mmol) at −78° C. The reaction mixture was stirred at this temperature for 1 h, left to warm to room temperature and stirred for 16 h. The reaction mixture was poured on ice cooled saturated NaHCO₃ solution, extracted with DCM. The organic phase was dried, filtered, the filtrate evaporated. The crude material was purified by chromatography on silica (0-50% EtOAc in Petrol) to give the title compound (94 mg, 48%) as an oil. MS: [M+H]⁺=254. ¹⁹F NMR: −185

Preparation 33: cis-3-Fluoro-4-methoxy-pyrrolidine

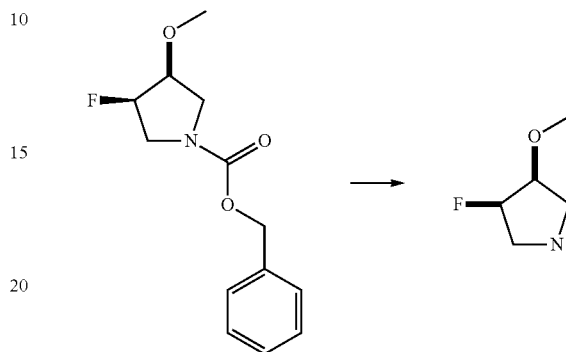

To a stirred solution of cis-3-fluoro-4-methoxy-pyrrolidine-1-carboxylic acid benzyl ester (94 mg, 0.37 mmol) in EtOH (5 mL) was added Pd/C (10%, 50 mg) and the mixture was hydrogenated for 1 h. The catalyst was filtered, the filtrate evaporated to afford colourless oil (31 mg, 70%). 1H NMR (400 MHz, CDCl3): 5.13 (2H, d), 4.08 (1H, d), 3.63-3.54 (1H, m), 3.50 (1H, d), 3.44 (5H, d).

Preparation 34: (2R,5S)-5-((R)-2,4-Dimethyl-3-oxo-piperazin-1-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester To (2R,5S)-4-{2-[6-(4-fluoro-benzyl)-3,3-dimethyl-2,3-dihydro-pyrrolo[3,2-b]pyridin-1-yl]-2-oxo-ethyl}-2-methyl-5-((R)-2-methyl-3-oxo-piperazin-1-ylmethyl)-piperazine-1-carboxylic acid tert-butyl ester (168 mg, 0.27 mmol) dissolved in anhydrous DMF (1.35 mL) cooled to 0° C. (ice bath) was added sodium hydride 60% in mineral oil (14 mg, 0.30 mmol). The reaction was stirred for 30 min at this temperature and methyl iodide (18 μL, 0.30 mmol) added. After stirring for 3 h, the reaction was poured into water, extracted with dichloromethane and the organic phase concentrated. The crude product was purified by column chromatography on silica gel (gradient elution, 0-100%, ethyl acetate—petrol) to give the title compound (101 mg) MS: [M+H]⁺ 637.

Preparation 35: 3,3-Dimethyl-6-propionyl-2,3-dihydro-pyrrolo[3,2-b]pyridine-1-carboxylic acid tert-butyl ester 6-Bromo-3,3-dimethyl-2,3-dihydro-pyrrolo[3,2-b]pyridine-1-carboxylic acid tert-butyl ester (1.33 g, 4.07 mmol) in THF (20.3 mL) was cooled to −78° C. under nitrogen and butyllithium (2.5 M in hexanes, 3.75 mL, 9.4 mmol) added. The reaction was stirred at this temperature for 30 minutes. To this was added N-methoxy-N-methyl-propionamide (0.71 g, 6.1 mmol) and the reaction was stirred for 1 h. Water and EtOAc were added and the organic layer separated, washed with brine (3×) and dried with sodium sulfate, filtered and concentrated. Chromatography (silica gel, gradient elution, 0-60%, EtOAc in petrol 40-60) gave the title compound (0.823 g), MS: [M+H]$^+$=305, as a 2:1 mixture with 3,3-dimethyl-2,3-dihydro-pyrrolo[3,2-b]pyridine-1-carboxylic acid tert-butyl ester.

The following compound was made following an analogous procedure to Preparation 35: 35A: 6-Butyryl-3,3-dimethyl-2,3-dihydro-pyrrolo[3,2-b]pyridine-1-carboxylic acid tert-butyl ester; [M+H]$^+$=319.

Preparation 36: 6-(1,1-Difluoro-propyl)-3,3-dimethyl-2,3-dihydro-pyrrolo[3,2-b]pyridine-1-carboxylic acid tert-butyl ester The product mixture from Preparation 35 (0.50 g) was dissolved in a THF solution of Deoxo-Fluor (50%, 1.64 g, 7.4 mmol) and was heated at 90° C. for 18 h. The reaction was cooled to room temperature and poured into saturated aqueous sodium carbonate. The mixture was extracted with DCM (3×), dried with sodium sulfate, filtered and concentrated. Chromatography (silica gel, gradient elution, 0-25%, EtOAc/petrol 40-60) gave the title compound (0.25 g). MS: [M+H]$^+$=327.

Preparation 37: 6-(1,1-Difluoro-propyl)-3,3-dimethyl-2,3-dihydro-1H-pyrrolo[3,2-b]pyridine 6-(1,1-Difluoro-propyl)-3,3-dimethyl-2,3-dihydro-pyrrolo[3,2-b]pyridine-1-carboxylic acid tert-butyl ester (0.245 g, 0.75 mmol) was dissolved in 5M aqueous HCl and MeOH (1:1, 10 mL) and the reaction was stirred at room temperature for 18 h. The solvent was removed in vacuo, to give the title compound (0.178 g) MS: [M+H]$^+$=227.

Preparation 38: 6-Butyl-3,3-dimethyl-5-oxy-2,3-dihydro-pyrrolo[3,2-c]pyridine-1-carboxylic acid tert-butyl ester A degassed mixture of 6-chloro-3,3-dimethyl-2,3-dihydro-pyrrolo[3,2-c]pyridine-1-carboxylic acid tert-butyl ester (2.82 g, 10 mmol), lithium bromide (2.58 g, 30 mmol), (1,3-diisopropylimidazol-2-ylidene)(3-chloropyridyl)palladium (II) dichloride (0.136 g, 0.2 mmol), butylzinc bromide (0.5 M in THF; 40 mL, 20 mmol), THF (30 mL) and NMP (30 mL) was stirred under nitrogen at 20° C. for 18 h. Mixture was poured into water (200 mL) and extracted with ether. Aqueous phase was treated with 10% aqueous citric acid (30 mL) then re-extracted with ether (100 mL). The combined ether layers were treated with petrol (50 mL) then washed with water (3×80 mL). The organic phase was dried (MgSO4) and evaporated to give a pale yellow oil (2.90 g). A mixture of this material and 3-chloroperbenzoic acid (3.0 g, 13.4 mmol) in DCM was stirred at 20° C. for 2 h. Further 3-chloroperbenzoic acid (1.0 g, 7.7 mmol) was added and stirring continued for 1 h. The mixture was then applied directly to a pre-packed silica cartridge. Chromatography (SiO$_2$ gradient elution, 0-20%, EtOAc in petrol) gave the title compound (1.725 g). MS: [M+H]$^+$=321.

Preparation 39: 6-(1-Hydroxy-butyl)-3,3-dimethyl-2,3-dihydro-pyrrolo[3,2-c]pyridine-1-carboxylic acid tert-butyl ester A mixture of 6-butyl-3,3-dimethyl-5-oxy-2,3-dihydro-pyrrolo[3,2-c]pyridine-1-carboxylic acid tert-butyl ester (1.72 g, 5.4 mmol) and acetic anhydride (10 mL) was stirred at 100° C. for 2 h then poured into ice-water (50 g). Resulting mixture was stirred for 1 h then treated with NaHCO$_3$. The mixture was extracted with DCM (3×50 mL) and the combined extracts were dried and evaporated to give an oil. This material was treated with water (2 mL), methanol (10 mL) and sodium hydroxide (0.28 g) and the mixture stirred for 2 h at 20° C. Mixture was poured into brine and extracted with DCM (3×50 mL). Combined organic extracts were dried and evaporated to give an oil. Chromatography (SiO$_2$, 0-50% ether in petrol gradient) gave the title compound (1.44 g). MS: [M+H]$^+$=321.

Preparation 40: 6-(1,1-Difluoro-butyl)-3,3-dimethyl-2,3-dihydro-pyrrolo[3,2-c]pyridine-1-carboxylic acid tert-butyl ester A mixture of 6-(1-hydroxy-butyl)-3,3-dimethyl-2,3-dihydro-pyrrolo[3,2-c]pyridine-1-carboxylic acid tert-butyl ester (1.44 g, 4.5 mmol) and manganese (IV) oxide (3.92, 45 mmol) in dichloromethane (30 mL) was stirred at 20° C. for 18 h. Solids were removed by filtration and filtrate evaporated to give a solid (1.19 g). A solution of this material in DCM (4 mL) was added to a stirred solution of DAST (3.61 g, 22.5 mmol) in DCM (8 mL) at −78° C. under nitrogen. Mixture was stirred at −70° C. for 1 h then at 20° C. for 40 h. Mixture was slowly poured into ice water (~80 g) and resulting two phase mixture neutralised with NaHCO$_3$. Resulting mixture was extracted with DCM (3×30 mL) and combined extracts dried and evaporated to give an oil. Chromatography (SiO$_2$, 0-40% ether in petrol gradient) gave the title compound (1.113 g). MS: [M+H]$^+$=341.

Preparation 41: 6-(1,1-Difluoro-butyl)-3,3-dimethyl-2,3-dihydro-1H-pyrrolo[3,2-c]pyridine A mixture of 6-(1,1-difluoro-butyl)-3,3-dimethyl-2,3-dihydro-pyrrolo[3,2-c]pyridine-1-carboxylic acid tert-butyl ester (1.113 g, 3.3 mmol) methanol (20 mL) and 5 M aqueous HCl (20 mL) was stirred at 20° C. for 72 h then evaporated in vacuo. The residue from evaporation was converted to the free base by partion between DCM and aqueous sodium hydrogen carbonate to give the title compound (0.799 g) as an oil. MS: [M+H]$^+$=241.

Preparation 42: 6-Chloro-3,3-dimethyl-2,3-dihydro-indole-1-carboxylic acid tert-butyl ester To 6-chloro-3,3-dimethyl-2,3-dihydro-1H-indole (10 g, 55.25 mmol) and di-tert-butyl carbonate (13.24 g, 60.77 mmol) in anhydrous THF (76 mL) was added triethylamine (30.8 mL, 221 mmol) at room temperature. The reaction was stirred at room temperature for 1 h after which time, 4-dimethylaminopyridine (50 mg) was added. The reaction was stirred for an additional 1 h and dimethylaminopyridine (100 mg) added followed by di-tert-butyl carbonate (6.0 g, 27.6 mmol). Left to stir overnight (18 h), and di-tert-butyl carbonate (6.0 g, 27.6 mmol) added. The reaction was stirred for 24 h and then concentrated. The crude product was purified by column chromatography on silica gel (gradient elution, 0-100%, ethyl acetate/petrol). To give the title compound (13 g). M+H=226 (-tBu).

Preparation 43: 6-(4-Fluoro-benzyl)-3,3-dimethyl-2,3-dihydro-indole-1-carboxylic acid tert-butyl ester 6-Chloro-3,3-dimethyl-2,3-dihydro-indole-1-carboxylic acid tert-butyl ester (10.99 g, 39.11 mmol) was dissolved in NMP/THF (1:1) (390 mL) and both (1,3-diisopropylimidazol-2-ylidene)(3-chloropyridyl)palladium(11) dichloride (720 mg, 1.06 mmol) and lithium bromide (7.2 g, 82.91 mmol) were added. After stirring for 5 min 0.5M 4-fluoro benzyl zinc chloride (391 mL, 195.55 mmol) was added at room temperature. After stirring at the same temperature for 1 h, the reaction was poured into ice/water (700 mL) and allowed to stir for 20 min. 5% aqueous citric acid (35 mL) was added and the aqueous extracted with diethyl ether (3×). The combined organic extracts were washed with water (3×), saturated brine solution (3×), dried over sodium sulfate, filtered and concentrated, the crude product was purified by column chromatography on silica gel (gradient elution, 0-50%, ethyl acetate/petrol), to give the title compound (7.3 g), MS: $[M+H]^+=300(-tBu)$ Preparation 44: 6-(4-Fluoro-benzyl)-3,3-dimethyl-2, 3-dihydro-1H-indole 6-(4-Fluoro-benzyl)-3,3-dimethyl-2,3-dihydro-indole-1-carboxylic acid tert-butyl ester (7.0 g, 19.72 mmol) was dissolved in methanol (247 mL) at 50° C. 5M HCl aq (247 mL) was added and the reaction stirred for 1 h. Concentrated HCl (50 mL) was added and the reaction stirred at 60° C. overnight. The reaction was concentrated in vacuo and the solid was triturated with diethyl ether. The solid was slurried in 1M NaOH (100 mL) and sodium hydroxide pellets added until pH 11. The resulting basic slurry was extracted with DCM (3×) and concentrated, to give the title compound (4.9 g) MS: $[M+H]^+=256$.

Preparation 45: 2-Chloro-1-[6-(4-fluoro-benzyl)-3, 3-dimethyl-2,3-dihydro-indol-1-yl]-ethanone 6-(4-Fluoro-benzyl)-3,3-dimethyl-2,3-dihydro-1H-indole (575 mg, 2.25 mmol) was dissolved in ether (11.28 mL) and cooled to −20° C. Pyridine (0.18 mL, 2.25 mmol) and chloro acetyl chloride (0.23 mL, 2.71 mmol) were added. The reaction was allowed to warm gently to room temperature overnight (18 h). Water (5.0 mL) was added and extracted with diethyl ether (2×6.0 mL). The combined organic extracts were dried over sodium sulfate, filtered and concentrated. The crude oil was purified by column chromatography on silica gel (gradient elution, 0-50%, ethyl acetate/petrol), to give the title compound (625 mg), 1H NMR (400 MHz, CDCl3): 8.10 (1H, s), 7.18 (2H, dd), 7.08 (1H, d), 7.03-6.85 (3H, m), 4.15 (2H, s), 3.95 (2H, s), 3.89 (2H, s), 1.38 (6H, s).

Preparation 46: (2R,5S)-4-{2-[6-(4-Fluoro-benzyl)-3,3-dimethyl-2,3-dihydro-indol-1-yl]-2-oxo-ethyl}-2-methyl-5-((R)-3-methyl-morpholin-4-ylmethyl)-piperazine-1-carboxylic acid tert-butyl ester 2-Chloro-1-[6-(4-fluoro-benzyl)-3,3-dimethyl-2,3-dihydro-indol-1-yl]-ethanone (200 mg, 0.60 mol), potassium iodide (201 mg, 1.21 mmol), potassium carbonate (334 mg, 2.42 mmol) and (2R,5S)-2-methyl-(2R,5S)-5-((3R)-3-methyl-morpholin-4-ylmethyl)-2-methyl-piperazine-1-carboxylic acid tert-butyl ester (189 mg, 0.60 mmol) were slurried in acetonitrile (3.0 mL). The reaction was stirred at room temperature for 2 h, diluted with dichloromethane and concentrated. The crude product was purified by column chromatography on silica gel (gradient elution, 0-100%, ethyl acetate/petrol), to give the title compound (350 mg), MS: $[M+H]^+=609$.

The compound listed below was prepared following an analogous method to that described in Preparation 46, with additional purification by chromatography as necessary: 46A: (2R,5S)-5-((3R,5R)-3,5-Dimethyl-morpholin-4-ylmethyl)-4-{2-[6-(4-fluoro-benzyl)-3,3-dimethyl-2,3-dihydro-indol-1-yl]-2-oxo-ethyl}-2-methyl-piperazine-1-carboxylic acid tert-butyl ester; MS: $[M+H]^+=623$.

Preparation 47: (3R,6S)-3,6-Dimethyl-piperazin-2-one ((S)-2-Amino-propyl)-carbamic acid tert-butyl ester hydrochloride (500 mg, 2.37 mmol) was added to a mixture of (S)-2-bromo-propionic acid (399 mg, 2.6 mmol), 1-ethyl-3-(3-dimethylaminopropyl) carbodiimide hydrochloride (600 mg, 3.1 mmol), 1-hydroxybenzotriazole hydrate (420 mg, 3.1 mmol) and N-ethylmorpholine (0.9 mL, 7.11 mmol) in DCM (10 mL) which was stirred at room temperature under a nitrogen atmosphere overnight. Water (20 mL) was added and the DCM layer was collected through a hydrophobic frit. The aqueous was further washed with DCM (2×10 mL) and the organic extracts were combined and evaporated. The crude was purified by chromatography, product elutes at approx 45% EtOAc in petrol 40:60 which was collected and evaporated to give [(S)-2-((S)-2-bromo-propionylamino)-propyl]carbamic acid tert-butyl ester as a solid (465 mg). 1H NMR (400 MHz, DMSO-d6): 8.08-7.92 (1H, m), 6.81 (1H, d), 4.50-4.37 (1H, m), 3.85-3.71 (1H, m), 3.07-2.84 (2H, m), 1.65 (d) and 1.60-1.46 (m); together 3H, 1.37 (9H, s), 0.99 (3H, t). This material was suspended in EtOAc (5 mL) and to this was added 4 M HCl in 1,4-dioxane (8 mL) and the sample was stirred at room temperature for 5 h. The mixture was evaporated and the residue suspended in acetonitrile (10 mL) and to this was added triethylamine (0.42 mL, 3 mmol) and the sample heated to 85° C. overnight. The reaction was cooled and evaporated then the residue was purified by SCX cartridge (washed with 3 column volumes of methanol, eluted with 2 column volumes of 2 M NH$_3$ in methanol) and product was collected and evaporated to give the title compound as a 70:30 mixture with a diastereomer (165 mg). 1H NMR (400 MHz, DMSO-d6): 7.48 (1H, d), 3.38 (1H, dd), 3.20-3.12 (1H, m), 2.86-2.76 (1H, m), 2.59 (1H, s), 1.18-1.12 (3H, m), 1.07 (3H, d).

Preparation 48: 3-Methyl-morpholine-3-carboxylic acid

3-Methyl-3-hydroxymethylmorpholine (*Archiv der Pharmazie and Berichte der Deutschen Pharmazeutischen Gesellschaft*, 1964, 297 (10), 632-8) (0.70 g, 5.34 mmol), di-t-Butyl dicarbonate (1.165 g, 5.34 mmol) and triethylamine (0.74 ml, 5.34 mmol) in DMF (10 ml) was stirred at room temperature overnight. Water was added (20 mL) and mixture extracted with EtOAc (2×30 mL). Combined organic extracts were washed with brine (30 mL) and solvent evaporated. Chromatography (0-50% EtOAc/Petrol gradient) gave a colourless oil (900 mg). This material (450 mg, 1.95 mmol) in acetone (2 mL) and NaHCO$_3$ (5% aq.

solution, 6 mL) was cooled to 0° C. then KBr (23 mg, 0.19 mmol) and TEMPO (334 mg, 2.14 mmol) added followed by NaOCl (5% aq. solution, 2.9 mL, 1.95 mmol) dropwise. Mixture was stirred at this temperature for 1 h and extra NaOCl (5% aq. solution, 2.9 mL, 1.95 mmol) added. After 1 h 5% NaHCO3 was added and mixture concentrated. The residue was extracted with $Et_2O$ then pH adjusted to 6 with addition of 1 M aqueous $KHSO_4$. Aqueous phase was extracted with EtOAc and solvent removed to give a white powder (90 mg). This material was dissolved in EtOAc (1 ml) and 4 M HCl in dioxane (2 mL) added. Mixture was stirred at room temperature for 5 h. Solvent was evaporated and product triturated with $Et_2O$ to give the title compound (60 mg). 1H NMR (400 MHz, Me-d3-OD): 4.24 (1H, d), 4.14-3.91 (1H, m), 3.91-3.80 (1H, m), 3.74 (1H, d), 3.51-3.36 (1H, m), 3.30 (1H, t), 1.60 (3H, s).

Preparation 49: (3,6-Dichloro-pyridazin-4-yl)-(2-methyl-allyl)-amine

Potassium tert-butoxide (157.5 g) was charged portionwise to a stirred solution of 3,6-dichloro-pyridazin-4-ylamine (210 g) in THF (3.36 L). After 15 minutes, 3-bromo-2-methylpropene (141.8 mL) was added dropwise over a period of 30 minutes, maintaining the temperature <25° C. The solution was allowed to stir at room temperature for 16 h, after which time the reaction was concentrated and the residue partitioned between DCM (6 L) and water (6 L). The aqueous phase was extracted with DCM (2×5 L). The combined organic phases were washed (brine, 5 L), dried with magnesium sulfate, filtered and concentrated. Chromatography (silica gel, eluting with 70:30 Heptane:-EtOAc) gave the title compound (211.7 g). $^1$H NMR (270 MHz, CDCl3): 6.49 (1H, s), 5.48 (1H, br s), 5.00 (1H, s), 4.91 (1H, s), 3.81 (2H, d, J=6 Hz), 1.80 (3H, s).

Preparation 50: (3,6-Dichloro-pyridazin-4-yl)-(2-methyl-allyl)-carbamic acid tert-butyl ester Di-tert-butyldicarbonate (267.5 mL) was charged to a stirred solution of (3,6-dichloro-pyridazin-4-yl)-(2-methyl-allyl)-amine (211.7 g) and 4-(dimethylamino)pyridine (23.65 g) in THF (4.54 L). After the addition, the solution was warmed to 60° C. and allowed to stir for 2 h. After this time, the solvent was removed in vacuo and the residue purified by column chromatography on silica gel, eluting with 75:25 Heptane:EtOAc, to give the title compound (296.9 g). MS: $[M+H]^+$=318.

Preparation 51: 3-Chloro-7,7-dimethyl-6,7-dihydro-pyrrolo[3,2-c]pyridazine-5-carboxylic acid tert-butyl ester (3,6-Dichloro-pyridazin-4-yl)-(2-methyl-allyl)-carbamic acid tert-butyl ester (239 g), $Bu_4NCl$ (251.8 g), sodium formate (64.2 g), $Et_3N$ (354 mL) and $Pd(OAc)_2$ (13 g) were dissolved in DMSO (6 L) and water (354 mL). The reaction mixture was heated to 100° C. and held at temperature for 10 minutes, after which time the reaction was complete and the mixture was allowed to cool to room temperature. The mixture was diluted with water (9 L) and extracted with EtOAc (4×3 L). The combined organic extracts were washed with brine (3 L). The emulsion was allowed to separate overnight and the interface back extracted with EtOAc (3 L). The combined organic extracts were dried with magnesium sulfate, filtered and concentrated. Chromatography on silica, eluting with a solvent gradient of 10% EtOAc in heptane to 20% EtOAc in heptane, gave the title compound (118 g) $[M+H]^+$=284.

Preparation 52: 5-Bromo-6-(4-fluoro-benzyl)-3,3-dimethyl-2,3-dihydro-indole-1-carboxylic acid tert-butyl ester 6-(4-Fluoro-benzyl)-3,3-dimethyl-2,3-dihydro-indole-1-carboxylic acid tert-butyl ester (2.93 g, 8.25 mmol) was dissolved in MeCN (11.3 mL) at room temperature. N-Bromo succinimide (1.47 g, 8.25 mmol) was added in one portion. The reaction was placed in an ice bath and stirred for 0.5 h. After warming to room temperature and stirring for 1 h the reaction was concentrated in vacuo. The residue was slurried in DCM and filtered. Chromatography on silica gel (gradient elution, 0-100%, EtOAC/petrol), gave the title compound (1.81 g) MS: $[M+H]^+$=377 (fragment).

Preparation 53: 5-Cyano-6-(4-fluoro-benzyl)-3,3-dimethyl-2,3-dihydro-indole-1-carboxylic acid tert-butyl ester To 5-bromo-6-(4-fluoro-benzyl)-3,3-dimethyl-2,3-dihydro-indole-1-carboxylic acid tert-butyl ester (1.61 g, 3.71 mmol) in DMF (5.1 mL) was added $Zn(CN)_2$ (217 mg, 1.85 mmol) and $Pd(PPh_3)_4$ (857 mg, 0.74 mmol). The reaction was degassed under nitrogen and then heated to 120° C. for 1.5 h. The reaction was cooled to room temperature, poured into water and extracted with ethyl acetate (3×). The combined organic extracts were concentrated in vacuo. Chromatography on silica gel (gradient elution, 0-100%, EtOAC/petrol), gave the title compound (1.33 g) MS: $[M+H]^+$=325 (fragment).

Preparation 54: 6-(4-Fluoro-benzyl)-3,3-dimethyl-2,3-dihydro-1H-indole-5-carbonitrile 5-Cyano-6-(4-fluoro-benzyl)-3,3-dimethyl-2,3-dihydro-indole-1-carboxylic acid tert-butyl ester (1.33 g, 3.50 mmol) was dissolved in 4M HCl-dioxane (35 mL). The reaction was stirred overnight and concentrated in vacuo. The residue was neutralised with saturated aqueous sodium bicarbonate and extracted with ethyl acetate (3×). The combined organic extracts were dried over sodium sulfate and concentrated. Chromatography on silica gel (gradient elution, 0-100%, EtOAc/petrol), gave the title compound (0.808 g) MS: $[M-H]^+$=279 (fragment).

Preparation 55: 1-(2-Chloro-acetyl)-6-(4-fluoro-benzyl)-3,3-di methyl-2,3-dihydro-1H-indole-5-carbonitrile To 6-(4-fluoro-benzyl)-3,3-dimethyl-2,3-dihydro-1H-indole-5-carbonitrile (701 mg, 2.50 mmol) dissolved in diethyl ether (12.52 mL) was added pyridine (0.20 mL, 2.50 mmol) and chloroacetyl chloride (0.33 mL, 3.0 mmol) at −20° C. The reaction was stirred at this temperature for 1 h. Water was added, the reaction extracted with ethyl acetate and the organic phase concentrated in vacuo. Chromatography on silica gel (gradient elution, 0-50%, EtOAc/petrol), gave the title compound (898 mg); $^1$H NMR (400 MHz, CDCl3): 8.21 (1H, s), 7.40 (1H, s), 7.28-7.21 (2H, m), 7.00 (2H, t), 4.16 (4H, d), 3.95 (2H, s), 1.40 (6H, s).

Preparation 56: (±)-6-[(4-Fluoro-phenyl)-hydroxy-methyl]-3,3-dimethyl-2,3-dihydro-pyrrolo[3,2-b]pyridine-1-carboxylic acid tert-butyl ester

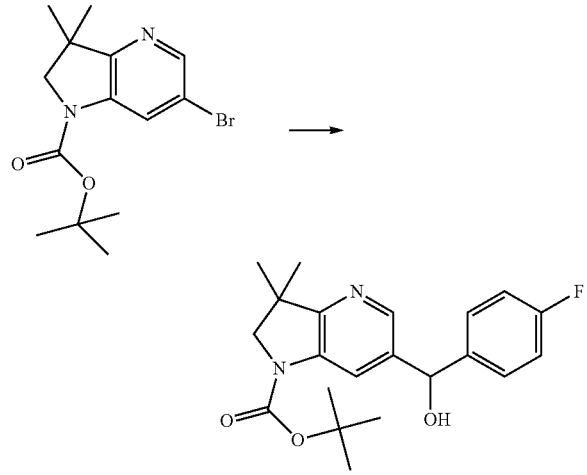

6-Bromo-3,3-dimethyl-2,3-dihydro-pyrrolo[3,2-b]pyridine-1-carboxylic acid tert-butyl ester (1.50 g, 4.59 mmol) was dissolved in anhydrous THF (22.95 mL) and cooled to −78° C. Butyllithium (2.5 M in hexanes, 2.75 mL, 6.89 mmol) was added dropwise. The reaction was stirred for 0.5 h at this temperature and 4-fluoro-benzaldehyde (738 μL, 6.89 mmol) was added dropwise. The reaction was stirred for 0.5 h at this temperature and quenched with saturated aqueous ammonium chloride, warming to room temperature. The solution was separated and extracted with ethyl acetate (3×). The combined organic extracts were dried over sodium sulfate and concentrated in vacuo. Chromatography on silica gel (gradient elution, 0-100%, ethyl acetate/petrol), gave the title compound (1.58 g) MS: [M+H]⁺=373.

Preparation 57A: 6-[(4-Fluoro-phenyl)-(R)-hydroxy-methyl]-3,3-di methyl-2,3-dihydro-pyrrolo[3,2-b]pyridine-1-carboxylic acid tert-butyl ester [faster eluting], and Preparation 57B: 6-[(4-Fluoro-phenyl)-(S)-hydroxy-methyl]-3,3-di methyl-2,3-dihydro-pyrrolo[3,2-b]pyridine-1-carboxylic acid tert-butyl ester [slower eluting]

(±)-6-[(4-Fluoro-phenyl)-hydroxy-methyl]-3,3-di methyl-2,3-dihydro-pyrrolo[3,2-b]pyridine-1-carboxylic acid tert-butyl ester was separated by chiral HPLC (heptane/ethanol (90:10), 0.2% DEA on a cellulose lux 2 column, to give the title compounds; MS: [M+H]⁺=373. Absolute stereochemistry determined by X-ray crystallography.

Preparation 58: (±)-(3,3-Dimethyl-2,3-dihydro-1H-pyrrolo[3,2-b]pyridin-6-yl)-(4-fluoro-phenyl)-methanol (±)-6-[(4-Fluoro-phenyl)-hydroxy-methyl]-3,3-di methyl-2,3-dihydro-pyrrolo[3,2-b]pyridine-1-carboxylic acid tert-butyl ester (100 mg, 0.27 mmol) was dissolved in a 1:1 mixture of 5 M aqueous HCl and MeOH (2.69 mL) and stirred for 1 h, after which time the mixture was heated to 50° C. for 18 h. The reaction was concentrated in vacuo and residue (dissolved in methanol) was loaded onto a NH₂ ion exchange column eluting with methanol. Appropriate fractions were concentrated in vacuo to give the title compound (53 mg) MS: [M+H]⁺=273.

The compounds in the following table were prepared starting from the appropriate substituted benzaldehyde following procedures similar or analogous to those of Preparations 56, 57A/B and 58, with chiral separation being carried out using the conditions indicated unless otherwise stated:

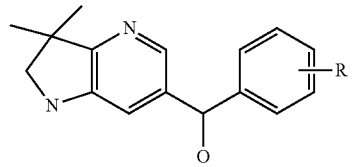

| Cpd. No. | Compound name | R | Chiral separation method | MS: [M + H]⁺ |
|---|---|---|---|---|
| 58A | (R or S)-(3,3-Dimethyl-2,3-dihydro-1H-pyrrolo[3,2-b]pyridin-6-yl)-(3-fluoro-phenyl)-methanol (faster eluting) | 3-F | Heptane/ethanol 90:10, 0.2% diethylamine, | 273 |
| 58B | (R or S)-(3,3-Dimethyl-2,3-dihydro-1H-pyrrolo[3,2-b]pyridin-6-yl)-(3-fluoro-phenyl)-methanol (slower eluting) | 3-F | lux-2 column | 273 |
| 58C | (R or S)-(2,4-Difluoro-phenyl)-(3,3-dimethyl-2,3-dihydro-1H-pyrrolo[3,2-b]pyridin-6-yl)-methanol (faster eluting) | 2,4-diF | Heptane/ethanol 90:10, 0.2% diethylamine, | 291 |
| 58D | (R or S)-(2,4-Difluoro-phenyl)-(3,3-dimethyl-2,3-dihydro-1H-pyrrolo[3,2-b]pyridin-6-yl)-methanol (slower eluting) | 2,4-diF | lux-2 column | 291 |
| 58E | (R or S)-(3,4-Difluoro-phenyl)-(3,3-dimethyl-2,3-dihydro-1H-pyrrolo[3,2-b]pyridin-6-yl)-methanol (faster eluting) | 3,4-diF | Heptane/ethanol 95:5, 0.2% diethylamine, | 291 |
| 58F | (R or S)-(3,4-Difluoro-phenyl)-(3,3-dimethyl-2,3-dihydro-1H-pyrrolo[3,2-b]pyridin-6-yl)-methanol (slower eluting) | 3,4-diF | lux-2 column | 291 |

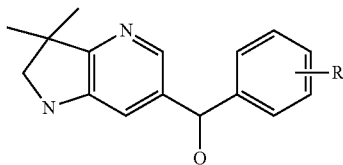

| Cpd. No. | Compound name | R | Chiral separation method | MS: [M + H]+ |
|---|---|---|---|---|
| 58G | (R or S)-(2,3-Difluoro-phenyl)-(3,3-dimethyl-2,3-dihydro-1H-pyrrolo[3,2-b]pyridin-6-yl)-methanol (faster eluting) | 2,3-diF | Heptane/ethanol 95:5, 0.2% diethylamine, | 291 |
| 58H | (R or S)-(2,3-Difluoro-phenyl)-(3,3-dimethyl-2,3-dihydro-1H-pyrrolo[3,2-b]pyridin-6-yl)-methanol (slower eluting) | 2,3-diF | lux-2 column | 291 |
| 58I | (R or S)-(2-Fluoro-phenyl)-(3,3-dimethyl-2,3-dihydro-1H-pyrrolo[3,2-b]pyridin-6-yl)-methanol (faster eluting) | 2-F | Heptane/ethanol 90:10, 0.2% diethylamine, | 273 |
| 58J | (R or S)-(2-Fluoro-phenyl)-(3,3-dimethyl-2,3-dihydro-1H-pyrrolo[3,2-b]pyridin-6-yl)-methanol (slower eluting) | 2-F | lux-2 column | 273 |
| 58O | (R or S)-(3,3-Dimethyl-2,3-dihydro-1H-pyrrolo[3,2-b]pyridin-6-yl)-phenyl-methanol (faster eluting) | H | Heptane/ethanol 90:10, 0.2% diethylamine, | 255 |
| 58P | (R or S)-(3,3-Dimethyl-2,3-dihydro-1H-pyrrolo[3,2-b]pyridin-6-yl)-phenyl-methanol (slower eluting) | H | lux-2 column | 255 |
| 58Q | (+)-(2,5-Difluoro-phenyl)-(3,3-dimethyl-2,3-dihydro-1H-pyrrolo[3,2-b]pyridin-6-yl)-methanol | 2,5-diF | Enantiomers not separated | 291 |
| 58R | (R or S)-(2,6-Difluoro-phenyl)-(3,3-dimethyl-2,3-dihydro-1H-pyrrolo[3,2-b]pyridin-6-yl)-methanol (faster eluting) | 2,6-diF | Heptane/ethanol 95:5, 0.2% diethylamine, | (a) |
| 58S | (R or S)-(2,6-Difluoro-phenyl)-(3,3-dimethyl-2,3-dihydro-1H-pyrrolo[3,2-b]pyridin-6-yl)-methanol (slower eluting) | 2,6-diF | lux-2 column | (b) |

Footnotes:
(a) 1H NMR (400 MHz, Me-d3-OD): 7.75 (1H, s), 7.41-7.29 (1H, m), 7.04-6.91 (3H, m), 6.17 (1H, s), 3.36 (2H, s), 1.32 (3H, s), 1.31 (3H, s).
(b) 1H NMR (400 MHz, Me-d3-OD): 7.75 (1H, s), 7.42-7.29 (1H, m), 7.04-6.91 (3H, m), 6.17 (1H, s), 3.36 (2H, s), 1.34-1.30 (6H, m).

Preparation 59:
3-Methoxymethyl-3-methyl-morpholine

A mixture of 3-hydroxymethyl-3-methyl-morpholine (1.3 g, 9.92 mmol), di-t-butyl dicarbonate (2.16 g, 9.92 mmol) and triethylamine (2.75 ml, 19.9 mmol) in DMF (15 mL) was stirred at ambient temperature overnight. Water (20 mL) was added and the mixture extracted with EtOAc (2×30 mL). Combined organic layers were washed with brine (30 mL) and solvent removed. Chromatography on silica gel (0-50% EtOAc/Petrol gradient) gave a colourless oil (1.9 g, 83%). To this material (1.00 g, 4.33 mmol) in DCM (54 mL) at 0° C. was added proton sponge (4.63 g, 21.7 mmol) followed by trimethyl oxonium tetrafluoroborate (2.99 g, 21.7 mmol) portionwise over 5 minutes. Mixture was allowed to warm to ambient temperature over 1 h, then was quenched with saturated aqueous NH4Cl and extracted with DCM. Solvent was concentrated then petrol was added and mixture filtered. Filtrate was concentrated and then purified by filtration through an SCX column to give a colourless oil (900 mg, 85%). This product was dissolved in EtOAc (2 mL) then 4 M HCl in dioxane (5 mL) was added and mixture stirred at ambient temperature overnight. Solvent was evaporated and product azetroped with toluene to give the title compound (860 mg) as a colourless oil. 1H NMR (400 MHz, CDCl3): 10.26 (1H, s), 9.32 (1H, s), 4.11-3.88 (2H, m), 3.80 (1H, d), 3.74-3.67 (2H, m), 3.64-3.57 (1H, m), 3.46 (3H, s), 3.27 (2H, s), 1.54 (3H, s).

Preparation 60: (2R,5S)-5-((3R,5R)-3,5-Dimethyl-morpholin-4-ylmethyl)-4-{2-[6-(1-hydroxy-butyl)-3,3-dimethyl-2,3-dihydro-pyrrolo[3,2-b]pyridin-1-yl]-2-oxo-ethyl}-2-methyl-piperazine-1-carboxylic acid tert-butyl ester (Two Separated Diastereomers of Unknown Absolute Stereochemistry where Indicated*)

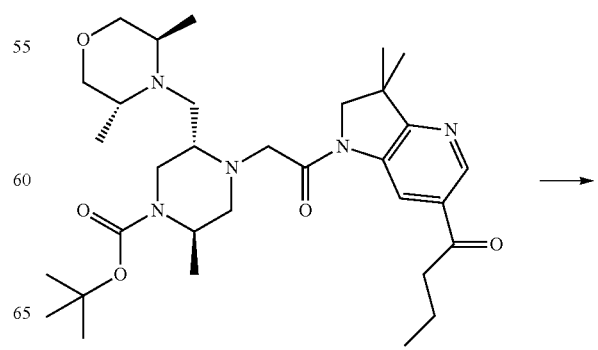

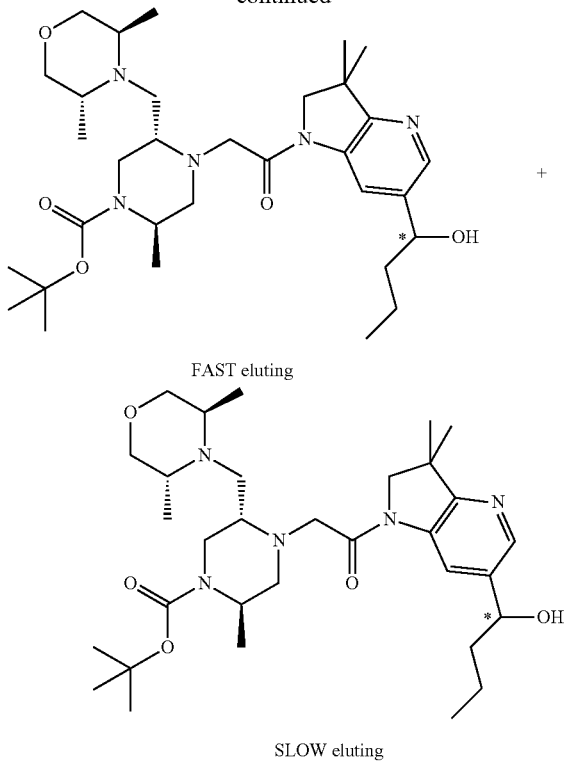

FAST eluting

SLOW eluting (2R,5S)-4-[2-(6-Butyryl-3,3-dimethyl-2,3-dihydro-pyrrolo[3,2-b]pyridin-1-yl)-2-oxo-ethyl]-5-((3R,5R)-3,5-dimethyl-morpholin-4-ylmethyl)-2-methyl-piperazine-1-carboxylic acid tert-butyl ester (668 mg, 1.14 mmol) was dissolved in methanol (10 mL). Sodium borohydride (86 mg, 2.28 mmol) was added and the reaction mixture was stirred for 1 h. The solvent was evaporated, water was added and the product was extracted with DCM. The organic phase was dried and evaporated to give an oil (0.65 g). Chiral HPLC separation using Heptane/Ethanol (60/40) with 0.2% diethylamine on a LUX2 column gave the title compounds as follows:

60A: FAST eluting, (211 mg) MS: [M+H]$^+$=588.
60B: SLOW eluting, (246 mg) MS: [M+H]$^+$=588.

Preparation 61: 2-(5-Chloro-3-fluoro-pyridin-2-yl)-2-methyl-propionitrile

A solution of sodium bis(trimethylsilyl)amide (610 mL, 40% in tetrahydrofuran, 1.326 mole) was added to a cooled solution of 5-chloro-2,3-difluoropyridine (198.2 g, 1.326 mole) and isobutyronitrile (238 mL, 2.65 mole) in toluene (2 L). The mixture was stirred under nitrogen at RT overnight before addition of saturated aqueous ammonium chloride (1 L). Phases were separated and the aqueous extracted with ethyl acetate (2×1 L). Combined organics were dried (MgSO$_4$) and concentrated in vacuo at 40° C. to give the title compound (259.8 g, 95%) 1H NMR (400 MHz, DMSO-d6): 8.57 (1H, dd), 8.24 (1H, dd), 1.74 (6H, bd).

Preparation 62: 2-(5-Chloro-3-fluoropyridin-2-yl)-2-methylpropylamine

Borane-tetrahydrofuran complex (1 M, 1.37 L, 1.365 mole) was added to a cooled solution of 2-(5-chloro-3-fluoropyridin-2-yl)-2-methylpropionitrile (135.6 g, 0.683 mole) in tetrahydrofuran (670 mL). The mixture was stirred under nitrogen at room temperature overnight before cooling in ice. The mixture was quenched by the addition of 5 M hydrochloric acid (335 mL). The resulting mixture was basified with 40% aqueous potassium hydroxide (460 mL) and the phases were separated. The basic aqueous phase was extracted with ethyl acetate (2×670 mL) and the combined organic extracts were washed with brine (670 mL), dried (MgSO$_4$) and concentrated in vacuo at 40° C. to give the title compound (102.9 g, 74%) 1H NMR (400 MHz, DMSO-d6): 8.44 (1H, t), 7.95 (1H, dd), 2.85 (2H, d), 1.29 (6H, d).

Preparation 63: 6-Chloro-3,3-dimethyl-2,3-dihydro-1H-pyrrolo[3,2-b]pyridine

A mixture of 2-(5-chloro-3-fluoropyridin-2-yl)-2-methyl-propylamine (33 g, 0.163 mole), potassium carbonate (122 g) and NMP (100 mL) were heated to 150° C. for 4 hours. The cooled mixture was diluted with water (330 mL) and extracted with toluene (3×300 mL) The combined organic extracts were washed with brine (160 mL), dried (MgSO4) and concentrated in vacuo at 40° C. to give crude material (24.8 g). Chromatography on silica eluting with 5-30% ethyl acetate/petrol gave the title compound (21 g, 71%) 1H NMR (400 MHz, DMSO-d6): 7.61 (1H, d), 6.75 (1H, d), 6.06 (1H, bs), 3.31 (2H, s), 1.21 (6H, s).

Preparation 64: 6-Chloro-3,3-dimethyl-2,3-dihydro-pyrrolo[3,2-b]pyridine-1-carboxylic acid tert-butyl ester Di-tertbutyldicarbonate (3.7 g, 17.1 mmol) was added to a mixture of 6-chloro-3,3-dimethyl-2,3-dihydro-1H-pyrrolo[3,2-b]pyridine (2.6 g, 14.2 mmol), tetrahydrofuran (26 mL) and 2 M sodium hydroxide (11.4 mL, 22.8 mmol) with stirring over the weekend. The biphasic mixture was diluted with water (20 mL) and extracted with ethyl acetate (2×20 mL). The combined organic extracts were dried (MgSO$_4$) and concentrated in vacuo at 40° C. to give crude material (6.02 g). Chromatography on silica eluting with 5-30% ethyl acetate/petrol gave the title compound (2.23 g, 55%); 1H NMR (400 MHz, DMSO-d6): 8.11 (1H, d), 7.85 (1H, bs), 3.77 (2H, s), 1.52 (9H, s), 1.28 (6H, s).

Preparation 65: 6-Bromo-3,3-dimethyl-2,3-dihydro-pyrrolo[3,2-b]pyridine-1-carboxylic acid tert-butyl ester (Alternative Procedure)

The title compound was synthesised from 5-bromo-2,3-difluoropyridine following analogous methods to those of Preparations 61-64 inclusive; analytical data were consistent with those obtained previously.

Preparation 66: (2R,5R)-2-(tert-Butyl-dimethyl-silanyloxymethyl)-5-methyl-morpholine Prepared using a similar procedure to that described in WO 2010/048013.

Preparation 67: (2R,5S)-5-[(2R,5R)-2-(tert-Butyl-dimethyl-silanyloxymethyl)-5-methyl-morpholin-4-ylmethyl]-2-methyl-piperazine-1-carboxylic acid tert-butyl ester Prepared from (2R,5R)-2-(tert-butyl-dimethyl-silanyloxymethyl)-5-methyl-morpholine (which may be prepared as described in Preparation 66) using an analogous procedure to that described in Preparations 21 and 22; MS: [M+H]$^+$=458

Preparation 68: (2R,5S)-5-[(2R,5R)-2-(tert-Butyl-dimethyl-silanyloxymethyl)-5-methyl-morpholin-4-ylmethyl]-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester (2R,5R)-5-Chloromethyl-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester (which may be prepared as described in Preparation 19) (0.140 g, 0.26 mmol), (2R,5R)-2-(tert-butyl-dimethyl-silanyloxymethyl)-5-methyl-morpholine (which may be prepared as described in Preparation 66) (0.126 g, 0.51 mmol), potassium carbonate (0.107 g, 0.77 mmol) and potassium iodide (0.094 g, 0.57 mmol) were slurried in MeCN (2.65 mL) and heated at reflux for 18 h. The reaction was cooled to room temperature and stirred for 48 h at the same temperature. The reaction was diluted with DCM, filtered and concentrated in vacuo. The crude product was purified by column chromatography on silica gel (gradient elution, 0-100%, ethyl acetate/petrol 40-60° C.), to give the title compound (165 mg); 1H NMR (400 MHz, Me-d3-OD): 8.21 (1H, s), 8.03 (1H, s), 7.21 (2H, dd), 6.99 (2H, t), 4.13 (1H, s), 4.04-3.72 (6H, m), 3.72-3.38 (5H, m), 3.22-3.09 (1H, m), 3.09-2.96 (2H, m), 2.87 (2H, d), 2.56 (1H, dd), 2.24 (1H, s), 2.16-2.02 (1H, m), 1.56-1.42 (9H, m), 1.36 (6H, s), 1.21-1.14 (3H, m), 0.96 (3H, d), 0.84 (9H, s), 0.01 (6H, d).

Preparation 69: (2R,5S)-5-[(2R,5R)-2-(tert-Butyl-dimethyl-silanyloxymethyl)-5-methyl-morpholin-4-ylmethyl]-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester Prepared from (2R,5S)-5-[(2R,5R)-2-(tert-butyl-dimethyl-silanyloxymethyl)-5-methyl-morpholin-4-ylmethyl]-2-methyl-piperazine-1-carboxylic acid tert-butyl ester using a method analogous to that of Preparation 23; $^1$H NMR (400 MHz, Me-d3-OD): 8.28 (1H, s), 8.08 (1H, s), 7.41-7.26 (1H, m), 7.01-6.89 (2H, m), 4.23-3.98 (6H, m), 3.98-3.82 (2H, m), 3.76-3.49 (5H, m), 3.19 (1H, t), 3.08 (2H, s), 2.93 (2H, d), 2.60 (1H, dd), 2.29 (1H, s), 2.17-2.03 (2H, m), 1.49 (9H, s), 1.40 (6H, s), 1.26-1.22 (3H, m), 1.00 (3H, d), 0.88 (9H, s), 0.05 (6H, d).

Preparation 70: 2-Chloro-1-[6-(4-fluoro-benzyl)-3,3-dimethyl-4-oxy-2,3-dihydro-pyrrolo[3,2-b]pyridin-1-yl]-ethanone

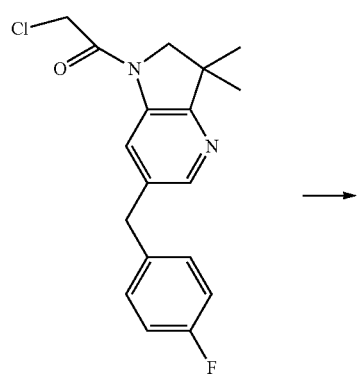

→

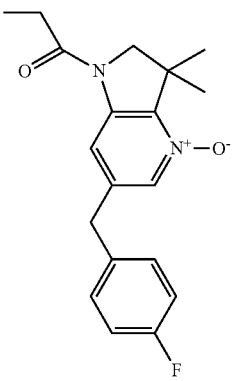

To a cooled solution (0° C.) of 2-chloro-1-[6-(4-fluoro-benzyl)-3,3-dimethyl-2,3-dihydro-pyrrolo[3,2-b]pyridin-1-yl]-ethanone (Preparation 17, 0.499 g, 1.5 mmol) in DCM (7.5 ml) was added mCPBA portionwise over 1 hour. The temperature was controlled below 5° C. The reaction was left to warm slowly to room temperature overnight. The reaction was quenched with a saturated solution of NaHCO$_3$ and the layers separated. The aqueous layer was extracted with DCM (twice). The combined organic layers were washed with brine, dried (MgSO$_4$) and concentrated under reduced pressure. The mixture was used directly in the next stage. [M+H] 349

Preparation of Compounds of Formula (I)

Compounds of formula (I) are prepared using deprotection methods analogous to those detailed below:

Method 1

A mixture of (2R,5S)-5-((3R,5R)-3,5-Dimethyl-morpholin-4-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester (0.073 g), ethyl acetate (5 mL) and HCl dioxane (4 M; 5 mL) was stirred at 20° C. for 18 h and resulting solid was collected by filtration to give 2-[(2R,5R)-2-{[(3R,5R)-3,5-dimethylmorpholin-4-yl]methyl}-5-methylpiperazin-1-yl]-1-{6-[(4-fluorophenyl)methyl]-3,3-di methyl-1H,2H,3H-pyrrolo[3,2-b]pyridin-1-yl}ethan-1-one dihydrochloride (Example 15)

Examples 1 to 63, 66-69, 71, 76, 87-88, 90 and 92-121

By following methods similar and/or analogous to those described above, the compounds set out in the Table below were prepared from the corresponding N-Boc protected derivatives, with any significant variations indicated below except where otherwise stated. Precursors for the N-Boc protected derivatives are identified (by preparation number or name) in the table below. The title compounds were either isolated directly as the free base or appropriate salt without further purification, or purified for example using mass-directed preparative HPLC, crystallization or trituration.

| Ex. | Structure | Name | Synthesis of Boc derivative | Deprotection Method | NMR Data | MS Data [M + H]+ |
|---|---|---|---|---|---|---|
| 1 | 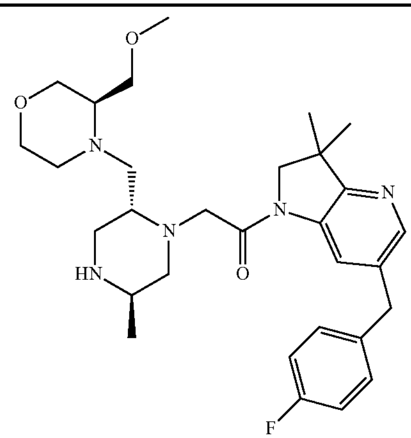 | 1-{6-[(4-Fluorophenyl)methyl]-3,3-dimethyl-1H,2H,3H-pyrrolo[3,2-b]pyridin-1-yl}-2-[(2R,5R)-2-{[(3R)-3-(methoxymethyl)morpholin-4-yl]methyl}-5-methylpiperazin-1-yl]ethan-1-one dihydrochloride | 19 + (R)-3-Methoxymethyl-morpholine, see Preparation 20 | 1 | 1H NMR (400 MHz, Me-d3-OD): 8.69 (1H, s), 8.45 (1H, s), 7.36 (2H, dd), 7.13 (2H, t), 4.28 (1H, d), 4.23 (3H, s), 4.19 (1H, s), 4.10 (3H, d), 3.99 (2H, s), 3.93-3.69 (5H, m), 3.69-3.56 (2H, m), 3.48 (3H, s), 3.25 (6H, s), 3.07-2.94 (1H, m), 1.61 (6H, d), 1.44 (3H, s). | 540 |
| 2 | 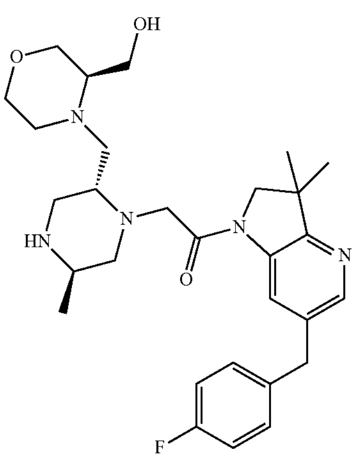 [SMILES: C[C@@H]1CN(CC(=O)N2CC(C)(C)c3ncc(Cc4ccc(F)cc4)cc32)[C@@H](CN2CCOC[C@H]2CO)CN1] | 1-{6-[(4-Fluorophenyl)methyl]-3,3-dimethyl-1H,2H,3H-pyrrolo[3,2-b]pyridin-1-yl}-2-[(2R,5R)-2-{[(3R)-3-(hydroxymethyl)morpholin-4-yl]methyl}-5-methylpiperazin-1-yl]ethan-1-one dihydrochloride | 19 + (R)-3-Methoxymethyl-morpholine, see Preparation 20 | 1 | 1H NMR (400 MHz, Me-d3-OD): 8.78 (1H, d), 8.40 (1H, d), 7.46-7.30 (2H, m), 7.21-7.06 (2H, m), 4.31-4.18 (4H, m), 4.18-3.94 (6H, m), 3.84 (4H, d), 3.69 (3H, s), 3.60 (2H, d), 3.48-3.38 (2H, m), 3.35 (2H, s), 3.28-3.16 (1H, m), 3.16-2.95 (1H, m), 1.62 (6H, d), 1.46-1.37 (3H, m). | 526 |

| Ex. | Structure | Name | Synthesis of Boc derivative | Deprotection Method | NMR Data | MS Data [M + H]+ |
|---|---|---|---|---|---|---|
| 3 | 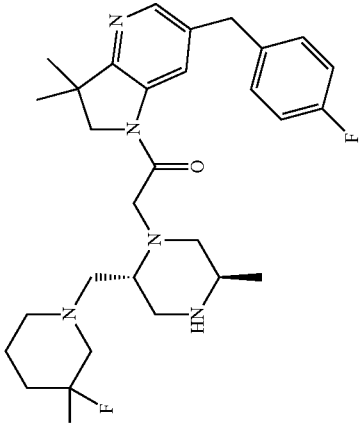 | 2-[(2R,5R)-2-[(3,3-Difluoropiperidin-1-yl)methyl]-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + 3,3-difluoropiperidine, see Preparation 20 | 1 | 1H NMR (400 MHz, Me-d3-OD): 8.75 (1H, s), 8.45 (1H, s), 7.46-7.29 (2H, m), 7.21-7.05 (2H, m), 4.31 (2H, s), 4.22 (2H, s), 4.20-4.06 (2H, m), 3.95 (1H, s), 3.88-3.56 (5H, m), 3.45 (2H, s), 3.24-3.12 (1H, m), 2.26 (2H, s), 2.04 (3H, s), 1.65 (6H, d), 1.38 (3H, d). | 530 |
| 4 | 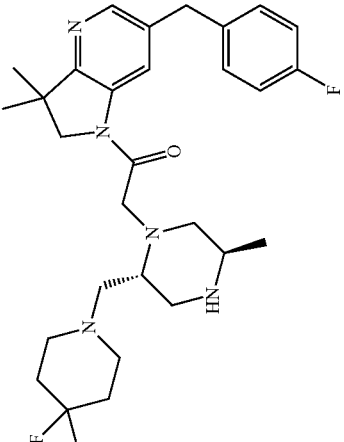 | 2-[(2R,5R)-2-[(4,4-Difluoropiperidin-1-yl)methyl]-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + 4,4-difluoropiperidine, see Preparation 20 | 1 | 1H NMR (400 MHz, Me-d3-OD): 8.78 (1H, s), 8.41 (1H, s), 7.35 (2H, dd), 7.10 (2H, t), 4.29 (2H, s), 4.22 (2H, s), 4.08 (2H, s), 4.05-3.79 (2H, m), 3.78-3.36 (8H, m), 3.31-3.01 (3H, m), 2.45 (4H, s), 1.63 (6H, d), 1.37 (3H, d). | 530 |

| Ex. | Structure | Name | Synthesis of Boc derivative | Deprotection Method | NMR Data | MS Data [M + H]+ |
|---|---|---|---|---|---|---|
| 5 | 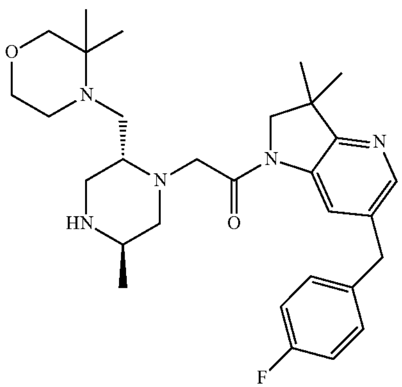 [SMILES: C[C@@H]1CN(CC(=O)N2CC(C)(C)c3ncc(Cc4ccc(F)cc4)cc32)[C@@H](CN2CCOCC2(C)C)CN1] | 2-[(2R,5R)-2-[(3,3-Dimethylmorpholin-4-yl)methyl]-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + 3,3-dimethylmorpholine, see Preparation 20 | 1 | 1H NMR (400 MHz, Me-d3-OD): 8.69 (1H, s), 8.53-8.40 (1H, m), 7.37 (2H, t), 7.13 (2H, t), 4.42 (1H, d), 4.31-4.21 (4H, m), 4.18 (1H, d), 4.07 (1H, d), 4.00 (1H, d), 3.85 (1H, d), 3.75 (1H, s), 3.68 (3H, s), 3.58 (2H, d), 3.52 (1H, d), 3.49-3.36 (1H, m), 3.10 (1H, d), 3.04-2.86 (2H, m), 1.63 (6H, d), 1.56 (6H, d), 1.43 (3H, s). | 524 |
| 6 | 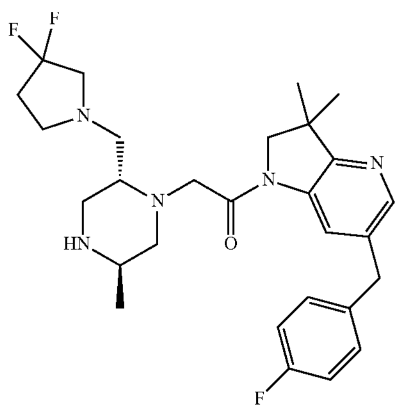 [SMILES: C[C@@H]1CN(CC(=O)N2CC(C)(C)c3ncc(Cc4ccc(F)cc4)cc32)[C@@H](CN2CCC(F)(F)C2)CN1] | 2-[(2R,5R)-2-[(3,3-Difluoropyrrolidin-1-yl)methyl]-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + 3,3-difluoropyrrolidine, see Preparation 20 | 1 | 1H NMR (400 MHz, Me-d3-OD): 8.79 (1H, s), 8.39 (1H, s), 7.43-7.29 (2H, m), 7.18-7.04 (2H, m), 4.26 (2H, s), 4.21 (2H, s), 4.07 (2H, d), 4.00-3.89 (2H, m), 3.82-3.70 (3H, m), 3.68 (2H, s), 3.64-3.56 (1H, m), 3.47-3.38 (2H, m), 3.26 (2H, m), 3.14 (1H, dd), 2.78-2.59 (2H, m), 1.62 (6H, d), 1.35 (3H, d). | 516 |

| Ex. | Structure | Name | Synthesis of Boc derivative | Deprotection Method | NMR Data | MS Data [M + H]+ |
|---|---|---|---|---|---|---|
| 7 | 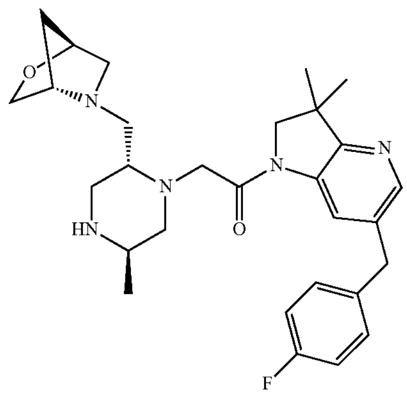 [SMILES: C[C@@H]1CN(CC(=O)N2CC(C)(C)c3ncc(Cc4ccc(F)cc4)cc32)[C@@H](CN2C[C@@H]3C[C@H]2CO3)CN1] | 1-{6-[(4-Fluorophenyl)methyl]-3,3-dimethyl-1H,2H,3H-pyrrolo[3,2-b]pyridin-1-yl}-2-[(2R,5R)-5-methyl-2-[(1S,4S)-2-oxa-5-azabicyclo[2.2.1]heptan-5-ylmethyl]piperazin-1-yl]ethan-1-one dihydrochloride | 19 + (1S,4S)-2-oxa-5-azabicyclo[2.2.1]heptane, see Preparation 20 | 1 | 1H NMR (400 MHz, Me-d3-OD): 8.74 (1H, s), 8.41 (1H, s), 7.44-7.30 (2H, m), 7.12 (2H, t), 4.80 (1H, s), 4.45 (1H, s), 4.30 (2H, s), 4.23 (2H, s), 4.20-4.08 (2H, m), 4.04 (1H, s), 3.89 (1H, d), 3.81 (1H, d), 3.70 (4H, d), 3.67-3.56 (2H, m), 3.44 (2H, d), 3.23-3.04 (1H, m), 2.35 (1H, d), 2.20 (1H, d), 1.64 (6H, d), 1.34 (3H, d). | 508 |
| 8 | 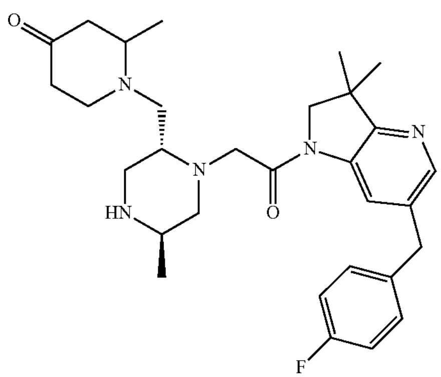 [SMILES: CC1CC(=O)CCN1C[C@H]1CN[C@H](C)CN1CC(=O)N1CC(C)(C)c2ncc(Cc3ccc(F)cc3)cc21] | 1-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}-2-methylpiperidin-4-one dihydrochloride | 19 + 2-methylpiperidin-4-one, see Preparation 20 | 1 | 1H NMR (400 MHz, Me-d3-OD): 8.78 (1H, d), 8.48-8.37 (1H, m), 7.36 (2H, d), 7.18-7.06 (2H, m), 4.34-4.23 (2H, m), 4.20 (3H, s), 4.13 (1H, d), 4.09-3.97 (1H, m), 3.83-3.69 (2H, m), 3.69-3.64 (2H, m), 3.60 (2H, d), 3.45 (1H, d), 3.27-3.18 (1H, m), 3.18-2.96 (2H, m), 2.27 (1H, t), 2.22-2.06 (2H, m), 2.01-1.86 (1H, s), 1.62 (6H, s), 1.49-1.38 (6H, m). | 522 |

| Ex. | Structure | Name | Synthesis of Boc derivative | Deprotection Method | NMR Data | MS Data [M + H]+ |
|---|---|---|---|---|---|---|
| 9 | 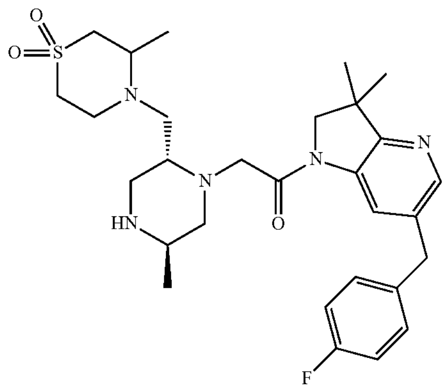 [SMILES: CC1CS(=O)(=O)CCN1C[C@H]1CN[C@H](C)CN1CC(=O)N1CC(C)(C)c2ncc(Cc3ccc(F)cc3)cc21] | 4-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}-3-methyl-1λ⁶,4-thiomorpholine-1,1-dione dihydrochloride | 19 + 3-methyl-1λ⁶,4-thiomorpholine-1,1-dione, see Preparation 20 | 1 | 1H NMR (400 MHz, Me-d3-OD): 8.81 (1H, s), 8.40 (1H, d), 7.35 (2H, t), 7.11 (2H, t), 4.31 (1H, d), 4.25 (2H, t), 4.23-4.17 (3H, m), 3.94 (2H, s), 3.67 (5H, s), 3.50 (3H, d), 3.43 (2H, s), 3.27-3.14 (3H, m), 1.62 (6H, s), 1.56-1.47 (3H, m), 1.43 (3H, dd). | 558 |
| 10 | 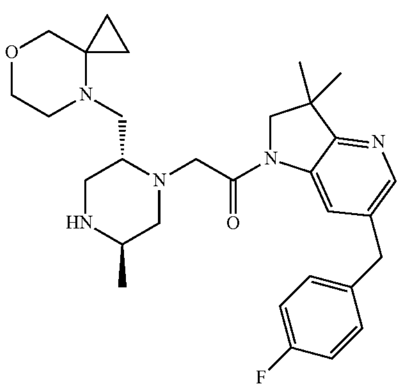 [SMILES: C[C@@H]1CN(CC(=O)N2CC(C)(C)c3ncc(Cc4ccc(F)cc4)cc32)[C@@H](CN2CCOCC23CC3)CN1] | 1-{6-[(4-Fluorophenyl)methyl]-3,3-dimethyl-1H,2H,3H-pyrrolo[3,2-b]pyridin-1-yl}-2-[(2R,5R)-5-methyl-2-{7-oxa-4-azaspiro[2.5]octan-4-ylmethyl}piperazin-1-yl]ethan-1-one dihydrochloride | 19 + 7-oxa-4-azaspiro[2.5]octane, see Preparation 20 | 1 | 1H NMR (400 MHz, Me-d3-OD): 8.66 (1H, s), 8.43 (1H, s), 7.37 (2H, dd), 7.15 (2H, t), 4.35-4.17 (6H, m), 4.17-4.03 (4H, m), 3.83 (3H, s), 3.75-3.64 (2H, m), 3.59 (3H, d), 3.45 (1H, s), 3.21 (1H, dd), 3.10-2.96 (1H, m), 1.60 (7H, s), 1.47 (4H, d), 1.17-1.01 (2H, m). | 522 |

| Ex. | Structure | Name | Synthesis of Boc derivative | Deprotection Method | NMR Data | MS Data [M + H]+ |
|---|---|---|---|---|---|---|
| 11 | 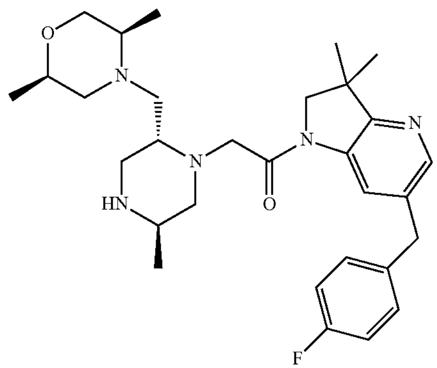 [SMILES: C[C@@H]1CN(CC(=O)N2CC(C)(C)c3ncc(Cc4ccc(F)cc4)cc32)[C@@H](CN2C[C@@H](C)OC[C@H]2C)CN1] | 2-[(2R,5R)-2-[[(2R,5R)-2,5-Dimethylmorpholin-4-yl]methyl]-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + (2R,5R)-2,5-dimethyl-morpholine, see Preparation 20 | 1 | 1H NMR (400 MHz, Me-d3-OD): 8.71 (1H, s), 8.44 (1H, s), 7.35 (2H, t), 7.12 (2H, t), 4.30 (2H, s), 4.23 (2H, s), 4.20-3.89 (5H, m), 3.80 (4H, s), 3.62 (1H, s), 3.47-3.39 (1H, m), 3.28 (2H, d), 3.22-3.00 (2H, m), 1.69-1.56 (7H, m), 1.56-1.44 (4H, m), 1.44-1.23 (6H, m). | 524 |
| 12 | 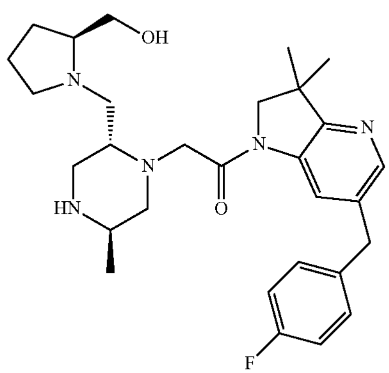 [SMILES: C[C@@H]1CN(CC(=O)N2CC(C)(C)c3ncc(Cc4ccc(F)cc4)cc32)[C@@H](CN2CCC[C@H]2CO)CN1] | 1-{6-[(4-Fluorophenyl)methyl]-3,3-dimethyl-1H,2H,3H-pyrrolo[3,2-b]pyridin-1-yl}-2-[(2R,5R)-2-[[(2S)-2-(hydroxymethyl)pyrrolidin-1-yl]methyl]-5-methylpiperazin-1-yl]ethan-1-one dihydrochloride | 19 + (2S)-2-(hydroxymethyl)pyrrolidine, see Preparation 20 | 1 | 1H NMR (400 MHz, Me-d3-OD): 8.59-8.52 (1H, m), 8.32 (1H, s), 7.32 (2H, dd), 7.15-7.05 (2H, m), 4.20-4.05 (6H, m), 3.98-3.82 (4H, m), 3.64-3.54 (2H, m), 3.54-3.43 (3H, m), 3.23-3.16 (1H, m), 3.01-2.92 (1H, m), 2.33-2.15 (2H, m), 1.88-1.79 (1H, m), 1.54 (6H, d), 1.38 (3H, d). | 510 |

| Ex. | Structure | Name | Synthesis of Boc derivative | Deprotection Method | NMR Data | MS Data [M + H]+ |
|---|---|---|---|---|---|---|
| 13 | 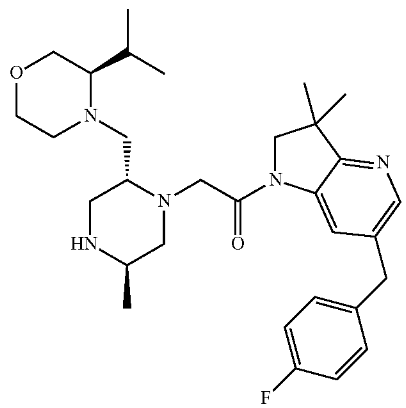 [SMILES: CC(C)[C@@H]1COCCN1C[C@H]1CN[C@H](C)CN1CC(=O)N1CC(C)(C)c2ncc(Cc3ccc(F)cc3)cc21] | 1-{6-[(4-Fluorophenyl)methyl]-3,3-dimethyl-1H,2H,3H-pyrrolo[3,2-b]pyridin-1-yl}-2-[(2R,5R)-5-methyl-2-{[(3R)-3-(propan-2-yl)morpholin-4-yl]methyl}piperazin-1-yl]ethan-1-one dihydrochloride | 19 + (3R)-3-(propan-2-yl)-morpholine, see Preparation 20 | 1 | 1H NMR (400 MHz, Me-d3-OD): 8.54 (1H, s), 8.42 (1H, s), 7.35 (2H, dd), 7.13 (2H, t), 4.44-4.31 (1H, m), 4.20 (4H, s), 4.15-3.91 (4H, m), 3.85-3.63 (7H, m), 3.40 (2H, d), 3.12 (2H, d), 2.97 (1H, d), 2.62 (1H, s), 1.64-1.52 (10H, m), 1.16 (3H, d), 0.97 (3H, d). | 538 |
| 14 | 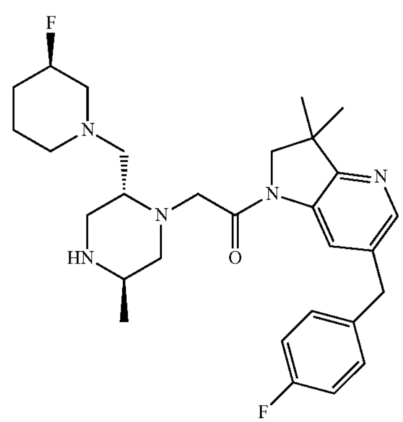 [SMILES: C[C@@H]1CN(CC(=O)N2CC(C)(C)c3ncc(Cc4ccc(F)cc4)cc32)[C@@H](CN2CCC[C@@H](F)C2)CN1] | 1-{6-[(4-Fluorophenyl)methyl]-3,3-dimethyl-1H,2H,3H-pyrrolo[3,2-b]pyridin-1-yl}-2-{[(2R,5R)-2-{[(3R)-3-fluoropiperidin-1-yl]methyl}-5-methylpiperazin-1-yl]ethan-1-one dihydrochloride | 19 + 29, see Preparation 20 | 1 | 1H NMR (400 MHz, Me-d3-OD): 8.86 (1H, s), 8.42 (1H, s), 7.34 (2H, t), 7.09 (2H, t), 5.08 (1H, d), 4.30 (2H, s), 4.25-4.15 (2H, m), 4.10 (2H, s), 3.85 (3H, s), 3.66-3.54 (2H, m), 3.54-3.45 (1H, m), 3.21-3.02 (2H, m), 2.28-1.89 (4H, m), 1.63 (6H, d), 1.38 (3H, d). | 512 |

-continued

| Ex. | Structure | Name | Synthesis of Boc derivative | Deprotection Method | NMR Data | MS Data [M + H]+ |
|---|---|---|---|---|---|---|
| 15 | 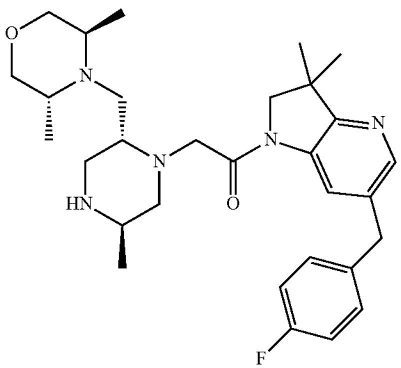 [SMILES: C[C@@H]1CN(CC(=O)N2CC(C)(C)c3ncc(Cc4ccc(F)cc4)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | See Preparation 20 | 1 | 1H NMR (400 MHz, Me-d3-OD): 8.65 (1H, s), 8.46 (1H, s), 7.43-7.31 (2H, m), 7.14 (2H, t), 4.29 (2H, s), 4.26-3.81 (9H, m), 3.81-3.54 (4H, m), 3.54-3.40 (2H, m), 3.27-3.06 (2H, m), 1.61 (6H, d), 1.52 (3H, d), 1.39 (3H, d), 1.13 (3H, d). | 524 |
| 16 | 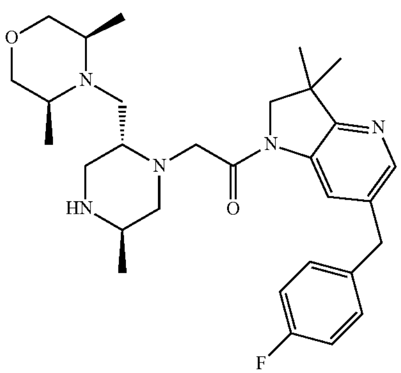 [SMILES: C[C@@H]1CN(CC(=O)N2CC(C)(C)c3ncc(Cc4ccc(F)cc4)cc32)[C@@H](CN2[C@H](C)COC[C@@H]2C)CN1] | 2-[(2R,5R)-2-{[(3R,5S)-3,5-Dimethylmorpholin-4-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + (3R,5S)-3,5-dimethyl-morpholine, see Preparation 20 | 1 | 1H NMR (400 MHz, Me-d3-OD): 8.73-8.52 (1H, m), 8.52-8.28 (1H, m), 7.41-7.29 (2H, m), 7.18-7.06 (2H, m), 4.33-3.93 (9H, m), 3.76 (3H, s), 3.66-3.51 (5H, m), 3.10 (2H, d), 1.63-1.23 (15H, m). | 524 |

-continued

| Ex. | Name | Structure | Synthesis of Boc derivative | Deprotection Method | NMR Data | MS Data [M + H]+ |
|---|---|---|---|---|---|---|
| 17 | 1-{6-[(4-Fluorophenyl)methyl]-3,3-dimethyl-1H,2H,3H-pyrrolo[3,2-b]pyridin-1-yl}-2-[(2R,5R)-5-methyl-2-{3-oxa-8-azabicyclo[3.2.1]octan-8-ylmethyl}piperazin-1-yl]ethan-1-one dihydrochloride | 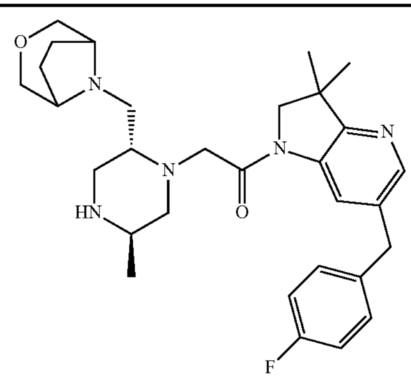 | 19 + 3-oxa-8-azabicyclo[3.2.1]octane, see Preparation 20 | 1 | 1H NMR (400 MHz, Me-d3-OD): 8.69 (1H, s), 8.43 (1H, s), 7.43-7.29 (2H, m), 7.19-7.06 (2H, m), 4.29-4.24 (2H, m), 4.21 (2H, s), 4.16-4.07 (3H, m), 4.07-3.87 (4H, m), 3.87-3.71 (2H, m), 3.65-3.53 (1H, m), 3.39 (3H, s), 3.31-3.05 (3H, m), 2.44-2.20 (5H, m), 1.62 (6H, d), 1.39 (3H, d). | 522 |
| 18 | 1-{6-[(4-Fluorophenyl)methyl]-3,3-dimethyl-1H,2H,3H-pyrrolo[3,2-b]pyridin-1-yl}-2-[(2R,5R)-5-methyl-2-{8-oxa-3-azabicyclo[3.2.1]octan-3-ylmethyl}piperazin-1-yl]ethan-1-one dihydrochloride | 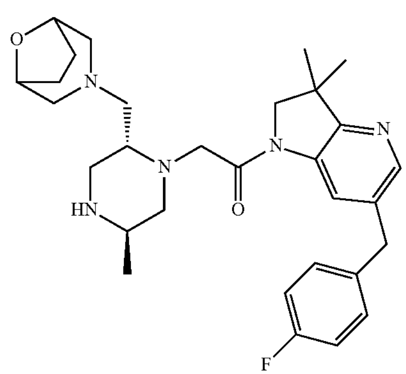 [SMILES: C[C@@H]1CN(CC(=O)N2CC(C)(C)c3ncc(Cc4ccc(F)cc4)cc32)[C@@H](CN2CC3CCC(C2)O3)CN1] | 19 + 8-oxa-3-azabicyclo[3.2.1]octane, see Preparation 20 | 1 | 1H NMR (400 MHz, Me-d3-OD): 8.62 (1H, s), 8.44 (1H, s), 7.39-7.27 (2H, m), 7.18-7.06 (2H, m), 4.66 (1H, d), 4.50 (1H, d), 4.30 (2H, s), 4.22 (2H, s), 4.15-4.05 (1H, m), 3.95 (1H, d), 3.90-3.74 (1H, m), 3.66-3.55 (2H, m), 3.46 (1H, m), 3.38 (2H, m), 3.27 (4H, d), 3.20-3.12 (2H, m), 2.32-2.03 (5H, m), 1.62 (6H, d), 1.31 (3H, d). | 522 |

-continued

| Ex. | Structure | Name | Synthesis of Boc derivative | Deprotection Method | NMR Data | MS Data [M + H]+ |
|---|---|---|---|---|---|---|
| 19 | 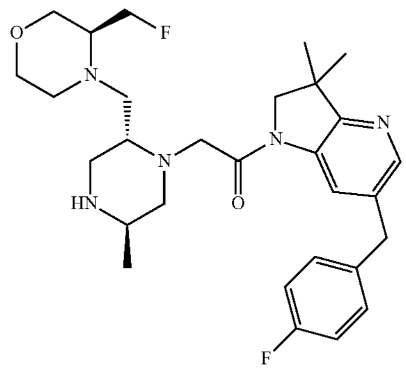 [SMILES: C[C@@H]1CN(CC(=O)N2CC(C)(C)c3ncc(Cc4ccc(F)cc4)cc32)[C@@H](CN2CCOC[C@H]2CF)CN1] | 2-[(2R,5R)-2-{[(3S)-3-(Fluoromethyl)morpholin-4-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + (3S)-3-(fluoromethyl)-morpholine, see Preparation 20 | 1 | 1H NMR (400 MHz, Me-d3-OD): 8.69 (1H, s), 8.44 (1H, s), 7.43-7.31 (2H, m), 7.13 (2H, t), 4.36-4.18 (6H, m), 4.18-4.07 (3H, m), 4.07-3.72 (9H, m), 3.60 (2H, d), 3.46 (2H, d), 3.27-3.17 (1H, m), 3.10-2.99 (1H, m), 1.61 (6H, d), 1.44 (3H, d). | 528 |
| 20 | 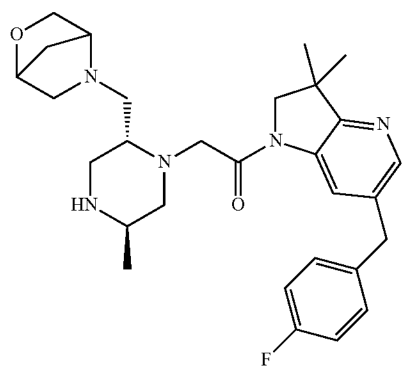 [SMILES: C[C@@H]1CN(CC(=O)N2CC(C)(C)c3ncc(Cc4ccc(F)cc4)cc32)[C@@H](CN2CC3CC2CO3)CN1] | 1-{6-[(4-Fluorophenyl)methyl]-3,3-dimethyl-1H,2H,3H-pyrrolo[3,2-b]pyridin-1-yl}-2-[(2R,5R)-5-methyl-2-{2-oxa-5-azabicyclo[2.2.1]heptan-5-ylmethyl}piperazin-1-yl]ethan-1-one dihydrochloride | 19 + 2-oxa-5-azabicyclo[2.2.1]heptane, see Preparation 20 | 1 | 1H NMR (400 MHz, Me-d3-OD): 8.75 (1H, s), 8.41 (1H, s), 7.48-7.29 (2H, m), 7.23-7.05 (2H, m), 4.80 (1H, s), 4.46 (1H, s), 4.32 (2H, s), 4.24 (2H, s), 4.15 (2H, d), 4.06 (1H, s), 3.88 (1H, d), 3.81 (1H, d), 3.74 (2H, s), 3.67-3.58 (1H, m), 3.46 (1H, d), 3.37 (2H, s), 3.31 (2H, d), 3.13 (1H, dd), 2.36 (1H, d), 2.19 (1H, d), 1.65 (6H, d), 1.35 (3H, d). | 508 |

| Ex. | Structure | Name | Synthesis of Boc derivative | Deprotection Method | NMR Data | MS Data [M + H]+ |
|---|---|---|---|---|---|---|
| 21 | 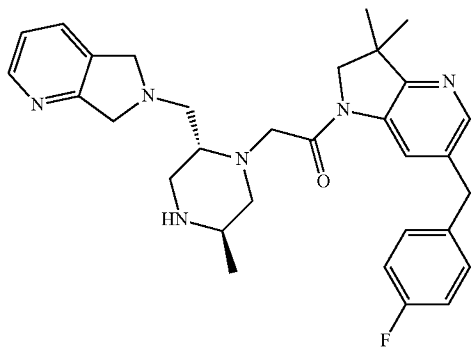 [SMILES: C[C@@H]1CN(CC(=O)N2CC(C)(C)c3ncc(Cc4ccc(F)cc4)cc32)[C@@H](CN2Cc3cccnc3C2)CN1] | 1-{6-[(4-Fluorophenyl)methyl]-3,3-dimethyl-1H,2H,3H-pyrrolo[3,2-b]pyridin-1-yl}-2-[(2R,5R)-5-methyl-2-{5H,6H,7H-pyrrolo[3,4-b]pyridin-6-ylmethyl}piperazin-1-yl]ethan-1-one dihydrochloride | 19 + (2R,5R)-5-methyl-2-{5H,6H,7H-pyrrolo[3,4-b]pyridine, see Preparation 20 | 1 | 1H NMR (400 MHz, Me-d3-OD): 8.74 (1H, s), 8.64 (1H, d), 8.33 (1H, s), 8.00 (1H, d), 7.58 (1H, t), 7.35-7.28 (2H, m), 7.12-7.04 (2H, m), 4.80 (2H, s), 4.29-3.45 (13H, m), 3.27-3.07 (2H, m), 1.58 (6H, d), 1.41-1.33 (3H, m). | 529 |
| 22 | 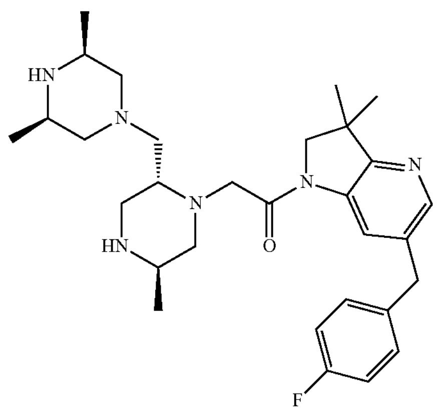 [SMILES: C[C@@H]1CN(CC(=O)N2CC(C)(C)c3ncc(Cc4ccc(F)cc4)cc32)[C@@H](CN2C[C@@H](C)N[C@@H](C)C2)CN1] | 2-[(2R,5R)-2-{[(3R,5S)-3,5-Dimethylpiperazin-1-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + (2R,6S)-2,6-dimethyl-piperazine-1-carboxylic acid tert-butyl ester, see Preparation 20 | 1 | 1H NMR (400 MHz, Me-d3-OD): 8.82 (1H, s), 8.37 (1H, s), 7.35 (2H, dd), 7.10 (2H, t), 4.35-4.17 (6H, m), 4.03 (1H, s), 3.67-3.51 (6H, m), 3.51-3.37 (2H, m), 3.28-3.20 (2H, m), 3.13-2.96 (1H, m), 2.73 (2H, d), 1.63 (6H, d), 1.41-1.31 (9H, m). | 523 |

-continued

| Ex. | Structure | Name | Synthesis of Boc derivative | Deprotection Method | NMR Data | MS Data [M + H]+ |
|---|---|---|---|---|---|---|
| 23 | 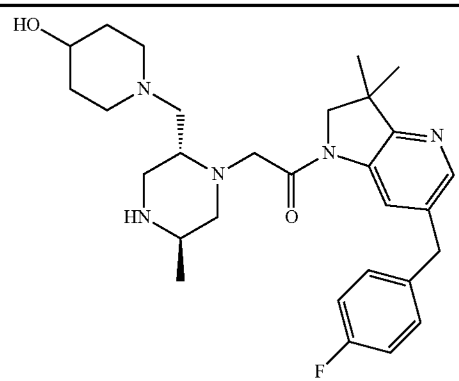 | 1-{6-[(4-Fluorophenyl)methyl]-3,3-dimethyl-1H,2H,3H-pyrrolo[3,2-b]pyridin-1-yl}-2-[(2R,5R)-2-[(4-hydroxypiperidin-1-yl)methyl]-5-methylpiperazin-1-yl]ethan-1-one dihydrochloride | 19 + 4-hydroxy-piperidine, see Preparation 20 | 1 | 1H NMR (400 MHz, Me-d3-OD): 8.88-8.66 (1H, m), 8.42 (1H, s), 7.36 (2H, s), 7.13 (2H, t), 4.36-4.26 (2H, m), 4.21 (3H, d), 4.04 (2H, s), 3.85 (2H, d), 3.66-3.46 (4H, m), 3.13-3.02 (1H, m), 2.10 (3H, d), 1.91 (2H, d), 1.63 (6H, d), 1.37 (3H, d). | 510 |
| 24 | 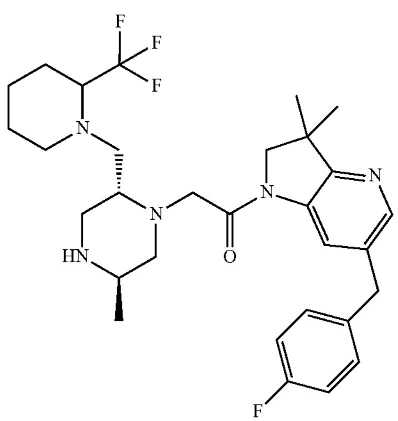 [SMILES: C[C@@H]1CN(CC(=O)N2CC(C)(C)c3ncc(Cc4ccc(F)cc4)cc32)[C@@H](CN2CCCCC2C(F)(F)F)CN1] | 1-{6-[(4-Fluorophenyl)methyl]-3,3-dimethyl-1H,2H,3H-pyrrolo[3,2-b]pyridin-1-yl}-2-[(2R,5R)-5-methyl-2-{[2-(R or S)(trifluoromethyl)piperidin-1-yl]methyl}piperazin-1-yl]ethan-1-one hydrochloride | 19 + (2-trifluoromethyl)-piperidine, see Preparation 20, then chromatographic separation | From slower eluting Boc diastereomer, 1 | 1H NMR (400 MHz, Me-d3-OD): 8.75 (1H, s), 8.39 (1H, s), 7.41-7.28 (2H, m), 7.10 (2H, t), 4.30 (1H, d), 4.26-4.09 (5H, m), 3.82 (1H, s), 3.67-3.54 (3H, m), 3.44 (1H, d), 3.28-3.08 (3H, m), 3.06-2.93 (1H, m), 2.85 (1H, d), 1.85 (2H, s), 1.62 (1H, d), 1.38 (3H, d). | 562 |

-continued

| Ex. | Structure | Name | Synthesis of Boc derivative | Deprotection Method | NMR Data | MS Data [M + H]+ |
|---|---|---|---|---|---|---|
| 25 | 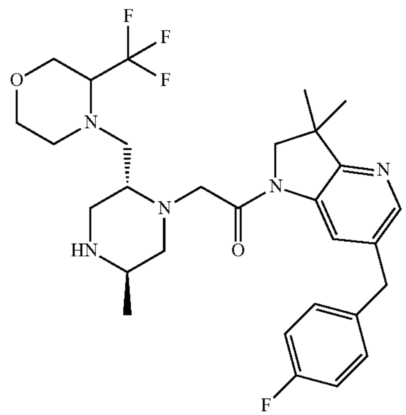 [SMILES: C[C@@H]1CN(CC(=O)N2CC(C)(C)c3ncc(Cc4ccc(F)cc4)cc32)[C@@H](CN2CCOCC2C(F)(F)F)CN1] | 1-{6-[(4-Fluorophenyl)methyl]-3,3-dimethyl-1H,2H,3H-pyrrolo[3,2-b]pyridin-1-yl}-2-[(2R,5R)-5-methyl-2-{[3-((R or S)]trifluoromethyl)morpholin-4-yl]methyl}piperazin-1-yl]ethan-1-one hydrochloride | 19 + 3-(trifluoromethyl)-morpholine, see Preparation 20, then chromatographic separation | From slower eluting Boc diastereomer, 1 | 1H NMR (400 MHz, Me-d3-OD): 8.76 (1H, s), 8.36 (1H, s), 7.33 (2H, dd), 7.09 (2H, t), 4.26-4.02 (7H, m), 3.91 (1H, d), 3.76 (2H, d), 3.63-3.44 (5H, m), 3.23-2.99 (4H, m), 2.88 (1H, dd), 2.61 (1H, d), 1.60 (6H, s), 1.34 (3H, d). | 564 |
| 26 | 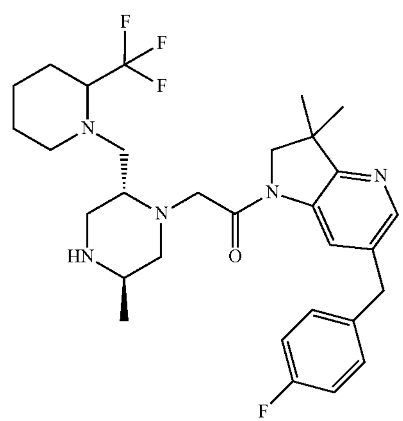 [SMILES: C[C@@H]1CN(CC(=O)N2CC(C)(C)c3ncc(Cc4ccc(F)cc4)cc32)[C@@H](CN2CCCCC2C(F)(F)F)CN1] | 1-{6-[(4-Fluorophenyl)methyl]-3,3-dimethyl-1H,2H,3H-pyrrolo[3,2-b]pyridin-1-yl}-2-[(2R,5R)-5-methyl-2-{[2-((R or S)]trifluoromethyl)piperidin-1-yl]methyl}piperazin-1-yl]ethan-1-one hydrochloride | 19 + (2-trifluoromethyl)-piperidine, see Preparation 20, then chromatographic separation | From faster eluting Boc diastereomer, 1 | 1H NMR (400 MHz, Me-d3-OD): 8.74 (1H, s), 8.37 (1H, s), 7.39-7.27 (2H, m), 7.15-7.04 (2H, m), 4.17 (6H, d), 4.08 (1H, d), 3.77 (2H, d), 3.66-3.47 (4H, m), 3.27-2.81 (7H, m), 1.59 (8H, d), 1.36 (3H, d). | 562 |

| Ex. | Structure | Name | Synthesis of Boc derivative | Deprotection Method | NMR Data | MS Data [M + H]+ |
|---|---|---|---|---|---|---|
| 27 | 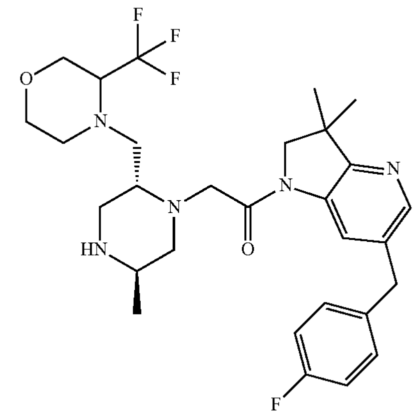 [SMILES: C[C@@H]1CN(CC(=O)N2CC(C)(C)c3ncc(Cc4ccc(F)cc4)cc32)[C@@H](CN2CCOCC2C(F)(F)F)CN1] | 1-{6-[(4-Fluorophenyl)methyl]-3,3-dimethyl-1H,2H,3H-pyrrolo[3,2-b]pyridin-1-yl}-2-[(2R,5R)-5-methyl-2-{[3-((R or S)]trifluoromethyl)morpholin-4-yl]methyl}piperazin-1-yl]ethan-1-one hydrochloride | 19 + 3-(trifluoromethyl)-morpholine, see Preparation 20, then chromatographic separation | From faster eluting Boc diastereomer, 1 | 1H NMR (400 MHz, Me-d3-OD): 8.76 (1H, s), 8.36 (1H, s), 7.38-7.27 (2H, m), 7.15-7.04 (2H, m), 4.20 (2H, s), 4.14 (2H, s), 4.06 (2H, s), 3.95 (1H, d), 3.91-3.75 (1H, m), 3.68 (3H, s), 3.51-3.42 (3H, m), 3.23 (1H, d), 3.18-3.06 (1H, m), 3.04-2.90 (2H, m), 2.84 (1H, d), 2.68 (1H, d), 1.60 (6H, d), 1.34 (3H, d). | 564 |
| 28 | 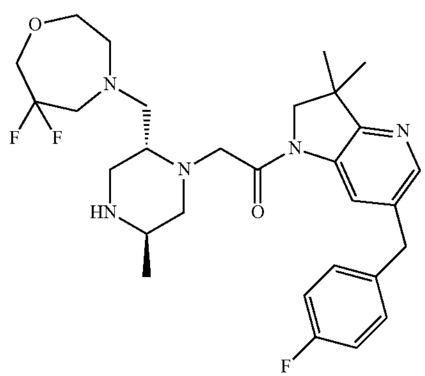 [SMILES: C[C@@H]1CN(CC(=O)N2CC(C)(C)c3ncc(Cc4ccc(F)cc4)cc32)[C@@H](CN2CCOCC(F)(F)C2)CN1] | 2-[(2R,5R)-2-[(6,6-Difluoro-1,4-oxazepan-4-yl)methyl]-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + 27, see Preparation 20 | 1 | 1H NMR (400 MHz, Me-d3-OD): 8.80 (1H, s), 8.41 (1H, s), 7.34 (2H, dd), 7.10 (2H, t), 4.27 (6H, d), 4.17-4.02 (1H, m), 4.02-3.69 (6H, m), 3.69-3.37 (5H, m), 3.00 (3H, d), 1.61 (6H, d), 1.39 (3H, d). | 546 |

-continued

| Ex. | Structure | Name | Synthesis of Boc derivative | Deprotection Method | NMR Data | MS Data [M + H]+ |
|---|---|---|---|---|---|---|
| 29 | 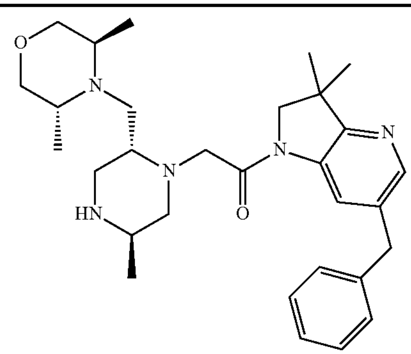 | 1-{6-Benzyl-3,3-dimethyl-1H,2H,3H-pyrrolo[3,2-b]pyridin-1-yl}-2-[(2R,5R)-3,5-{[(3R,5R)-3,5-dimethylmorpholin-4-yl]methyl}-5-methylpiperazin-1-yl]ethan-1-one dihydrochloride | 17A + 22, see Preparation 23 | 1 | 1H NMR (400 MHz, Me-d3-OD): 8.75 (1H, s), 8.50 (1H, s), 7.45-7.29 (5H, m), 4.33 (2H, s), 4.25 (3H, d), 4.15-3.98 (2H, m), 3.94 (2H, s), 3.89-3.71 (3H, m), 3.25-3.07 (2H, m), 1.64 (6H, s), 1.51 (3H, d), 1.39 (3H, d), 1.31-1.15 (1H, m), 1.10 (3H, d). | 506 |
| 30 | 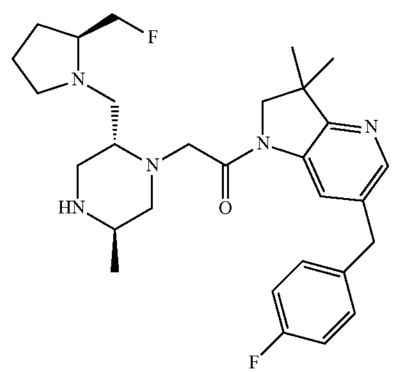 [SMILES: C[C@@H]1CN(CC(=O)N2CC(C)(C)c3ncc(Cc4ccc(F)cc4)cc32)[C@@H](CN2CCC[C@H]2CF)CN1] | 2-[(2R,5R)-2-{[(2S)-2-(Fluoromethyl)pyrrolidin-1-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + (2S)-2-(fluoromethyl)-pyrrolidine, see Preparation 20 | 1 | 1H NMR (400 MHz, Me-d3-OD): 8.70 (1H, s), 8.40 (1H, s), 7.34 (2H, dd), 7.12 (2H, t), 4.82-4.52 (2H, m), 4.32-4.17 (5H, m), 4.10-3.72 (6H, m), 3.58 (1H, s), 3.25 (1H, dd), 3.10-2.97 (1H, m), 2.45-2.31 (1H, m), 2.24 (1H, s), 2.05-2.02 (1H, m), 2.02-1.91 (1H, m), 1.60 (6H, s), 1.40 (3H, d). | 512 |

| Ex. | Structure | Name | Synthesis of Boc derivative | Deprotection Method | NMR Data | MS Data [M + H]+ |
|---|---|---|---|---|---|---|
| 31 | 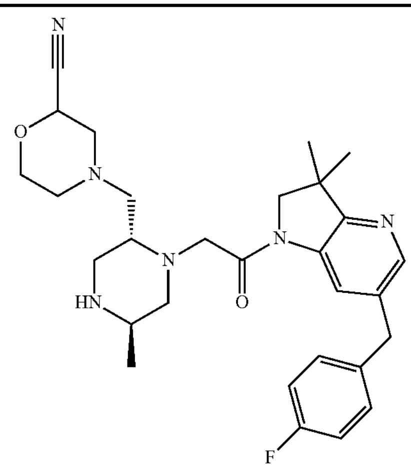 | 4-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}morpholine-2-carbonitrile | 19 + morpholine-2-carbonitrile, see Preparation 20 | 1, then purified by HPLC (basic method) | 1H NMR (400 MHz, Me-d3-OD): 8.31-8.21 (1H, m), 8.06 (1H, d), 7.33-7.19 (2H, m), 7.11-6.98 (2H, m), 4.22-4.11 (1H, m), 4.07-3.87 (4H, m), 3.87-3.72 (1H, m), 3.72-3.43 (2H, m), 3.02 (1H, d), 2.97-2.78 (4H, m), 2.78-2.69 (1H, m), 2.69-2.61 (1H, m), 2.61-2.54 (1H, m), 2.54-2.48 (1H, m), 2.48-2.21 (2H, m), 2.21-2.05 (2H, m), 1.45-1.35 (6H, m), 1.05 (3H, d). | 521 |
| 32 | 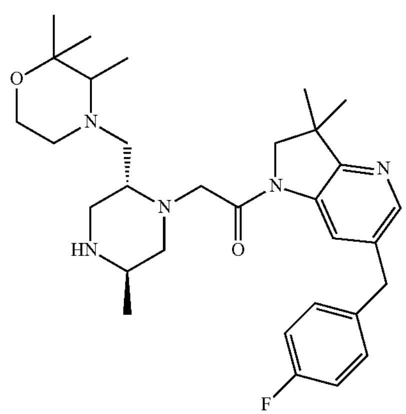 [SMILES: CC1N(C[C@H]2CN[C@H](C)CN2CC(=O)N2CC(C)(C)c3ncc(Cc4ccc(F)cc4)cc32)CCOC1(C)C] | 1-{6-[(4-Fluorophenyl)methyl]-3,3-dimethyl-1H,2H,3H-pyrrolo[3,2-b]pyridin-1-yl}-2-[(2R,5R)-5-methyl-2-[(2,2,3-trimethylmorpholin-4-yl)methyl]piperazin-1-yl]ethan-1-one dihydrochloride | 19 + 2,2,3-trimethylmorpholine, see Preparation 20 | 1 | 1H NMR (400 MHz, Me-d3-OD): 8.65 (1H, s), 8.46 (1H, d), 7.34 (2H, d), 7.18-7.06 (2H, m), 4.33-3.55 (13H, m), 3.40 (2H, s, hidden by solvent (1H) 3.27 (1H, s), 3.24-2.94 (2H, m), 1.71-1.29 (18H, m). | 538 |

| Ex. | Structure | Name | Synthesis of Boc derivative | Deprotection Method | NMR Data | MS Data [M + H]+ |
|---|---|---|---|---|---|---|
| 33 | 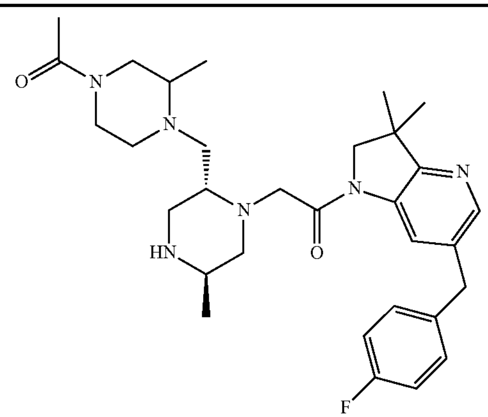 | 2-[(2R,5R)-2-[(4-Acetyl-2-methylpiperazin-1-yl)methyl]-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 19 + 4-acetyl-2-methylpiperazine, see Preparation 20 | 1 | 1H NMR (400 MHz, Me-d3-OD): 8.76 (1H, d), 8.45 (1H, d), 7.36 (2H, t), 7.11 (2H, t), 4.35-4.03 (8H, m), 4.03-3.91 (1H, m), 3.82 (3H, s), 3.61 (2H, s), 3.40 (2H, d), 3.20 (5H, s), 2.25 (3H, s), 1.64 (6H, s), 1.42 (6H, d). | 551 |
| 34 | 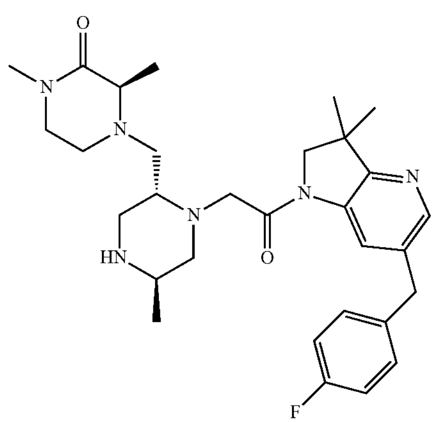 [SMILES: C[C@@H]1CN(CC(=O)N2CC(C)(C)c3ncc(Cc4ccc(F)cc4)cc32)[C@@H](CN2CCN(C)C(=O)[C@H]2C)CN1] | (3R)-4-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}-1,3-dimethylpiperazin-2-one dihydrochloride | See Preparation 34 | 1 | 1H NMR (400 MHz, Me-d3-OD): 8.77 (1H, s), 8.41 (1H, s), 7.35 (2H, dd), 7.12 (2H, t), 4.28 (2H, s), 4.23 (2H, s), 4.09 (1H, d), 3.91 (2H, s), 3.79-3.59 (8H, m), 3.52 (1H, d), 3.47-3.36 (2H, m), 3.27-3.06 (1H, m), 3.04 (3H, s), 1.67 (3H, d), 1.63 (6H, s), 1.40 (3H, d). | 537 |

-continued

| Ex. | Structure | Name | Synthesis of Boc derivative | Deprotection Method | NMR Data | MS Data [M + H]+ |
|---|---|---|---|---|---|---|
| 35 | 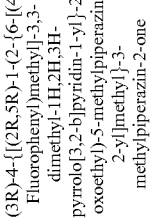 | (3R)-4-{[(2R,5R)-1-(2-{6-[(4-Fluorophenyl)methyl]-3,3-dimethyl-1H,2H,3H-pyrrolo[3,2-b]pyridin-2-yl}-2-oxoethyl)-5-methylpiperazin-2-yl]methyl}-3-methylpiperazin-2-one | 19 + 3-methylpiperazin-2-one, see Preparation 20 | 1, then purified by HPLC (basic method) | 1H NMR (400 MHz, Me-d3-OD): 8.25 (1H, s), 8.05 (1H, s), 7.25 (2H, dd), 7.04 (2H, t), 3.99 (2H, s), 3.96-3.72 (4H, m), 3.22-2.76 (9H, m), 2.68-2.44 (2H, m), 2.39-2.26 (1H, m), 2.16 (1H, dd), 1.38 (6H, d), 1.34 (3H, d), 1.06 (3H, d). | 523 |
| 36 | 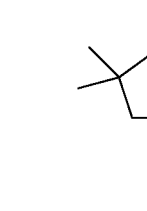 | 1-{6-[(4-Fluorophenyl)methyl]-1H,2H,3H-3,3-dimethyl-pyrrolo[3,2-b]pyridin-1-yl}-2-[(2R,5R)-5-methyl-2-{[(2S)-2-(trifluoromethyl)pyrrolidin-1-yl]methyl}piperazin-1-yl]ethan-1-one | 19 + (2S)-2-(trifluoromethyl)-pyrrolidine, see Preparation 20 | 1, purified by flash chromatography | 1H NMR (400 MHz, Me-d3-OD): 8.22 (1H, s), 8.07 (1H, s), 7.24 (2H, dd), 7.03 (2H, t), 4.18 (1H, d), 4.00 (2H, s), 3.86 (2H, s), 3.80 (1H, d), 3.39 (1H, d), hidden bend solvent (1H), 3.28-3.05 (4H, m), 2.99 (1H, dd), 2.77 (2H, quintet), 2.57 (1H, d), 2.42-2.30 (1H, m), 2.08-1.89 (1H, m), 1.89-1.67 (2H, m), 1.67-1.48 (1H, m), 1.38 (6H, d), 1.22 (3H, d). | 548 |

| Ex. | Structure | Name | Synthesis of Boc derivative | Deprotection Method | NMR Data | MS Data [M + H]+ |
|---|---|---|---|---|---|---|
| 37 | 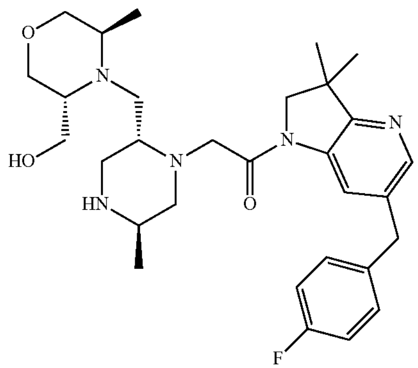 [SMILES: C[C@@H]1CN(CC(=O)N2CC(C)(C)c3ncc(Cc4ccc(F)cc4)cc32)[C@@H](CN2[C@H](CO)COC[C@H]2C)CN1] | 1-{6-[(4-Fluorophenyl)methyl]-1H,2H,3H-pyrrolo[3,2-b]pyridin-1-yl}-2-{[(3R,5R)-3-[(2R,5R)-2-(hydroxymethyl)-5-methylmorpholin-4-yl]methyl]-5-methylpiperazin-1-yl]ethan-1-one, dihydrochloride | 19 + 25, see Preparation 20 | 1 | 1H NMR (400 MHz, Me-d3-OD): 8.94-8.80 (1H, m), 8.45-8.32 (1H, m), 7.38 (2H, t), 7.12 (2H, t), 4.34-4.26 (2H, m), 4.23 (3H, s), 4.14-4.08 (2H, m), 4.02-3.91 (2H, m), 3.91-3.80 (3H, m), 3.80-3.70 (2H, m), 3.66-3.43 (6H, m), 3.38 (1H, d), 3.31-3.18 (1H, m), 3.13 (1H, dd), 1.65 (6H, d), 1.52-1.35 (6H, m). | 540 |
| 38 | 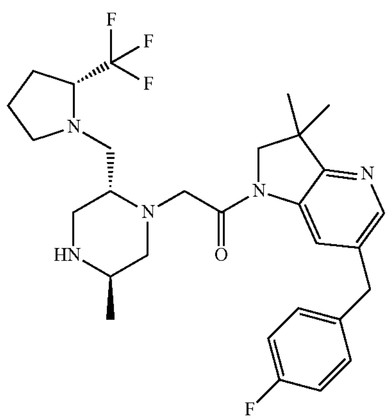 [SMILES: C[C@@H]1CN(CC(=O)N2CC(C)(C)c3ncc(Cc4ccc(F)cc4)cc32)[C@@H](CN2CCC[C@@H]2C(F)(F)F)CN1] | 1-{6-[(4-Fluorophenyl)methyl]-1H,2H,3H-pyrrolo[3,2-b]pyridin-1-yl}-2-{[(2R,5R)-5-methyl-2-{[(2R)-2-(trifluoromethyl)pyrrolidin-1-yl]methyl}piperazin-1-yl]ethan-1-one | 19 + (2R)-2-(trifluoromethyl)-pyrrolidine, see Preparation 20 | 1, purified by flash chromatography | 1H NMR (400 MHz, Me-d3-OD): 8.24 (1H, s), 8.08 (1H, s), 7.24 (2H, t), 7.03 (2H, t), 4.03-3.89 (4H, m), 3.83 (1H, d), 3.67-3.53 (2H, m), 3.38 (1H, d), 3.31-3.22 (2H, m), 3.22-3.13 (1H, m), 3.12-2.99 (2H, m), 2.89-2.80 (1H, m), 2.80-2.52 (2H, m), 2.44-2.34 (1H, m), 2.15-1.93 (1H, m), 1.93-1.76 (3H, m), 1.40 (6H, d), 1.32-1.25 (3H, m). | 548 |

| Ex. | Structure | Name | Synthesis of Boc derivative | Deprotection Method | NMR Data | MS Data [M + H]+ |
|---|---|---|---|---|---|---|
| 39 | 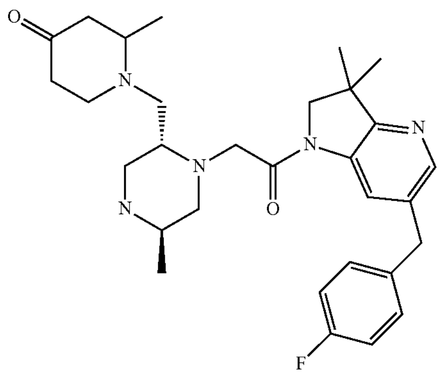 [SMILES: CC1CC(=O)CCN1C[C@H]1CN[C@H](C)CN1CC(=O)N1CC(C)(C)c2ncc(Cc3ccc(F)cc3)cc21] | (2R or 2S)-1-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}-2-methylpiperidin-4-one dihydrochloride | N/A | HPLC<sup>e</sup> separation of example 8, faster eluting | 1H NMR (400 MHz, Me-d3-OD): 8.76-8.66 (1H, m), 8.43-8.33 (1H, m), 7.34 (2H, s), 7.11 (2H, t), 4.19 (4H, s), 4.15-3.93 (2H, m), 3.76 (1H, d), 3.68 (2H, d), 3.64-3.56 (2H, m), 3.56-3.49 (2H, m), 3.44 (2H, d), 3.17-2.95 (2H, m), 2.31-2.11 (2H, m), 2.01 (2H, d), 1.59 (6H, s), 1.57-1.40 (6H, m). | 522 |
| 40 | 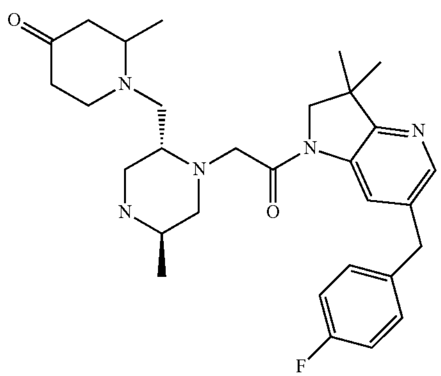 [SMILES: CC1CC(=O)CCN1C[C@H]1CN[C@H](C)CN1CC(=O)N1CC(C)(C)c2ncc(Cc3ccc(F)cc3)cc21] | (2S)-1-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}-2-methylpiperidin-4-one dihydrochloride | N/A | HPLC<sup>e</sup> separation of example 8, slower eluting | 1H NMR (400 MHz, Me-d3-OD): 8.71 (1H, s), 8.41 (1H, s), 7.41-7.29 (2H, m), 7.17-7.05 (2H, m), 4.31-4.10 (6H, m), 3.87-3.65 (3H, m), 3.60 (2H, s), 3.52 (2H, d), 3.47-3.40 (2H, m), 3.13-2.96 (2H, m), 2.41-2.19 (2H, m), 2.11 (2H, dd), 1.59 (6H, s), 1.46 (3H, d), 1.40 (3H, d). | 522 |

| Ex. | Structure | Name | Synthesis of Boc derivative | Deprotection Method | NMR Data | MS Data [M + H]+ |
|---|---|---|---|---|---|---|
| 41 | 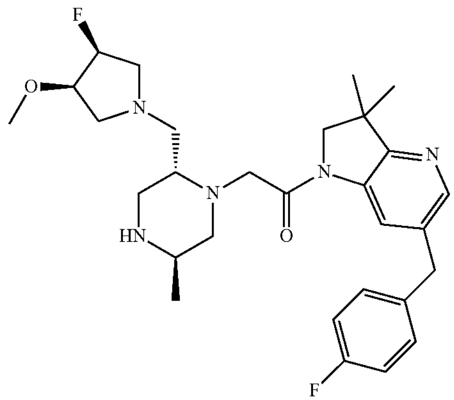 [SMILES: CO[C@@H]1CN(C[C@H]2CN[C@H](C)CN2CC(=O)N2CC(C)(C)c3ncc(Cc4ccc(F)cc4)cc32)C[C@@H]1F] | 2-[(2R,5R)-2-{[(3S,4R)-3-Fluoro-4-methoxypyrrolidin-1-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride and 2-[(2R,5R)-2-{[(3R,4S)-3-fluoro-4-methoxypyrrolidin-1-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride (1:1 mixture) | 19 + 33, see Preparation 20 | 1 | 1H NMR (400 MHz, Me-d3-OD): 8.71 (1H, d), 8.38 (1H, s), 7.38-7.28 (2H, m), 7.17-7.04 (2H, m), 5.52-5.44 (1H, m), 5.36 (1H, s), 4.39-4.12 (6H, m), 4.12-3.93 (3H, m), 3.92-3.69 (5H, m), 3.59 (1H, s), 3.53-3.43 (4H, m), 3.18-3.07 (1H, m), 1.61 (6H, d), 1.34 (3H, dd). | 528 |
| 42 | 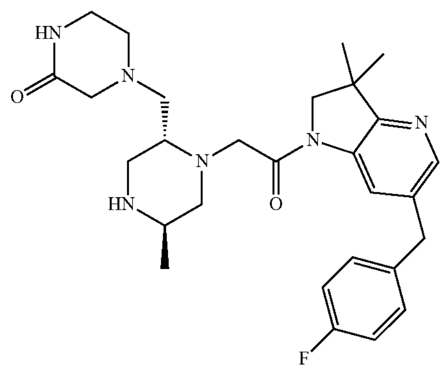 [SMILES: C[C@@H]1CN(CC(=O)N2CC(C)(C)c3ncc(Cc4ccc(F)cc4)cc32)[C@@H](CN2CCNC(=O)C2)CN1] | 4-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}piperazin-2-one dihydrochloride | 19 + piperazin-2-one, see Preparation 20 | 1 | 1H NMR (400 MHz, Me-d3-OD): 8.77 (1H, s), 8.37 (1H, s), 7.36 (2H, s), 7.18-7.06 (2H, m), 4.23 (4H, d), 4.11 (2H, s), 3.89 (3H, s), 3.68 (2H, d), 3.59 (5H, m), 3.46 (2H, d), 3.22 (4H, d), 1.62 (6H, s), 1.37 (3H, s). | 509 |

| Ex. | Structure | Name | Synthesis of Boc derivative | Deprotection Method | NMR Data | MS Data [M + H]+ |
|---|---|---|---|---|---|---|
| 43 | 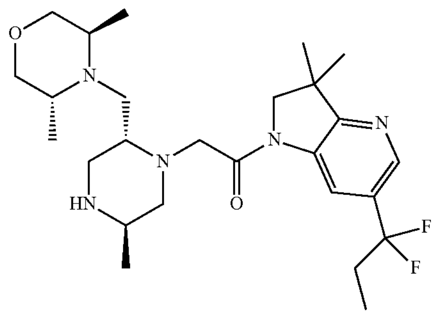 [SMILES: CCC(F)(F)c1cnc2c(c1)N(C(=O)CN1C[C@@H](C)NC[C@@H]1CN1[C@H](C)COC[C@H]1C)CC2(C)C] | 1-[6-(1,1-Difluoropropyl)-3,3-dimethyl-1H,2H,3H-pyrrolo[3,2-b]pyridin-1-yl]-2-[(2R,5R)-2-{[(3R,5R)-3,5-dimethylmorpholin-4-yl]methyl}-5-methylpiperazin-1-yl]ethan-1-one, dihydrochloride | 17C + 22, see Preparation 23 | 1 | 1H NMR (400 MHz, Me-d3-OD): 8.67 (1H, d), 8.49 (1H, s), 4.34-4.07 (7H, m), 4.06-3.89 (2H, m), 3.87-3.70 (4H, m), 3.64 (1H, s), 3.26 (1H, d), 3.21-3.12 (1H, m), 2.38-2.20 (2H, m), 1.59-1.51 (9H, m), 1.41 (3H, d), 1.31-1.23 (3H, m), 1.05 (3H, t). | 494 |
| 44 | 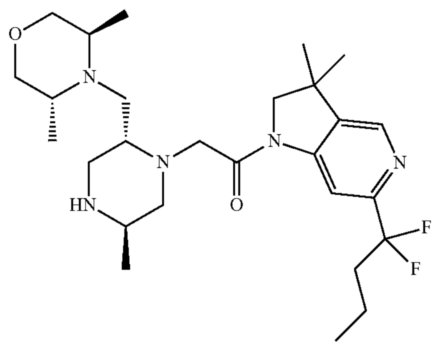 [SMILES: CCCC(F)(F)c1cc2c(cn1)C(C)(C)CN2C(=O)CN1C[C@@H](C)NC[C@@H]1CN1[C@H](C)COC[C@H]1C] | 1-[6-(1,1-Difluorobutyl)-3,3-dimethyl-1H,2H,3H-pyrrolo[3,2-c]pyridin-1-yl]-2-[(2R,5R)-2-{[(3R,5R)-3,5-dimethylmorpholin-4-yl]methyl}-5-methylpiperazin-1-yl]ethan-1-one, dihydrochloride | 17D + 22, see Preparation 23 | 1 | 1H NMR (400 MHz, Me-d3-OD): 8.66 (1H, s), 8.46 (1H, s), 4.24 (3H, d), 4.20-4.07 (3H, m), 4.05-3.91 (2H, m), 3.85-3.69 (4H, m), 3.67-3.60 (1H, m), 3.49-3.38 (2H, m), 3.27 (1H, s), 3.19-3.09 (1H, m), 2.39-2.25 (2H, m), 1.61-1.45 (11H, m), 1.41 (3H, d), 1.32 (3H, d), 1.01 (3H, t). | 508 |
| Ref Eg 45 | 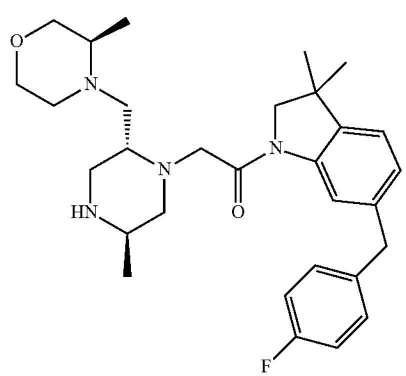 [SMILES: C[C@@H]1CN(CC(=O)N2CC(C)(C)c3ccc(Cc4ccc(F)cc4)cc32)[C@@H](CN2CCOC[C@H]2C)CN1] | 1-{6-[(4-Fluorophenyl)methyl]-3,3-dimethyl-2,3-dihydro-1H-indol-1-yl}-2-[(2R,5R)-2-{[(3R)-3-methylmorpholin-4-yl]methyl}piperazin-1-yl]ethan-1-one, dihydrochloride | See Preparation 46 | 1 | 1H NMR (400 MHz, Me-d3-OD): 7.90 (1H, s), 7.29-7.15 (3H, m), 7.12 (1H, d), 7.09-6.97 (2H, m), 4.07-3.92 (8H, m), 3.86 (2H, d), 3.80-3.64 (4H, m), 3.64-3.55 (2H, m), 3.44 (3H, d), 3.24 (2H, d), 3.06 (2H, d), 1.45-1.39 (8H, m), 1.30-1.15 (2H, m). | 509 |

| Ex. | Structure | Name | Synthesis of Boc derivative | Deprotection Method | NMR Data | MS Data [M + H]+ |
|---|---|---|---|---|---|---|
| 46 | 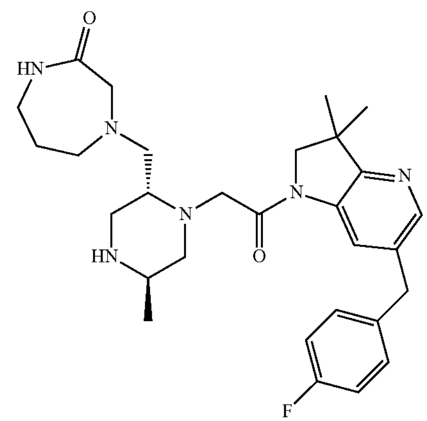 [SMILES: C[C@@H]1CN(CC(=O)N2CC(C)(C)c3ncc(Cc4ccc(F)cc4)cc32)[C@@H](CN2CCCNC(=O)C2)CN1] | 4-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}-1,4-diazepan-2-one, dihydrochloride | 19 + 1,4-diazepan-2-one, see Preparation 20 | 1 | 1H NMR (400 MHz, Me-d3-OD): 8.84 (1H, s), 8.40-8.31 (1H, m), 7.43-7.29 (2H, m), 7.10 (2H, t), 4.28-4.17 (5H, m), 4.08 (3H, d), 3.97-3.83 (1H, m), 3.68 (2H, s), 3.67-3.54 (4H, m), 3.44-3.35 (4H, m), 3.20-3.11 (1H, m), 2.09 (2H, s), 1.62 (6H, d), 1.40-1.32 (3H, m). | 523 |
| 47 | 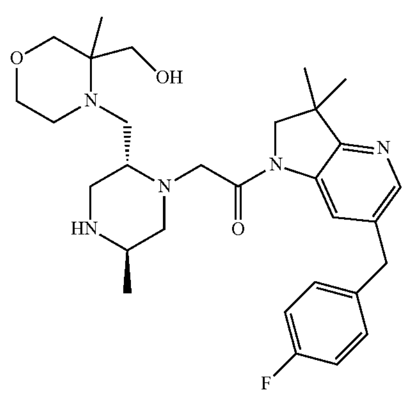 | 1-{6-[(4-Fluorophenyl)methyl]-3,3-dimethyl-1H,2H,3H-pyrrolo[3,2-b]pyridin-1-yl}-2-[(2R,5R)-2-{[3-(hydroxymethyl)-3-methylmorpholin-4-yl]methyl}-5-methylpiperazin-1-yl]ethan-1-one, dihydrochloride | 19 + 3-(hydroxymethyl)-3-methylmorpholine, see Preparation 20 | 1 | 1H NMR (400 MHz, Me-d3-OD): 8.79 (1H, s), 8.43 (1H, s), 7.38 (2H, s), 7.13 (2H, s), 4.26 (5H, s), 4.00 (4H, s), 3.81 (4H, s), 3.71-3.40 (6H, m), 3.25-2.84 (3H, m), 1.67 (6H, s), 1.48 (6H, s). | 540 |

-continued

| Ex. | Structure | Name | Synthesis of Boc derivative | Deprotection Method | NMR Data | MS Data [M + H]+ |
|---|---|---|---|---|---|---|
| 48 | 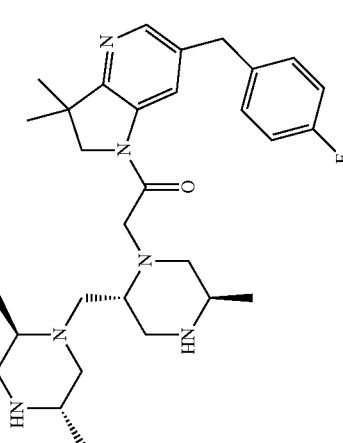 | (3R,6S)-4-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}-3,6-dimethylpiperazin-2-one, dihydrochloride, 70:30 mixture with a diastereomer | 19 + 47, see Preparation 20 | 1 | 1H NMR (400 MHz, Me-d3-OD): 8.89-8.76 (1H, m), 8.40 (1H, d), 7.37 (2H, s), 7.12 (2H, s), 4.30 (2H, s), 4.22 (4H, s), 4.05 (3H, s), 3.79-3.58 (5H, m), 3.58-3.39 (3H, m), 3.22 (1H, s), 1.83-1.60 (9H, m), 1.50-1.39 (3H, m), 1.33 (3H, d). | 537 |
| 49 | 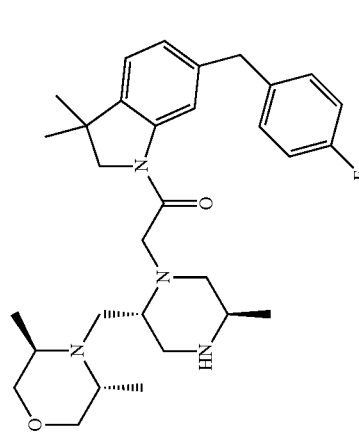 | 2-[(2R,5R)-2-{[(3R,5R)-3,5-Dimethylmorpholin-4-yl]methyl}-5-methylpiperazin-1-yl]-1-{6-[(4-fluorophenyl)methyl]-3,3-dimethyl-2,3-dihydro-1H-indol-1-yl}ethan-1-one, dihydrochloride | See Preparation 46A | 1 | 1H NMR (400 MHz, Me-d3-OD): 7.90 (1H, s), 7.28-7.17 (3H, m), 7.14 (1H, d), 7.09-7.00 (2H, m), 4.07-3.91 (9H, m), 3.80 (1H, d), 3.72-3.51 (7H, m), 3.46-3.40 (1H, m), 3.21-3.08 (2H, m), 1.51 (3H, d), 1.41 (6H, d), 1.39-1.31 (3H, m), 1.07 (3H, d). | 523 |

| Ex. | Structure | Name | Synthesis of Boc derivative | Deprotection Method | NMR Data | MS Data [M + H]+ |
|---|---|---|---|---|---|---|
| 50 | 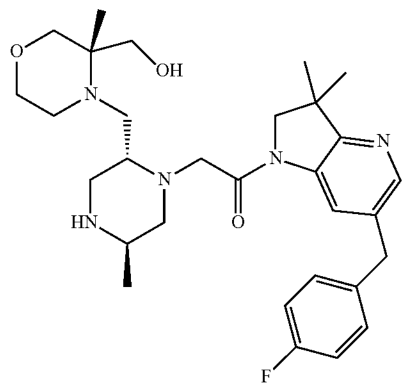 [SMILES: C[C@@H]1CN(CC(=O)N2CC(C)(C)c3ncc(Cc4ccc(F)cc4)cc32)[C@@H](CN2CCOC[C@]2(C)CO)CN1] | 1-{6-[(4-Fluorophenyl)methyl]-3,3-dimethyl-1H,2H,3H-pyrrolo[3,2-b]pyridin-1-yl}-2-{[(2R,5R)-2-{[(3S)-3-(hydroxymethyl)-3-methylmorpholin-4-yl]methyl}-5-methylpiperazin-1-yl]ethan-1-one, dihydrochloride | 19, see Preparation 20, then chromatographic separation | 1 | 1H NMR (400 MHz, Me-d3-OD): 8.63-8.45 (1H, m), 8.37-8.28 (1H, m), 7.31 (2H, dd), 7.09 (2H, t), 4.12 (5H, d), 4.04-3.70 (8H, m), 3.57 (6H, d), 3.42 (2H, d), 3.10 (1H, dd), 2.95 (1H, dd), 1.53 (6H, s), 1.50-1.37 (6H, m). | 540 |
| 51 | 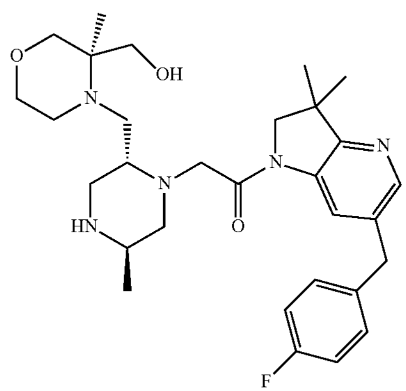 [SMILES: C[C@@H]1CN(CC(=O)N2CC(C)(C)c3ncc(Cc4ccc(F)cc4)cc32)[C@@H](CN2CCOC[C@@]2(C)CO)CN1] | 1-{6-[(4-Fluorophenyl)methyl]-3,3-dimethyl-1H,2H,3H-pyrrolo[3,2-b]pyridin-1-yl}-2-{[(2R,5R)-2-{[(3R)-3-(hydroxymethyl)-3-methylmorpholin-4-yl]methyl}-5-methylpiperazin-1-yl]ethan-1-one, dihydrochloride | 19, see Preparation 20, then chromatographic separation | 1 | 1H NMR (400 MHz, Me-d3-OD): 8.58 (1H, s), 8.38 (1H, s), 7.34 (2H, dd), 7.17-7.06 (2H, m), 4.22-4.06 (6H, m), 4.06-3.89 (3H, m), 3.89-3.73 (3H, m), 3.63-3.37 (7H, m), 3.18-2.95 (2H, m), 2.90 (1H, dd), 1.57 (6H, d), 1.49 (3H, d), 1.45 (3H, s). | 540 |

-continued

| Ex. | Structure | Name | Synthesis of Boc derivative | Deprotection Method | NMR Data | MS Data [M + H]+ |
|---|---|---|---|---|---|---|
| 52 | 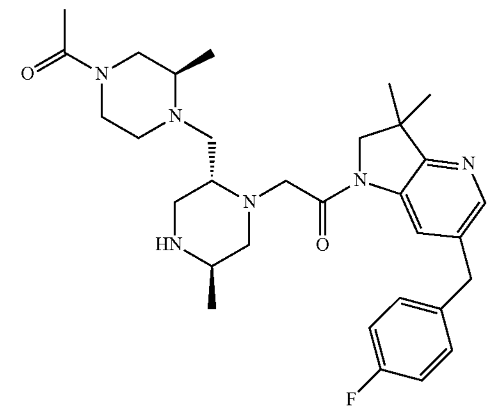 [SMILES: CC(=O)N1CCN(C[C@H]2CN[C@H](C)CN2CC(=O)N2CC(C)(C)c3ncc(Cc4ccc(F)cc4)cc32)[C@H](C)C1] | 2-[(2R,5R)-2-[[(2R)-4-Acetyl-2-methylpiperazin-1-yl]methyl]-5-methylpiperazin-1-yl]-1-{6-[(4-fluorophenyl)methyl]-3,3-dimethyl-1H,2H,3H-pyrrolo[3,2-b]pyridin-1-yl}ethan-1-one, dihydrochloride | 19 + (2R)-4-acetyl-2-methylpiperazine, see Preparation 20 | 1 | 1H NMR (400 MHz, Me-d3-OD): 8.67 (1H, d), 8.42 (1H, d), 7.34 (2H, dd), 7.10 (2H, t), 4.33-4.07 (7H, m), 3.88-3.71 (3H, m), 3.66-3.55 (2H, m), 3.55-3.36 (4H, m), 3.20 (4H, d), 2.24 (3H, s), 1.61 (6H, s), 1.48-1.35 (6H, m). | 551 |
| 53 | 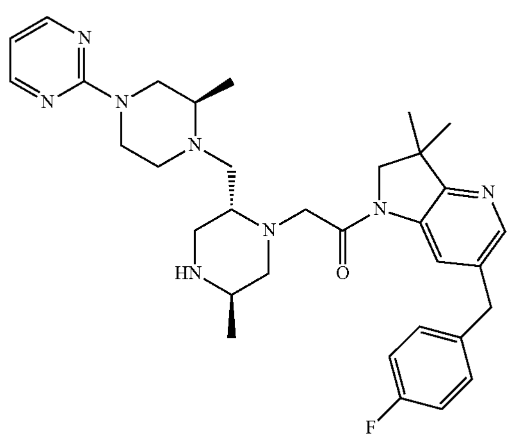 [SMILES: C[C@@H]1CN(CC(=O)N2CC(C)(C)c3ncc(Cc4ccc(F)cc4)cc32)[C@@H](CN2CCN(c3ncccn3)C[C@H]2C)CN1] | 1-{6-[(4-Fluorophenyl)methyl]-3,3-dimethyl-1H,2H,3H-pyrrolo[3,2-b]pyridin-1-yl]-2-[(2R,5R)-5-methyl-2-{[(2R)-2-methyl-4-(pyrimidin-2-yl)piperazin-1-yl]methyl}piperazin-1-yl]ethan-1-one, dihydrochloride | 19 + (2R)-2-methyl-4-(pyrimidin-2-yl)piperazine, see Preparation 20 | 1 | 1H NMR (400 MHz, Me-d3-OD): 8.79 (1H, s), 8.63 (2H, d), 8.43 (1H, s), 7.34 (2H, dd), 7.05 (2H, t), 6.99 (1H, t), 4.37-4.26 (2H, m), 4.20 (5H, d), 4.09-3.36 (10H, m), 3.28 (2H, d), 3.19-3.04 (1H, m), 1.64 (6H, s), 1.55-1.39 (6H, m). | 587 |

-continued

| Ex. | Structure | Name | Synthesis of Boc derivative | Deprotection Method | NMR Data | MS Data [M + H]+ |
|---|---|---|---|---|---|---|
| 54 | 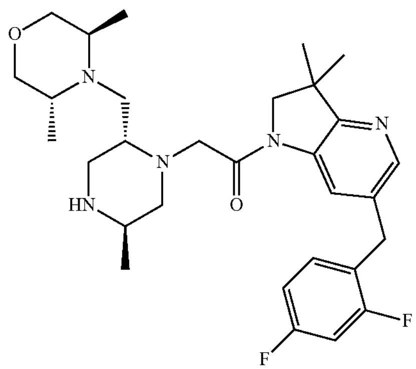 [SMILES: C[C@@H]1CN(CC(=O)N2CC(C)(C)c3ncc(Cc4ccc(F)cc4F)cc32)[C@@H](CN2[C@H](C)COC[C@H]2C)CN1] | 1-{6-[(2,4-Difluorophenyl)methyl]-3,3-dimethyl-1H,2H,3H-pyrrolo[3,2-b]pyridin-1-yl}-2-[(2R,5R)-2-{[(3R,5R)-3,5-dimethylmorpholin-4-yl]methyl}-5-methylpiperazin-1-yl]ethan-1-one, dihydrochloride | 17F + 22, see Preparation 23 | 1 | 1H NMR (400 MHz, Me-d3-OD): 8.73 (1H, s), 8.49 (1H, s), 7.56-7.44 (1H, m), 7.12-6.98 (2H, m), 4.38-4.28 (2H, m), 4.26 (2H, s), 4.24-4.19 (1H, m), 4.14-4.06 (2H, m), 3.98 (2H, s), 3.89 (1H, d), 3.79 (2H, d), 3.76-3.59 (3H, m), 3.54-3.48 (1H, m), 3.37 (2H, d), 3.23 (1H, d), 3.15 (1H, dd), 1.61 (6H, s), 1.54 (3H, d), 1.40 (3H, d), 1.19 (3H, d). | 542 |
| 55 | 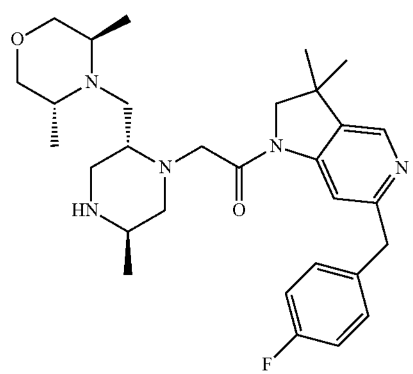 [SMILES: C[C@@H]1CN(CC(=O)N2CC(C)(C)c3cnc(Cc4ccc(F)cc4)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(4-fluorophenyl)methyl]-3,3-dimethyl-1H,2H,3H-pyrrolo[3,2-c]pyridin-1-yl}ethan-1-one, dihydrochloride | 17B + 22, see Preparation 23 | 1 | 1H NMR (400 MHz, Me-d3-OD): 8.66 (1H, s), 8.09 (1H, s), 7.46-7.36 (2H, m), 7.20 (2H, t), 4.41 (2H, s), 4.27 (2H, s), 4.20 (2H, d), 4.08-3.99 (1H, m), 3.93 (2H, s), 3.91-3.65 (5H, m), 3.65-3.57 (1H, m), 3.49-3.35 (3H, m), 3.29-3.20 (1H, m), 3.09 (1H, dd), 1.55 (6H, s), 1.51 (3H, d), 1.40 (3H, d), 1.20 (3H, d). | 524 |

| Ex. | Structure | Name | Synthesis of Boc derivative | Deprotection Method | NMR Data | MS Data [M + H]+ |
|---|---|---|---|---|---|---|
| 56 | 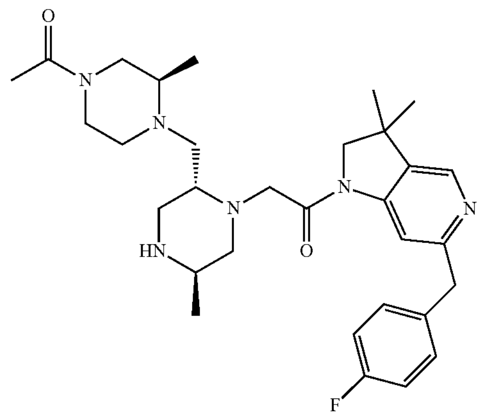 [SMILES: CC(=O)N1CCN(C[C@H]2CN[C@H](C)CN2CC(=O)N2CC(C)(C)c3cnc(Cc4ccc(F)cc4)cc32)[C@H](C)C1] | 2-[(2R,5R)-2-{[(2R)-4-Acetyl-2-methylpiperazin-1-yl]methyl}-5-methylpiperazin-1-yl]-1-{6-[(4-fluorophenyl)methyl]-3,3-dimethyl-1H,2H,3H-pyrrolo[3,2-c]pyridin-1-yl}ethan-1-one, dihydrochloride | 17B + 22B, see Preparation 23 | 1 | 1H NMR (400 MHz, Me-d3-OD): 8.61 (1H, s), 8.11 (1H, d), 7.40 (2H, dd), 7.15 (2H, t), 4.39 (2H, s), 4.34-4.06 (5H, m), 3.91-3.56 (5H, m), 3.41 (2H, d), 3.33-3.16 (6H, m), 3.07 (1H, d), 2.24 (3H, s), 1.55 (6H, s), 1.51-1.36 (6H, m). | 551 |
| 57 | 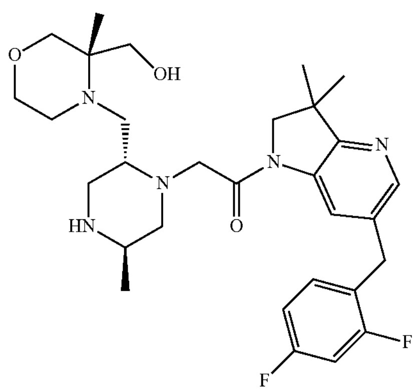 [SMILES: C[C@@H]1CN(CC(=O)N2CC(C)(C)c3ncc(Cc4ccc(F)cc4F)cc32)[C@@H](CN2CCOC[C@]2(C)CO)CN1] | 1-{6-[(2,4-Difluorophenyl)methyl]-3,3-dimethyl-1H,2H,3H-pyrrolo[3,2-b]pyridin-1-yl}-2-[(2R,5R)-2-{[(3S)-3-(hydroxymethyl)-3-methylmorpholin-4-yl]methyl}-5-methylpiperazin-1-yl]ethan-1-one, dihydrochloride | 17F + 22C, see Preparation 23 | 1, separated by preparative HPLC | 1H NMR (400 MHz, Me-d3-OD): 8.60 (1H, s), 8.40 (1H, s), 7.52-7.41 (1H, m), 7.08-6.96 (2H, m), 4.30-4.13 (5H, m), 4.13-3.74 (8H, m), 3.74-3.68 (1H, m), 3.65-3.52 (5H, m), 3.48-3.37 (1H, m), 3.17-3.07 (1H, m), 3.03 (1H, d), 2.90 (1H, dd), 1.56 (6H, d), 1.50 (3H, d), 1.46 (3H, s). | 558 |

| Ex. | Structure | Name | Synthesis of Boc derivative | Deprotection Method | NMR Data | MS Data [M + H]+ |
|---|---|---|---|---|---|---|
| 58 | 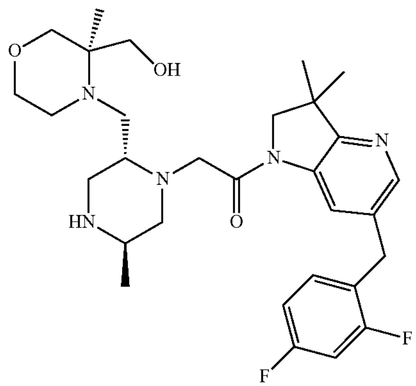 [SMILES: C[C@@H]1CN(CC(=O)N2CC(C)(C)c3ncc(Cc4ccc(F)cc4F)cc32)[C@@H](CN2CCOC[C@@]2(C)CO)CN1] | 1-{6-[(2,4-Difluorophenyl)methyl]-3,3-dimethyl-1H,2H,3H-pyrrolo[3,2-b]pyridin-1-yl}-2-[(2R,5R)-2-{[(3R)-3-(hydroxymethyl)-3-methylmorpholin-4-yl]methyl}-5-methylpiperazin-1-yl]ethan-1-one, dihydrochloride | 17F + 22C, see Preparation 23 | 1, separated by preparative HPLC | 1H NMR (400 MHz, Me-d3-OD): 8.24 (1H, s), 8.13 (1H, s), 7.41-7.28 (1H, m), 7.02-6.89 (2H, m), 4.13-3.35 (16H, m), 3.24-3.02 (1H, m), 3.02-2.81 (3H, m), 2.81-2.45 (2H, m), 1.41 (6H, d), 1.32 (3H, s), 1.19-0.86 (3H, m). | 558 |
| 59 | 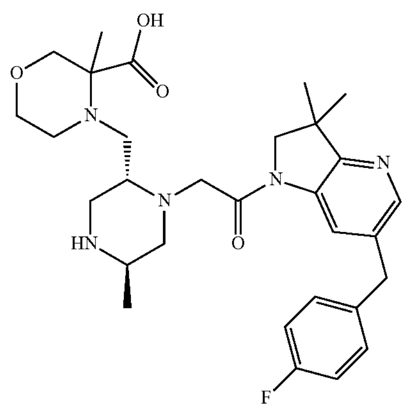 [SMILES: C[C@@H]1CN(CC(=O)N2CC(C)(C)c3ncc(Cc4ccc(F)cc4)cc32)[C@@H](CN2CCOCC2(C)C(=O)O)CN1] | 4-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}-3-methylmorpholine-3-carboxylic acid, dihydrochloride | 19 + 48, see Preparation 20 | 1 | 1H NMR (400 MHz, Me-d3-OD): 8.80 (1H, s), 8.40-8.32 (1H, m), 7.34 (2H, t), 7.10 (2H, t), 4.48 (1H, t), 4.38-4.24 (1H, m), 4.20 (4H, s), 4.06 (1H, d), 3.93 (2H, d), 3.89-3.80 (2H, m), 3.78-3.73 (1H, m), 3.73-3.69 (1H, m), 3.64-3.56 (1H, m), 3.56-3.37 (3H, m), 3.30-3.16 (2H, m), 3.11-2.99 (1H, m), 1.74-1.57 (9H, m), 1.38-1.29 (3H, m). | 554 |

| Ex. | Structure | Name | Synthesis of Boc derivative | Deprotection Method | NMR Data | MS Data [M + H]+ |
|---|---|---|---|---|---|---|
| 60 | 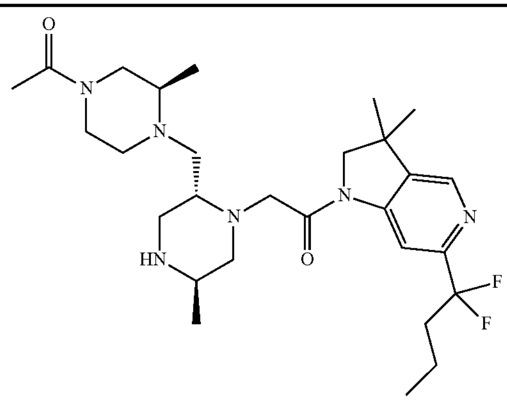 | 2-[(2R,5R)-2-[[(2R)-4-Acetyl-2-methylpiperazin-1-yl]methyl]-5-methylpiperazin-1-yl]-1-[6-(1,1-difluorobutyl)-3,3-dimethyl-1H,2H,3H-pyrrolo[3,2-c]pyridin-1-yl]ethan-1-one, dihydrochloride | 17D + 22B, see Preparation 23 | 1 | 1H NMR (400 MHz, Me-d3-OD): 8.76-8.68 (1H, m), 8.54 (1H, s), 4.32 (2H, s), 4.26-3.72 (8H, m), 3.68-3.36 (6H, m), 3.28 (2H, d), 3.16-3.00 (1H, m), 2.44-2.24 (2H, m), 2.20 (3H, d), 1.73-1.53 (10H, m), 1.45-1.37 (3H, m), 1.04 (3H, t). | 535 |
| 61 | 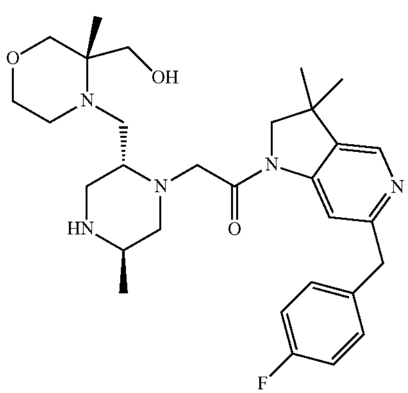 [SMILES: C[C@@H]1CN(CC(=O)N2CC(C)(C)c3cnc(Cc4ccc(F)cc4)cc32)[C@@H](CN2CCOC[C@]2(C)CO)CN1] | 1-[6-[(4-Fluorophenyl)methyl]-3,3-dimethyl-1H,2H,3H-pyrrolo[3,2-c]pyridin-1-yl]-2-[(2R,5R)-2-[[(3S)-3-(hydroxymethyl)-3-methylmorpholin-4-yl]methyl]-5-methylpiperazin-1-yl]ethan-1-one, dihydrochloride | 17B + 22C, see Preparation 23 | 1, separated by preparative HPLC | 1H NMR (400 MHz, Me-d3-OD): 8.39 (1H, s), 7.97 (1H, s), 7.32 (2H, dd), 7.15-7.03 (2H, m), 4.23 (2H, s), 4.20-3.98 (4H, m), 3.90-3.68 (3H, m), 3.68-3.66 (3H, m), 3.66-3.35 (7H, m), 3.05-2.74 (3H, m), 1.48 (6H, s), 1.43-1.29 (3H, m), 1.05 (3H, s). | 540 |

| Ex. | Structure | Name | Synthesis of Boc derivative | Deprotection Method | NMR Data | MS Data [M + H]+ |
|---|---|---|---|---|---|---|
| 62 | 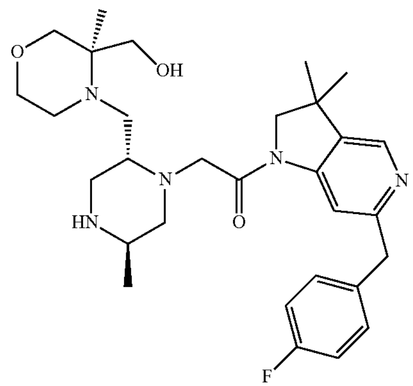 [SMILES: C[C@@H]1CN(CC(=O)N2CC(C)(C)c3cnc(Cc4ccc(F)cc4)cc32)[C@@H](CN2CCOC[C@@]2(C)CO)CN1] | 1-{6-[(4-Fluorophenyl)methyl]-3,3-dimethyl-1H,2H,3H-pyrrolo[3,2-c]pyridin-1-yl}-2-{(2R,5R)-2-{[(3R)-3-(hydroxymethyl)-3-methylmorpholin-4-yl]methyl}-5-methylpiperazin-1-yl]ethan-1-one, dihydrochloride | 17B + 22C, see Preparation 23 | 1, separated by preparative HPLC | 1H NMR (400 MHz, Me-d3-OD): 8.26 (1H, s), 7.88 (1H, s), 7.26 (2H, dd), 7.02 (2H, t), 4.09 (2H, s), 3.93 (3H, d), 3.71 (1H, d), 3.64-3.45 (5H, m), 3.45-3.36 (1H, m), 3.29-3.10 (3H, m), 3.00 (1H, dd), 2.84-2.55 (5H, m), 2.50 (1H, dd), 1.44 (6H, d), 1.20 (3H, d), 0.99 (3H, s). | 540 |
| 63 | 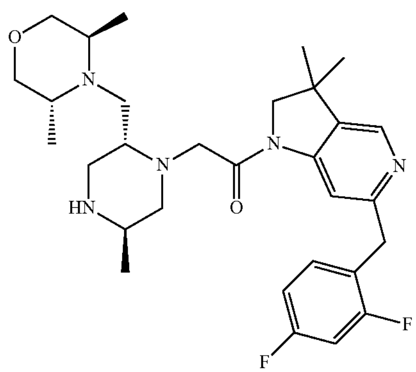 [SMILES: C[C@@H]1CN(CC(=O)N2CC(C)(C)c3cnc(Cc4ccc(F)cc4F)cc32)[C@@H](CN2[C@H](C)COC[C@H]2C)CN1] | 1-{6-[(2,4-Difluorophenyl)methyl]-3,3-dimethyl-1H,2H,3H-pyrrolo[3,2-c]pyridin-1-yl}-2-{(2R,5R)-2-{[(3R,5R)-3,5-dimethylmorpholin-4-yl]methyl}-5-methylpiperazin-1-yl]ethan-1-one, dihydrochloride | 17B + 22, see Preparation 23 | 1 | 1H NMR (400 MHz, Me-d3-OD): 8.67 (1H, s), 8.13 (1H, s), 7.61-7.50 (1H, m), 7.19-7.05 (2H, m), 4.50-4.35 (2H, m), 4.28 (2H, s), 4.25-4.13 (2H, m), 4.07 (1H, dd), 3.94 (2H, s), 3.91-3.70 (4H, m), 3.66-3.57 (1H, m), 3.55-3.42 (3H, m), 3.39 (1H, dd), 3.31-3.20 (2H, m), 3.10 (1H, dd), 1.55 (6H, s), 1.52 (3H, d), 1.41 (3H, d), 1.23 (3H, d). | 542 |

| Ex. | Structure | Name | Synthesis of Boc derivative | Deprotection Method | NMR Data | MS Data [M + H]+ |
|---|---|---|---|---|---|---|
| 66 | 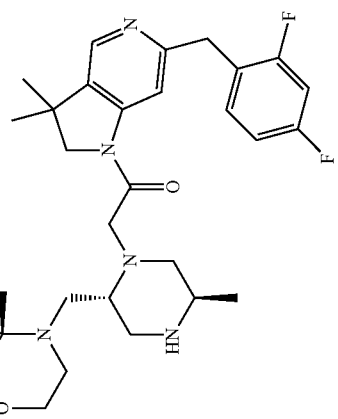 | 1-{6-[(2,4-Difluorophenyl)methyl]-3,3-dimethyl-1H,2H,3H-pyrrolo[3,2-c]pyridin-1-yl}-2-[(2R,5R)-2-{[(3S)-3-(hydroxymethyl)-3-methylmorpholin-4-yl]methyl}-5-methylpiperazin-1-yl]ethan-1-one dihydrochloride [slower eluting diastereomer] | 17E + 22E, Preparation 23 | a1, then HPLC separation then HCl salt formation | 1H NMR (400 MHz, Me-d3-OD): 8.34 (1H, s), 7.92 (1H, s), 7.42-7.30 (1H, m), 7.04-6.91 (2H, m), 4.18 (2H, s), 4.09-3.77 (4H, m), 3.77-3.36 (8H, m), 3.28 (1H, s), 3.10 (1H, s), 3.00-2.46 (6H, m), 1.46 (6H, d), 1.32 (3H, s), 1.03 (3H, s). | 558 |
| 67 | 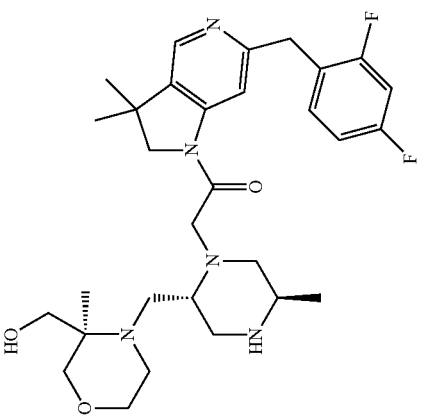 | 1-{6-[(2,4-Difluorophenyl)methyl]-3,3-dimethyl-1H,2H,3H-pyrrolo[3,2-c]pyridin-1-yl}-2-[(2R,5R)-2-{[(3R)-3-(hydroxymethyl)-3-methylmorpholin-4-yl]methyl}-5-methylpiperazin-1-yl]ethan-1-one dihydrochloride [faster eluting diastereomer] | 17E + 22E, Preparation 23 | a1, then HPLC separation then HCl salt formation | 1H NMR (400 MHz, Me-d3-OD): 8.25 (1H, s), 7.86 (1H, s), 7.37-7.26 (1H, m), 7.01-6.87 (2H, m), 4.11 (3H, d), 4.04-3.93 (2H, m), 3.90 (1H, d), 3.67 (1H, d), 3.63-3.51 (2H, m), 3.46 (2H, d), 3.38 (2H, d), 3.30-3.06 (2H, m), 3.06-2.96 (1H, m), 2.96-2.81 (2H, m), 2.80-2.60 (2H, m), 2.60-2.45 (1H, m), 2.38 (1H, dd), 1.44 (6H, d), 1.25 (3H, d), 0.94 (3H, s). | 558 |

| Ex. | Structure | Name | Synthesis of Boc derivative | Deprotection Method | NMR Data | MS Data [M + H]+ |
|---|---|---|---|---|---|---|
| 68 | 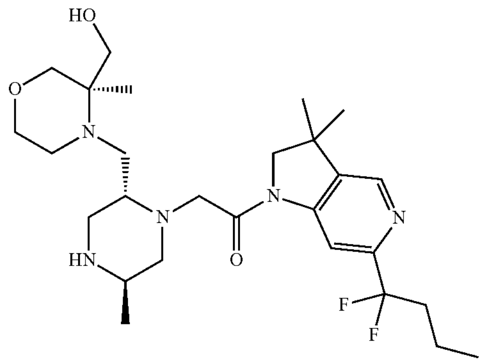 [SMILES: CCCC(F)(F)c1cc2c(cn1)C(C)(C)CN2C(=O)CN1C[C@@H](C)NC[C@@H]1CN1CCOC[C@@]1(C)CO] | 1-[6-(1,1-Difluorobutyl)-3,3-dimethyl-1H,2H,3H-pyrrolo[3,2-c]pyridin-1-yl)-2-[(2R,5R)-2-{[(3R)-3-(hydroxymethyl)-3-methylmorpholin-4-yl]methyl}-5-methylpiperazin-1-yl]ethan-1-one dihydrochloride [faster eluting diastereomer] | 17D + 22E, Preparation 23 | b1, then HPLC separation then HCl salt formation | 1H NMR (400 MHz, Me-d3-OD): 8.57 (1H, s), 8.48-8.32 (1H, m), 4.26-4.03 (7H, m), 3.98 (3H, dd), 3.83 (1H, d), 3.74-3.53 (6H, m), 3.19-3.05 (2H, m), 2.99-2.87 (1H, m), 2.38-2.22 (2H, m), 1.57-1.42 (15H, m), 1.00 (3H, t). | 524 |
| 69 | 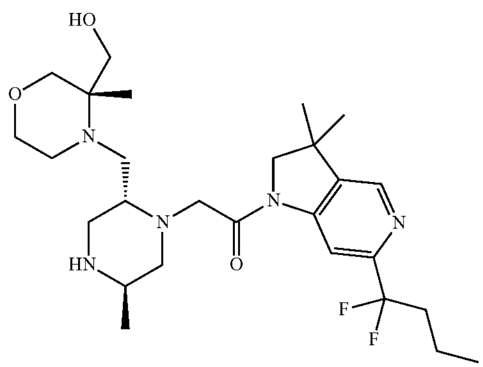 [SMILES: CCCC(F)(F)c1cc2c(cn1)C(C)(C)CN2C(=O)CN1C[C@@H](C)NC[C@@H]1CN1CCOC[C@]1(C)CO] | 1-[6-(1,1-Difluorobutyl)-3,3-dimethyl-1H,2H,3H-pyrrolo[3,2-c]pyridin-1-yl)-2-[(2R,5R)-2-{[(3S)-3-(hydroxymethyl)-3-methylmorpholin-4-yl]methyl}-5-methylpiperazin-1-yl]ethan-1-one dihydrochloride [slower eluting diastereomer] | 17D + 22E, Preparation 23 | b1, then HPLC separation then HCl salt formation | 1H NMR (400 MHz, Me-d3-OD): 8.41 (1H, s), 8.29 (1H, s), 4.12-3.88 (3H, m), 3.79 (1H, d), 3.63 (2H, t), 3.58-3.43 (4H, m), 3.26 (3H, dd), 3.05 (1H, dd), 2.92-2.61 (5H, m), 2.55 (1H, dd), 2.32-2.16 (2H, m), 1.58-1.29 (9H, m), 1.24 (3H, d), 1.03 (3H, s), 0.96 (3H, t). | 524 |

| Ex. | Structure | Name | Synthesis of Boc derivative | Deprotection Method | NMR Data | MS Data [M + H]+ |
|---|---|---|---|---|---|---|
| 71 | 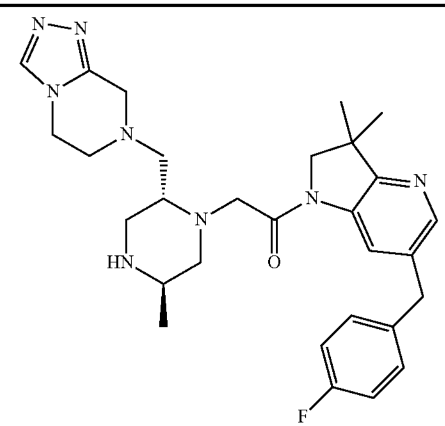 | 1-{6-[(4-Fluorophenyl)methyl]-3,3-dimethyl-1H,2H,3H-pyrrolo[3,2-b]pyridin-1-yl}-2-[(2R,5R)-5-methyl-2-{5H,6H,7H,8H-[1,2,4]triazolo[4,3-a]pyrazin-7-ylmethyl}piperazin-1-yl]ethan-1-one dihydrochloride | 19 + 5,6,7,8-Tetrahydro-[1,2,4]triazolo[1,5-a]pyrazine, Preparation 20 | 1 | 1H NMR (400 MHz, Me-d3-OD): 9.36 (1H, s), 8.76 (1H, s), 8.34 (1H, s), 7.35 (2H, dd), 7.15-7.05 (2H, m), 4.43-4.29 (3H, m), 4.29-4.12 (7H, m), 4.04 (1H, s), 3.76-3.63 (2H, m), 3.55-3.41 (1H, m), 3.28-3.18 (4H, m), 2.90 (1H, dd), 1.57 (6H, d), 1.39 (3H, d). | 533 |
| 76 | 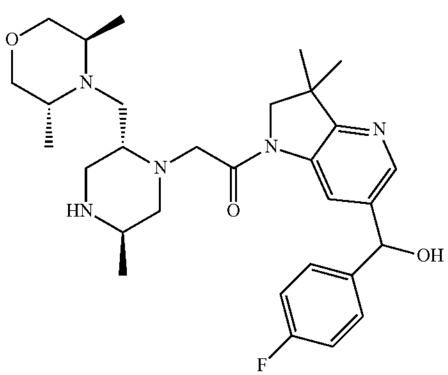 [SMILES: C[C@@H]1CN(CC(=O)N2CC(C)(C)c3ncc(C(O)c4ccc(F)cc4)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(4-fluorophenyl)(hydroxy)methyl]-3,3-dimethyl-1H,2H,3H-pyrrolo[3,2-b]pyridin-1-yl}ethan-1-one dihydrochloride | 17K + 22, Preparation 23 | 1 | 1H NMR (400 MHz, Me-d3-OD): 8.68 (1H, s), 8.54 (1H, d), 7.48 (2H, dd), 7.20-7.10 (2H, m), 6.01 (1H, s), 4.26 (2H, d), 4.20-4.14 (1H, m), 4.10-4.02 (2H, m), 3.99 (2H, d), 3.91-3.81 (1H, m), 3.72 (3H, s), 3.67-3.57 (2H, m), 3.52-3.45 (1H, m), 3.22 (2H, dd), 3.18-3.07 (2H, m), 1.61-1.56 (6H, m), 1.53 (3H, d), 1.39 (3H, dd), 1.19-1.08 (3H, m). | 540 |

-continued

| Ex. | Structure | Name | Synthesis of Boc derivative | Deprotection Method | NMR Data | MS Data [M + H]+ |
|---|---|---|---|---|---|---|
| 87 | 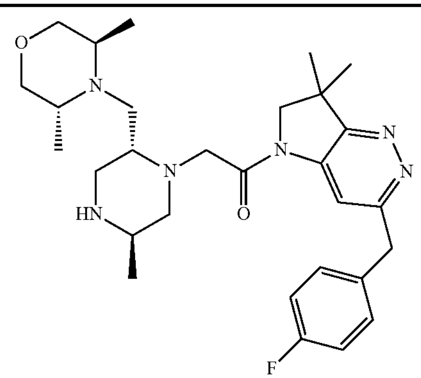 | 2-[(2R,5R)-2-{[(3R,5R)-3,5-Dimethylmorpholin-4-yl]methyl}-5-methylpiperazin-1-yl]-1-{3-[(4-fluorophenyl)methyl]-7,7-dimethyl-5H,6H,7H-pyrrolo[3,2-c]pyridazin-5-yl}ethan-1-one dihydrochloride | 17G + 22, Preparation 23 | 1 | 1H NMR (400 MHz, Me-d3-OD): 8.10 (1H, s), 7.44 (2H, dd), 7.24-7.14 (2H, m), 4.47 (2H, s), 4.31 (2H, s), 4.30-4.15 (2H, m), 4.08-3.69 (7H, m), 3.67-3.35 (5H, m), 3.31-3.19 (2H, m), 3.08 (1H, dd), 1.59 (6H, d), 1.52 (3H, s), 1.39 (3H, d), 1.22 (3H, d). | 525 |
| 88 | 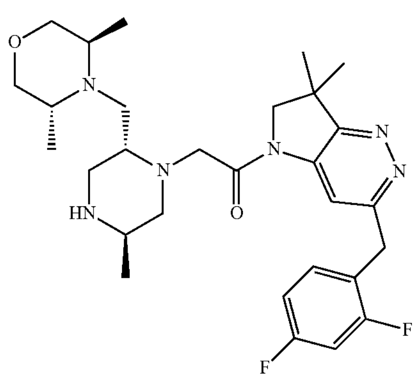 | 1-{3-[(2,4-Difluorophenyl)methyl]-7,7-dimethyl-5H,6H,7H-pyrrolo[3,2-c]pyridazin-5-yl}-2-[(2R,5R)-2-{[(3R,5R)-3,5-dimethylmorpholin-4-yl]methyl}-5-methylpiperazin-1-yl]ethan-1-one dihydrochloride | 17H + 22, Preparation 23 | 1 | 1H NMR (400 MHz, Me-d3-OD): 8.18 (1H, s), 7.65-7.54 (1H, m), 7.19-7.06 (2H, m), 4.52 (2H, s), 4.36 (2H, s), 4.33-4.18 (2H, m), 4.16-3.96 (2H, m), 3.96-3.71 (6H, m), 3.67-3.55 (2H, m), 3.48-3.37 (2H, m), 3.31-3.20 (2H, m), 3.16-3.03 (1H, m), 1.65-1.56 (6H, m), 1.56-1.49 (3H, m), 1.40 (3H, d), 1.27 (3H, d). | 543 |

| Ex. | Structure | Name | Synthesis of Boc derivative | Deprotection Method | NMR Data | MS Data [M + H]+ |
|---|---|---|---|---|---|---|
| 90 | 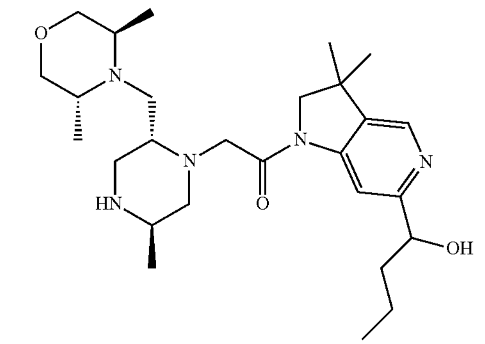 [SMILES: CCCC(O)c1cc2c(cn1)C(C)(C)CN2C(=O)CN1C[C@@H](C)NC[C@@H]1CN1[C@H](C)COC[C@H]1C] | 2-[(2R,5R)-2-{[(3R,5R)-3,5-Dimethylmorpholin-4-yl]methyl}-5-methylpiperazin-1-yl]-1-[6-(1-hydroxybutyl)-3,3-dimethyl-1H,2H,3H-pyrrolo[3,2-c]pyridin-1-yl]ethan-1-one dihydrochloride | 17N + 22, Preparation 23 | 1 | 1H NMR (400 MHz, Me-d3-OD): 8.58 (1H, s), 8.47 (1H, s), 4.24-3.90 (4H, m), 3.90-3.49 (4H, m), 3.35-3.30 (12H, m), 3.15 (2H, t), 3.05-2.83 (4H, m), 2.83-2.67 (1H, m), 2.67-2.46 (2H, m), 1.81-1.67 (2H, m), 1.29-1.20 (3H, m), 1.07-0.98 (9H, m). | 488 |
| 92 | 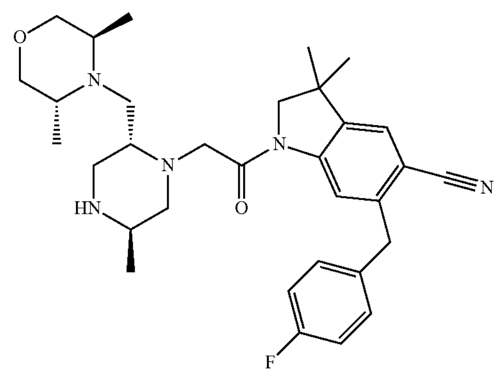 [SMILES: C[C@@H]1CN(CC(=O)N2CC(C)(C)c3cc(C#N)c(Cc4ccc(F)cc4)cc32)[C@@H](CN2[C@H](C)COC[C@H]2C)CN1] | 1-{2-[(2R,5R)-2-{[(3R,5R)-3,5-Dimethylmorpholin-4-yl]methyl}-5-methylpiperazin-1-yl]acetyl}-6-[(4-fluorophenyl)methyl]-3,3-dimethyl-2,3-dihydro-1H-indole-5-carbonitrile dihydrochloride | 55 + 22, Preparation 23 | 1 | 1H NMR (400 MHz, Me-d3-OD): 8.03 (1H, s), 7.70 (1H, s), 7.35-7.25 (2H, m), 7.16-7.05 (2H, m), 4.24 (2H, d), 4.12-3.97 (5H, m), 3.95 (2H, d), 3.85-3.78 (1H, m), 3.67-3.55 (4H, m), 3.45-3.35 (2H, m), 3.29-3.17 (2H, m), 3.10 (1H, dd), 1.50 (3H, d), 1.44 (6H, d), 1.37 (3H, d), 1.10 (3H, d). | 548 |

| Ex. | Structure | Name | Synthesis of Boc derivative | Deprotection Method | NMR Data | MS Data [M + H]+ |
|---|---|---|---|---|---|---|
| 93 | 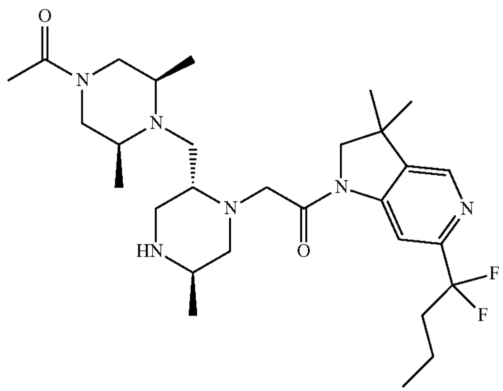 [SMILES: CCCC(F)(F)c1cc2c(cn1)C(C)(C)CN2C(=O)CN1C[C@@H](C)NC[C@@H]1CN1[C@H](C)CN(C(C)=O)C[C@@H]1C] | 2-[(2R,5R)-2-{[(2R,6S)-4-Acetyl-2,6-dimethylpiperazin-1-yl]methyl}-5-methylpiperazin-1-yl]-1-{6-(1,1-difluorobutyl)-3,3-dimethyl-1H,2H,3H-pyrrolo[3,2-c]pyridin-1-yl]ethan-1-one dihydrochloride | 17D + 22F, Preparation 23 | 1 | 1H NMR (400 MHz, Me-d3-OD): 8.64 (1H, s), 8.44 (1H, s), 4.31-4.22 (1H, m), 4.20 (2H, s), 4.18-4.05 (2H, m), 4.05-3.69 (5H, m), 3.61 (3H, d), 3.53-3.36 (3H, m), 3.27-3.19 (1H, m), 3.15-3.01 (1H, m), 2.41-2.24 (2H, m), 2.24-2.14 (3H, m), 1.70-1.50 (14H, m), 1.49-1.45 (3H, m), 1.01 (3H, t). | 549 |
| 94 | 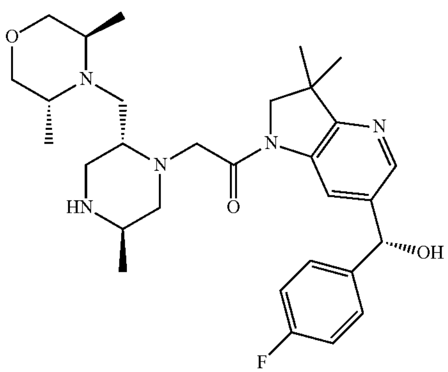 [SMILES: C[C@@H]1CN(CC(=O)N2CC(C)(C)c3ncc([C@H](O)c4ccc(F)cc4)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(R)-(4-fluorophenyl)(hydroxy)methyl]-3,3-dimethyl-1H,2H,3H-pyrrolo[3,2-b]pyridin-1-yl}ethan-1-one L-lactate [racemate is Example 76] | 17K + 22, Preparation 23 | "HPLC separation of Ex 76 then lactate salt formation | 1H NMR (400 MHz, Me-d3-OD): 8.35 (1H, d), 8.24 (1H, d), 7.41 (2H, dd), 7.07 (2H, t), 5.86 (1H, s), 4.09 (1H, q), 4.01-3.84 (4H, m), 3.55-3.40 (4H, m), 3.31-3.23 (1H, m), 3.23-3.10 (2H, m), 3.10-2.95 (4H, m), 2.89-2.74 (3H, m), 2.29 (1H, dd), 1.42 (6H, d), 1.36 (3H, s), 1.28 (3H, d), 0.97 (6H, d). | 540 |

-continued

| Ex. | Structure | Name | Synthesis of Boc derivative | Deprotection Method | NMR Data | MS Data [M + H]+ |
|---|---|---|---|---|---|---|
| 95 | 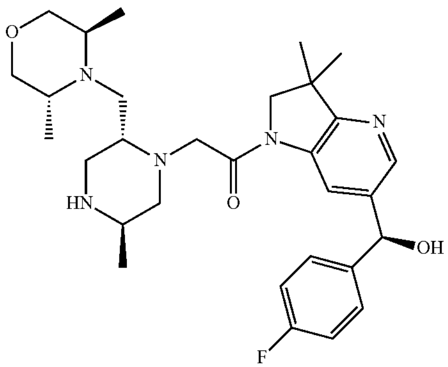 [SMILES: C[C@@H]1CN(CC(=O)N2CC(C)(C)c3ncc([C@@H](O)c4ccc(F)cc4)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(S)-(4-fluorophenyl)(hydroxy)methyl]-3,3-dimethyl-1H,2H,3H-pyrrolo[3,2-b]pyridin-1-yl}ethan-1-one dihydrochloride [racemate is Example 76] | 17M + 22, Preparation 23 | 1 | 1H NMR (400 MHz, Me-d3-OD): 8.79 (1H, s), 8.60 (1H, s), 7.50 (2H, dd), 7.16 (2H, t), 6.04 (1H, s), 4.32 (2H, s), 4.24 (1H, d), 4.19-3.96 (4H, m), 3.88 (1H, d), 3.82-3.55 (5H, m), 3.54-3.40 (1H, m), 3.28-3.08 (2H, m), 1.63 (6H, d), 1.53 (3H, d), 1.38 (3H, d), 1.10 (3H, d). | 540 |
| 96 | 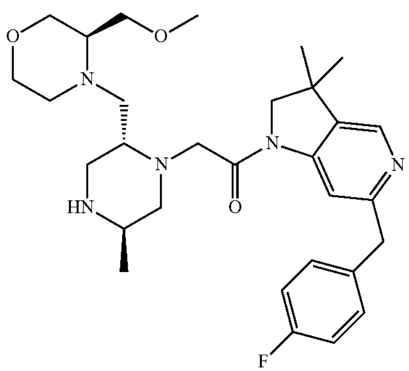 [SMILES: COC[C@@H]1COCCN1C[C@H]1CN[C@H](C)CN1CC(=O)N1CC(C)(C)c2cnc(Cc3ccc(F)cc3)cc21] | 1-{6-[(4-Fluorophenyl)methyl]-3,3-dimethyl-1H,2H,3H-pyrrolo[3,2-c]pyridin-1-yl}-2-[(2R,5R)-2-{[(3R)-3-(methoxymethyl)morpholin-4-yl]methyl}-5-methylpiperazin-1-yl]ethan-1-one dihydrochloride | 17B + 22D, Preparation 23 | 1 | 1H NMR (400 MHz, Me-d3-OD): 8.62 (1H, s), 8.08 (1H, s), 7.41 (2H, dd), 7.24-7.13 (2H, m), 4.40 (2H, s), 4.38-3.87 (9H, m), 3.87-3.68 (5H, m), 3.67-3.41 (5H, m), 3.20 (2H, s), 3.05-2.91 (1H, m), 1.54 (6H, d), 1.46 (3H, s). | 540 |

| Ex. | Structure | Name | Synthesis of Boc derivative | Deprotection Method | NMR Data | MS Data [M + H]+ |
|---|---|---|---|---|---|---|
| 97 | 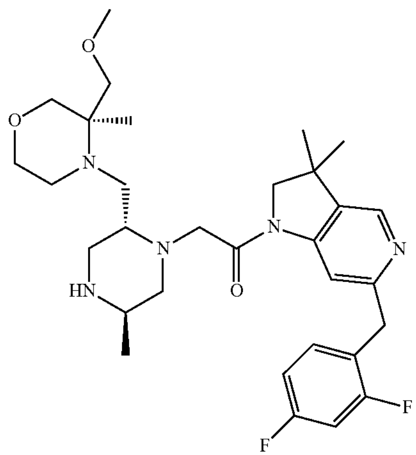 [SMILES: COC[C@]1(C)COCCN1C[C@H]1CN[C@H](C)CN1CC(=O)N1CC(C)(C)c2cnc(Cc3ccc(F)cc3F)cc21] | 1-{6-[(2,4-Difluorophenyl)methyl]-3,3-dimethyl-1H,2H,3H-pyrrolo[3,2-c]pyridin-1-yl}-2-[(2R,5R)-2-{[(3R)-3-(methoxymethyl)-3-methylmorpholin-4-yl]methyl}-5-methylpiperazin-1-yl]ethan-1-one dihydrochloride | 17E + 22G, Preparation 23 | $d_1$, chiral HPLC separation then HCl salt formation | 8.26 (1H, s), 7.87 (1H, s), 7.35-7.26 (1H, m), 6.99-6.88 (2H, m), 4.33-4.22 (1H, m), 4.11 (2H, s), 4.04-3.86 (3H, m), 3.67-3.47 (3H, m), 3.45-3.37 (1H, m), 3.25-3.06 (7H, m), 2.97 (1H, dd), 2.82 (1H, dd), 2.78-2.71 (1H, m), 2.71-2.58 (2H, m), 2.54-2.43 (1H, m), 2.30-2.20 (1H, m), 1.44 (6H, d), 1.18 (3H, d), 0.93 (3H, s). | 572 |
| 98 | 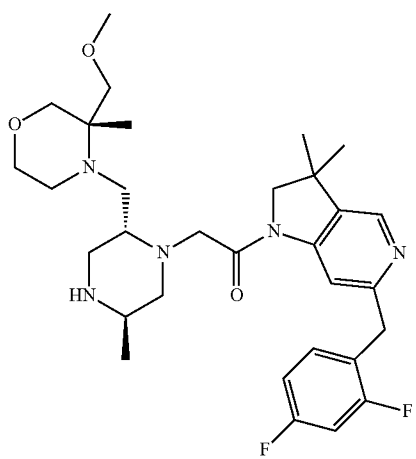 [SMILES: COC[C@@]1(C)COCCN1C[C@H]1CN[C@H](C)CN1CC(=O)N1CC(C)(C)c2cnc(Cc3ccc(F)cc3F)cc21] | 1-{6-[(2,4-Difluorophenyl)methyl]-3,3-dimethyl-1H,2H,3H-pyrrolo[3,2-c]pyridin-1-yl}-2-[(2R,5R)-2-{[(3S)-3-(methoxymethyl)-3-methylmorpholin-4-yl]methyl}-5-methylpiperazin-1-yl]ethan-1-one dihydrochloride | 17E + 22G, Preparation 23 | $d_1$, chiral HPLC separation then HCl salt formation | 1H NMR (400 MHz, Me-d3-OD): 8.26 (1H, s), 7.86 (1H, s), 7.37-7.26 (1H, m), 7.00-6.88 (2H, m), 4.12 (2H, s), 3.98-3.92 (2H, m), 3.89 (1H, d), 3.74 (1H, d), 3.58 (2H, t), 3.55-3.49 (1H, m), 3.46 (1H, d), 3.37 (1H, d), 3.29 (3H, s), 3.22 (3H, d), 3.03-2.96 (1H, m), 2.85-2.74 (2H, m), 2.69 (1H, t), 2.65-2.57 (2H, m), 2.47 (1H, dd), 1.44 (6H, d), 1.23 (3H, d), 0.99 (3H, s). | 572 |

| Ex. | Structure | Name | Synthesis of Boc derivative | Deprotection Method | NMR Data | MS Data [M + H]+ |
|---|---|---|---|---|---|---|
| 99 | 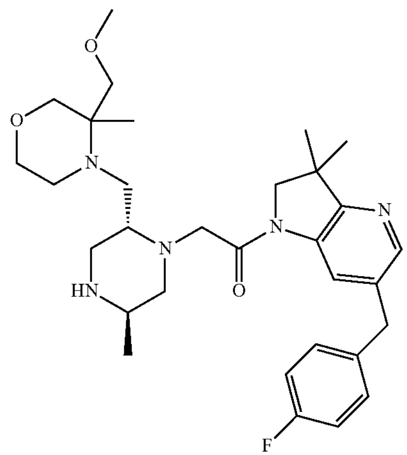 [SMILES: COCC1(C)COCCN1C[C@H]1CN[C@H](C)CN1CC(=O)N1CC(C)(C)c2ncc(Cc3ccc(F)cc3)cc21] | 1-{6-[(4-Fluorophenyl)methyl]-3,3-dimethyl-1H,2H,3H-pyrrolo[3,2-b]pyridin-1-yl]-2-[(2R,5R)-2-[[3-(methoxymethyl)-3-methylmorpholin-4-yl]methyl]-5-methylpiperazin-1-yl]ethan-1-one dihydrochloride Faster eluting, unassigned stereochemistry on morpholine | 17 + 22G, Preparation 23 | $d_1$, chiral HPLC separation then HCl salt formation | 1H NMR (400 MHz, Me-d3-OD): 8.45 (1H, s), 8.36 (1H, s), 7.32 (2H, dd), 7.11 (2H, t), 4.36-4.19 (2H, m), 4.15 (3H, s), 4.11-3.89 (5H, m), 3.86 (2H, s), 3.83-3.71 (1H, m), 3.70-3.46 (6H, m), 3.46-3.34 (3H, m), 3.08 (1H, d), 3.03-2.86 (2H, m), 1.54 (9H, d), 1.50 (3H, s). | 554 |
| 100 | 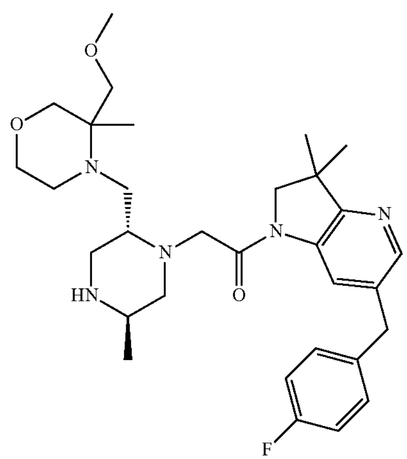 [SMILES: COCC1(C)COCCN1C[C@H]1CN[C@H](C)CN1CC(=O)N1CC(C)(C)c2ncc(Cc3ccc(F)cc3)cc21] | 1-{6-[(4-Fluorophenyl)methyl]-3,3-dimethyl-1H,2H,3H-pyrrolo[3,2-b]pyridin-1-yl]-2-[(2R,5R)-2-[[3-(methoxymethyl)-3-methylmorpholin-4-yl]methyl]-5-methylpiperazin-1-yl]ethan-1-one dihydrochloride Slower eluting, unassigned stereochemistry on morpholine | 17 + 22G, Preparation 23 | $d_1$, chiral HPLC separation then HCl salt formation | 1H NMR (400 MHz, Me-d3-OD): 8.42 (2H, s), 7.32 (2H, dd), 7.10 (2H, t), 4.18-4.05 (5H, m), 3.96 (4H, m), 3.74 (4H, s), 3.57 (5H, s), 3.43 (4H, s), 3.17-3.02 (2H, m), 2.96 (1H, dd), 1.64-1.37 (12H, m). | 554 |

| Ex. | Structure | Name | Synthesis of Boc derivative | Deprotection Method | NMR Data | MS Data [M + H]+ |
|---|---|---|---|---|---|---|
| 101 | 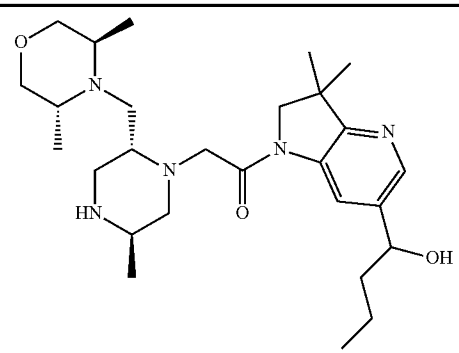 | 2-[(2R,5R)-2-{[(3R,5R)-3,5-Dimethylmorpholin-4-yl]methyl}-5-methylpiperazin-1-yl]-1-[6-(1-(R or S)-hydroxybutyl)-3,3-dimethyl-1H,2H,3H-pyrrolo[3,2-b]pyridin-1-yl]ethan-1-one dihydrochloride [epimer mixture is Example 89] | See preparation 60; derives from slower eluting isomer 60B | 1 | 1H NMR (400 MHz, Me-d3-OD): 9.09 (1H, s), 8.44 (1H, s), 5.00-4.91 (1H, m), 4.44-4.23 (3H, m), 4.22-3.90 (6H, m), 3.79 (4H, dd), 3.65 (1H, dd), 3.40 (3H, d), 3.26 (1H, d), 3.18 (1H, dd), 1.84-1.71 (2H, m), 1.65 (7H, d), 1.56 (4H, d), 1.40 (4H, d), 1.34-1.23 (3H, m), 1.00 (3H, t). | 488 |
| 102 | 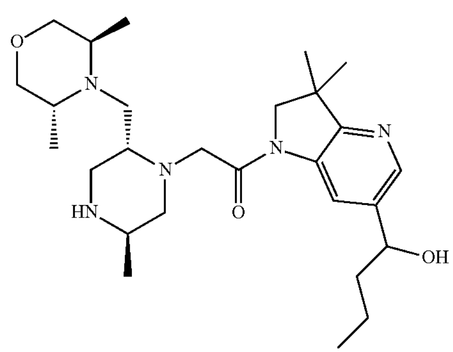 [SMILES: CCCC(O)c1cnc2c(c1)N(C(=O)CN1C[C@@H](C)NC[C@@H]1CN1[C@H](C)COC[C@H]1C)CC2(C)C] | 2-[(2R,5R)-2-{[(3R,5R)-3,5-Dimethylmorpholin-4-yl]methyl}-5-methylpiperazin-1-yl]-1-[6-(1-(R or S)-hydroxybutyl)-3,3-dimethyl-1H,2H,3H-pyrrolo[3,2-b]pyridin-1-yl]ethan-1-one dihydrochloride [epimer mixture is Example 89] | See preparation 60; derives from faster eluting isomer 60A | 1 | 1H NMR (400 MHz, Me-d3-OD): 9.09 (1H, s), 8.44 (1H, s), 4.94 (1H, t), 4.43-4.23 (3H, m), 4.23-4.06 (4H, m), 4.05-3.91 (2H, m), 3.91-3.58 (5H, m), 3.53-3.36 (3H, m), 3.24-3.11 (1H, m), 1.83-1.70 (2H, m), 1.65 (6H, d), 1.58-1.45 (5H, m), 1.42 (3H, d), 1.31 (3H, d), 1.00 (3H, t). | 488 |

| Ex. | Structure | Name | Synthesis of Boc derivative | Deprotection Method | NMR Data | MS Data [M + H]+ |
|---|---|---|---|---|---|---|
| 103 | 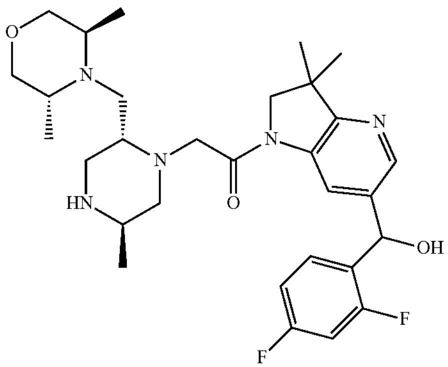 [SMILES: C[C@@H]1CN(CC(=O)N2CC(C)(C)c3ncc(C(O)c4ccc(F)cc4F)cc32)[C@@H](CN2[C@H](C)COC[C@H]2C)CN1] | (R or S)-1-{6-[(2,4-Difluorophenyl)(hydroxy)methyl]-3,3-dimethyl-1H,2H,3H-pyrrolo[3,2-b]pyridin-1-yl}-2-[(2R,5R)-2-{[(3R,5R)-3,5-dimethylmorpholin-4-yl]methyl}-5-methylpiperazin-1-yl]ethan-1-one dihydrochloride | 17T + 22, Preparation 23 | 1 | 1H NMR (400 MHz, Me-d3-OD): 8.85 (1H, s), 8.59 (1H, s), 7.73-7.61 (1H, m), 7.13-6.99 (2H, m), 6.27 (1H, s), 4.37-4.17 (3H, m), 4.17-3.95 (4H, m), 3.95-3.57 (5H, m), 3.57-3.43 (1H, m), 3.27-3.09 (2H, m), 1.63 (6H, d), 1.54 (3H, d), 1.39 (3H, d), 1.16 (3H, d). | 558 |
| 104 | 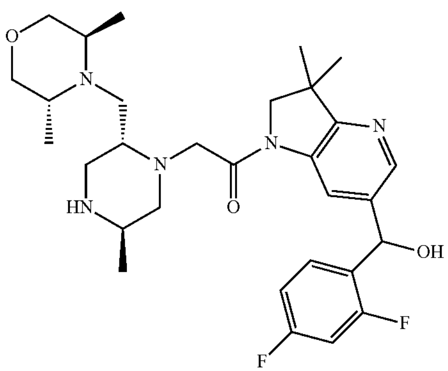 [SMILES: C[C@@H]1CN(CC(=O)N2CC(C)(C)c3ncc(C(O)c4ccc(F)cc4F)cc32)[C@@H](CN2[C@H](C)COC[C@H]2C)CN1] | (R or S)-1-{6-[(2,4-Difluorophenyl)(hydroxy)methyl]-3,3-dimethyl-1H,2H,3H-pyrrolo[3,2-b]pyridin-1-yl}-2-[(2R,5R)-2-{[(3R,5R)-3,5-dimethylmorpholin-4-yl]methyl}-5-methylpiperazin-1-yl]ethan-1-one dihydrochloride | 17S + 22, Preparation 23 | 1 | 1H NMR (400 MHz, Me-d3-OD): 8.87 (1H, s), 8.61-8.52 (1H, m), 7.72 (1H, d), 7.69 (1H, d), 7.15-6.97 (2H, m), 6.25 (1H, s), 4.39-4.28 (2H, m), 4.28-4.06 (3H, m), 4.06-3.94 (2H, m), 3.94-3.69 (4H, m), 3.69-3.47 (2H, m), 3.42 (2H, m), 3.29-3.07 (2H, m), 1.63 (6H, d), 1.54 (3H, d), 1.40 (3H, d), 1.22 (3H, d). | 558 |

| Ex. | Structure | Name | Synthesis of Boc derivative | Deprotection Method | NMR Data | MS Data [M + H]+ |
|---|---|---|---|---|---|---|
| 105 | 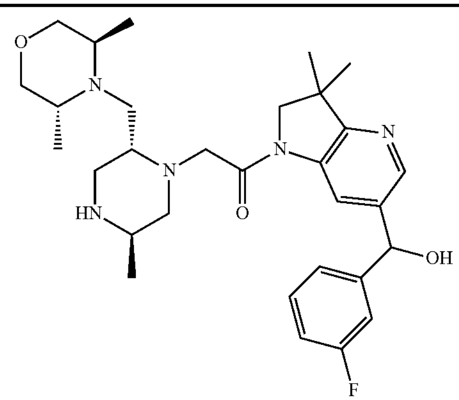 | 2-[(2R,5R)-2-{[(3R,5R)-3,5-Dimethylmorpholin-4-yl]methyl}-5-methylpiperazin-1-yl]-1-{6-[(R or S)-(3-fluorophenyl)(hydroxy)methyl]-3,3-dimethyl-1H,2H,3H-pyrrolo[3,2-b]pyridin-1-yl}ethan-1-one dihydrochloride | 17R + 22, Preparation 23 | 1 | 1H NMR (400 MHz, Me-d3-OD): 8.86 (1H, s), 8.63 (1H, s), 7.51-7.38 (1H, m), 7.33 (1H, d), 7.25 (1H, d), 7.16-7.04 (1H, m), 6.07 (1H, s), 4.40-4.20 (3H, m), 4.20-3.95 (4H, m), 3.95-3.57 (6H, m), 3.50 (1H, t), 3.27-3.09 (2H, m), 1.64 (6H, d), 1.53 (3H, d), 1.39 (3H, d), 1.10 (3H, d). | 540 |
| 106 | 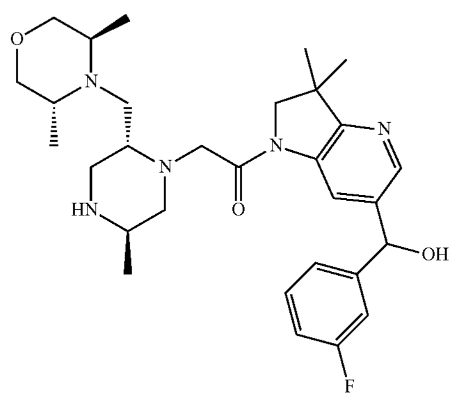 [SMILES: C[C@@H]1CN(CC(=O)N2CC(C)(C)c3ncc(C(O)c4cccc(F)c4)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(R or S)-(3-fluorophenyl)(hydroxy)methyl]-3,3-dimethyl-1H,2H,3H-pyrrolo[3,2-b]pyridin-1-yl}ethan-1-one dihydrochloride | 17Q + 22, Preparation 23 | 1 | 1H NMR (400 MHz, Me-d3-OD): 8.82 (1H, d), 8.58 (1H, d), 7.49-7.37 (1H, m), 7.35-7.20 (2H, m), 7.14-7.03 (1H, m), 6.05 (1H, s), 4.36-4.26 (2H, m), 4.26-4.15 (1H, m), 4.15-4.05 (2H, m), 4.05-3.94 (2H, m), 3.89 (1H, d), 3.84-3.67 (3H, m), 3.67-3.45 (3H, m), 3.22 (1H, d), 3.14 (1H, dd), 1.61 (6H, s), 1.53 (3H, d), 1.39 (3H, d), 1.16 (3H, d). | 540 |

-continued

| Ex. | Structure | Name | Synthesis of Boc derivative | Deprotection Method | NMR Data | MS Data [M + H]+ |
|---|---|---|---|---|---|---|
| 107 | 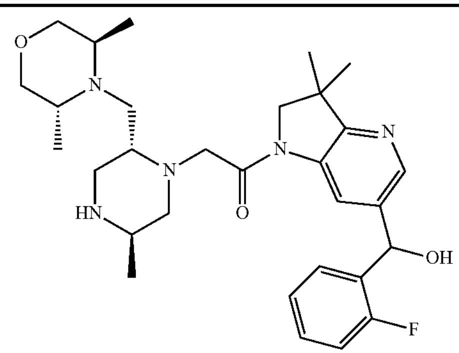 | 2-[(2R,5R)-2-{[(3R,5R)-3,5-Dimethylmorpholin-4-yl]methyl}-5-methylpiperazin-1-yl]-1-{6-[(R or S)-(2-fluorophenyl)(hydroxy)methyl]-3,3-dimethyl-1H,2H,3H-pyrrolo[3,2-b]pyridin-1-yl}ethan-1-one dihydrochloride | 17I + 22, Preparation 23 | 1 | 1H NMR (400 MHz, Me-d3-OD): 8.86 (1H, s), 8.61 (1H, s), 7.70-7.59 (1H, m), 7.46-7.33 (1H, m), 7.28 (1H, t), 7.16 (1H, t), 6.31 (1H, s), 4.38-4.18 (3H, m), 4.13-4.05 (2H, m), 4.00 (2H, s), 3.94-3.56 (6H, m), 3.56-3.42 (1H, m), 3.37 (3H, d), 3.28-3.09 (2H, m), 1.62 (6H, d), 1.53 (3H, d), 1.39 (3H, d), 1.13 (3H, d). | 540 |
| 108 | 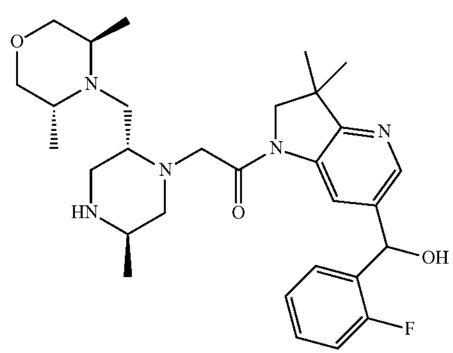 [SMILES: C[C@@H]1CN(CC(=O)N2CC(C)(C)c3ncc(C(O)c4ccccc4F)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(R or S)-(2-fluorophenyl)(hydroxy)methyl]-3,3-dimethyl-1H,2H,3H-pyrrolo[3,2-b]pyridin-1-yl}ethan-1-one dihydrochloride | 17Z + 22, Preparation 23 | 1 | 1H NMR (400 MHz, Me-d3-OD): 8.81 (1H, s), 8.56 (1H, s), 7.74-7.64 (1H, m), 7.45-7.34 (1H, m), 7.30 (1H, t), 7.13 (1H, dd), 6.27 (1H, s), 4.34-4.24 (2H, m), 4.22-4.17 (1H, m), 4.14-4.05 (2H, m), 3.99 (2H, s), 3.90-3.84 (1H, m), 3.74 (3H, d), 3.65-3.51 (2H, m), 3.38 (1H, s), 3.34-3.34 (2H, m), 3.23 (1H, d), 3.16-3.10 (1H, m), 1.60 (6H, d), 1.53 (3H, d), 1.39 (3H, d), 1.17 (3H, d). | 540 |

| Ex. | Structure | Name | Synthesis of Boc derivative | Deprotection Method | NMR Data | MS Data [M + H]+ |
|---|---|---|---|---|---|---|
| 109 | 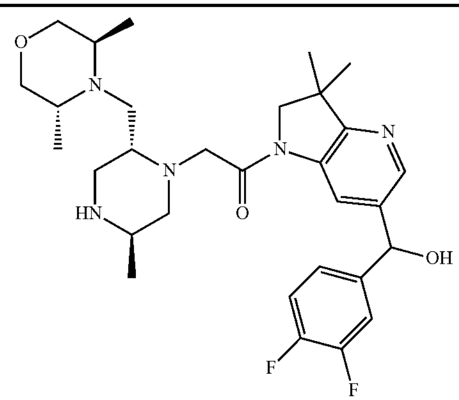 | (R or S)-1-{6-[(3,4-Difluorophenyl)(hydroxy)methyl]-3,3-dimethyl-1H,2H,3H-pyrrolo[3,2-b]pyridin-1-yl}-2-[(2R,5R)-2-{[(3R,5R)-3,5-dimethylmorpholin-4-yl]methyl}-5-methylpiperazin-1-yl]ethan-1-one dihydrochloride | 17W + 22, Preparation 23 | 1 | 1H NMR (400 MHz, Me-d3-OD): 8.86 (1H, s), 8.61 (1H, s), 7.49-7.39 (1H, m), 7.39-7.27 (2H, m), 6.06 (1H, s), 4.35 (2H, s), 4.27 (1H, d), 4.13 (1H, d), 4.08-3.87 (4H, m), 3.87-3.57 (5H, m), 3.57-3.47 (1H, m), 3.31-3.09 (2H, m), 1.65 (6H, d), 1.54 (3H, d), 1.40 (3H, d), 1.14 (3H, d). | 558 |
| 110 | 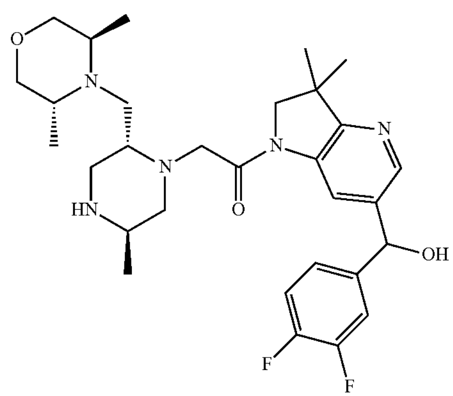 [SMILES: C[C@@H]1CN(CC(=O)N2CC(C)(C)c3ncc(C(O)c4ccc(F)c(F)c4)cc32)[C@@H](CN2[C@H](C)COC[C@H]2C)CN1] | (R or S)-1-{6-[(3,4-Difluorophenyl)(hydroxy)methyl]-3,3-dimethyl-1H,2H,3H-pyrrolo[3,2-b]pyridin-1-yl}-2-[(2R,5R)-2-{[(3R,5R)-3,5-dimethylmorpholin-4-yl]methyl}-5-methylpiperazin-1-yl]ethan-1-one dihydrochloride | 17U + 22, Preparation 23 | 1 | 1H NMR (400 MHz, Me-d3-OD): 8.90 (1H, s), 8.58 (1H, s), 7.49-7.39 (1H, m), 7.39-7.26 (2H, m), 6.06 (1H, s), 4.42-4.32 (2H, m), 4.26 (1H, d), 4.15 (1H, d), 4.11-4.05 (1H, m), 4.05-3.87 (3H, m), 3.87-3.79 (2H, m), 3.74 (1H, s), 3.67-3.50 (2H, m), 3.43 (2H, d), 3.30-3.09 (2H, m), 1.68-1.62 (6H, m), 1.53 (3H, d), 1.41 (3H, d), 1.22 (3H, d). | 558 |

| Ex. | Structure | Name | Synthesis of Boc derivative | Deprotection Method | NMR Data | MS Data [M + H]+ |
|---|---|---|---|---|---|---|
| 111 | 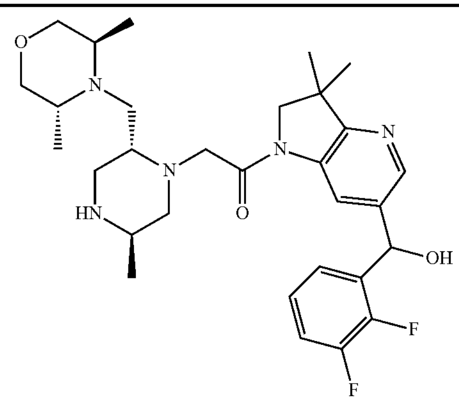 | (R or S)-1-{6-[(2,3-Difluorophenyl)(hydroxy)methyl]-3,3-dimethyl-1H,2H,3H-pyrrolo[3,2-b]pyridin-1-yl}-2-[(2R,5R)-2-{[(3R,5R)-3,5-dimethylmorpholin-4-yl]methyl}-5-methylpiperazin-1-yl]ethan-1-one dihydrochloride | 17Y + 22, Preparation 23 | 1 | 1H NMR (400 MHz, Me-d3-OD): 8.94 (1H, s), 8.63 (1H, s), 7.51-7.40 (1H, m), 7.37-7.21 (2H, m), 6.35 (1H, s), 4.36 (2H, s), 4.28 (1H, d), 4.20-4.04 (2H, m), 4.01 (2H, s), 3.92 (1H, s), 3.88-3.59 (5H, m), 3.53 (1H, t), 3.39 (2H, s), 3.27-3.11 (2H, m), 1.65 (6H, s), 1.54 (3H, d), 1.40 (3H, d), 1.15 (3H, d). | 558 |
| 112 | 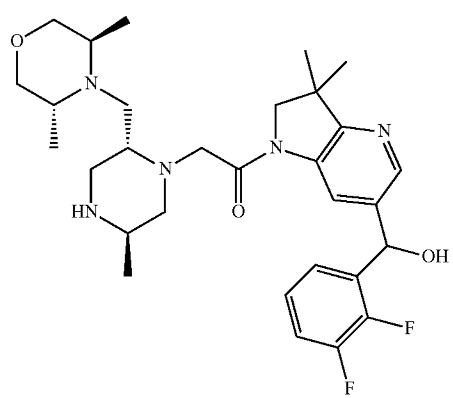 [SMILES: C[C@@H]1CN(CC(=O)N2CC(C)(C)c3ncc(C(O)c4cccc(F)c4F)cc32)[C@@H](CN2[C@H](C)COC[C@H]2C)CN1] | (R or S)-1-{6-[(2,3-Difluorophenyl)(hydroxy)methyl]-3,3-dimethyl-1H,2H,3H-pyrrolo[3,2-b]pyridin-1-yl}-2-[(2R,5R)-2-{[(3R,5R)-3,5-dimethylmorpholin-4-yl]methyl}-5-methylpiperazin-1-yl]ethan-1-one dihydrochloride | 17X + 22, Preparation 23 | 1 | 1H NMR (400 MHz, Me-d3-OD): 8.86 (1H, s), 8.57 (1H, s), 7.53-7.43 (1H, m), 7.36-7.23 (2H, m), 6.30 (1H, s), 4.37-4.27 (2H, m), 4.22 (1H, d), 4.11 (2H, d), 4.06-3.95 (2H, m), 3.90 (1H, d), 3.79 (2H, d), 3.72 (1H, d), 3.68-3.45 (2H, m), 3.40 (1H, d), 3.29-3.21 (1H, m), 3.21-3.08 (1H, d), 1.61 (6H, d), 1.53 (3H, d), 1.40 (3H, d), 1.20 (3H, d). | 558 |

| Ex. | Name | Synthesis of Boc derivative | Deprotection Method | NMR Data | MS Data [M + H]+ |
|---|---|---|---|---|---|
| 113 | 2-[(2R,5R)-2-[[(3R,5R)-3,5-Dimethylmorpholin-4-yl]methyl]-5-methylpiperazin-1-yl]-1-((R or S)-6-[hydroxy(phenyl)methyl]-3,3-dimethyl-1H,2H,3H-pyrrolo[3,2-b]pyridin-1-yl]ethan-1-one dihydrochloride | 17EE and 22, Preparation 23 | 1 | 1H NMR (400 MHz, Me-d3-OD): 8.89 (1H, s), 8.59 (1H, s), 7.53-7.30 (5H, m), 6.05 (1H, s), 4.33 (2H, s), 4.24 (1H, d), 4.19-4.13 (1H, m), 4.10-4.05 (1H, m), 3.96 (2H, s), 3.87 (1H, d), 3.84-3.75 (2H, m), 3.72 (1H, s), 3.66-3.59 (1H, m), 3.54 (1H, t), 3.48-3.34 (3H, m), 3.28-3.08 (2H, m), 1.64 (6H, s), 1.52 (3H, d), 1.40 (3H, d), 1.19 (3H, d). | 522 |
| 114 | 2-[(2R,5R)-2-[[(3R,5R)-3,5-Dimethylmorpholin-4-yl]methyl]-5-methylpiperazin-1-yl]-1-((R or S)-6-[hydroxy(phenyl)methyl]-3,3-dimethyl-1H,2H,3H-pyrrolo[3,2-b]pyridin-1-yl]ethan-1-one dihydrochloride | 17FF and 22, Preparation 23 | 1 | 1H NMR (400 MHz, Me-d3-OD): 8.79 (1H, s), 8.61 (1H, s), 7.49-7.35 (5H, m), 6.03 (1H, s), 4.31 (2H, s), 4.23 (1H, d), 4.12-4.07 (1H, m), 4.07-4.02 (1H, m), 3.99 (2H, s), 3.87 (1H, d), 3.75 (1H, s), 3.72-3.59 (3H, m), 3.46-3.36 (4H, m), 3.22-3.10 (2H, m), 1.63 (6H, d), 1.52 (3H, d), 1.38 (3H, d), 1.06 (3H, d). | 522 |

| Ex. | Structure | Name | Synthesis of Boc derivative | Deprotection Method | NMR Data | MS Data [M + H]+ |
|---|---|---|---|---|---|---|
| 115 | 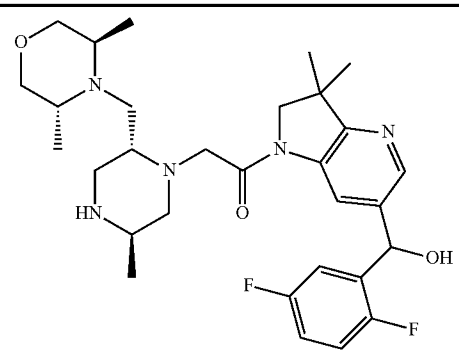 | 1-{(R or S)-6-[(2,5-Difluorophenyl)(hydroxy)methyl]-3,3-dimethyl-1H,2H,3H-pyrrolo[3,2-b]pyridin-1-yl}-2-{[(2R,5R)-2-{[(3R,5R)-3,5-dimethylmorpholin-4-yl]methyl}-5-methylpiperazin-1-yl]ethan-1-one dihydrochloride | 17GG and 22, Preparation 23, fast eluting isomer. | 1 | 1H NMR (400 MHz, Me-d3-OD): 8.78 (1H, s), 8.55 (1H, s), 7.50-7.40 (1H, m), 7.21-7.08 (2H, m), 6.23 (1H, s), 4.33-3.95 (8H, m), 3.89 (1H, d), 3.79-3.68 (3H, m), 3.67-3.53 (2H, m), 3.22 (1H, d), 3.18-3.08 (1H, m), 1.59 (6H, d), 1.54 (3H, d), 1.39 (3H, d), 1.16 (3H, d). | 558 |
| 116 | 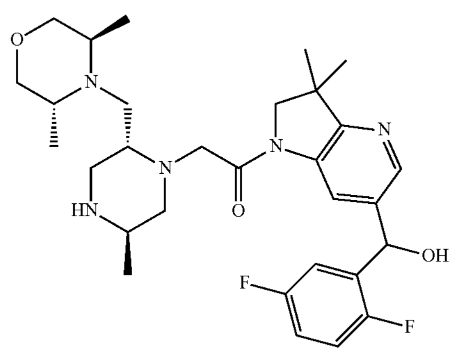 [SMILES: C[C@@H]1CN(CC(=O)N2CC(C)(C)c3ncc(C(O)c4cc(F)ccc4F)cc32)[C@@H](CN2[C@H](C)COC[C@H]2C)CN1] | 1-{(R or S)-6-[(2,5-Difluorophenyl)(hydroxy)methyl]-3,3-dimethyl-1H,2H,3H-pyrrolo[3,2-b]pyridin-1-yl}-2-{[(2R,5R)-2-{[(3R,5R)-3,5-dimethylmorpholin-4-yl]methyl}-5-methylpiperazin-1-yl]ethan-1-one dihydrochloride | 17GG + 22, Preparation 23, slow eluting isomer | 1 | 1H NMR (400 MHz, Me-d3-OD): 8.58 (1H, s), 8.51 (1H, s), 7.45-7.35 (1H, m), 7.20-7.06 (2H, m), 6.20 (1H, s), 4.26-4.04 (5H, m), 4.01 (2H, s), 3.87 (1H, d), 3.80-3.48 (6H, m), 3.23 (1H, d), 3.18-3.07 (1H, m), 1.57-1.50 (9H, m), 1.38 (3H, d), 1.17 (3H, d). | 558 |

| Ex. | Structure | Name | Synthesis of Boc derivative | Deprotection Method | NMR Data | MS Data [M + H]+ |
|---|---|---|---|---|---|---|
| 117 | 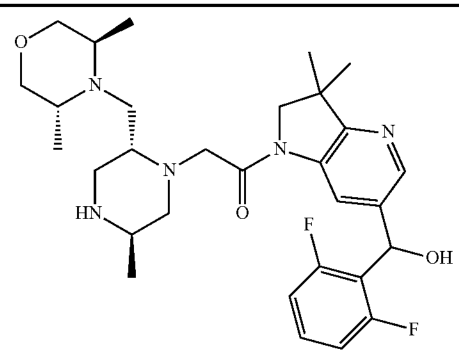 | 1-{(R or S)-6-[(2,6-Difluorophenyl)(hydroxy)methyl]-3,3-dimethyl-1H,2H,3H-pyrrolo[3,2-b]pyridin-1-yl}-2-{[(2R,5R)-2-{[(3R,5R)-3,5-dimethylmorpholin-4-yl]methyl}-5-methylpiperazin-1-yl]ethan-1-one dihydrochloride | 17HH + 22, Preparation 23 | 1 | 1H NMR (400 MHz, Me-d3-OD): 8.98 (1H, s), 8.52 (1H, s), 7.52-7.41 (1H, m), 7.06 (2H, t), 6.44 (1H, s), 4.33 (2H, s), 4.23 (1H, d), 4.15 (1H, s), 4.12-4.08 (1H, m), 3.94 (2H, s), 3.91-3.83 (1H, m), 3.83-3.69 (3H, m), 3.67-3.55 (2H, m), 3.52-3.34 (3H, m), 3.28-3.07 (2H, m), 1.63 (6H, s), 1.53 (3H, d), 1.41 (3H, d), 1.28 (3H, d). | 588 |
| 118 | 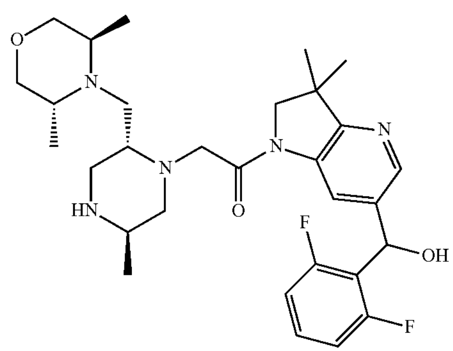 [SMILES: C[C@@H]1CN(CC(=O)N2CC(C)(C)c3ncc(C(O)c4c(F)cccc4F)cc32)[C@@H](CN2[C@H](C)COC[C@H]2C)CN1] | 1-{(R or S)-6-[(2,6-Difluorophenyl)(hydroxy)methyl]-3,3-dimethyl-1H,2H,3H-pyrrolo[3,2-b]pyridin-1-yl}-2-{[(2R,5R)-2-{[(3R,5R)-3,5-dimethylmorpholin-4-yl]methyl}-5-methylpiperazin-1-yl]ethan-1-one dihydrochloride | 17II + 22, Preparation 23 | 1 | 1H NMR (400 MHz, Me-d3-OD): 8.86 (1H, s), 8.60 (1H, s), 7.55-7.42 (1H, m), 7.18-7.01 (2H, m), 6.45 (1H, s), 4.35 (2H, s), 4.25 (1H, d), 4.21-4.10 (1H, m), 4.10-4.02 (1H, m), 4.00 (2H, s), 3.96-3.84 (1H, m), 3.84-3.56 (5H, m), 3.26-3.08 (2H, m), 1.65 (6H, d), 1.54 (3H, d), 1.40 (3H, d), 1.06 (3H, d). | 558 |

-continued

| Ex. | Structure | Name | Synthesis of Boc derivative | Deprotection Method | NMR Data | MS Data [M + H]+ |
|---|---|---|---|---|---|---|
| 119 | 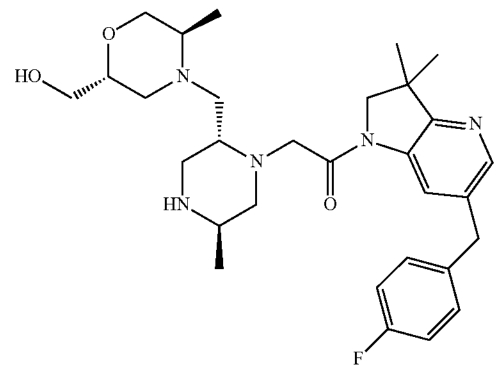 [SMILES: C[C@@H]1CN(CC(=O)N2CC(C)(C)c3ncc(Cc4ccc(F)cc4)cc32)[C@@H](CN2C[C@H](CO)OC[C@H]2C)CN1] | 1-{6-[(4-Fluorophenyl)methyl]-3,3-dimethyl-1H,2H,3H-pyrrolo[3,2-b]pyridin-1-yl}-2-{[(2R,5R)-2-(hydroxymethyl)-5-methylmorpholin-4-yl]methyl}-5-methylpiperazin-1-yl]ethan-1-one, dihydrochloride | Preparation 68 (or Preparation 69) | 1 | 1H NMR (400 MHz, Me-d3-OD): 8.74 (1H, s), 8.44 (1H, s), 7.37 (2H, dd), 7.14 (2H, t), 4.41-4.18 (5H, m), 4.18-4.03 (3H, m), 3.95-3.75 (3H, m), 3.75-3.67 (2H, m), 3.64-3.42 (5H, m), 3.30-3.19 (1H, m), 3.19-3.09 (2H, m), 3.04 (1H, dd), 1.63 (6H, s), 1.46 (3H, d), 1.30 (3H, d). | 540 |
| 120 | 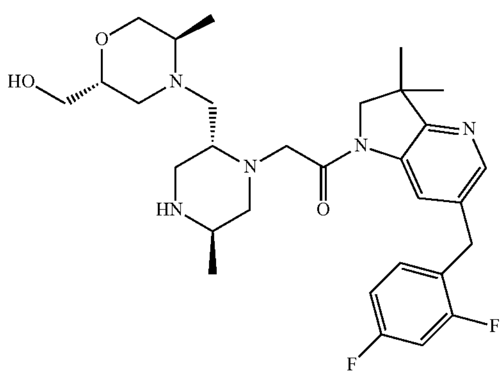 [SMILES: C[C@@H]1CN(CC(=O)N2CC(C)(C)c3ncc(Cc4ccc(F)cc4F)cc32)[C@@H](CN2C[C@H](CO)OC[C@H]2C)CN1] | 1-{6-[(2,4-Difluorophenyl)methyl]-3,3-dimethyl-1H,2H,3H-pyrrolo[3,2-b]pyridin-1-yl}-2-{[(2R,5R)-2-(hydroxymethyl)-5-methylmorpholin-4-yl]methyl}-5-methylpiperazin-1-yl]ethan-1-one, dihydrochloride | Preparation 23 Precursors - Preparations 67, 22C | 1 | 1H NMR (400 MHz, Me-d3-OD): 8.72 (1H, s), 8.44 (1H, s), 7.54-7.44 (1H, m), 7.10-6.99 (2H, m), 4.31-4.01 (9H, m), 3.99-3.89 (1H, m), 3.82 (2H, d), 3.73-3.57 (4H, m), 3.57-3.41 (3H, m), 3.29-3.20 (1H, m), 3.20-3.09 (2H, m), 3.04 (1H, dd), 1.60 (6H, s), 1.46 (3H, d), 1.32 (3H, d). | 558 |

| Ex. | Structure | Name | Synthesis of Boc derivative | Deprotection Method | NMR Data | MS Data [M + H]+ |
|---|---|---|---|---|---|---|
| 121 | 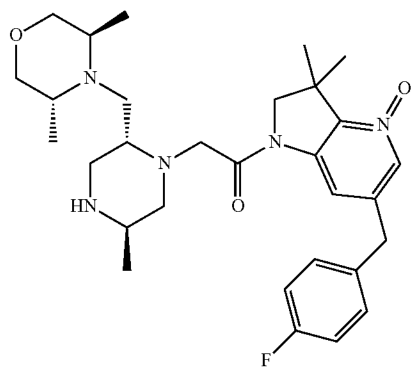 [SMILES: C[C@@H]1CN(CC(=O)N2CC(C)(C)c3c2cc(Cc2ccc(F)cc2)c[n+]3[O-])[C@@H](CN2[C@H](C)COC[C@H]2C)CN1] | 1-{2-[(2R,5R)-2-{[(3R,5R)-3,5-Dimethylmorpholin-4-yl]methyl}-5-methylpiperazin-1-yl]acetyl}-6-[(4-fluorophenyl)methyl]-3,3-dimethyl-1H,2H,3H-pyrrolo[3,2-b]pyridin-4-oxide dihydrochloride | Preparation 23, Precursors Preparation 70, 22 | 1 | 1H NMR (400 MHz, Me-d3-OD): 8.32 (2H, d), 7.35 (2H, dd), 7.17-7.07 (2H, m), 4.33-4.21 (2H, m), 4.15 (2H, s), 4.12-3.99 (2H, m), 3.99-3.91 (2H, m), 3.91-3.79 (2H, m), 3.79-3.69 (4H, m), 3.67-3.55 (2H, m), 3.55-3.35 (3H, m), 3.28-3.07 (2H, m), 1.69 (6H, d), 1.52 (3H, d), 1.39 (3H, d), 1.14 (3H, d) | 540 |

[a]HPLC diastereomer separation using a ChiralPak-IC column eluting with 50:50 heptane-ethanol containing 0.1% diethylamine
[b]HPLC diastereomer separation using a ChiralPak-IC column eluting with 80:20 heptane-ethanol containing 0.1% diethylamine
[c]HPLC diastereomer separation using a Lux cellulose column eluting with 50:50 heptane-ethanol containing 0.2% diethylamine
[d]HPLC diastereomer separation using a Lux cellulose-2 column eluting with 30:70 heptane-ethanol containing 0.2% diethylamine
[e]HPLC diastereomer separation using ChiralPak AD-H (Daicel) 250 x 20 x 5 mm, 1:1 Heptane-IPA + 0.2% diethylamine

Examples 64-91

The following compounds can be made using the methods described herein.

In particular Preparations 20 or 23 could be used with the appropriate intermediates. The required intermediates are commercially available or can be synthesised using the methods analogous to those described herein.

| Prophetic Example | Compound Structure | Name |
|---|---|---|
| 64 | 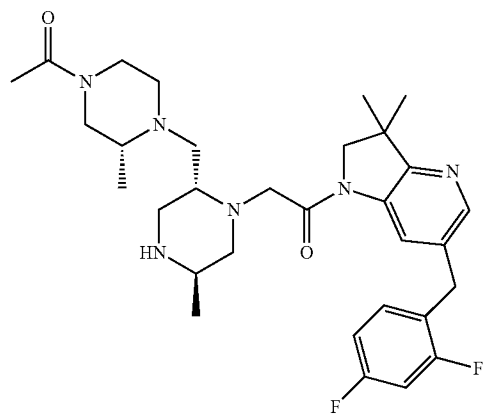 [SMILES: CC(=O)N1CCN(C[C@H]2CN[C@H](C)CN2CC(=O)N2CC(C)(C)c3ncc(Cc4ccc(F)cc4F)cc32)[C@H](C)C1] | 2-[(2R,5R)-2-{[(2R)-4-Acetyl-2-methylpiperazin-1-yl]methyl}-5-methylpiperazin-1-yl]-1-{6-[(2,4-difluorophenyl)methyl]-3,3-dimethyl-1H,2H,3H-pyrrolo[3,2-b]pyridin-1-yl}ethan-1-one |
| 65 | 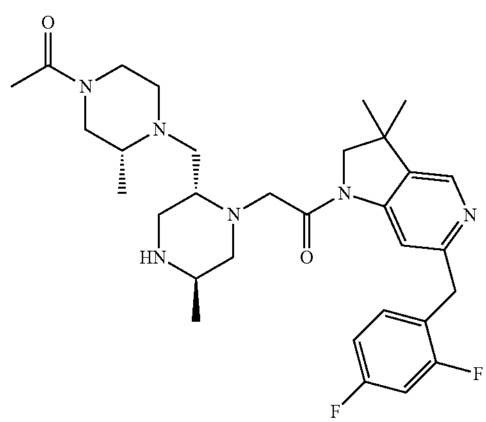 [SMILES: CC(=O)N1CCN(C[C@H]2CN[C@H](C)CN2CC(=O)N2CC(C)(C)c3cnc(Cc4ccc(F)cc4F)cc32)[C@H](C)C1] | 2-[(2R,5R)-2-{[(2R)-4-Acetyl-2-methylpiperazin-1-yl]methyl}-5-methylpiperazin-1-yl]-1-{6-[(2,4-difluorophenyl)methyl]-3,3-dimethyl-1H,2H,3H-pyrrolo[3,2-c]pyridin-1-yl}ethan-1-one |
| 66 | 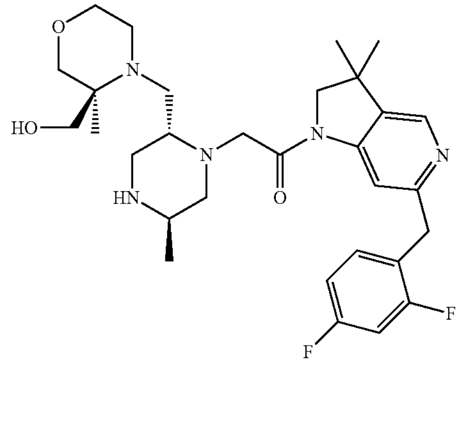 [SMILES: C[C@@H]1CN(CC(=O)N2CC(C)(C)c3cnc(Cc4ccc(F)cc4F)cc32)[C@@H](CN2CCOC[C@]2(C)CO)CN1] | 1-{6-[(2,4-Difluorophenyl)methyl]-3,3-dimethyl-1H,2H,3H-pyrrolo[3,2-c]pyridin-1-yl}-2-[(2R,5R)-2-{[(3S)-3-(hydroxymethyl)-3-methylmorpholin-4-yl]methyl}-5-nnethylpiperazin-1-yl]ethan-1-one |

| Prophetic Example | Compound Structure | Name |
|---|---|---|
| 67 | 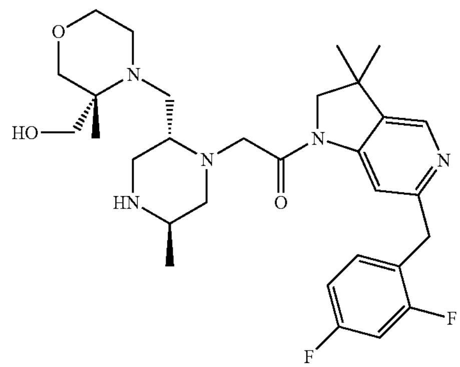 [SMILES: C[C@@H]1CN(CC(=O)N2CC(C)(C)c3cnc(Cc4ccc(F)cc4F)cc32)[C@@H](CN2CCOC[C@@]2(C)CO)CN1] | 1-{6-[(2,4-Difluorophenyl)methyl]-3,3-dimethyl-1H,2H,3H-pyrrolo[3,2-c]pyridin-1-yl}-2-[(2R,5R)-2-{[(3R)-3-(hydroxymethyl)-3-methylmorpholin-4-yl]methyl}-5-methylpiperazin-1-yl]ethan-1-one |
| 68 | 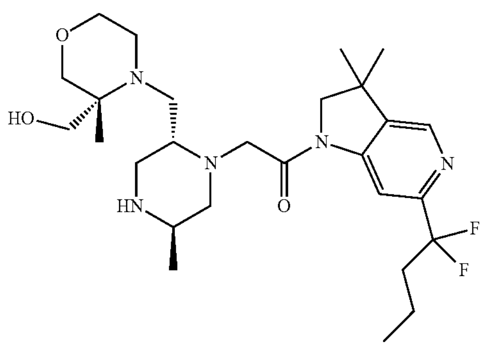 [SMILES: CCCC(F)(F)c1cc2c(cn1)C(C)(C)CN2C(=O)CN1C[C@@H](C)NC[C@@H]1CN1CCOC[C@@]1(C)CO] | 1-[6-(1,1-Difluorobutyl)-3,3-dimethyl-1H,2H,3H-pyrrolo[3,2-c]pyridin-1-yl]-2-[(2R,5R)-2-{[(3R)-3-(hydroxymethyl)-3-methylmorpholin-4-yl]methyl}-5-methylpiperazin-1-yl]ethan-1-one |
| 69 | 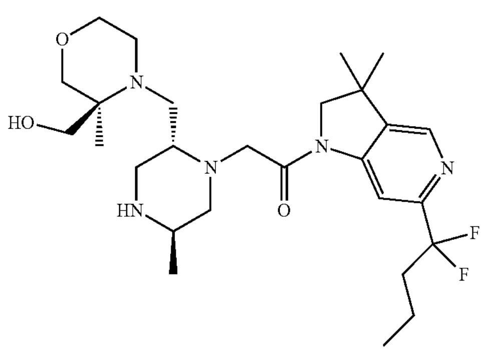 [SMILES: CCCC(F)(F)c1cc2c(cn1)C(C)(C)CN2C(=O)CN1C[C@@H](C)NC[C@@H]1CN1CCOC[C@]1(C)CO] | 1-[6-(1,1-Difluorobutyl)-3,3-dimethyl-1H,2H,3H-pyrrolo[3,2-c]pyridin-1-yl]-2-[(2R,5R)-2-{[(3S)-3-(hydroxymethyl)-3-methylmorpholin-4-yl]methyl}-5-methylpiperazin-1-yl]ethan-1-one |
| 70 | 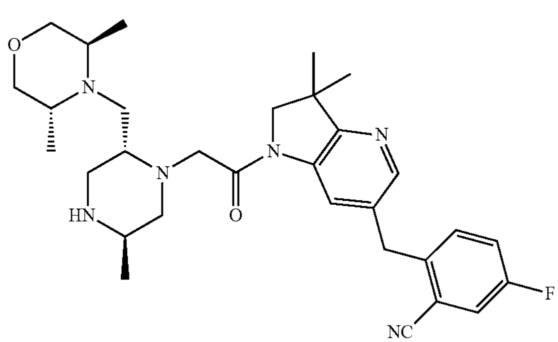 [SMILES: C[C@@H]1CN(CC(=O)N2CC(C)(C)c3ncc(Cc4ccc(F)cc4C#N)cc32)[C@@H](CN2[C@H](C)COC[C@H]2C)CN1] | 2-[(1-{2-[(2R,5R)-2-{[(3R,5R)-3,5-Dimethylmorpholin-4-yl]methyl}-5-methylpiperazin-1-yl]acetyl}-3,3-dimethyl-1H,2H,3H-pyrrolo[3,2-b]pyridin-6-yl)methyl]-5-fluorobenzonitrile |

| Prophetic Example | Compound Structure | Name |
|---|---|---|
| 71 | 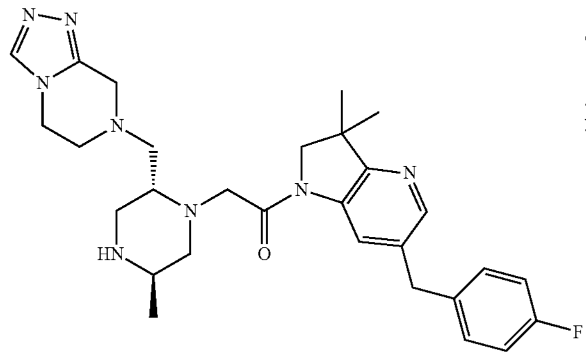 [SMILES: C[C@@H]1CN(CC(=O)N2CC(C)(C)c3ncc(Cc4ccc(F)cc4)cc32)[C@@H](CN2CCn3cnnc3C2)CN1] | 1-{6-[(4-Fluorophenyl)methyl]-3,3-dimethyl-1H,2H,3H-pyrrolo[3,2-b]pyridin-1-yl}-2-[(2R,5R)-5-methyl-2-{5H,6H,7H,8H-[1,2,4]triazolo[4,3-a]pyrazin-7-ylmethyl}piperazin-1-yl]ethan-1-one |
| 72 | 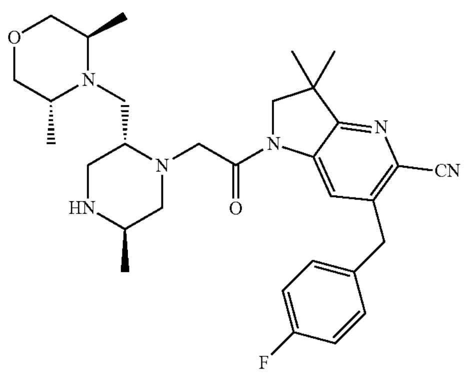 [SMILES: C[C@@H]1CN(CC(=O)N2CC(C)(C)c3nc(C#N)c(Cc4ccc(F)cc4)cc32)[C@@H](CN2[C@H](C)COC[C@H]2C)CN1] | 1-{2-[(2R,5R)-2-{[(3R,5R)-3,5-Dimethylmorpholin-4-yl]methyl}-5-methylpiperazin-1-yl]acetyl}-6-[(4-fluorophenyl)methyl]-3,3-dimethyl-1H,2H,3H-pyrrolo[3,2-b]pyridine-5-carbonitrile |
| 73 | 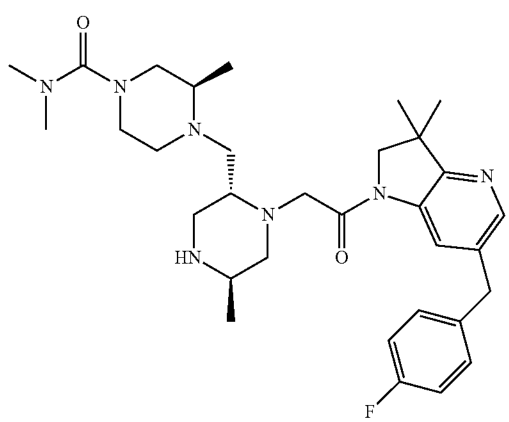 [SMILES: C[C@@H]1CN(CC(=O)N2CC(C)(C)c3ncc(Cc4ccc(F)cc4)cc32)[C@@H](CN2CCN(C(=O)N(C)C)C[C@H]2C)CN1] | (3R)-4-{[(2R,5R)-1-(2-{6-[(4-Fluorophenyl)methyl]-3,3-dimethyl-1H,2H,3H-pyrrolo[3,2-b]pyridin-1-yl}-2-oxoethyl)-5-methylpiperazin-2-yl]methyl}-N,N,3-trimethylpiperazine-1-carboxamide |
| 74 | 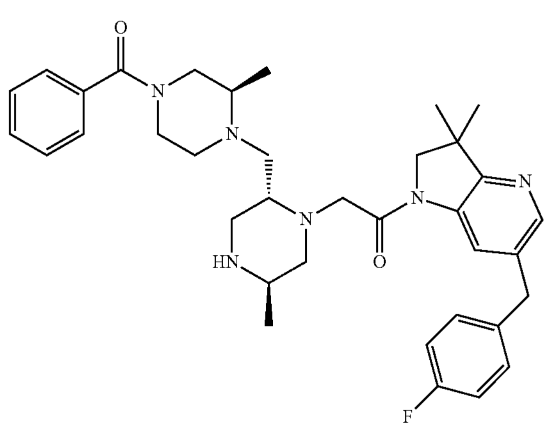 [SMILES: C[C@@H]1CN(CC(=O)N2CC(C)(C)c3ncc(Cc4ccc(F)cc4)cc32)[C@@H](CN2CCN(C(=O)c3ccccc3)C[C@H]2C)CN1] | 2-[(2R,5R)-2-{[(2R)-4-Benzoyl-2-methylpiperazin-1-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one |

| Prophetic Example | Compound Structure | Name |
|---|---|---|
| 75 | 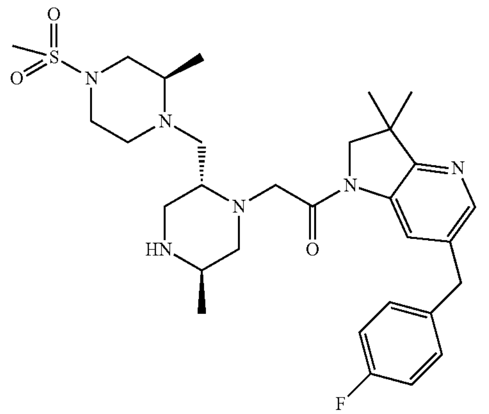 [SMILES: C[C@@H]1CN(CC(=O)N2CC(C)(C)c3ncc(Cc4ccc(F)cc4)cc32)[C@@H](CN2CCN(S(C)(=O)=O)C[C@H]2C)CN1] | 1-{6-[(4-Fluorophenyl)methyl]-3,3-dimethyl-1H,2H,3H-pyrrolo[3,2-b]pyridin-1-yl}-2-[(2R,5R)-2-{[(2R)-4-methanesulfonyl-2-methylpiperazin-1-yl]methyl}-5-methylpiperazin-1-yl]ethan-1-one |
| 76 | 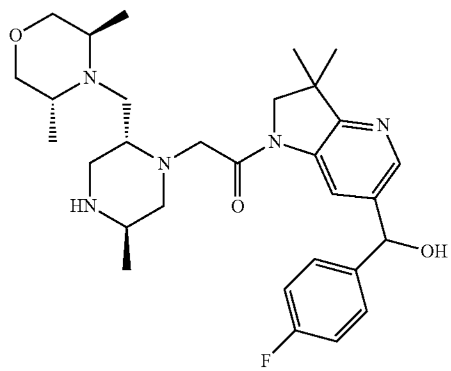 [SMILES: C[C@@H]1CN(CC(=O)N2CC(C)(C)c3ncc(C(O)c4ccc(F)cc4)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(R)-(4-fluorophenyl)(hydroxy)methyl]-3,3-dimethyl-1H,2H,3H-pyrrolo[3,2-b]pyridin-1-yl}ethan-1-one and 2-[(2R,5R)-2-{[(3R,5R)-3,5-Dimethylmorpholin-4-yl]methyl}-5-methylpiperazin-1-yl]-1-{6-[(S)-(4-fluorophenyl)(hydroxy)methyl]-3,3-dimethyl-1H,2H,3H-pyrrolo[3,2-b]pyridin-1-yl}ethan-1-one |
| 77 | 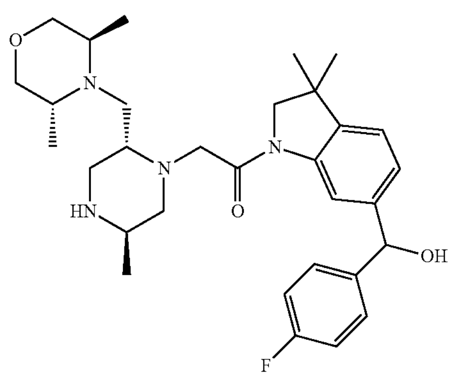 [SMILES: C[C@@H]1CN(CC(=O)N2CC(C)(C)c3ccc(C(O)c4ccc(F)cc4)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(S)-(4-fluorophenyl)(hydroxy)methyl]-3,3-dimethyl-2,3-dihydro-1H-indol-1-yl}ethan-1-one and 2-[(2R,5R)-2-{[(3R,5R)-3,5-dimethylmorpholin-4-yl]methyl}-5-methylpiperazin-1-yl]-1-{6-[(R)-(4-fluorophenyl)(hydroxy)methyl]-3,3-dimethyl-2,3-dihydro-1H-indol-1-yl}ethan-1-one |
| 78 | 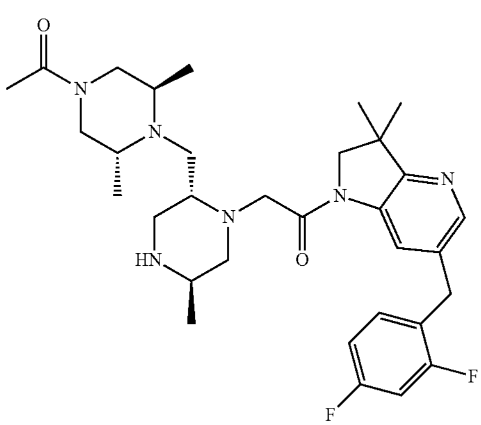 [SMILES: CC(=O)N1C[C@@H](C)N(C[C@H]2CN[C@H](C)CN2CC(=O)N2CC(C)(C)c3ncc(Cc4ccc(F)cc4F)cc32)[C@H](C)C1] | 2-[(2R,5R)-2-{[(2R,6R)-4-Acetyl-2,6-dimethylpiperazin-1-yl]methyl}-5-methylpiperazin-1-yl]-1-{6-[(2,4-difluorophenyl)methyl]-3,3-dimethyl-1H,2H,3H-pyrrolo[3,2-b]pyridin-1-yl}ethan-1-one |

| Prophetic Example | Compound Structure | Name |
|---|---|---|
| 79 | 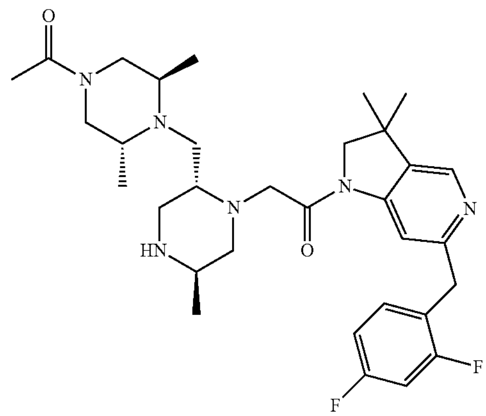 [SMILES: CC(=O)N1C[C@@H](C)N(C[C@H]2CN[C@H](C)CN2CC(=O)N2CC(C)(C)c3cnc(Cc4ccc(F)cc4F)cc32)[C@H](C)C1] | 2-[(2R,5R)-2-{[(2R,6R)-4-Acetyl-2,6-dimethylpiperazin-1-yl]methyl}-5-methylpiperazin-1-yl]-1-{6-[(2,4-difluorophenyl)methyl]-3,3-dimethyl-1H,2H,3H-pyrrolo[3,2-c]pyridin-1-yl}ethan-1-one |
| 80 | 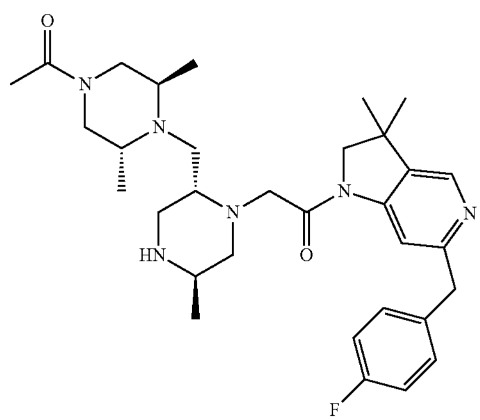 [SMILES: CC(=O)N1C[C@@H](C)N(C[C@H]2CN[C@H](C)CN2CC(=O)N2CC(C)(C)c3cnc(Cc4ccc(F)cc4)cc32)[C@H](C)C1] | 2-[(2R,5R)-2-{[(2R,6R)-4-Acetyl-2,6-dimethylpiperazin-1-yl]methyl}-5-methylpiperazin-1-yl]-1-{6-[(4-fluorophenyl)methyl]-3,3-dimethyl-1H,2H,3H-pyrrolo[3,2-c]pyridin-1-yl}ethan-1-one |
| 81 | 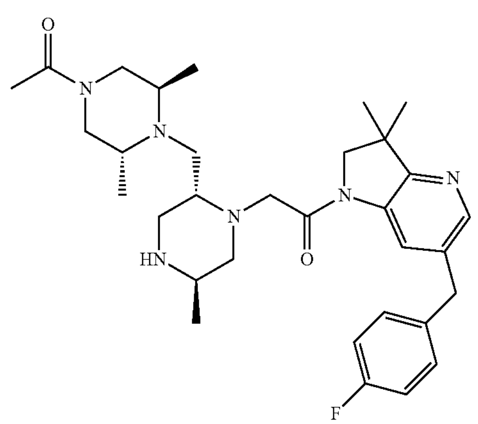 [SMILES: CC(=O)N1C[C@@H](C)N(C[C@H]2CN[C@H](C)CN2CC(=O)N2CC(C)(C)c3ncc(Cc4ccc(F)cc4)cc32)[C@H](C)C1] | 2-[(2R,5R)-2-{[(2R,6R)-4-Acetyl-2,6-dimethylpiperazin-1-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one |

| Prophetic Example | Compound Structure | Name |
|---|---|---|
| 82 | 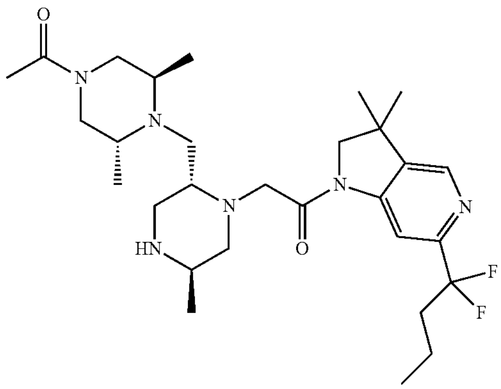 [SMILES: CCCC(F)(F)c1cc2c(cn1)C(C)(C)CN2C(=O)CN1C[C@@H](C)NC[C@@H]1CN1[C@H](C)CN(C(C)=O)C[C@H]1C] | 2-[(2R,5R)-2-{[(2R,6R)-4-Acetyl-2,6-dimethylpiperazin-1-yl]methyl}-5-methylpiperazin-1-yl]-1-[6-(1,1-difluorobutyl)-3,3-dimethyl-1H,2H,3H-pyrrolo[3,2-c]pyridin-1-yl]ethan-1-one |
| 83 | 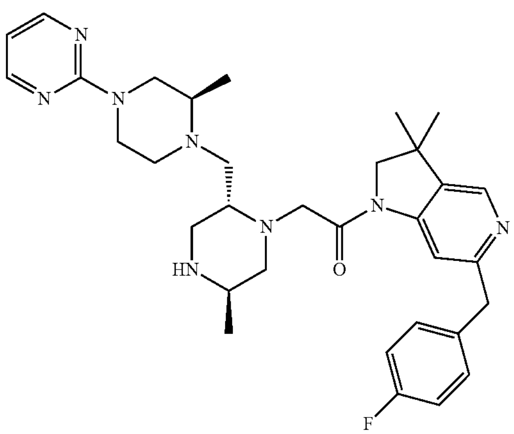 [SMILES: C[C@@H]1CN(CC(=O)N2CC(C)(C)c3cnc(Cc4ccc(F)cc4)cc32)[C@@H](CN2CCN(c3ncccn3)C[C@H]2C)CN1] | 1-{6-[(4-Fluorophenyl)methyl]-3,3-dimethyl-1H,2H,3H-pyrrolo[3,2-c]pyridin-1-yl}-2-[(2R,5R)-5-methyl-2-{[(2R)-2-methyl-4-(pyrimidin-2-yl)piperazin-1-yl]methyl}piperazin-1-yl]ethan-1-one |
| 84 | 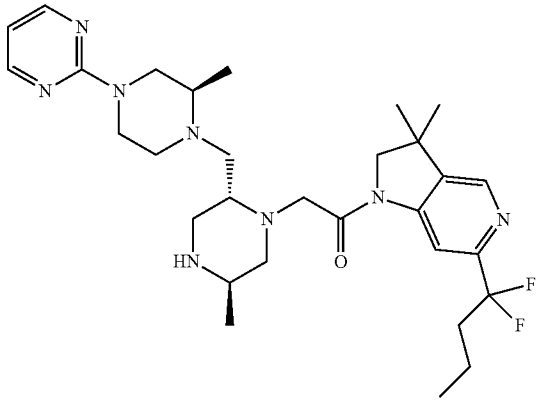 [SMILES: CCCC(F)(F)c1cc2c(cn1)C(C)(C)CN2C(=O)CN1C[C@@H](C)NC[C@@H]1CN1CCN(c2ncccn2)C[C@H]1C] | 1-[6-(1,1-Difluorobutyl)-3,3-dimethyl-1H,2H,3H-pyrrolo[3,2-c]pyridin-1-yl]-2-[(2R,5R)-5-methyl-2-{[(2R)-2-methyl-4-(pyrimidin-2-yl)piperazin-1-yl]methyl}piperazin-1-yl]ethan-1-one |

| Prophetic Example | Compound Structure | Name |
|---|---|---|
| 85 | 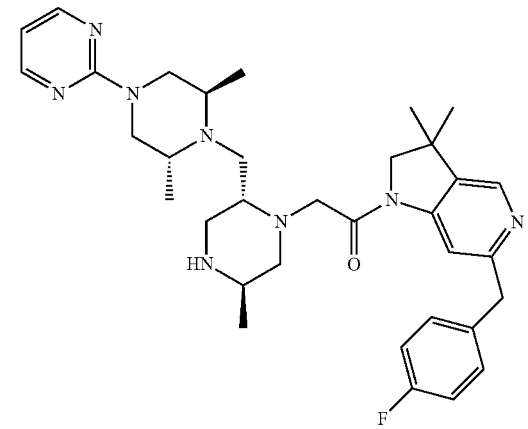 [SMILES: C[C@@H]1CN(CC(=O)N2CC(C)(C)c3cnc(Cc4ccc(F)cc4)cc32)[C@@H](CN2[C@H](C)CN(c3ncccn3)C[C@H]2C)CN1] | 2-[(2R,5R)-2-{[(2R,6R)-2,6-Dimethyl-4-(pyrimidin-2-yl)piperazin-1-yl]methyl}-5-methylpiperazin-1-yl]-1-{6-[(4-fluorophenyl)methyl]-3,3-dimethyl-1H,2H,3H-pyrrolo[3,2-c]pyridin-1-yl}ethan-1-one |
| 86 | 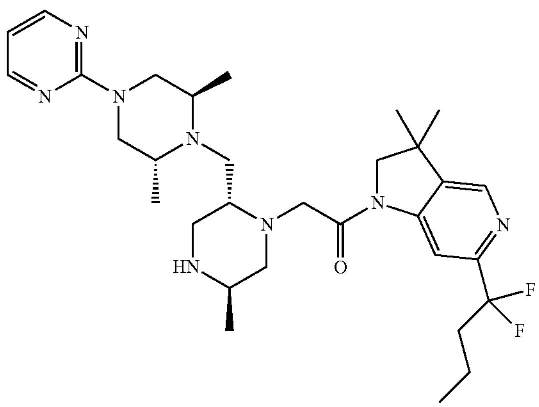 [SMILES: CCCC(F)(F)c1cc2c(cn1)C(C)(C)CN2C(=O)CN1C[C@@H](C)NC[C@@H]1CN1[C@H](C)CN(c2ncccn2)C[C@H]1C] | 1-[6-(1,1-Difluorobutyl)-3,3-dimethyl-1H,2H,3H-pyrrolo[3,2-c]pyridin-1-yl]-2-[(2R,5R)-2-{[(2R,6R)-2,6-dimethyl-4-(pyrimidin-2-yl)piperazin-1-yl]methyl}-5-methylpiperazin-1-yl]ethan-1-one |
| 87 | 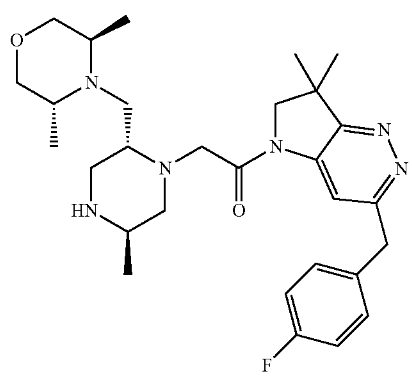 [SMILES: C[C@@H]1CN(CC(=O)N2CC(C)(C)c3nnc(Cc4ccc(F)cc4)cc32)[C@@H](CN2[C@H](C)COC[C@H]2C)CN1] | 2-[(2R,5R)-2-{(3R,5R)-3,5-Dimethylmorpholin-4-yl}methyl-5-methylpiperazin-1-yl]-1-{3-[(4-fluorophenyl)methyl]-7,7-dimethyl-5H,6H,7H-pyrrolo[3,2-c]pyridazin-5-yl}ethan-1-one |
| 88 | 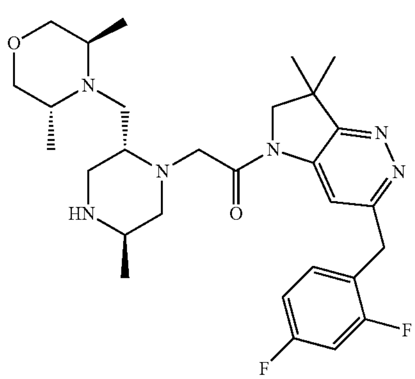 [SMILES: C[C@@H]1CN(CC(=O)N2CC(C)(C)c3nnc(Cc4ccc(F)cc4F)cc32)[C@@H](CN2[C@H](C)COC[C@H]2C)CN1] | 1-{3-[(2,4-Difluorophenyl)methyl]-7,7-dimethyl-5H,6H,7H-pyrrolo[3,2-c]pyridazin-5-yl-2-[(2R,5R)-2-{[(3R,5R)-3,5-dimethylmorpholin-4-yl]methyl}-5-methylpiperazin-1-yl]ethan-1-one |

| Prophetic Example | Compound Structure | Name |
|---|---|---|
| 89 | 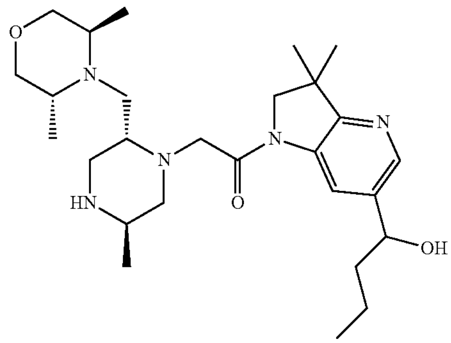 [SMILES: CCCC(O)c1cnc2c(c1)N(C(=O)CN1C[C@@H](C)NC[C@@H]1CN1[C@H](C)COC[C@H]1C)CC2(C)C] | 2-[(2R,5R)-2-{[(3R,5R)-3,5-Dimethylmorpholin-4-yl]methyl}-5-methylpiperazin-1-yl]-1-{6-[(1S)-1-hydroxybutyl]-3,3-dimethyl-1H,2H,3H-pyrrolo[3,2-b]pyridin-1-yl}ethan-1-one And 2-[(2R,5R)-2-{[(3R,5R)-3,5-dimethylmorpholin-4-yl]methyl}-5-methylpiperazin-1-yl]-1-{6-[(1R)-1-hydroxybutyl]-3,3-dimethyl-1H,2H,3H-pyrrolo[3,2-b]pyridin-1-yl}ethan-1-one |
| 90 | 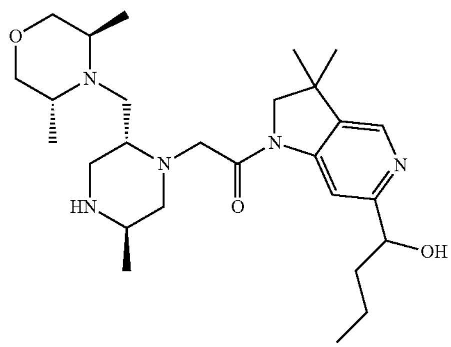 [SMILES: CCCC(O)c1cc2c(cn1)C(C)(C)CN2C(=O)CN1C[C@@H](C)NC[C@@H]1CN1[C@H](C)COC[C@H]1C] | 2-[(2R,5R)-2-{[(3R,5R)-3,5-Dimethylmorpholin-4-yl]methyl}-5-methylpiperazin-1-yl]-1-{6-[(1S)-1-hydroxybutyl]-3,3-dimethyl-1H,2H,3H-pyrrolo[3,2-c]pyridin-1-yl}ethan-1-one And 2-[(2R,5R)-2-{[(3R,5R)-3,5-dimethylmorpholin-4-yl]methyl}-5-methylpiperazin-1-yl]-1-{6-[(1R)-1-hydroxybutyl]-3,3-dimethyl-1H,2H,3H-pyrrolo[3,2-c]pyridin-1-yl}ethan-1-one |
| 91 | 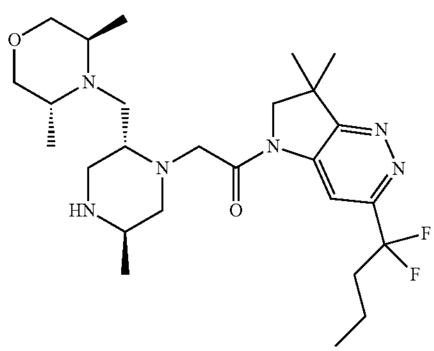 [SMILES: CCCC(F)(F)c1cc2c(nn1)C(C)(C)CN2C(=O)CN1C[C@@H](C)NC[C@@H]1CN1[C@H](C)COC[C@H]1C] | 1-[3-(1,1-Difluorobutyl)-7,7-dimethyl-5H,6H,7H-pyrrolo[3,2-c]pyridazin-5-yl]-2-[(2R,5R)-2-{[(3R,5R)-3,5-dimethylmorpholin-4-yl]methyl}-5-methylpiperazin-1-yl]ethan-1-one |

Biological Assays

Expression and Purification of XIAP, cIAP-1 and cIAP-2 BIR3 Domains

The recombinant BIR3 domain of human XIAP (residues 252-350) fused to a His-tag, human cIAP-1 (residues 267-363) fused to a GST-tag and human cIAP-2 (residues 244-337) fused to a His-tag were overexpressed from *Escherichia coli* cells grown in TB medium. Protein was isolated from lysates using Ni-NTA affinity chromatography (XIAP/cIAP-2) or glutathione sepharase 4B affinity chromatography (cIAP-1). Affinity tags for XIAP and cIAP-1 were cleaved with thrombin in 25 mM HEPES pH 7.5, 100 mM NaCl, 50 µM Zn(OAc)$_2$ and 1 mM Ca(OAc)$_2$ followed by purification of BIR3 domains by size-exclusion chromatography. The His-tag was uncleaved for cIAP-2 and the protein was not concentrated above 3 mg/ml due to aggregation induced covalent self-oligomerization issues. The purified protein was stored in 25 mM Tris pH 7.5, 100 mM NaCl at −80° C.

XIAP, cIAP-1 and cIAP-2 In Vitro Competitive Displacement Binding Assays

Modified SMAC peptides and compounds were tested for their ability to displace the fluorescent tracer from either XIAP, cIAP-1 or cIAP-2. BIR3 domains of cIAP-1, cIAP-2 and XIAP were incubated with test compounds or SMAC based peptides and their respective peptide probes (Peptide Protein Research) in assay buffer (50 mM Hepes pH 7.5, 0.025% Tween-20, 0.01% BSA, and 1 mM DTT). Positive controls consisted of BIR3 proteins and tracer (no inhibition) and negative controls contained tracer only (100% inhibition). The samples were incubated at room temperature for 1 hr (XIAP and cIAP-2) or 3 hrs (cIAP-1) prior to being read in the BMG Pherastar in Fluorescence Polarization mode (FP 485 nm, 520 nm, 520 nm). $IC_{50}$ values were determined from dose-response plots using nonlinear least-squares analysis.

| Final conditions for XIAP, cIAP-1 and cIAP-2 assays | | | |
|---|---|---|---|
| Protein | Protein Conc | Peptide Probe | Peptide Conc |
| XIAP | 20 nM | AbuRPFK(5&6FAM)-amide | 5 nM |
| cIAP-1 | 4 nM | AbuRPFK(5&6FAM)-amide | 2 nM |
| cIAP-2 | 20 nM | AVPWK(5&6FAM)-amide | 2 nM |

The compounds of Examples 1-36, 38, 41-46, 48-62, 66-69, 71, 76, 87-88, 90, 92-112, 114 and 116-117 have IC50 values of less than 1 µM or provide at least 50% inhibition of the activity at a concentration of 1 µM in the XIAP assay and have IC50 values of less than 0.1 µM or provide at least 50% inhibition of the activity at a concentration of 0.1 µM in the cIAP1 assay. The compounds of Examples 15, 35, 43-45, 53-56, 58, 60-62, 66-69, 92-93, 95, 98, 100, 103-105, 107-109 and 114 have IC50 values of less than 0.1 µM or provide at least 50% inhibition of the activity at a concentration of 0.1 µM in the XIAP and cIAP1 assays. Preferred compounds of the invention have IC50 values of less than 0.01 µM against XIAP and/or cIAP1 and/or cIAP2. Data for the compounds of the invention in the above assays are provided in Table 1.

Anti-Proliferative Activity

Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds (in 0.1% DMSO v/v) for a further 72 hours. At the end of the incubation period 10% (v/v) Alamar Blue is added and incubated for a further 6 hours prior to determination of fluorescent product at 535 nM ex/590 nM em.

The anti-proliferative activities of compounds of the invention can be determined by measuring the ability of the compounds to inhibit growth in 3 cancer cell lines:

EVSA-T (human breast carcinoma) DSMZ cat. no. ACC 433

MDA-MB-231 (human breast carcinoma) ECACC cat. no. 92020424

HCT116 (human colon carcinoma) ECACC cat. no. 91091005 (insensitive cell line used as a control for non-specific cytotoxicity)

Many compounds of the invention were found to have $EC_{50}$ values of less than 0.01 µM in EVSA-T cell line assays (and less than 0.1 µM against the MDA-MB-231 cell line) and preferred compounds have $EC_{50}$ values of less than 0.001 µM in EVSA-T cell assays (and less than 0.01 µM against the MDA-MB-231 cell line) and $EC_{50}$>10 µM against HCT116 cells. In an assay using the cell line EVSA-T, Examples 1-63, 66-69, 71, 76, 87-88, 90, 92-116 and 119-121 have an $EC_{50}$ of less than 1 µM. Data for the compounds of the invention in the above assays are provided in Table 1.

HEK293-XIAP-Caspase-9 Immunoprecipitation (IP) MSD Assay Protocol

Stable HEK293-XIAP-Caspase-9 cells were plated out into 96-well plates [200 µl/well at 1×10$^6$ cells/ml in cultured complete medium (DMEM+10% FBS+0.5 mg/ml Geneticin (Invitrogen)] and left overnight at 37° C. to recover. Compounds were added to duplicate wells in 0.1% DMSO for 2 h at 37° C. Cells were lysed in 50 µl 1×MSD lysis buffer (1% Triton X-100 in 20 mM Tris.Cl (pH 7.6), 150 mM NaCl including protease inhibitors) for 20 min rocking at room temperature. Streptavidin high bind MSD plate (L15SB-2) were coated with biotinylated anti-FLAG M2 antibody (Sigma F9291) at 25 µl/well with a 5 µg/ml dilution of antibody in PBS for 1 h, shaking; followed by blocking for 1 h with 150 µl 3% BSA/TBST. Cell lysate (25 µl) was added to the 96-well anti-FLAG coated MSD plate and placed on shaker for 4 h at room temperature. After washing 4 times with 150 µl TBST (20 mM Tris.Cl (pH 7.6), 150 mM NaCl, 0.1% Tween-20), anti-Caspase-9 [CST#9505] diluted to 5 µl/ml in MSD blocking buffer (3% BSA/TBST) was added overnight at 4° C. After washing plates 4 times with 150 µl TBST, anti-rabbit-sulfo tag (MSD cat no. $R^{32}AB-1$), diluted to 2 µg/ml in MSD blocking buffer, was added for 2 hours at RT. Plates were washed 4 times with 150 µl TBST, and 150 µl/well 1×MSD read buffer ($R^{92}TC-2$) added before reading each plate.

$EC_{50}$ values were determined from dose-response plots using nonlinear least-squares analysis. Many compounds of the invention were found to have $EC_{50}$ values of less than 1 µM in and preferred compounds have $EC_{50}$ values of less than 0.1 µM.

TABLE 1

| Eg. | Xiap\|IC50 or PI\|µM | cIAP1\|IC50 or PI\|µM | EVSA-T prolif\|µM |
|---|---|---|---|
| 1 | 35% @0.04 | 98% @0.012 | 0.0029 |
| 2 | 40% @0.04 | 98% @0.012 | 0.0017 |
| 3 | 37% @0.04 | 98% @0.012 | 0.0068 |
| 4 | 58% @0.12 | 93% @0.012 | 0.0068 |
| 5 | 41% @0.04 | 98% @0.012 | 0.0003 |
| 6 | 52% @0.12 | 90% @0.012 | 0.0046 |
| 7 | 0.16 | 80% @0.012 | 0.0062 |
| 8 | 56% @0.12 | 93% @0.012 | 0.003 |
| 9 | 61% @0.12 | 93% @0.012 | 0.0021 |
| 10 | 41% @0.04 | 97% @0.012 | 0.00042 |
| 11 | 66% @0.12 | 100% @0.012 | 0.0028 |
| 12 | 0.15 | 85% @0.012 | 0.0016 |
| 13 | 59% @0.12 | 98% @0.012 | 0.0012 |
| 14 | 62% @0.12 | 98% @0.012 | 0.0046 |
| 15 | 54% @0.04 | 98% @0.012 | 0.00017 |
| 16 | 56% @0.12 | 99% @0.012 | 0.00089 |
| 17 | 58% @0.12 | 98% @0.012 | 0.0038 |
| 18 | 35% @0.04 | 97% @0.012 | 0.0018 |
| 19 | 43% @0.04 | 99% @0.012 | 0.00065 |
| 20 | 0.14 | 90% @0.012 | 0.0028 |
| 21 | 54% @0.12 | 94% @0.012 | 0.0037 |
| 22 | 40% @0.04 | 94% @0.012 | 0.03 |
| 23 | 56% @0.12 | 92% @0.012 | 0.0038 |
| 24 | 0.13 | 96% @0.012 | 0.013 |
| 25 | 0.12 | 96% @0.012 | 0.0012 |
| 26 | 0.21 | 94% @0.012 | 0.12 |
| 27 | 0.13 | 90% @0.012 | 0.015 |
| 28 | 61% @0.12 | 94% @0.012 | 0.0031 |
| 29 | 47% @0.04 | 96% @0.012 | 0.0004 |

TABLE 1-continued

| Eg. | Xiap\|IC50 or PI\|μM | cIAP1\|IC50 or PI\|μM | EVSA-T prolif\|μM |
|---|---|---|---|
| 30 | 58% @0.12 | 97% @0.012 | 0.0012 |
| 31 | 58% @0.12 | 96% @0.012 | 0.0011 |
| 32 | 42% @0.04 | 104% @0.012 | 0.0007 |
| 33 | 38% @0.04 | 99% @0.012 | 0.00046 |
| 34 | 42% @0.04 | 100% @0.012 | 0.00085 |
| 35 | 54% @0.04 | 96% @0.012 | 0.0019 |
| 36 | 38% @0.04 | 99% @0.012 | 0.012 |
| 37 | | | 0.0028 |
| 38 | 0.48 | 88% @0.012 | 0.034 |
| 39 | | | 0.0054 |
| 40 | | | 0.0028 |
| 41 | 56% @0.12 | 97% @0.012 | 0.006 |
| 42 | 44% @0.04 | 95% @0.012 | 0.011 |
| 43 | 62% @0.04 | 69% @0.012 | 0.0083 |
| 44 | 78% @0.04 | 93% @0.012 | 0.001 |
| 45 | 52% @0.04 | 98% @0.012 | 0.0035 |
| 46 | 0.13 | 94% @0.012 | 0.036 |
| 47 | | | 0.0009 |
| 48 | 49% @0.04 | 96% @0.012 | 0.0043 |
| 49 | 44% @0.04 | 100% @0.012 | 0.0011 |
| 50 | 44% @0.04 | 100% @0.012 | 0.0013 |
| 51 | 44% @0.04 | 99% @0.012 | 0.0022 |
| 52 | 49% @0.04 | 100% @0.012 | 0.001 |
| 53 | 59% @0.04 | 99% @0.012 | 0.00061 |
| 54 | 59% @0.04 | 98% @0.012 | 96% at 0.001 |
| 55 | 59% @0.04 | 97% @0.012 | 0.00023 |
| 56 | 70% at 0.04 | 100% at 0.012 | 0.00042 |
| 57 | 41% @0.04 | 95% @0.012 | 0.0026 |
| 58 | 51% @0.04 | 98% @0.012 | 0.00070 |
| 59 | 0.34 | 68% @0.012 | 0.042 |
| 60 | 74% @0.04 | 91% @0.012 | 0.0067 |
| 61 | 57% @0.04 | 99% @0.012 | 0.0060 |
| 62 | 60% @0.04 | 97% @0.012 | 0.0011 |
| 63 | | | 0.00048 |
| 66 | 78% @0.04 | 100% @0.012 | 0.0008 |
| 67 | 65% @0.04 | 98% @0.012 | 0.0037 |
| 68 | 69% @0.04 | 77% @0.012 | 0.022 |
| 69 | 71% @0.04 | 84% @0.012 | 0.0056 |
| 71 | 64% @0.12 | 97% @0.012 | 0.098 |
| 76 | 49% @0.04 | 94% @0.012 | 0.0041 |
| 87 | 0.14 | 97% @0.012 | 0.00066 |
| 88 | 0.22 | 79% @0.012 | 0.00024 |
| 90 | 68% @0.12 | 94% @0.012 | 0.029 |
| 92 | 54% @0.04 | 100% @0.012 | 0.0027 |
| 93 | 50% @0.04 | 80% @0.012 | 0.0071 |
| 94 | 65% @0.12 | 96% @0.012 | 0.002 |
| 95 | 77% @0.04 | 94% @0.012 | 0.0031 |
| 96 | 49% @0.04 | 100% @0.012 | 0.0017 |
| 97 | 44% @0.04 | 96% @0.012 | 0.0023 |
| 98 | 62% @0.04 | 98% @0.012 | 0.0073 |
| 99 | 51% @0.12 | 90% @0.012 | 0.0015 |
| 100 | 56% @0.04 | 99% @0.012 | 0.00092 |
| 101 | 47% @0.04 | 74% @0.012 | 0.031 |
| 102 | 36% @0.04 | 86% @0.012 | 0.0058 |
| 103 | 69% @0.04 | 97% @0.012 | 0.0028 |
| 104 | 70% @0.04 | 110% @0.012 | 0.0013 |
| 105 | 60% @0.04 | 73% @0.012 | 0.035 |
| 106 | 42% @0.04 | 88% @0.012 | 0.0043 |
| 107 | 57% @0.04 | 79% @0.012 | 0.0071 |
| 108 | 66% @0.04 | 97% @0.012 | 0.0027 |
| 109 | 64% @0.04 | 93% @0.012 | 0.0097 |
| 110 | 39% @0.04 | 99% @0.012 | 0.0028 |
| 111 | 45% @0.04 | 82% @0.012 | 0.025 |
| 112 | 47% @0.04 | 90% @0.012 | 0.02 |
| 113 | | | 0.0094 |
| 114 | 82% @0.04 | 83% @0.012 | 0.024 |
| 115 | | | 0.0095 |
| 116 | 47% @0.04 | 70% @0.012 | 0.055 |
| 117 | 41% @0.04 | 85% @0.012 | |
| 119 | | | 0.00032 |
| 120 | | | 0.0003 |
| 121 | | | 0.00037 |

Where more than one data point has been obtained, the table above shows an average (e.g. geometric mean) of these data points (to 2 significant figures).

The invention claimed is:
1. A compound of formula (I):

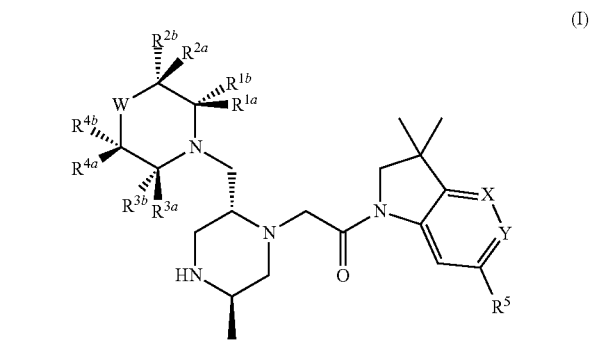

or a tautomeric or stereochemically isomeric form, N-oxide, pharmaceutically acceptable salt or solvate thereof; wherein X is CH and Y is $CR^9$, or one of X or Y is $CR^9$ and the other is nitrogen, or X and Y are nitrogen;

W is either absent or selected from $CR^6R^7$, $CH_2$—$CH_2$, $CH_2$—O, O—$CH_2$, C=O, $SO_2$, O, $NR^8$, $CH_2$—$NR^8$ and $NR^8$—$CH_2$;

when W is $CR^6R^7$, $CH_2$—$CH_2$, $CH_2$—O, O—$CH_2$, C=O, $SO_2$, $CH_2$—$NR^8$ or $NR^8$—$CH_2$, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, when W is $NR^8$, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^2b$ and $R^{3b}$, or $R^2b$ and $R^{4b}$, or $R^{3b}$ and $R^{4b}$ can join together to form a $C_{1-4}$ bridged alkyl group, or $R^{2a/2b}$ or $R^{4a/4b}$ can join together with the nitrogen atom at W to form a fused heterocyclic group with 5 or 6 ring members which can be optionally substituted by one or more substituents $R^{10}$, provided that when X and Y are other than both nitrogen, $R^{4a}$ and $R^{4b}$ do not together represent =O when $R^5$ is 1,1-difluoroethyl and $R^8$ is methyl;

when W is O, then $R^{1a}$, $R^{1b}$, $R^{2a}$, $R^{2b}$, $R^{3a}$, $R^{3b}$, $R^{4a}$, and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, provided that when X and Y are other than both nitrogen:
$R^{1a}$, $R^{1b}$, $R^{2a}$, $R^{2b}$, $R^{3a}$, $R^{3b}$, $R^{4a}$ and $R^{4b}$ are not all hydrogen, or when one of $R^{1a}$ or $R^{1b}$ or $R^{3a}$ or $R^{3b}$ is methyl or ethyl the remaining $R^{1a}$, $R^{1b}$, $R^{2a}$, $R^{2b}$, $R^{3a}$, $R^{3}$b, $R^{4a}$ and $R^{4b}$ groups are not all hydrogen, or when $R^{2a}$ and $R^{4a}$ are methyl then $R^{1a}$, $R^{1b}$, $R^{2b}$, $R^{3a}$, $R^{3b}$ and $R^{4b}$ are not all hydrogen, or $R^{1a}$ or $R^{3b}$ is not methoxymethyl when $R^5$ is 1,1-difluoropropyl;

when W is absent, then $R^{1a}$, $R^{1b}$, $R^{2a}$, $R^{2b}$, $R^{3a}$, $R^{3b}$, $R^{4a}$ and $R^{4b}$ are independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile, or $R^{2a}$ and $R^{2b}$, or $R^{4a}$ and $R^{4b}$ can together represent =O, or $R^{1a}$ and $R^{1b}$, $R^{2a}$ and $R^{2b}$, $R^{3a}$ and $R^{3b}$ or $R^{4a}$ and $R^{4b}$ can join together to form cyclopropyl or oxetanyl, or $R^{1a}$ and $R^{3a}$, or $R^{1a}$ and $R^{2a}$, or $R^{2a}$ and $R^{3a}$, or $R^{2a}$ and $R^{4a}$, or $R^{3a}$ and $R^{4a}$, or $R^{1b}$ and $R^{3b}$, or $R^{1b}$ and $R^{2b}$, or $R^{2b}$ and $R^{3b}$, or $R^{2b}$ and $R^{4b}$, or $R^{3b}$ and $R^{4b}$ can join together to form a $C_{1-4}$ bridged alkyl group, or $R^{2a/2b}$ and $R^{4a/4b}$ can join together to form a fused phenyl or pyridinyl group which can be optionally substituted by one or more substituents $R^{10}$, provided that when X and Y are other than both nitrogen:
$R^{1a}$, $R^{1b}$, $R^{2a}$, $R^{2b}$, $R^{3a}$, $R^{3b}$, $R^{4a}$ and $R^{4b}$ are not all hydrogen, or when one of $R^{2a}$ or $R^{2b}$ or $R^{4a}$ or $R^{4b}$ is fluorine the remaining $R^{1a}$, $R^{1b}$, $R^{2a}$, $R^{2b}$, $R^{3a}$, $R^{3b}$, $R^{4a}$ and $R^{4b}$ groups are not all hydrogen, or when $R^{2a}$ and $R^{2b}$, or $R^{4a}$ and $R^{4b}$ join to form =O then the remaining $R^{1a}$, $R^{1b}$, $R^{2a}$, $R^{2b}$, $R^{3a}$, $R^{3b}$, $R^{4a}$ and $R^{4b}$ groups are not all hydrogen, or $R^{2a}$ and $R^{2b}$, or $R^{4a}$ and $R^{4b}$ are not both fluorine when $R^5$ is 2,4-difluorobenzyl;

$R^5$ is selected from: benzyl optionally substituted on the phenyl group by one or two substituents selected from fluorine and nitrile, and optionally substituted on the methylene by hydroxyl; and $C_{2-4}$ alkyl substituted by one or two substituents selected from fluorine and hydroxyl;

$R^6$ and $R^7$ are independently selected from hydrogen, hydroxyl and fluorine;

$R^8$ is selected from hydrogen, $C_{1-4}$ alkyl, —$SO_2$-$C_{1-4}$ alkyl, —$SO_2$—NH($C_{1-4}$ alkyl), —$SO_2$—N($C_{1-4}$ alkyl)$_2$, —C(=O)—NH—$SO_2$-$C_{1-4}$ alkyl, —C(=O)—NH—$SO_2$-phenyl, —C(=O)—N($C_{1-4}$ alkyl)$_2$, pyrimidinyl, —C(=O)-phenyl, —C(=O)—$C_{3-6}$ cycloalkyl and —C(=O)—$C_{1-4}$ alkyl, wherein the alkyl or cyclic groups can be optionally substituted by one or more $R^{10}$;

$R^9$ is selected from hydrogen and nitrile; and $R^{10}$ is independently selected from hydrogen, halogen, $C_{1-4}$ alkyl, carboxyl, hydroxyl, hydroxy$C_{1-4}$ alkyl, $C_{1-4}$ alkyoxy, $C_{3-6}$ cycloalkyl, halo$C_{1-4}$ alkyl, methoxymethyl and nitrile.

2. A compound as defined in claim 1, wherein X and Y are both nitrogen; X is nitrogen and Y is $CR^9$; or X is $CR^9$ and Y is nitrogen, or a tautomeric or stereochemically isomeric form, N-oxide, pharmaceutically acceptable salt or solvate thereof.

3. A compound as defined in claim 2, wherein X is nitrogen and Y is CH, or a tautomeric or stereochemically isomeric form, N-oxide, pharmaceutically acceptable salt or solvate thereof.

4. A compound as defined in claim 1, wherein W is either absent or is selected from $CR^6R^7$, $CH_2$—O, C=O, $SO_2$, O, $NR^8$ and $CH_2$—$NR^8$, or a tautomeric or stereochemically isomeric form, N-oxide, pharmaceutically acceptable salt or solvate thereof.

5. A compound as defined in claim 1, wherein W represents O, or a tautomeric or stereochemically isomeric form, N-oxide, pharmaceutically acceptable salt or solvate thereof.

6. A compound as defined in claim 1, wherein $R^{1a}$, $R^{1b}$, $R^{2a}$, $R^{2b}$, $R^{3a}$, $R^{3b}$, $R^{4a}$ and $R^{4b}$ independently represent hydrogen or $C_{1-4}$ alkyl, or a tautomeric or stereochemically isomeric form, N-oxide, pharmaceutically acceptable salt or solvate thereof.

7. A compound as defined in claim 1, wherein $R^{1a}$ and $R^{3b}$ both represents methyl and $R^{1b}$, $R^{2a}$, $R^{2b}$, $R^{3a}$, $R^{4a}$ and $R^{4b}$ each represent hydrogen, or a tautomeric or stereochemically isomeric form, N-oxide, pharmaceutically acceptable salt or solvate thereof.

8. A compound as defined in claim 1, wherein when W represents $NR^8$:

$R^{1a}$ and $R^{1b}$ both represent hydrogen or one represents hydrogen and the other represents $C_{1-4}$ alkyl;

$R^{2a}$ and $R^{2b}$ both represent hydrogen or one represents hydrogen and the other represents $C_{1-4}$ alkyl or $R^{2a}$ and $R^{2b}$ together represent =O;

$R^{3a}$ and $R^{3b}$ both represent hydrogen or one represents hydrogen and the other represents $C_{1-4}$ alkyl;

$R^{4a}$ and $R^{4b}$ both represent hydrogen or one represents hydrogen and the other represents $C_{1-4}$ alkyl or $R^{4a}$ and $R^{4b}$ together represent =O;

or $R^{2a}$/$R^{2b}$ join together with the nitrogen atom at W to form a fused heteroaromatic group with 5 or 6 ring members which can be optionally substituted by one or more substituents $R^{10}$;

$R^8$ represents hydrogen, $C_{1-4}$ alkyl, —$SO_2$-$C_{1-4}$ alkyl, —C(=O)—N($C_{1-4}$ alkyl)$_2$, pyrimidinyl, —C(=O)-phenyl or —C(=O)—$C_{1-4}$ alkyl, or a tautomeric or stereochemically isomeric form, N-oxide, pharmaceutically acceptable salt or solvate thereof.

9. A compound as defined in claim 1, wherein when W represents $NR^8$, $R^8$ represents hydrogen, $C_{1-4}$ alkyl, —$SO_2$-$C_{1-4}$ alkyl, —C(=O)—N($C_{1-4}$ alkyl)$_2$, pyrimidinyl, —C(=O)-phenyl or —C(=O)—$C_{1-4}$ alkyl, or a tautomeric or stereochemically isomeric form, N-oxide, pharmaceutically acceptable salt or solvate thereof.

10. A compound as defined in claim 1, wherein when W is $NR^8$, $R^8$ is —C(=O)-methyl, $R^{3b}$ is methyl, $R^{1a}$ is hydrogen or methyl, and $R^{1b}$, $R^{2a}$, $R^{2b}$, $R^{3a}$, $R^{4a}$ and $R^{4b}$ are hydrogen, or a tautomeric or stereochemically isomeric form, N-oxide, pharmaceutically acceptable salt or solvate thereof.

11. A compound as defined in claim 1, wherein when W represents O:

$R^{1a}$ and $R^{1b}$ both represent hydrogen or $C_{1-4}$ alkyl or one represents hydrogen and the other represents $C_{1-4}$ alkyl, hydroxyC$_{1-4}$ alkyl, haloC$_{1-4}$ alkyl or methoxymethyl, or one represents C$_{1-4}$ alkyl and the other represents hydroxyC$_{1-4}$ alkyl or carboxyl;

R$^{2a}$ and R$^{2b}$ both represent hydrogen or C$_{1-4}$ alkyl or one represents hydrogen and the other represents nitrile;

R$^{1a}$ and R$^{3b}$ both represent hydrogen or one represents hydrogen and the other represents C$_{1-4}$ alkyl or hydroxyC$_{1-4}$ alkyl or one represents C$_{1-4}$ alkyl and the other represents hydroxyC$_{1-4}$ alkyl;

R$^{4a}$ and R$^{4b}$ both represent hydrogen or one represents hydrogen and the other represents C$_{1-4}$ alkyl;

or R$^{1a}$ and R$^{1b}$ join together to form cyclopropyl;

or R$^{1a}$ and R$^{1a}$ or R$^{1b}$ and R$^{3b}$ join together to form a C$_{1-4}$ bridged alkyl group;

or R$^{2a}$ and R$^{1a}$ or R$^{2b}$ and R$^{3b}$ join together to form a C$_{1-4}$ bridged alkyl group;

or R$^{1a}$ and R$^{4a}$ or R$^{1b}$ and R$^{4b}$ join together to form a C$_{1-4}$ bridged alkyl group;

or R$^{2a}$ and R$^{4a}$ or R$^{2b}$ and R$^{4b}$ join together to form a C$_{1-4}$ bridged alkyl group, or a tautomeric or stereochemically isomeric form, N-oxide, pharmaceutically acceptable salt or solvate thereof.

12. A compound as defined in claim 11, wherein W is O and R$^{1a}$ and R$^{3b}$ are methyl, or a tautomeric or stereochemically isomeric form, N-oxide, pharmaceutically acceptable salt or solvate thereof.

13. A compound as defined in claim 12, wherein W is O, R$^{1a}$ and R$^{3b}$ are methyl, and R$^{1b}$, R$^{2a}$, R$^{2b}$, R$^{3a}$, R$^{4a}$ and R$^{4b}$ are hydrogen, or a tautomeric or stereochemically isomeric form, N-oxide, pharmaceutically acceptable salt or solvate thereof.

14. A compound as defined in claim 1, wherein R$^5$ is selected from benzyl optionally substituted on the phenyl group by one or two fluorines or one fluorine and one nitrile, wherein the methylene is optionally substituted by a hydroxyl group or R$^5$ is selected from C$_{2-4}$ alkyl substituted by one or two fluorines, or a tautomeric or stereochemically isomeric form, N-oxide, pharmaceutically acceptable salt or solvate thereof.

15. A compound as defined in claim 1, wherein the compound of formula (I) is a compound of formula (If):

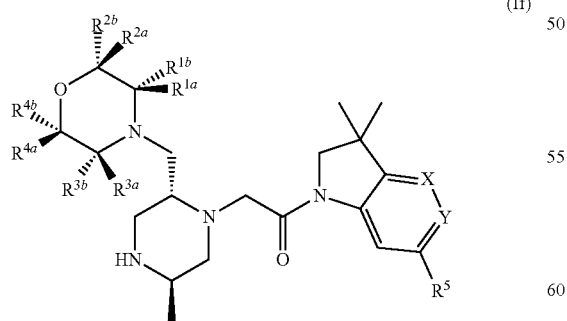

or a tautomeric or stereochemically isomeric form, N-oxide, pharmaceutically acceptable salt or solvate thereof.

16. A compound as defined in claim 1, wherein the compound of formula (I) is a compound of formula (Ij):

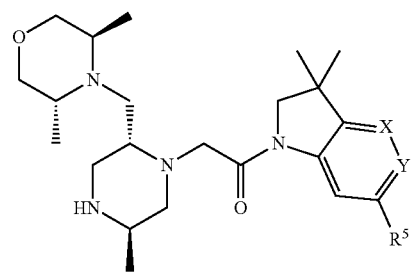

or a tautomeric or stereochemically isomeric form, N-oxide, pharmaceutically acceptable salt or solvate thereof.

17. A compound as defined in claim 1, wherein the compound is selected from:

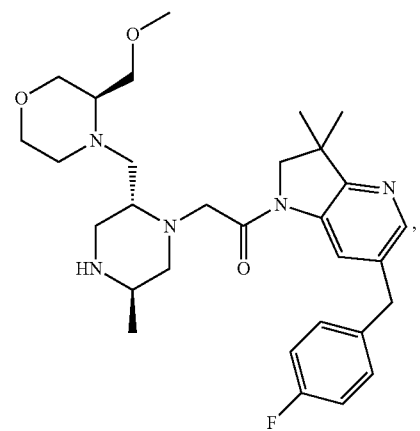

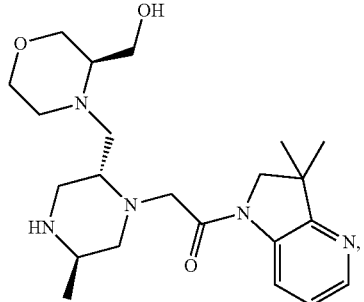

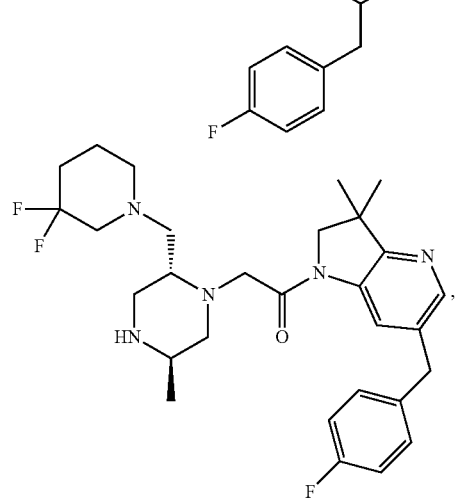

251
-continued
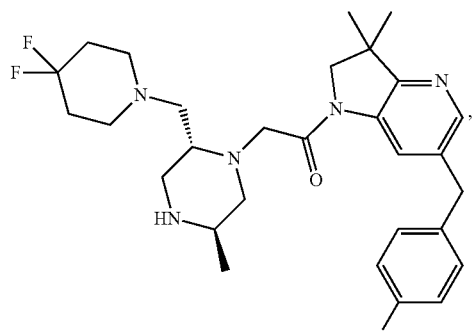
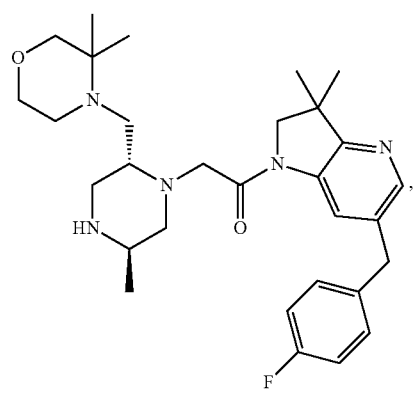
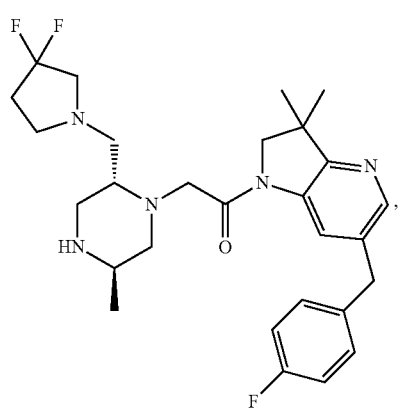
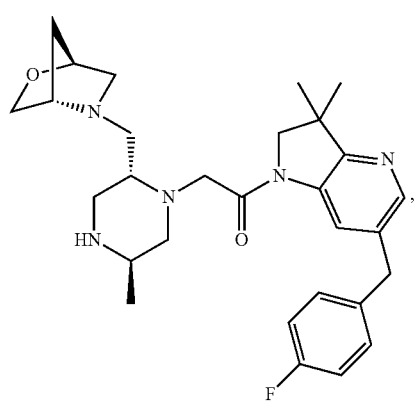
252
-continued
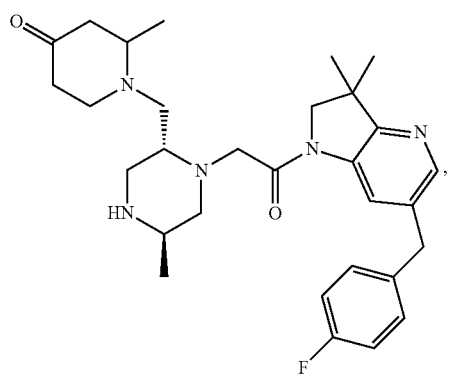
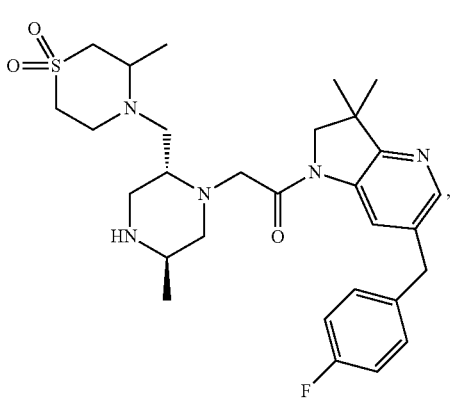
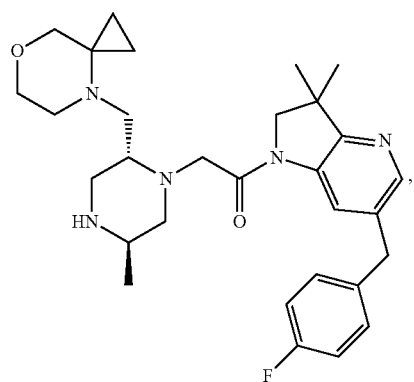
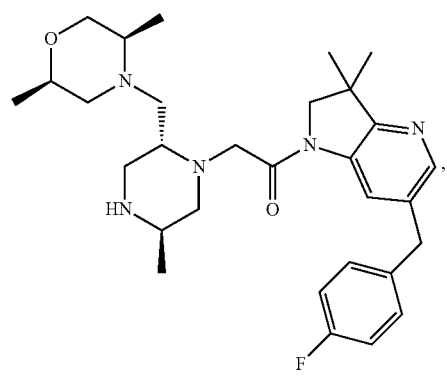

253
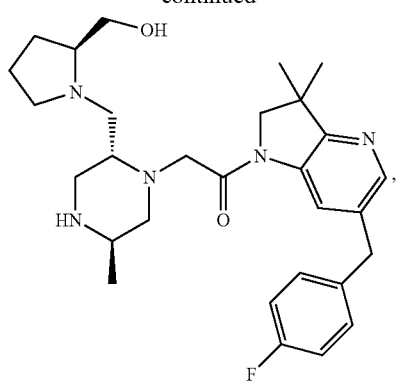
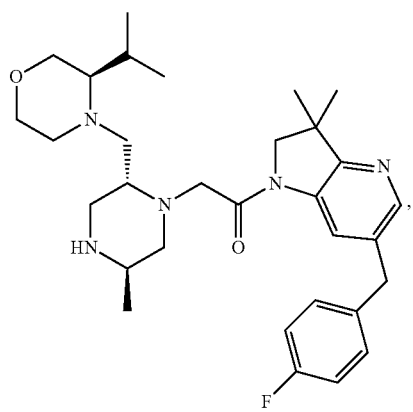
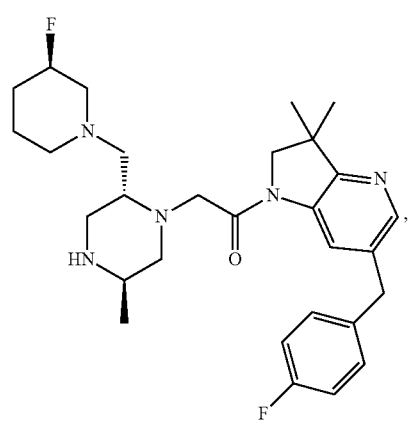
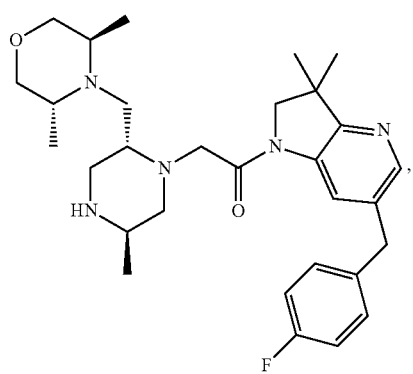
254
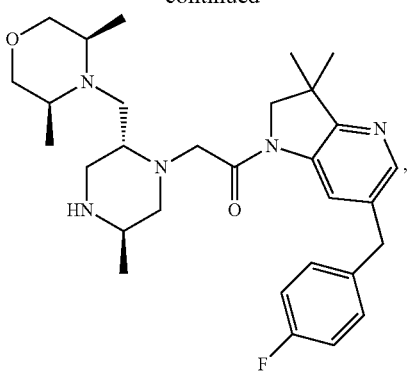
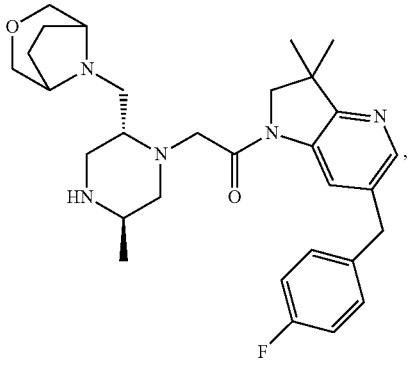
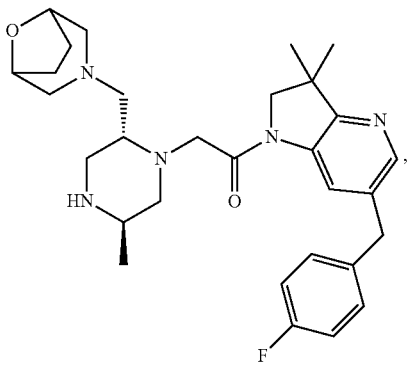
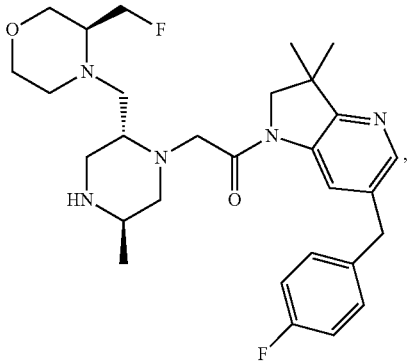

255
-continued
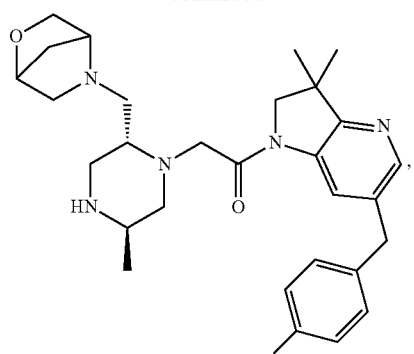
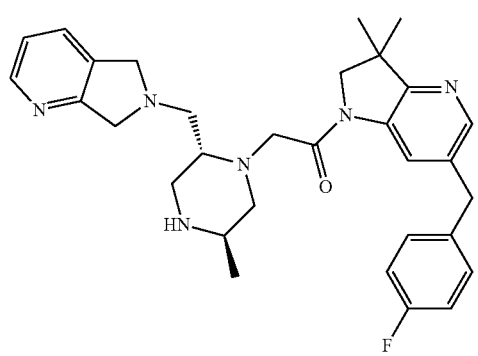
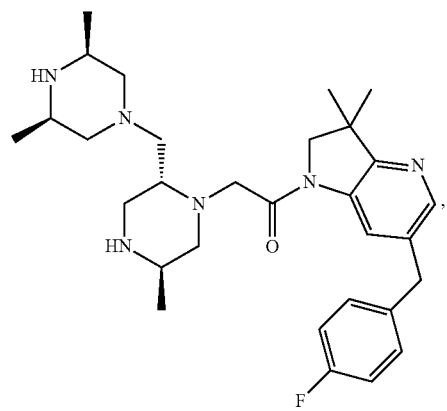
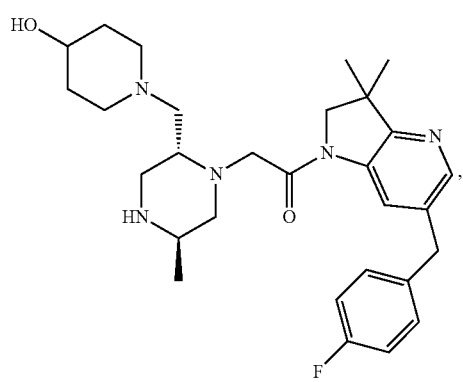
256
-continued
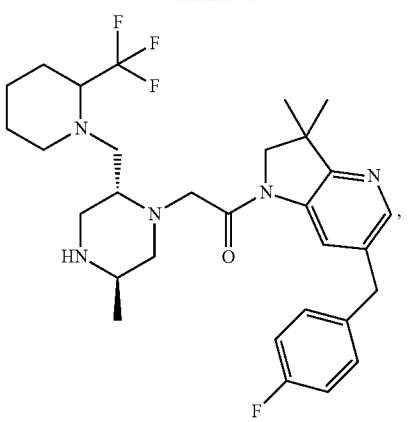
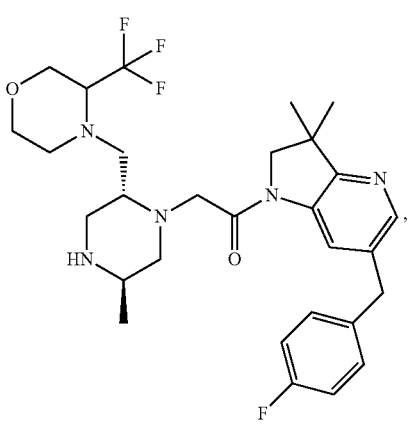
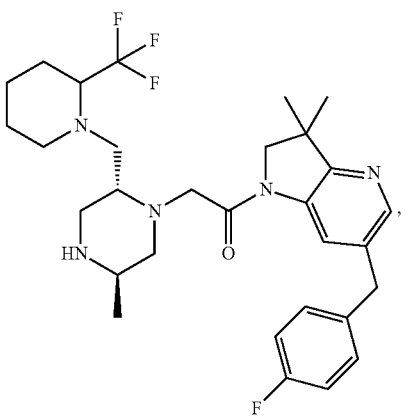
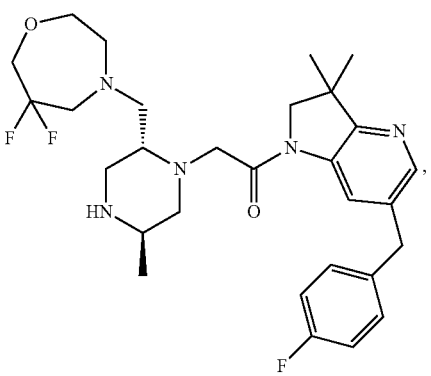

257
-continued
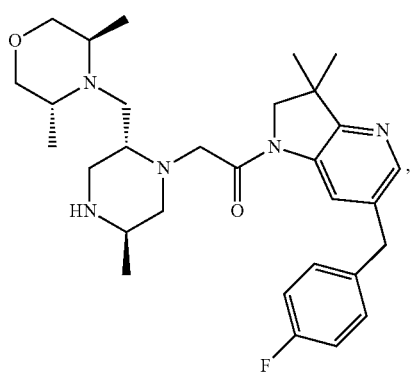
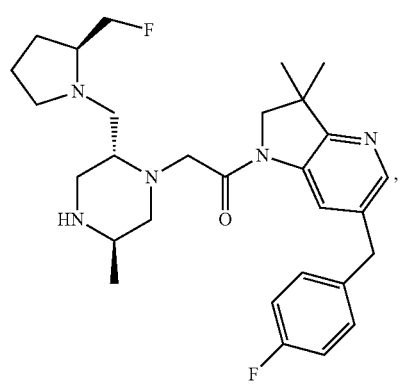
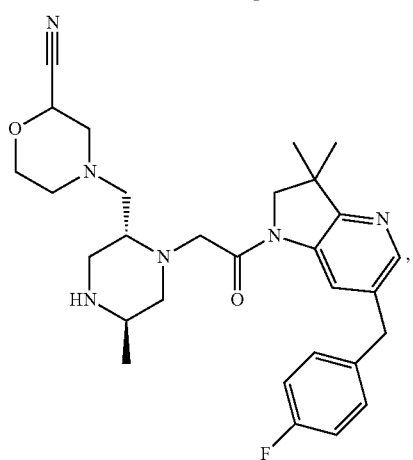
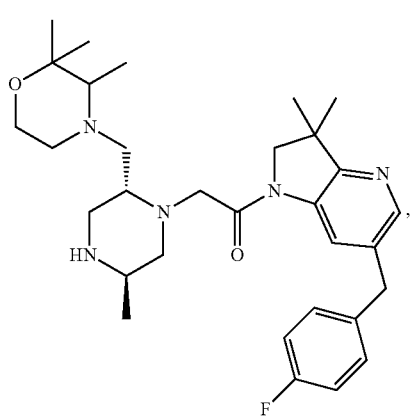
258
-continued
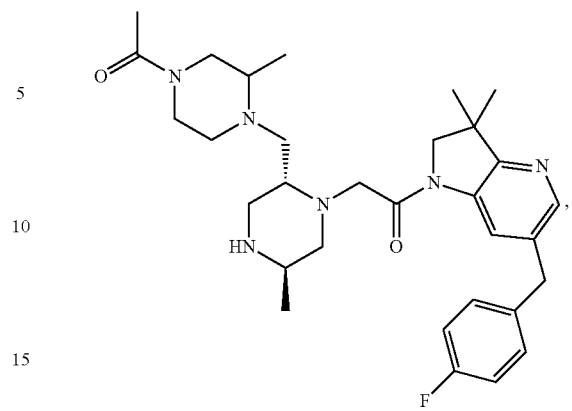
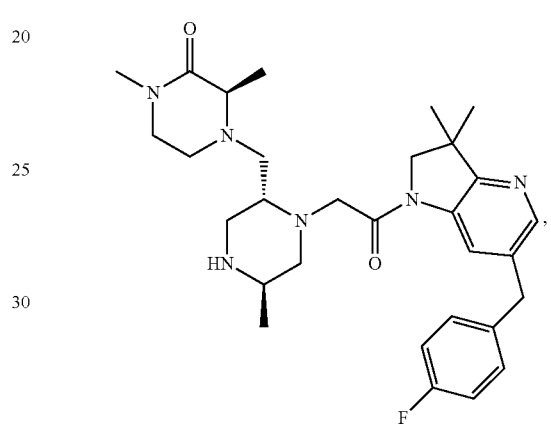
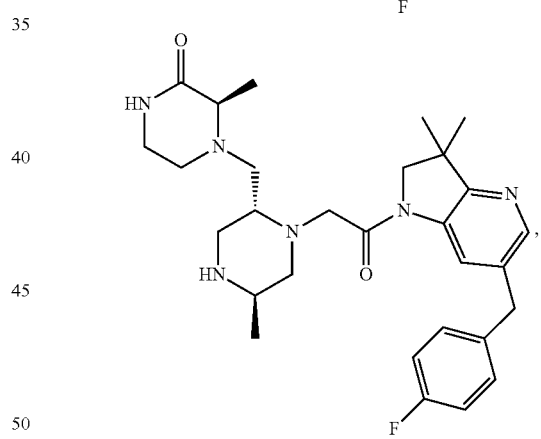
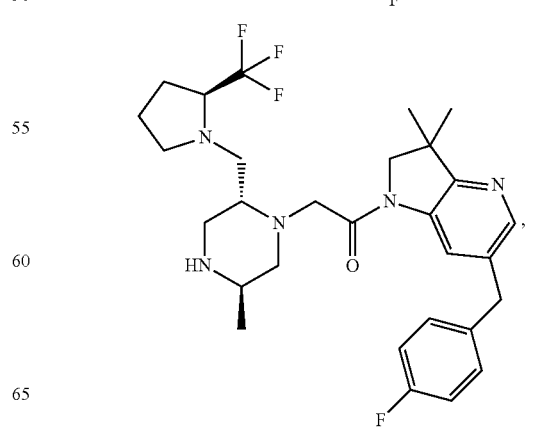

259
-continued
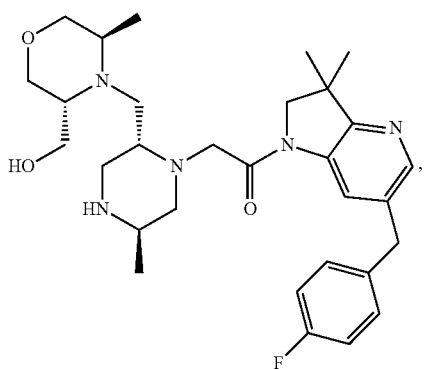
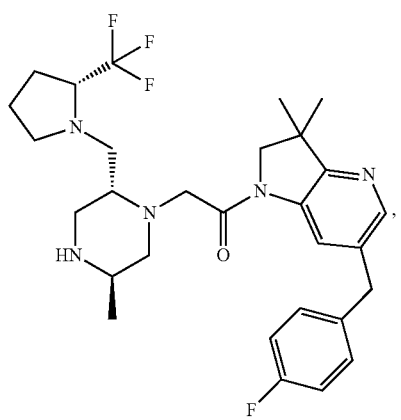
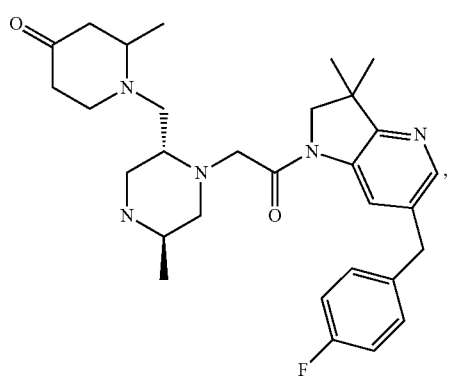
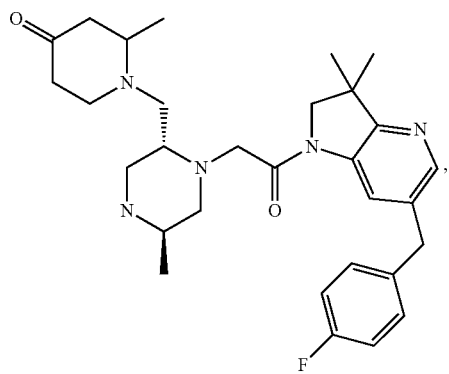
260
-continued
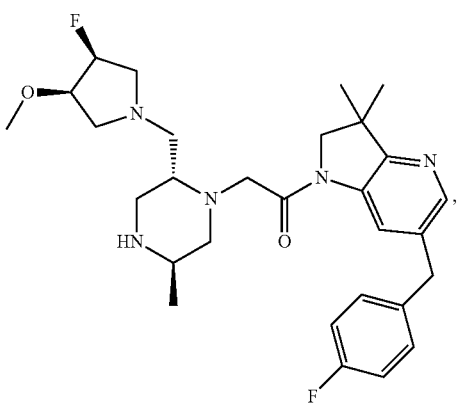
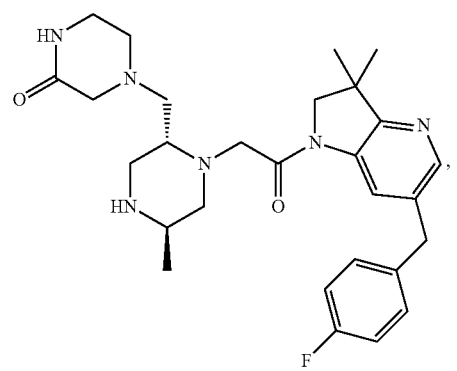
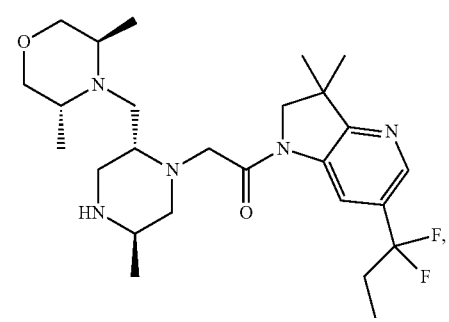
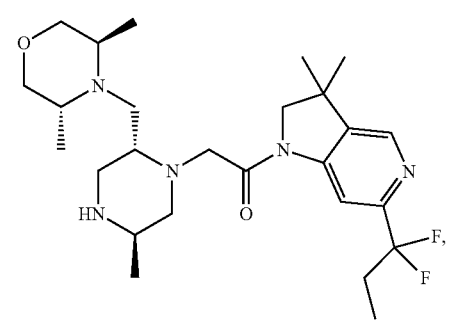

261
-continued
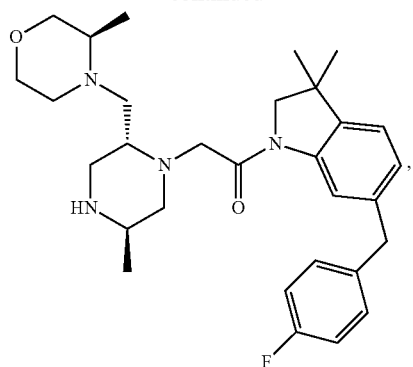
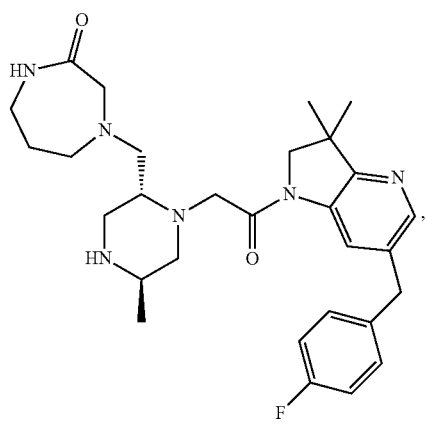
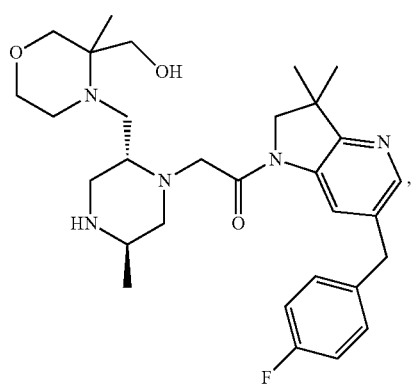
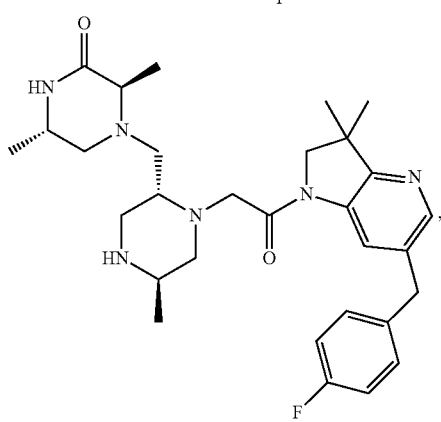
262
-continued
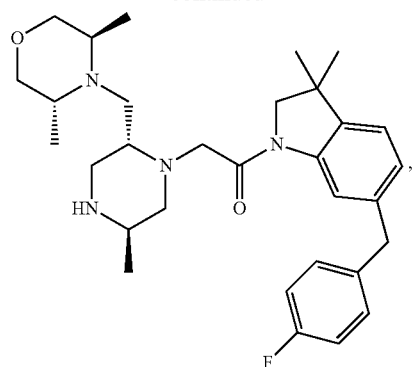
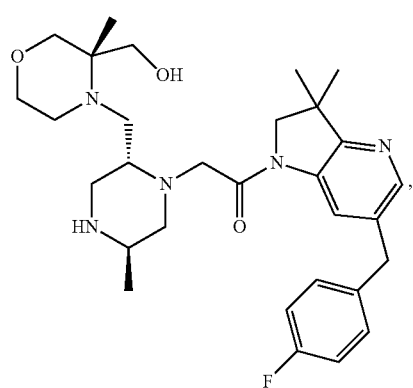
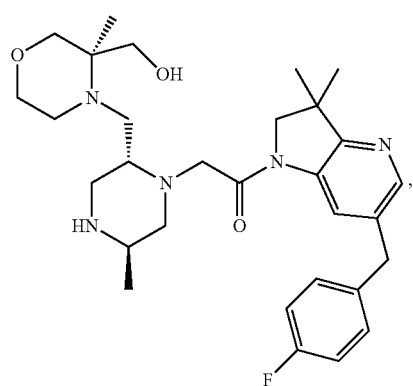
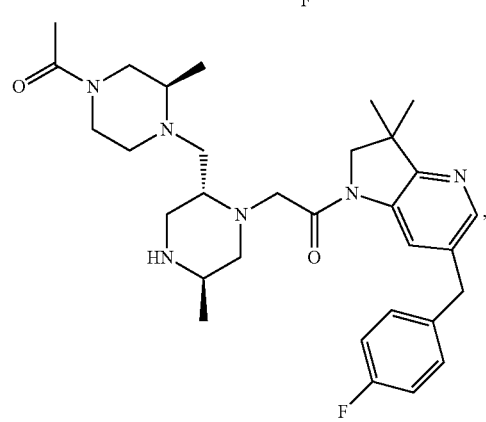

263
-continued
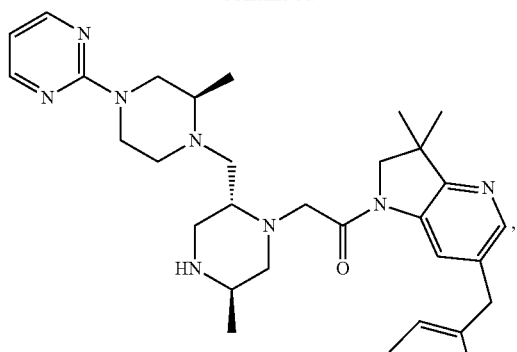
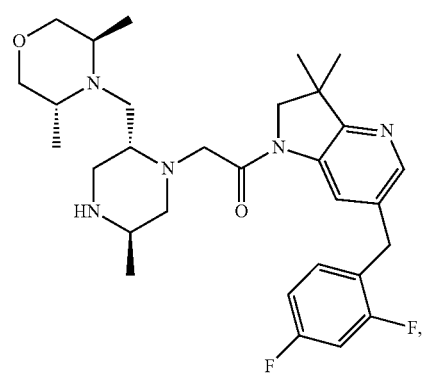
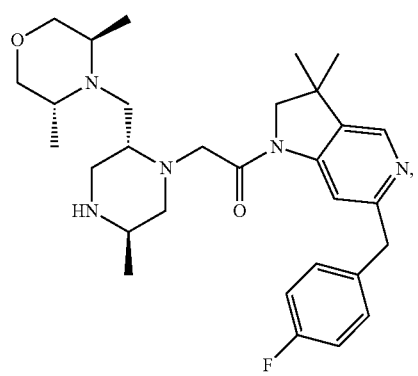
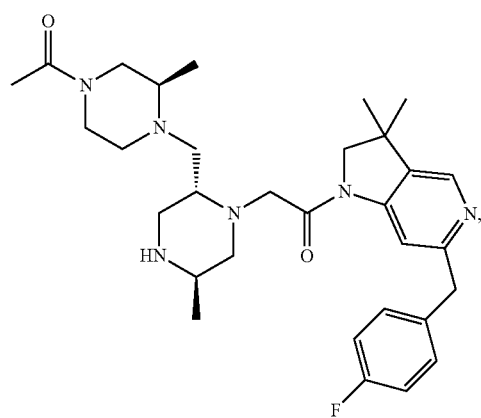
264
-continued
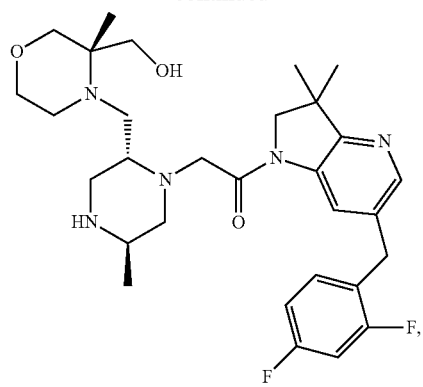
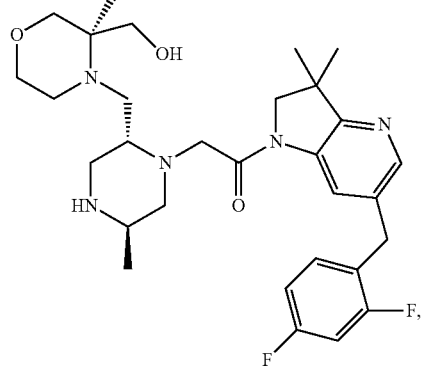
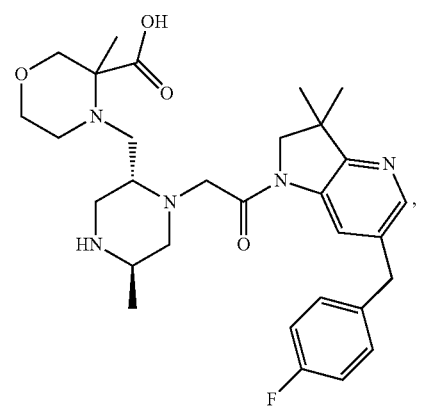
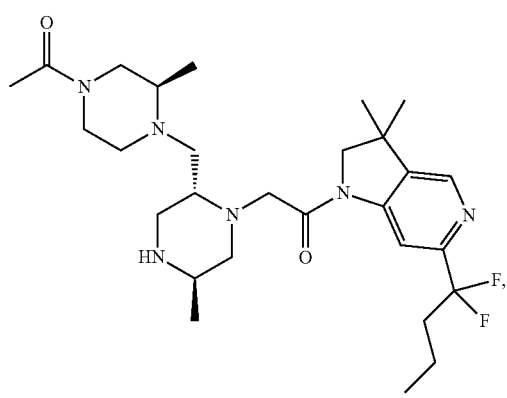

265
-continued
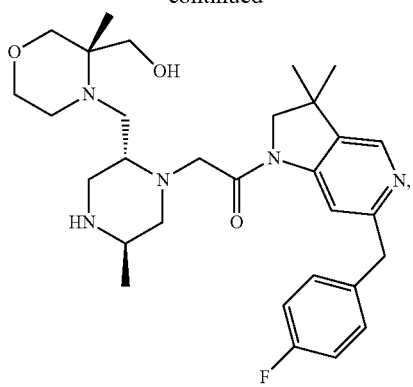
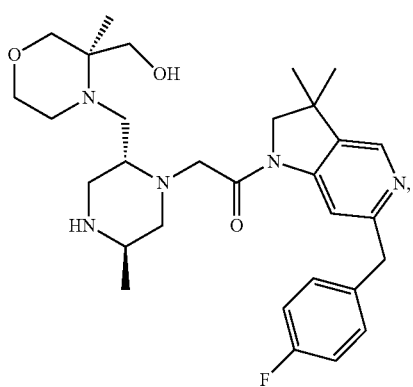
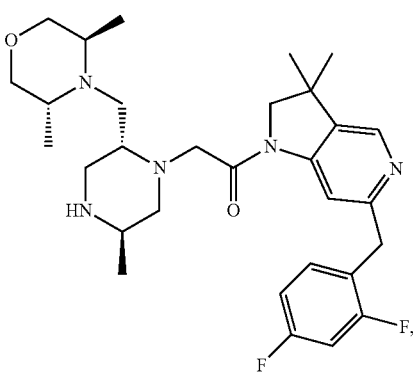
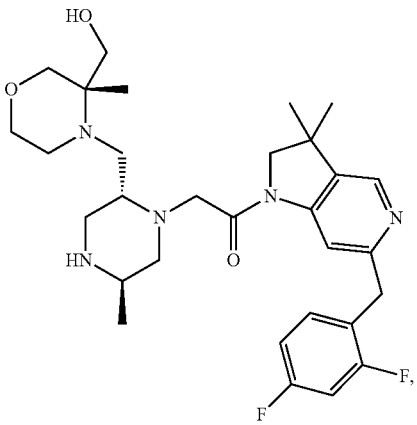
266
-continued
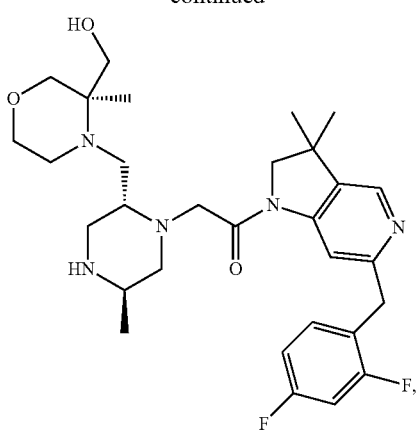
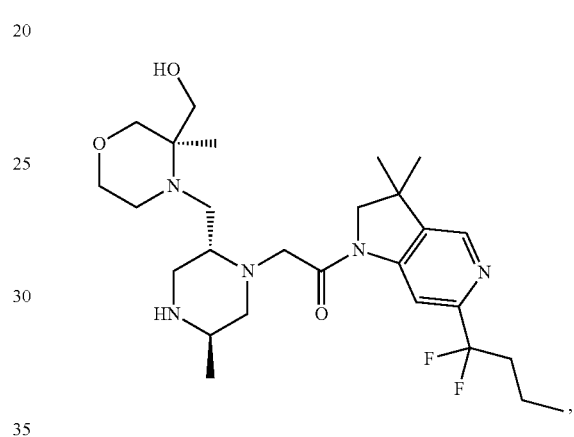
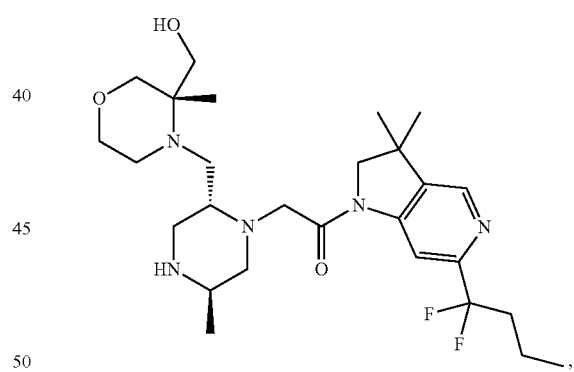
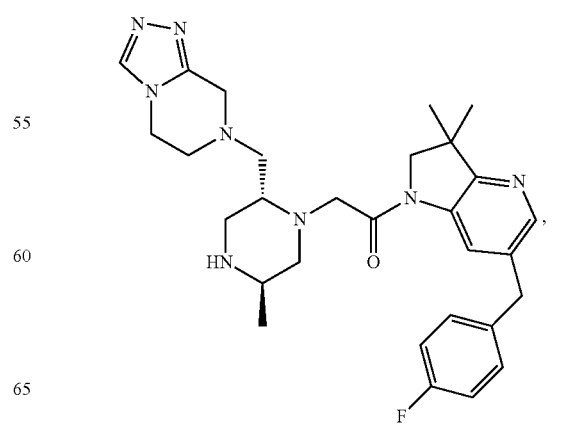

267
-continued
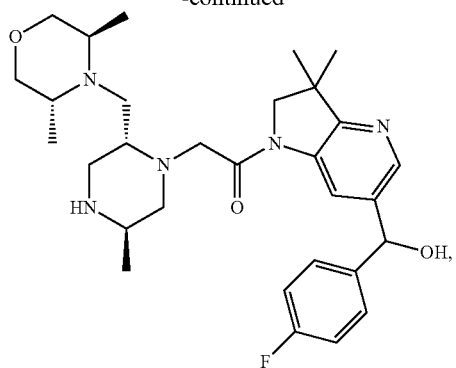
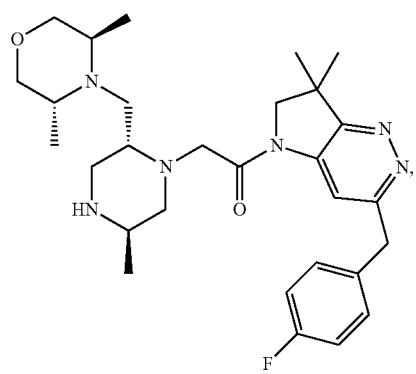
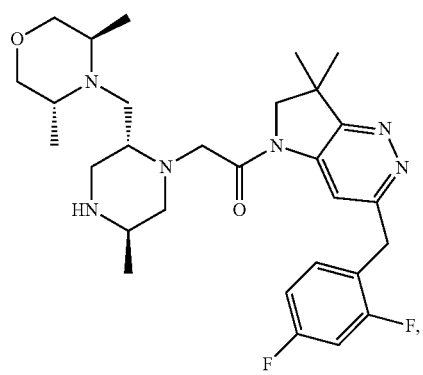
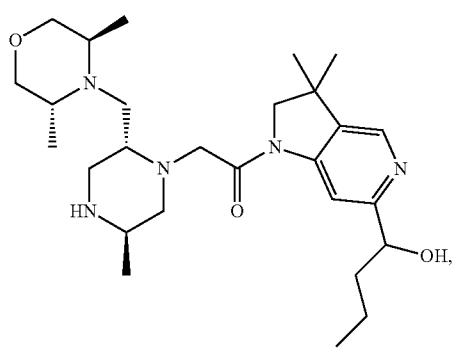
268
-continued
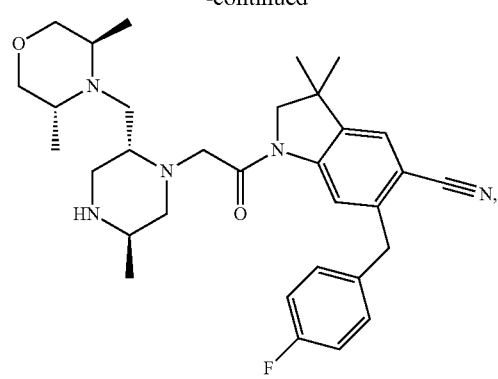
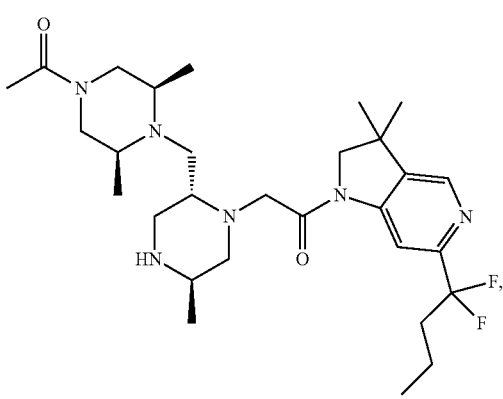
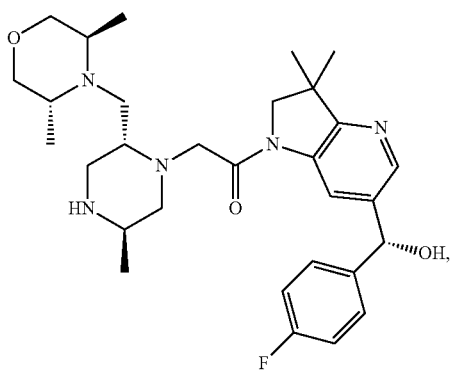
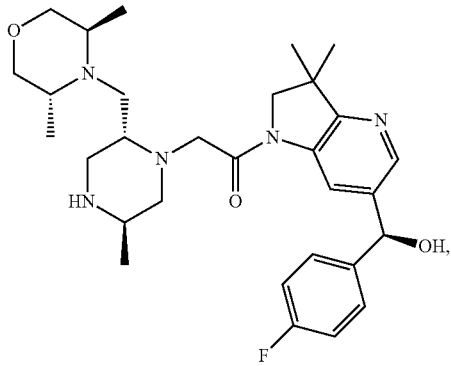

269
-continued
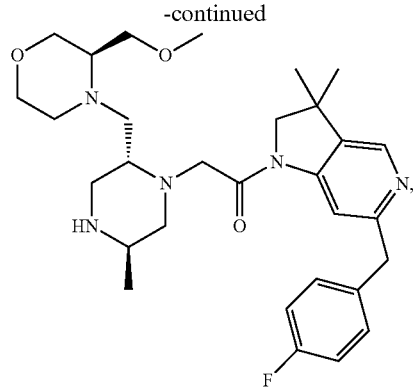
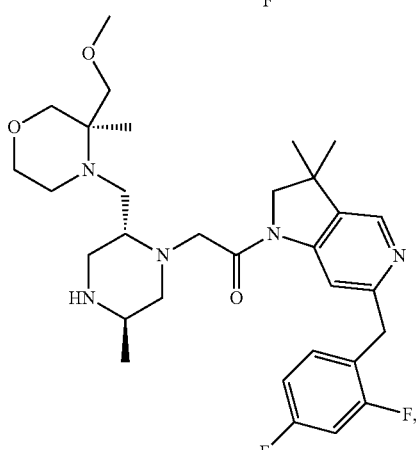
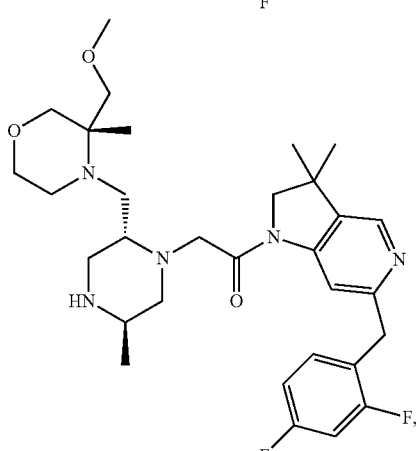
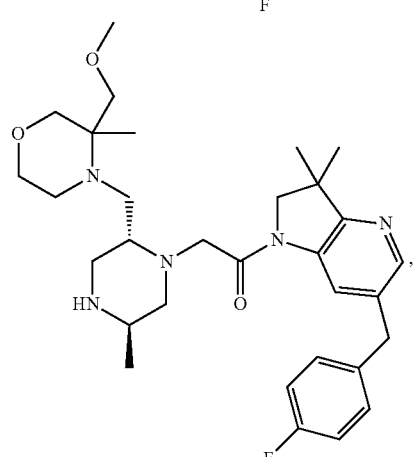
270
-continued
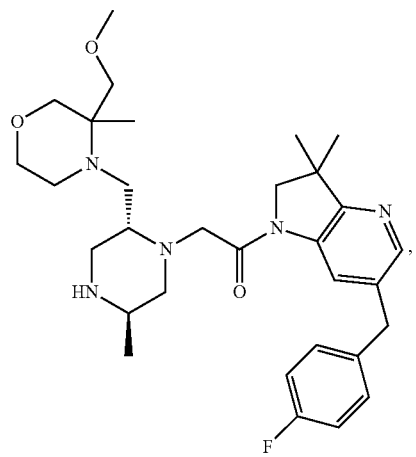
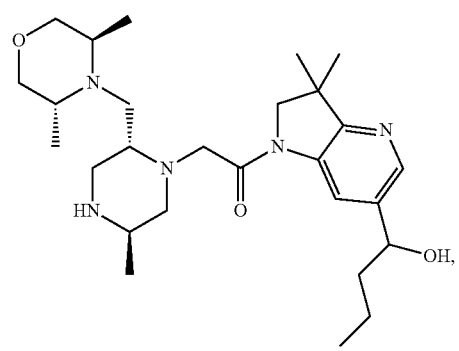
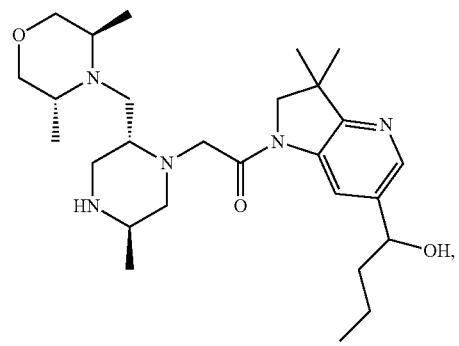
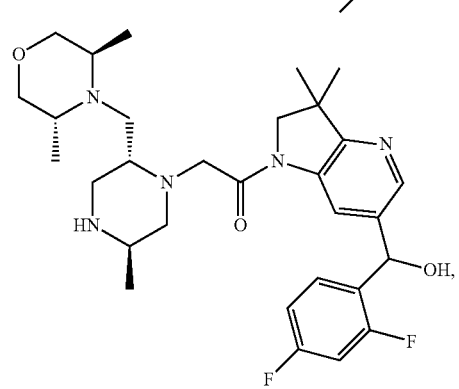

| 271 -continued | 272 -continued |
|---|---|
| 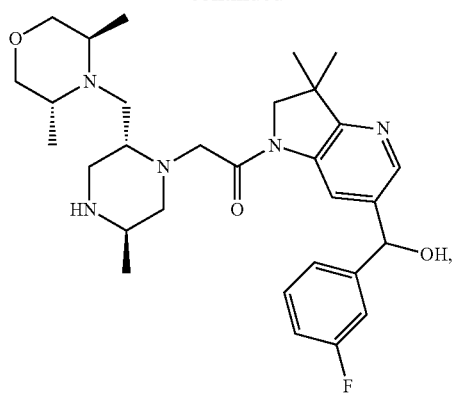 | 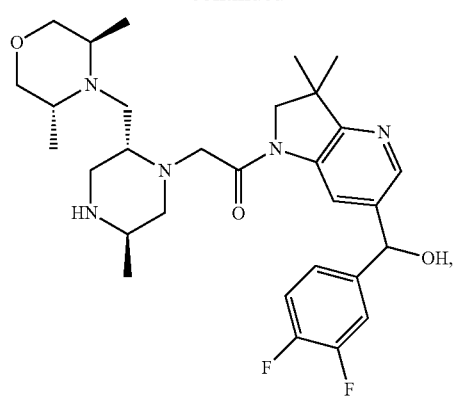 |
| 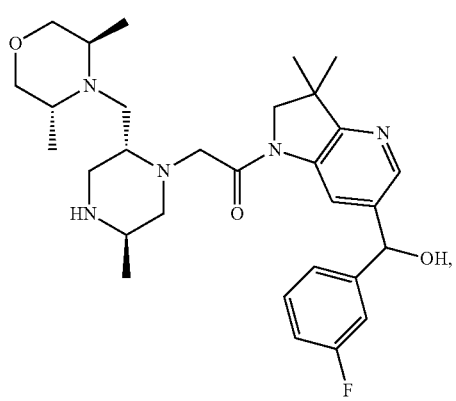 | 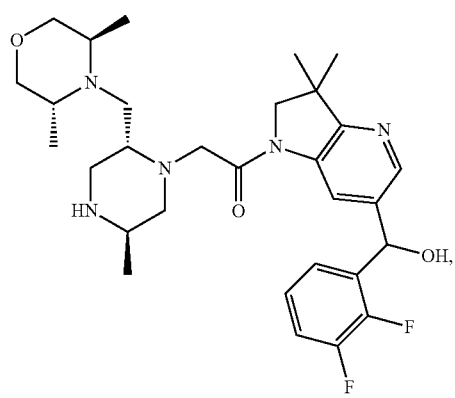 |
| 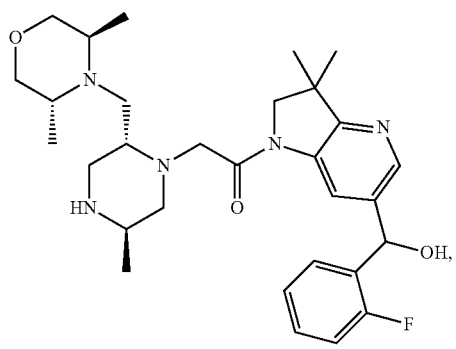 | 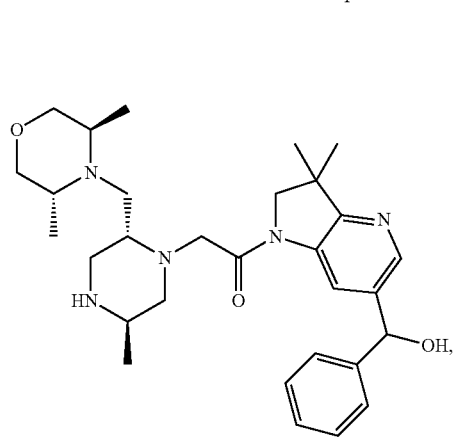 |
| 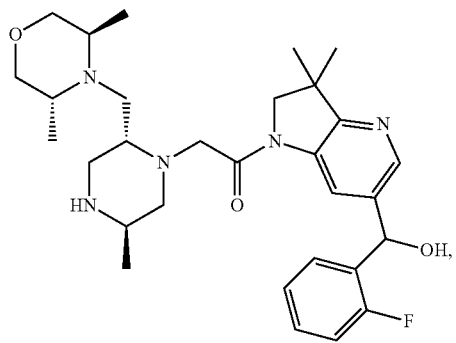 | 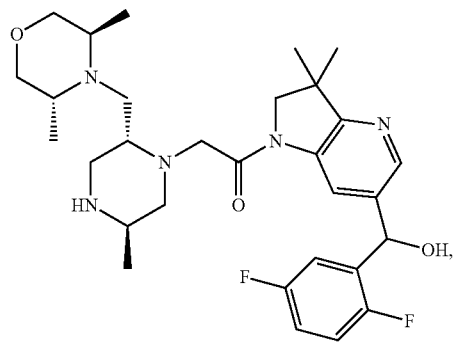 |

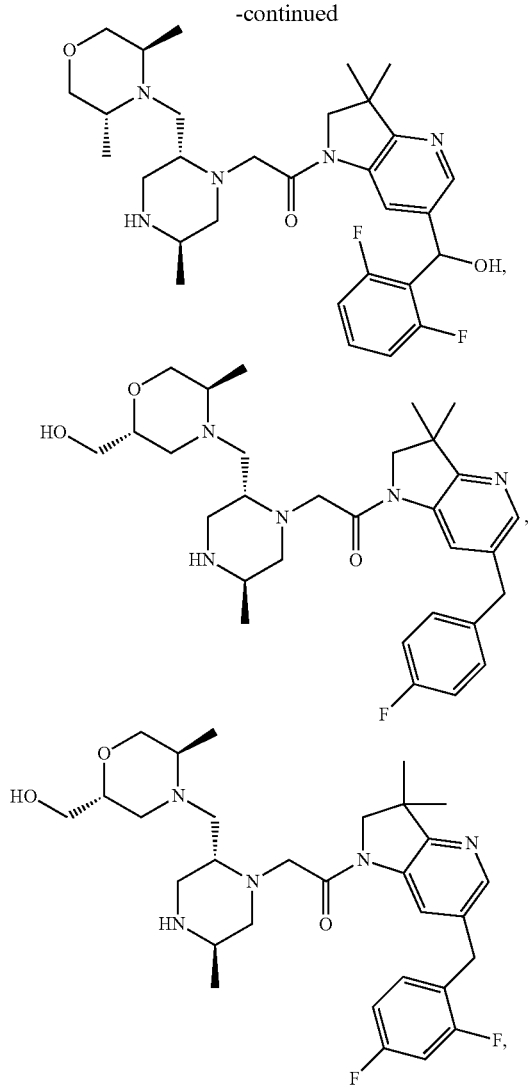

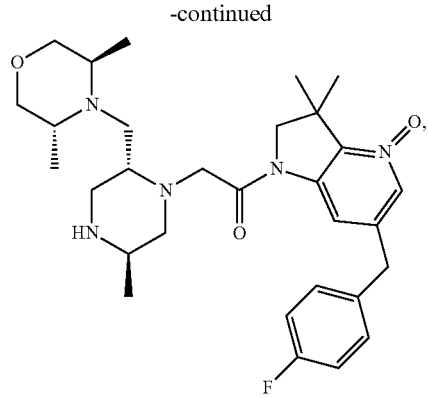

or a tautomeric or stereochemically isomeric form, N-oxide, pharmaceutically acceptable salt or solvate thereof.

18. A pharmaceutical composition comprising a compound of formula (I) as defined in claim 1, or a tautomeric or stereochemically isomeric form, N-oxide, pharmaceutically acceptable salt or solvate thereof.

19. A method of treating a disease state or condition mediated by inhibitor of apoptosis protein (IAP), the method comprising administering to a subject in need thereof a compound of formula (I) as defined in claim 1, or a tautomeric or stereochemically isomeric form, N-oxide, pharmaceutically acceptable salt or solvate thereof.

20. A method of inhibiting the activity of inhibitor of apoptosis protein (IAP), the method comprising contacting the IAP with a compound of formula (I) as defined in claim 1, or a tautomeric or stereochemically isomeric form, N-oxide, pharmaceutically acceptable salt or solvate thereof.

\* \* \* \* \*

UNITED STATES PATENT AND TRADEMARK OFFICE
CERTIFICATE OF CORRECTION

PATENT NO. : 9,617,248 B2  
APPLICATION NO. : 14/436319  
DATED : April 11, 2017  
INVENTOR(S) : Chessari et al.

Page 1 of 1

It is certified that error appears in the above-identified patent and that said Letters Patent is hereby corrected as shown below:

In the Claims

Column 249, Line 6: Claim 11, Delete "$R^{1a}$ and $R^{3b}$" and insert -- $R^{3a}$ and $R^{3b}$ --

Column 249, Line 13: Claim 11, Delete "or $R^{1a}$ and $R^{1a}$" and insert -- or $R^{1a}$ and $R^{3a}$ --

Column 249, Line 15: Claim 11, Delete "or $R^{2a}$ and $R^{1a}$" and insert -- or $R^{2a}$ and $R^{3a}$ --

Signed and Sealed this  
Twenty-seventh Day of June, 2017

Joseph Matal  
*Performing the Functions and Duties of the*  
*Under Secretary of Commerce for Intellectual Property and*  
*Director of the United States Patent and Trademark Office*